(12) United States Patent
Musicki et al.

(10) Patent No.: US 10,752,617 B2
(45) Date of Patent: *Aug. 25, 2020

(54) INDAZOLE SULFONAMIDE DERIVATIVES AS INVERSE AGONISTS OF RETINOID-RELATED ORPHAN RECEPTOR GAMMA (ROR GAMMA (T))

(71) Applicant: GALDERMA RESEARCH & DEVELOPMENT, Biot (FR)

(72) Inventors: Branislav Musicki, Nice (FR); Gilles Ouvry, Biot (FR); Etienne Thoreau, Saint Vallier de Thiey (FR); Claire Bouix-Peter, Vallauris (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,115

(22) Filed: Mar. 8, 2019

(65) Prior Publication Data

US 2019/0202819 A1    Jul. 4, 2019

Related U.S. Application Data

(63) Continuation of application No. 15/537,678, filed as application No. PCT/EP2015/080689 on Dec. 18, 2015, now Pat. No. 10,246,440.

(30) Foreign Application Priority Data

Dec. 19, 2014  (FR) ..................................... 14 63035
Jul. 3, 2015   (FR) ..................................... 15 56341

(51) Int. Cl.
| | |
|---|---|
| *C07D 231/56* | (2006.01) |
| *C07D 401/06* | (2006.01) |
| *C07D 403/04* | (2006.01) |
| *C07D 405/04* | (2006.01) |
| *C07D 405/06* | (2006.01) |
| *C07D 405/12* | (2006.01) |
| *C07D 405/14* | (2006.01) |
| *C07D 401/04* | (2006.01) |
| *C07D 403/06* | (2006.01) |
| *C07D 407/04* | (2006.01) |
| *C07D 409/04* | (2006.01) |
| *C07D 409/06* | (2006.01) |
| *C07D 417/06* | (2006.01) |
| *C07D 471/10* | (2006.01) |
| *C07D 209/34* | (2006.01) |
| *C07D 215/36* | (2006.01) |
| *C07D 307/79* | (2006.01) |
| *A61K 31/416* | (2006.01) |
| *A61P 17/10* | (2006.01) |
| *A61P 17/06* | (2006.01) |
| *A61P 17/04* | (2006.01) |
| *C07D 413/06* | (2006.01) |
| *C07D 235/26* | (2006.01) |
| *C07D 401/14* | (2006.01) |

(52) U.S. Cl.
CPC ............ *C07D 413/06* (2013.01); *A61P 17/04* (2018.01); *A61P 17/06* (2018.01); *A61P 17/10* (2018.01); *C07D 209/34* (2013.01); *C07D 215/36* (2013.01); *C07D 231/56* (2013.01); *C07D 235/26* (2013.01); *C07D 307/79* (2013.01); *C07D 401/04* (2013.01); *C07D 401/06* (2013.01); *C07D 401/14* (2013.01); *C07D 403/04* (2013.01); *C07D 403/06* (2013.01); *C07D 405/04* (2013.01); *C07D 405/06* (2013.01); *C07D 405/12* (2013.01); *C07D 405/14* (2013.01); *C07D 407/04* (2013.01); *C07D 409/04* (2013.01); *C07D 409/06* (2013.01); *C07D 417/06* (2013.01); *C07D 471/10* (2013.01)

(58) Field of Classification Search
CPC .. C07D 231/56; C07D 401/06; C07D 403/04; C07D 405/04; C07D 405/06; C07D 405/14; C07D 413/06; A61K 31/416; A61P 17/10
USPC ........................... 548/361.1, 358.1; 514/412
See application file for complete search history.

(56) References Cited

U.S. PATENT DOCUMENTS

10,246,440 B2 *   4/2019   Musicki ............... C07D 405/14
2008/0004288 A1   1/2008   Santhakumar et al.

FOREIGN PATENT DOCUMENTS

| WO | WO-2006/052190 A1 | 5/2006 |
|---|---|---|
| WO | WO-2011/137089 A1 | 11/2011 |
| WO | WO-2013/160418 A1 | 10/2013 |

(Continued)

OTHER PUBLICATIONS

International Search Report dated Mar. 7, 2016 corresponding to International Patent Application No. PCT/EP2015/080689, 6 pages.

(Continued)

*Primary Examiner* — Venkataraman Balasubramanian
(74) *Attorney, Agent, or Firm* — Foley & Lardner LLP; S. Talapatra

(57) ABSTRACT

Indazole sulfonamide derivatives of formula (I), the pharmaceutically acceptable addition salts thereof, the hydrates and/or solvates thereof, and the use of same as inverse agonists of retinoid-related orphan receptor gamma RORγt are described. Pharmaceutical compositions including such compounds, as well as the use thereof for the topical and/or oral treatment of RORγt receptor-mediated inflammatory diseases, in particular acne, psoriasis and/or atopic dermatitis are also described.

19 Claims, No Drawings

(56) References Cited

FOREIGN PATENT DOCUMENTS

WO     WO-2014/090712 A1     6/2014

OTHER PUBLICATIONS

Zhang et al., "Discovery of 2-oxo-1, 2-dihydrobenzo[cd]indole-6-sulfonamide derivatives as new RORγ inhibitors using virtual screening, synthesis and biological evaluation", European J. Med. Chem., vol. 78, Mar. 2014, pp. 431-444, XP028847891.
Chemical Abstracts Registry No. 1328091-23-1, indexed in the Registry file on STN CAS Online on Sep. 4, 2011. (Year : 2011).
Chemical Abstracts Registry No. 914244-66-9, indexed in the Registry file on STN CAS Online on Nov. 29, 2006. (Year : 2006).
Chemical Abstracts Registry No. 924168-33-2, indexed in the Registry file on STN CAS Online on Mar. 1, 2007. (Year: 2007).
Chemical Abstracts Registry No. 950052-33-2, indexed in the Registry file on STN CAS Online on Oct. 10, 2007. (Year : 2007).

\* cited by examiner

INDAZOLE SULFONAMIDE DERIVATIVES AS INVERSE AGONISTS OF RETINOID-RELATED ORPHAN RECEPTOR GAMMA (ROR GAMMA (T))

CROSS-REFERENCE TO RELATED APPLICATIONS

This application is a continuation of U.S. application Ser. No. 15/537,678, filed Jun. 19, 2017, which is the National Stage of PCT/EP2015/080689, filed Dec. 18, 2015, published on Jun. 23, 2016 as WO 2016/097391 A1, which claims priority to French Application No. 1463035, filed Dec. 19, 2014 and to French Application No. 1556341, filed Jul. 3, 2015. The contents of these applications are herein incorporated by reference in their entirety.

The present invention relates to particular bicyclic sulfonamide derivatives, to the pharmaceutically acceptable addition salts thereof, hydrates thereof and/or solvates thereof, and also to the use thereof as inverse agonist of the retinoid-related orphan receptor gamma RORγt.

The invention also relates to a pharmaceutical composition comprising such compounds and also to the use thereof for the topical and/or oral treatment of inflammatory diseases mediated by the RORγt receptors, especially acne, atopic dermatitis and/or psoriasis.

The nuclear receptors form a large family (known as a superfamily) of transcription factors which correspond to proteins that are capable of being activated by a ligand, of binding to specific DNA sequences and of regulating the transcription of target genes. Thus, these receptors are involved in the regulation of a wide variety of biological functions, including growth, development, reproduction, differentiation and metabolism in a multitude of living organisms.

The first members of this superfamily that were identified and described in the scientific literature are the nuclear receptors of steroid hormones such as the glucocorticoid receptors and the estrogen receptors. This superfamily also comprises among its members many receptors for which no ligand has been identified. These nuclear receptors are known as "orphan receptors".

Retinoid-related orphan receptors thus constitute a subfamily of nuclear receptors. This subfamily is composed of three members each having an intrinsic expression profile: ROR alpha (known as RORα), ROR beta (known as ROM and ROR gamma (known as RORγ). Two isoforms of the orphan receptors RORγ have already been identified, namely RORγ1, which is expressed in a variety of tissues such as the thymus, the kidneys, muscles and the liver, and RORγ2 (also known as RORγt), which is expressed exclusively in the cells of the immune system.

In particular, the receptor RORγt plays an important regulating role in cell differentiation of the Th17 lymphocytes which correspond to helper T lymphocytes whose function is to ensure the defence of the body against a large number of extracellular pathogens such as bacteria and fungal infections.

However, it has been demonstrated that the Th17 lymphocytes are also involved in a wide variety of inflammatory disorders, such as acne, and of autoimmune diseases such as psoriasis, rheumatoid arthritis or multiple sclerosis (Peck A, Mellins E D. Precarious balance; Th17 cells in host defense. Infect. Immun. 2010 January; 78(1): 32-8; Suarez-Farinas: J. Allergy Clin. Immunol. 2014; J. Invest. Dermatol. 2008, 128(11), 2625).

Specifically, the Th17 lymphocytes produce numerous cytokines which have distinct profiles, such as interleukin-17A (IL-17A), interleukin-17F (IL-17F), interleukin-26 (IL-26), interleukin-21 (IL-21), interleukin-22 (IL-22) and TNFα, the development, survival and proliferation of which depend on interleukin-23 (IL-23). These cytokines are capable of activating different types of effector cells, such as keratinocytes, thus leading to their hyperproliferation and to the additional production of pro-inflammatory cytokines, chemokines and antimicrobial peptides, which in turn recruit and activate other immune system cells in the inflamed skin, which may lead to amplification of the immune response.

Thus, activation of the Th17 lymphocytes is responsible for the recruitment of cytokines, especially of interleukin-17 (IL17), and of other types of pro-inflammatory cells, which will lead to the mediation of inflammatory disorders such as acne and/or of autoimmune diseases such as psoriasis.

Experiments conducted on mice show that a decrease in the level of expression of the RORγt receptor leads to a decrease in the activity of the Th17 lymphocytes, which consequently makes it possible to greatly reduce the expression of interleukin-17 (IL-17) (Ivanov I I, McKenzie B S, Zhou L, Tadokoro C E, Lepelley A, Lafaille J J, Cua D J, Littman D R: Cell 2006, 126, 1121-1133) and to efficiently treat inflammatory disorders and autoimmune diseases mediated by these cytokines, especially those for which high levels of interleukin-17 (IL-17) are detected.

To this end, patent application WO 2013/160 418 describes sulfonamide compounds used as inverse agonists of the RORγt receptor in order to be able to treat inflammatory disorders and autoimmune diseases. Similarly, other compounds have also been developed as inverse agonists of the RORγt receptor, such as those described in patent applications WO 2014/090 712, WO 2014/008 214, WO 2013/169 588, WO 2013/160 419, WO 2013/1 002 027, WO 2013/092 939, WO 2013/092 941, WO 2013/085 890 and WO 2012/100 732.

There is thus a real need to develop novel compounds as inverse agonists of the RORγt receptor in order to be able to efficiently treat diseases mediated by such a receptor, especially inflammatory disorders such as acne, and/or autoimmune diseases such as psoriasis or atopic dermatitis.

This aim is achieved by means of the use of particular bicyclic sulfonamide derivatives as described below, which make it possible to modulate the activity of the RORγt receptor and consequently to efficiently treat inflammatory disorders and autoimmune diseases of certain pathologies.

One subject of the present invention is thus especially one or more compounds of formula (Ia), the pharmaceutically acceptable addition salts thereof, hydrates thereof and/or solvates thereof:

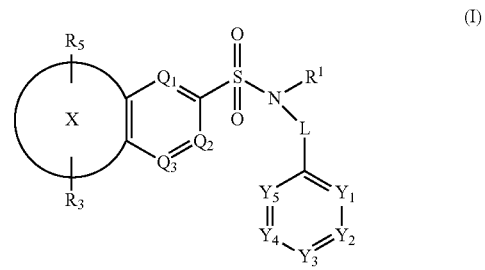

in which formula (I):
L represents a single bond or a methylene group $CH_2$,

X represents a cyclic radical chosen from the radicals $X_1$ and $X_2$ below:

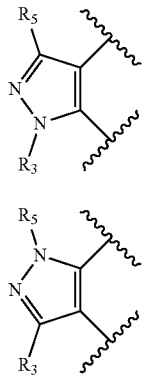

one or two of the elements $Y^1$, $Y^2$, $Y^3$, $Y^4$ and $Y^5$ represent(s) a nitrogen atom and the other elements correspond to a group $—CR^2$, or each of the elements $Y^1$, $Y^2$, $Y^3$, $Y^4$ and $Y^5$ corresponds to a group $—CR^2$, one or two of the elements $Q^1$, $Q^2$ and $Q^3$ represent(s) a nitrogen atom and the other element(s) correspond(s) to a group $—CR^{2a}$, or each of the elements $Q^1$, $Q^2$ and $Q^3$ corresponds to a group $—CR^{2a}$, $R^1$ represents a linear or branched $C_3$-$C_5$ alkyl radical, optionally substituted with a hydroxyl group and/or a halogen atom, a $C_3$-$C_5$ cycloalkyl radical, a linear or branched $C_2$-$C_5$ alkenyl radical, a $(C_1)$alkyl$(C_3$-$C_5)$ cycloalkyl radical, a $C_4$-$C_5$ heterocycloalkyl radical, a $(C_1)$alkyl$(C_4$-$C_6)$heterocycloalkyl radical, $R^2$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a cyano group $—CN$, a radical $—C(=O)R'^2$ with $R'^2$ denoting a $C_1$-$C_3$ alkoxy radical, a $—CF_3$ radical; said alkyl, alkenyl and alkoxy radicals possibly being substituted with one or more halogen atoms, $R^{2a}$ represents a hydrogen atom or a halogen atom, a linear or branched $C_1$-$C_5$ alkyl radical, a linear or branched $C_2$-$C_4$ alkenyl radical, a $C_1$-$C_4$ alkoxy radical, a $—CN$ group, a hydroxyl group $—OH$, a group $—CH(R^{3a})OH$, a carboxylic group $—COOH$, a carbamoyl group $—CONR^{2c}R^{2d}$, an amido group $—NR^{2c}COR^{2d}$, a group $—SO_2R^{2c}$, a group $—SOR^{2c}$, a group $—S(=O)(=NH—R^{2c})$, said alkyl, alkenyl and alkoxy radicals possibly being substituted with one or more halogen atoms, $R^{2c}$ and $R^{2d}$, which may be identical or different, represent a hydrogen atom or a linear or branched $C_1$-$C_5$ alkyl radical;

$R^{3a}$ represents a hydrogen atom or a linear or branched $C_1$-$C_5$ alkyl radical, $R^3$ represents a hydrogen atom, a halogen atom, a group $(CHR^6)_n—(Z)O—(CHR'^6)_p—R^7$, a group $CH=R^7$ or a group $—C=CH—R^7$, n, o and p, which may be identical or different, represent zero or a natural integer ranging from 1 to 3, $—Z$ represents a divalent group chosen from a methylene group $—CH_2—$, an amino group $—NH—$ and an oxygen atom $—O—$, $R^6$ and $R'^6$, which may be identical or different, represent a hydrogen atom, a methyl group $—CH_3$, a group $—OH$, a $C_1$ hydroxyalkyl group, a carboxylic function $—COOH$, $R^7$ represents:
a hydrogen atom or a halogen atom,
a group $COOR'^7$ with $R'^7$ denoting $(C_1)$alkyl$(C_6)$heterocycle,
a non-cationic heterocyclic radical optionally substituted with one or more halogen atoms, one or more linear or branched $C_1$-$C_3$ alkyl groups, one or more $—OH$ groups, one or more carbonyl functions, one or more linear or branched $C_1$-$C_4$ hydroxyalkyl groups, one or more amino groups, one or more groups $—C(=O)R^{7a}$, one or more groups $S(=O)_2R^{7a}$; $R^{7a}$ representing a linear or branched $C_1$-$C_3$ alkyl radical, a linear or branched $C_1$-$C_3$ alkoxy radical, or an amino radical $N(R^{8a})(R^{8b})$,
a non-cationic $C_3$-$C_6$ cycloalkyl radical optionally substituted with one or more $C_1$ alkyl radicals, one or more halogen atoms, a cyano group $—CN$ or one or more groups $—COR^9$; $R^9$ denoting a linear or branched $C_1$-$C_3$ alkoxy radical, or a hydroxyl group,
an aromatic or heteroaromatic, non-cationic radical optionally substituted with one or more halogen atoms, one or more linear or branched $C_1$-$C_3$ alkyl groups optionally substituted with one or more halogen atoms, one or more $C_1$-$C_3$ alkoxy groups, one or more amino groups $—NR^{11}R^{12}$, one or more groups $—COR^{11}$, one or more groups $—COOR^{11}$, one or more amido groups $—CONR^{11}R^{12}$, one or more groups $—SOR^{11}$, one or more groups $—SO_2R^{11}$, one or more groups $—NHCOR^{11}$, one or more groups $—NHCOOR^{11}$, one or more groups $—SO_2NR^{11}R^{12}$ or one or more $—CN$ groups; $R^{11}$ and $R^{12}$, which may be identical or different, representing a hydrogen atom, a hydroxyl radical $—OH$, a linear or branched $C_1$-$C_3$ alkyl radical optionally substituted with one or more halogen atoms;
when $R^3$ represents a group $—CH=R^7$ or a group $—C=CH—R^7$, then $R^7$ does not represent a hydrogen atom, a halogen atom or a group $COOR'^7$,
$R^5$ represents a hydrogen atom or a halogen atom, a linear or branched $C_1$-$C_3$ alkyl radical optionally substituted with one or more halogen atoms; an amino radical $—NH_2$, a $C_4$-$C_5$ heterocyclic radical, an $OCH_2—(C_4$-$C_5)$heterocyclic radical, a radical $CH_2R'^{7a}$ with $R'^{7a}$ denoting a $C_1$ alkoxy radical, a hydroxyl group-$OH$, a $—CH_2COOH$ group, a group $—CH(R^{5b})OH$, an amino group $—NH_2$, a carboxylic group $—COOH$, a $—CN$ group, a thioxo function,
$R^{5b}$ represents a hydrogen atom, a linear or branched $C_1$-$C_3$ alkyl radical optionally substituted with one or more carboxylic functions; a cyclopropyl radical,
$R^{8a}$ and $R^{8b}$, which may be identical or different, denote a hydrogen atom, a linear or branched $C_1$-$C_3$ alkyl radical or a cyclopropyl radical.

The compound(s) according to the invention thus correspond to bicyclic sulfonamide derivatives, and thus to one or more sulfonamide compounds bearing in their structure at least two rings that are fused to each other.

In other words, X is a cyclic radical fused to the aromatic nucleus, comprising the elements $Q^1$, $Q^2$ and $Q^3$ as defined above.

In accordance with the definition of formula (I), the endocyclic bond between the cyclic radical $X_1$ or $X_2$, as represented above, and the aromatic nucleus comprising the elements $Q_1$ to $Q_3$ is a double bond. Thus, the double bond is common between the cyclic radical $X_1$ or $X_2$ and the aromatic nucleus comprising the elements $Q_1$ to $Q_3$.

The compounds according to the invention make it possible to modulate, i.e. to inhibit, the activity of the RORγt receptor.

A subject of the present invention is also the compound(s) as defined previously, as medicament and cosmetic.

Another subject of the invention relates to the compound(s) as defined previously for their use in the treatment of diseases mediated by the RORγt receptor, especially inflammatory disorders and/or autoimmune diseases mediated by the RORγt receptor.

Moreover, the invention also relates to a pharmaceutical composition comprising, in a pharmaceutically acceptable medium, one or more compounds of formula (I) as defined previously, pharmaceutically acceptable addition salts thereof, hydrates thereof and/or solvates thereof.

The present invention also relates to the pharmaceutical composition as described previously, for its use in the treatment of diseases mediated by the RORγt receptor, especially inflammatory disorders and/or autoimmune diseases.

Finally, the invention relates to a method for treating diseases mediated by the RORγt receptor, comprising the administration, especially topically or orally, of a therapeutically effective amount of one or more compounds as defined above to a patient.

Other subjects, characteristics, aspects and advantages of the invention will emerge even more clearly on reading the description and the examples that follow.

According to one embodiment, in formula (I):
$R^3$ represents a hydrogen atom, a group $(CHR^6)_n-(Z)_o-(CHR'^6)_p-R^7$, a group $CH=R^7$ or a group $-C=CH-R^7$, and
$R^5$ represents a hydrogen atom or a halogen atom, a linear or branched $C_1$-$C_3$ alkyl radical optionally substituted with one or more halogen atoms; an amino radical $-NH_2$, a radical $CH_2R'^{7a}$ with $R'^7a$ denoting a $C_1$ alkoxy radical, a hydroxyl group $-OH$, a $-CH_2COOH$ group, a group $-CH(R^{5b})OH$, an amino group $-NH_2$, a carboxylic group $-COOH$, a $-CN$ group, a thioxo function.

According to one embodiment, in formula (I), L represents a single bond.

According to another embodiment, in formula (I), L represents a methylene group $-CH_2$.

Preferentially, in formula (I), L represents a single bond.

Preferably:
when $R^5$ is linked to the nitrogen atom, then $R^5$ represents a hydrogen atom or a $-CH_2COOH$ group,
when $R^5$ is linked to a carbon atom belonging to the cyclic radical X, then $R^5$ represents a hydroxyl group $-OH$, a group $-CH(R^{5b})OH$, an amino group $-NH_2$, a carboxylic group $-COOH$, a halogen atom or a $-CN$ group.

Preferentially, when $X=X_1$, then $R^3$ is other than a halogen atom and when $X=X_2$, then $R^5$ represents a hydrogen atom or a linear or branched $C_1$-$C_3$ alkyl radical optionally substituted with one or more halogen atoms.

More preferentially, $R^3$ and $R^5$ are different.

Even more preferentially, $R^3$ represents a hydrogen atom or a group $(CHR^6)_n-(Z)_o-(CHR'^6)_p-R^7$.

According to one embodiment, $R^3$ represents a hydrogen atom or a group $(CHR^6)_n-(Z)_o-(CHR'^6)_p-R^7$ and $R^5$ represents a hydrogen atom or a linear or branched $C_1$-$C_3$ alkyl radical, optionally substituted with one or more halogen atoms.

Preferably, $R^{11}$ and $R^{12}$ are other than an $-OH$ group.

According to one embodiment, in formula (I), $R^3$ represents a hydrogen atom.

According to one embodiment, in formula (I), $R^3$ represents a group $(CHR^6)_n-(Z)_o-(CHR'^6)_p-R^7$.

According to one embodiment, in formula (I), the indices n, o and p, which may be identical or different, denote zero.

According to one embodiment, in formula (I), the indices n, o and p, which may be identical or different, denote a natural integer ranging from 1 to 3.

According to one embodiment, in formula (I), the indices n and p denote zero and the index o is equal to 1.

According to one embodiment, in formula (I), Z represents a methylene group $-CH_2$.

According to one embodiment, in formula (I), Z represents a divalent group-O—.

According to one embodiment, in formula (I), Z represents a divalent group-NH—.

According to one embodiment, in formula (I), $R^3$ represents a group $Z-R^7$, with Z having the meaning described previously.

According to a particular embodiment, in formula (I), $R^3$ represents a group-$CH_2$—$R^7$.

According to a particular embodiment, in formula (I), $R^3$ represents a group-O—$R^7$.

According to a particular embodiment, in formula (I), $R^3$ represents a group-NH—$R^7$.

According to one embodiment, in formula (I), $R^7$ represents a heterocyclic radical chosen from the following heterocycles:

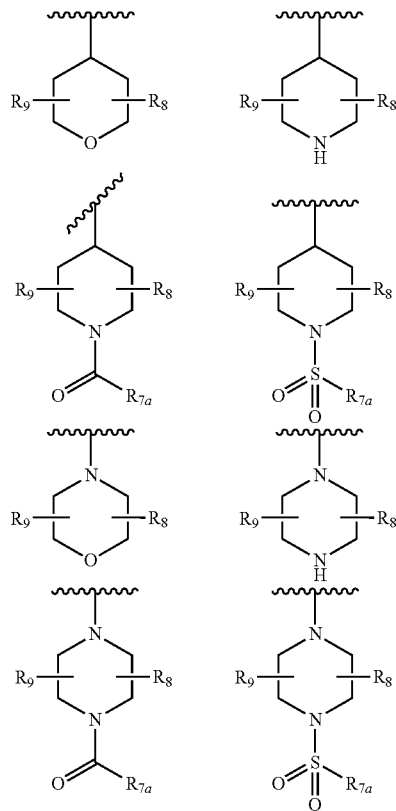

-continued

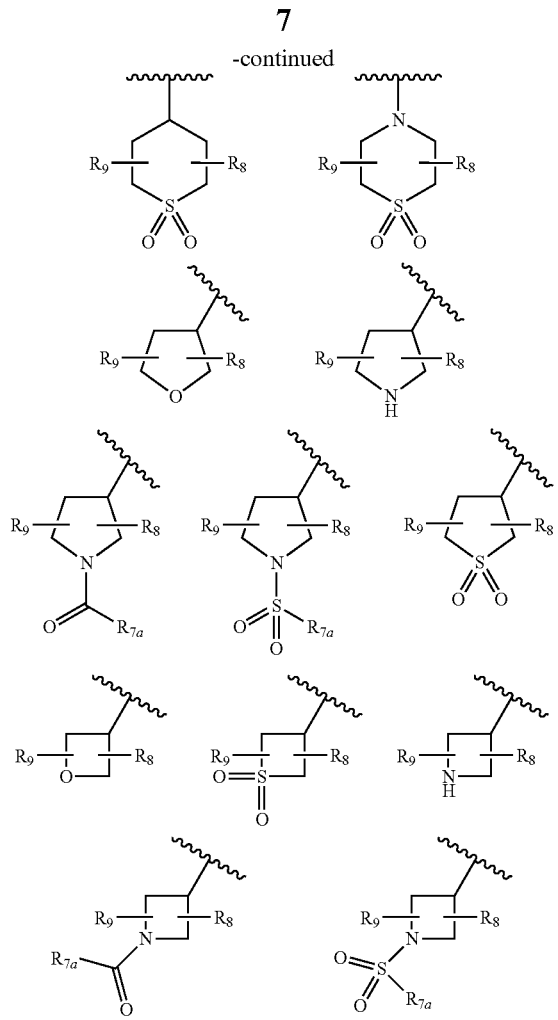

in which:

R$_{7a}$ represents a linear or branched C$_1$-C$_3$ alkyl radical, a linear or branched C$_1$-C$_3$ alkoxy radical or an amino radical N(R$^{8a}$)(R$^{8b}$), R$^{8a}$ and R$^{8b}$, which may be identical or different, denote a hydrogen atom, a linear or branched C$_1$-C$_3$ alkyl radical or a cyclopropyl radical, R$_8$ and R$_9$, which may be identical or different, represent a hydrogen atom, a linear or branched C$_1$-C$_3$ alkyl radical, a hydroxyl group —OH, a carbonyl function =O, a C$_1$ hydroxyalkyl radical (—CH$_2$OH), an amino group NH$_2$, R$_8$ and R$_9$ can form, together with the carbon atoms to which they are attached, a 5- to 7-membered carbocyclic ring.

According to one embodiment, in formula (I), R$^7$ represents an aromatic or heteroaromatic radical chosen from:

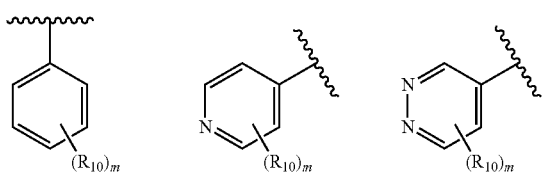

-continued in which:

R$_{10}$ represents a hydrogen atom or a halogen atom, one linear or branched C$_1$-C$_3$ alkyl group optionally substituted with one or more halogen atoms, one C$_1$-C$_3$ alkoxy group, one amino group —NR$^{11}$R$^{12}$, one group —COR$^{11}$, one group —COOR$^{11}$, one amido group —CONR$^{11}$R$^{12}$, one group —SOR$^{11}$, one group —SO$_2$R$^{11}$, one group —NHCOR$^{11}$, one group —NHCOOR$^{11}$, one group —SO$_2$R$^{11}$R$^{12}$ or one —CN group; R$^{11}$ and R$^{12}$, which may be identical or different, representing a hydrogen atom or a linear or branched C$_1$-C$_3$ alkyl radical optionally substituted with one or more halogen atoms, m denotes zero or a natural integer ranging from 1 to 3.

Preferably, R$^{11}$ and R$^{12}$ are other than an —OH group.

Preferentially, R$^7$ represents an aromatic or heteroaromatic radical as defined previously, optionally substituted with one or more methyl groups —CH$_3$, one or more methoxy groups —OCH$_3$, one or more hydroxyl groups —OH, one or more amino groups —NH$_2$, one or more —CH$_2$OH groups, one or more cyano groups —CN, one or more halogen atoms or one or more carbonyl functions.

According to one embodiment, the index m is equal to zero.

According to one embodiment, the index m denotes a natural integer ranging from 1 to 3.

Preferentially, the index m is equal to 1.

According to one embodiment, in formula (I), each of the elements Y$^1$, Y$^2$, Y$^3$, Y$^4$ and Y$^5$ corresponds to a group —CR$^2$ with R$^2$ having the same meaning as that described previously.

According to one embodiment, in formula (I), each of the elements Y$^1$, Y$^2$, Y$^3$, Y$^4$ and Y$^5$ corresponds to a group —CR$^2$ with R$^2$ representing a hydrogen atom.

According to one embodiment, in formula (I), each of the elements Y$^1$, Y$^2$, Y$^3$, Y$^4$ and Y$^5$ corresponds to a group —CR$^2$ with R$^2$ representing a linear or branched C$_1$-C$_5$ alkyl radical.

According to one embodiment, in formula (I), each of the elements Q$^1$, Q$^2$ and Q$^3$ represents a group —CR$^{2a}$ with R$^{2a}$ having the same meaning as that described previously.

According to one embodiment, in formula (I), each of the elements Q$^1$, Q$^2$ and Q$^3$ represents a group —CR$^{2a}$ with R$^{2a}$ representing a hydrogen atom.

According to one embodiment, in formula (I), Q$^1$ and Q$^2$ represent a group —CR$^{2a}$ with R$^{2a}$ representing a hydrogen atom and $Q^3$ represents a group —$CR^{2a}$ with $R^{2a}$ representing a linear or branched $C_1$-$C_5$ alkyl radical.

According to one embodiment, in formula (I), IV represents a linear or branched $C_3$-$C_5$ alkyl radical, preferably a branched $C_3$-$C_5$ and more preferentially branched $C_4$ alkyl radical.

According to one embodiment, in formula (I), IV represents a $C_3$-$C_5$ cycloalkyl radical, preferably cyclopropyl.

According to one embodiment, in formula (I), $R^1$ represents a linear or branched $C_2$-$C_5$ alkenyl radical.

According to one embodiment, in formula (I), $R^1$ represents a $CH_2$—($C_3$-$C_5$)cycloalkyl radical.

According to one embodiment, in formula (I), $R^1$ represents a $C_4$-$C_5$ heterocycloalkyl radical.

According to one embodiment, in formula (I), $R^1$ represents a $CH_2$—($C_4$-$C_6$)heterocycloalkyl radical, in particular a $CH_2$—($C_4$-$C_5$)heterocycloalkyl radical.

Preferentially, $R^1$ represents a linear or branched $C_3$-$C_5$ alkyl radical, or a $CH_2$—($C_4$-$C_5$)heterocycloalkyl radical.

According to one embodiment, $R^5$ represents a hydrogen atom.

Preferably, the compound(s) of formula (I) are chosen from the compound(s) of formula (II), the pharmaceutically acceptable addition salts thereof, hydrates thereof and/or solvates thereof:

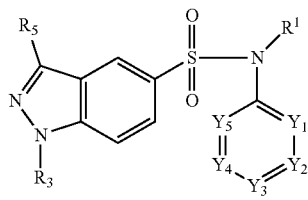

(II)

in which formula (II) $R^1$, $R^3$, $R^5$ and $Y^1$ to $Y^5$ have the same meanings as in formula (I) described previously.

Preferentially, $R^3$ represents a group $(CHR^6)_n$—$(Z)_o$—$(CHR'^6)_p$—$R^7$ with $R^6$, $Z$, $R'^6$, $R^7$ and the indices n, o and p having the same meanings as those indicated previously.

More preferentially, $R^3$ represents a group $CH_2$—$R^7$ with $R^7$ representing a non-cationic heterocyclic radical.

Preferably, the compound(s) of formula (I) are chosen from the compound(s) of formula (III), the pharmaceutically acceptable addition salts thereof, hydrates thereof and/or solvates thereof:

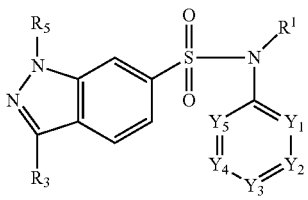

(III)

in which formula (III) $R^1$, $R^3$, $R^5$ and $Y^1$ to $Y^5$ have the same meanings as in formula (I) described previously.

Preferentially, in formula (III), $R_5$ represents a hydrogen atom or a linear or branched $C_1$-$C_3$ alkyl radical optionally substituted with one or more halogen atoms.

The compounds of formula (I) may be in the form of pharmaceutically acceptable salts. Examples of pharmaceutically acceptable salts are described in Berge et al., 1977, "Sels pharmaceutiquement acceptables" [Pharmaceutically acceptable salts], J. Pharm. Sci., Vol. 66, pages 1-19.

In particular, when the compounds of formula (I) according to the invention are in the form of salts, then the electrical neutrality of said compounds is ensured by an external cationic counterion Y which may be organic or mineral.

Y may be chosen from suitable inorganic cations such as alkali metal ions, especially $Na^+$, $K^+$, alkaline-earth metal ions, especially $Ca^{2+}$, $Mg^{2+}$, or alternatively other cations such as the aluminum ion $Al^{3+}$.

Y may be chosen from suitable organic cations such as the ammonium ion $NH_4+$, substituted ammonium ions such as $NH_3R^+$, $NHR_2^+$, $NR_4^+$ with R representing a $C_1$-$C_4$ alkyl radical.

In particular, the substituted ammonium ions are those chosen from derivatives of ethylamine, diethylamine, dicyclohexylamine, triethylamine, butylamine, ethylenediamine, ethanolamine, diethanolamine, piperazine, benzylamine, phenylbenzylamine, choline, meglumine and tromethamine, and amino acids such as lysine and arginine.

An example of a quaternary ammonium ion may be the ion $N^+$ $(CH_3)_4$.

The compound(s) according to the invention may be in the form of the solvates thereof.

For the purposes of the present invention, the term "solvate" means a complex of solute (i.e. the compound according to the invention or the salt of said compound) and of solvent.

If the solvent is water, then the solvate may suitably be considered as a hydrate, for example, a hemihydrate, a monohydrate, a dihydrate, a trihydrate, etc.

For example, the solvates and/or hydrates may be obtained directly at the end of the synthetic process, the target compound being isolated in the form of a hydrate, for example a monohydrate or hemihydrate, or in the form of a solvate of the reaction solvent and/or purification solvent.

Unless otherwise indicated, any reference to a compound according to the invention also includes the solvate or the hydrate of the corresponding compound.

Typical processes for the preparation and identification of hydrates and solvates are well known to those skilled in the art: see, for example, pages 202-209 of K J Guillory, "Generation of Polymorphs, Hydrates, Solvates, and Amorphous Solids" in Polymorphism in Pharmaceutical Solids, edition. Harry G. Britain, Vol. 95, Marcel Dekker, Inc., New York, 1999.

The hydrates and solvates may be isolated and characterized via methods known in the art, such as thermogravimetric analysis (TGA), TGA-mass spectroscopy, TGA-infrared spectroscopy, x-ray powder diffraction, Karl Fischer titration, high-resolution x-ray diffraction, and the like.

Preferably, the compound(s) of formula (Ia) are chosen from the compounds as described in the tables below, and also the pharmaceutically acceptable addition salts thereof, hydrates thereof and/or solvates thereof:

TABLE 1

| | | IC50 hRORg | IC50 hCD4/IL17 |
|---|---|---|---|
| 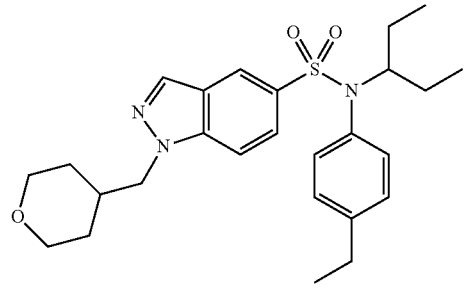 [SMILES: CCc1ccc(N(C(CC)CC)S(=O)(=O)c2ccc3c(cnn3CC3CCOCC3)c2)cc1] | 1-(tetrahydropyran-4-ylmethyl)-1H-indazole-5-sulfonic acid (4-ethylphenyl)(1-ethylpropyl)amide Compound 1 | B | B |
| 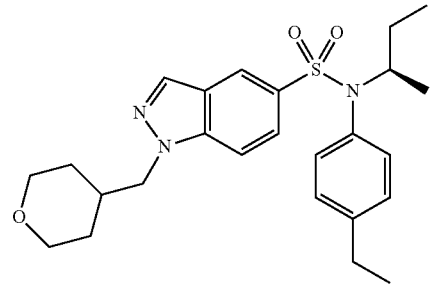 [SMILES: CCc1ccc(N([C@H](C)CC)S(=O)(=O)c2ccc3c(cnn3CC3CCOCC3)c2)cc1] | 1-(tetrahydropyran-4-ylmethyl)-1H-indazole-5-sulfonic acid ((R)-sec-butyl)(4-ethylphenyl)amide Compound 2 | B | ND |
| 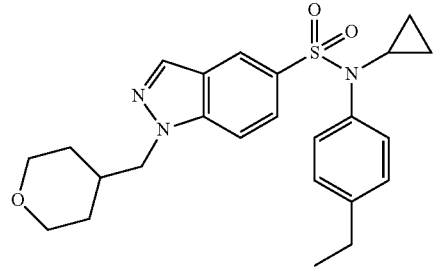 [SMILES: CCc1ccc(N(C2CC2)S(=O)(=O)c2ccc3c(cnn3CC3CCOCC3)c2)cc1] | 1-(tetrahydropyran-4-ylmethyl)-1H-indazole-5-sulfonic acid cyclopropyl(4-ethylphenyl)amide Compound 3 | C | ND |
| 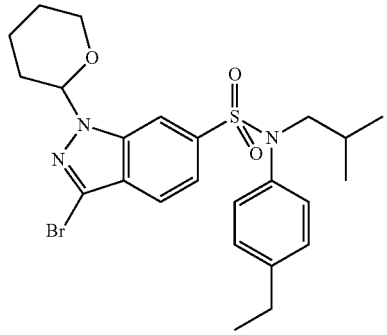 [SMILES: CCc1ccc(N(CC(C)C)S(=O)(=O)c2ccc3c(Br)nn(C4CCCCO4)c3c2)cc1] | 3-bromo-1-(tetrahydropyran-2-yl)-1H-indazole-6-sulfonic acid (4-ethylphenyl) isobutylamide Compound 4 | C | ND |
| 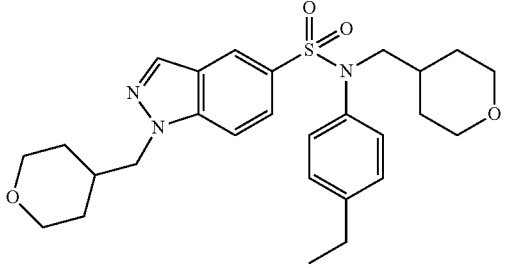 [SMILES: CCc1ccc(N(CC2CCOCC2)S(=O)(=O)c2ccc3c(cnn3CC3CCOCC3)c2)cc1] | 1-(tetrahydropyran-4-ylmethyl)-1H-indazole-5-sulfonic acid (4-ethylphenyl)(tetrahy-dropyran-4-ylmethyl)amide Compound 5 | C | ND |

TABLE 1-continued

| | | IC50 hRORg | IC50 hCD4/IL17 |
|---|---|---|---|
| 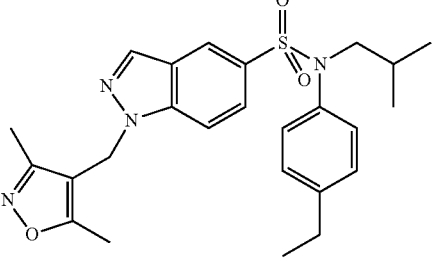 | 1-((3,5-dimethylisoxazol-4-yl)methyl)-N-(4-ethylphenyl)-N-isobutyl-1H-indazole-5-sulfonamide Compound 6 | B | ND |
| 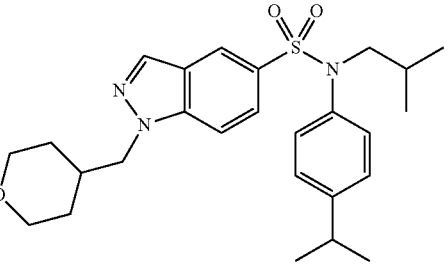 | 1-(tetrahydropyran-4-ylmethyl)-1H-indazole-5-sulfonic acid butyl(4-isopropylphenyl)amide Compound 7 | B | ND |
| 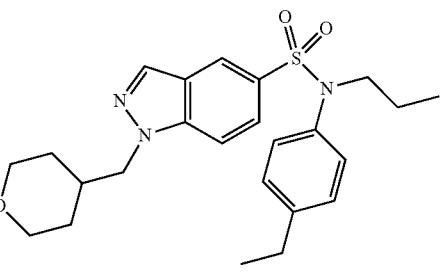 | 1-(tetrahydropyran-4-ylmethyl)-1H-indazole-5-sulfonic acid (4-ethylphenyl)propyl Compound 8 | C | ND |
| 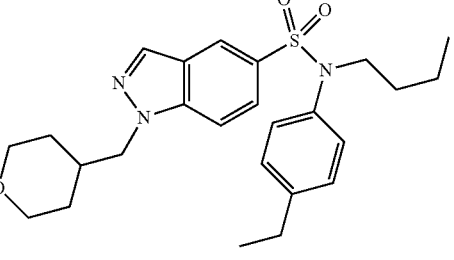 | 1-(tetrahydropyran-4-ylmethyl)-1H-indazole-5-sulfonic acid butyl(4-ethylphenyl)amide Compound 9 | C | ND |
| 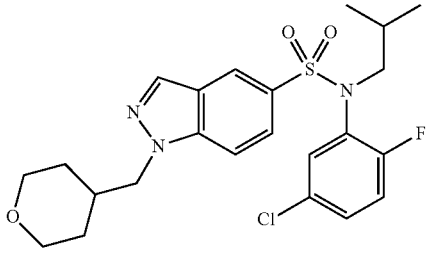 [SMILES: CC(C)CN(c1cc(Cl)ccc1F)S(=O)(=O)c1ccc2c(cnn2CC2CCOCC2)c1] | 1-(tetrahydropyran-4-ylmethyl)-1H-indazole-5-sulfonic acid (5-chloro-2-fluorophenyl)isobutylamide Compound 10 | C | ND |

TABLE 1-continued

| Structure | Name | IC50 hRORg | IC50 hCD4/IL17 |
|---|---|---|---|
| | 1-(tetrahydropyran-4-ylmethyl)-1H-indazole-5-sulfonic acid (2,5-dimethylphenyl)isobutylamide Compound 11 | B | ND |
| | 1-(tetrahydropyran-4-ylmethyl)-1H-indazole-5-sulfonic acid (3-methoxypyridin-2-yl)isobutylamide Compound 12 | C | ND |
| | 1-(tetrahydropyran-4-ylmethyl)-1H-indazole-5-sulfonic acid (4-butyl-2-methylphenyl)isobutylamide Compound 13 | B | ND |
| | N-(4-ethylphenyl)-N-isobutyl-1-((tetrahydro-2H-pyran-4-yl)methyl)-1H-indazole-5-sulfonamide Compound 14 | C | ND |
| | 3-amino-1H-indazole-5-sulfonic acid (4-ethylphenyl)isobutylamide Compound 15 | C | ND |

TABLE 1-continued

| Structure | Name | IC50 hRORg | IC50 hCD4/IL17 |
|---|---|---|---|
| | 1-(tetrahydropyran-4-ylmethyl)-1H-indazole-5-sulfonic acid (4-ethylphenyl)oxetan-3-ylmethylamide Compound 16 | C | ND |
| | 1-(1-acetylpyrrolidin-3-yl)-1H-indazole-5-sulfonic acid (4-ethylphenyl)isobutylamide Compound 17 | B | ND |
| | 3-(tetrahydropyran-4-ylmethoxy)-1-(tetrahydropyran-4-ylmethyl)-1H-indazole-5-sulfonic acid (4-ethylphenyl)isobutylamide Compound 18 | C | ND |
| | 1-(3,5-dimethylisoxazol-4-ylmethyl)-1H-indazole-5-sulfonic acid (4-ethylphenyl)isobutylamide Compound 19 | C | ND |
| | 1-((1-acetylpyrrolidin-3-yl)methyl)-N-(4-ethylphenyl)-N-isobutyl-1H-indazole-5-sulfonamide Compound 20 | C | ND |

TABLE 1-continued

| | | IC50 hRORg | IC50 hCD4/IL17 |
|---|---|---|---|
| 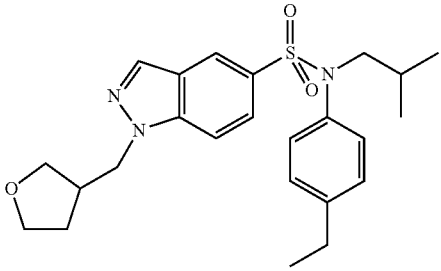 [SMILES: CCc1ccc(N(CC(C)C)S(=O)(=O)c2ccc3c(cnn3CC3CCOC3)c2)cc1] | N-(4-ethylphenyl)-N-isobutyl-1-((tetrahydrofuran-3-yl)methyl)-1H-indazole-5-sulfonamide Compound 21 | C | ND |
| 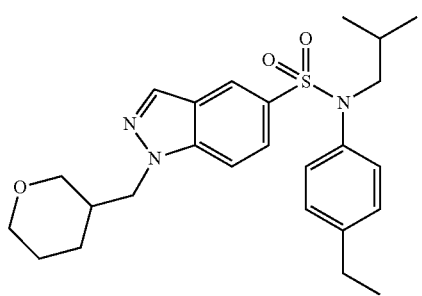 [SMILES: CCc1ccc(N(CC(C)C)S(=O)(=O)c2ccc3c(cnn3CC3CCCOC3)c2)cc1] | N-(4-ethylphenyl)-N-isobutyl-1-((tetrahydro-2H-pyran-3-yl)methyl)-1H-indazole-5-sulfonamide Compound 22 | C | ND |
| 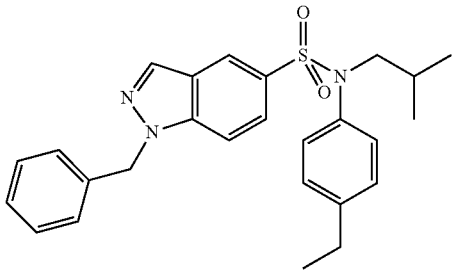 [SMILES: CCc1ccc(N(CC(C)C)S(=O)(=O)c2ccc3c(cnn3Cc3ccccc3)c2)cc1] | 1-benzyl-N-(4-ethylphenyl)-N-isobutyl-1H-indazole-5-sulfonamide Compound 23 | C | ND |
| 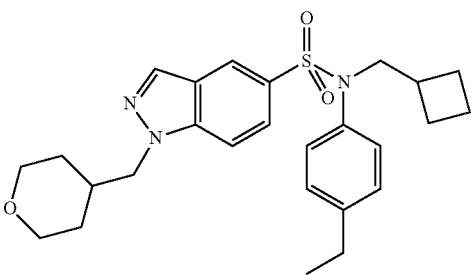 [SMILES: CCc1ccc(N(CC2CCC2)S(=O)(=O)c2ccc3c(cnn3CC3CCOCC3)c2)cc1] | N-(cyclobutylmethyl)-N-(4-ethylphenyl)-1-((tetrahydro-2H-pyran-4-yl)methyl)-1H-indazole-5-sulfonamide Compound 24 | B | ND |
| 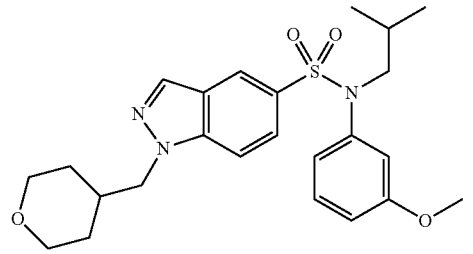 [SMILES: COc1cccc(N(CC(C)C)S(=O)(=O)c2ccc3c(cnn3CC3CCOCC3)c2)c1] | 1-(tetrahydropyran-4-ylmethyl)-1H-indazole-5-sulfonic acid (3-methoxyphenyl)isobutylamide Compound 25 | C | ND |

TABLE 1-continued

| Structure | Name | IC50 hRORg | IC50 hCD4/IL17 |
|---|---|---|---|
| | 1-(tetrahydropyran-4-ylmethyl)-1H-indazole-5-sulfonic acid (3-methylphenyl) isobutylamide Compound 26 | C | ND |
| | 1-(tetrahydropyran-4-ylmethyl)-1H-indazole-5-sulfonic acid (2,4-dimethylphenyl) isobutylamide Compound 27 | B | ND |
| | 1-(tetrahydropyran-4-ylmethyl)-1H-indazole-5-sulfonic acid (3,5-dimethylphenyl) isobutylamide Compound 28 | C | ND |
| | N-(4-ethylphenyl)-N-isopropyl-1-((tetrahydro-2H-pyran-4-yl)methyl)-1H-indazole-5-sulfonamide Compound 29 | C | ND |
| | 1-(tetrahydropyran-4-ylmethyl)-1H-indazole-5-sulfonic acid sec-butyl(4-ethylphenyl)amide Compound 30 | B | ND |

TABLE 1-continued

| | | IC50 hRORg | IC50 hCD4/IL17 |
|---|---|---|---|
| 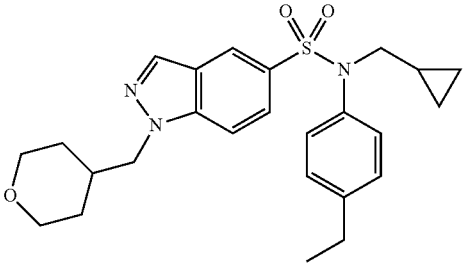 [SMILES: CCc1ccc(N(CC2CC2)S(=O)(=O)c2ccc3c(cnn3CC3CCOCC3)c2)cc1] | N-(cyclopropylmethyl)-N-(4-ethylphenyl)-1-((tetrahydro-2H-pyran-4-yl)methyl)-1H-indazole-5-sulfonamide Compound 31 | C | ND |
| 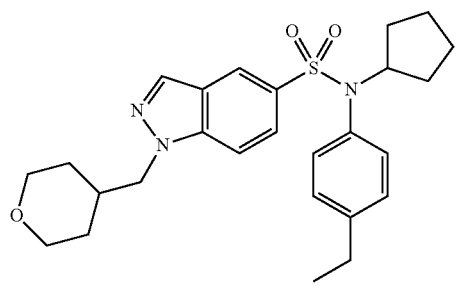 [SMILES: CCc1ccc(N(C2CCCC2)S(=O)(=O)c2ccc3c(cnn3CC3CCOCC3)c2)cc1] | 1-(tetrahydropyran-4-ylmethyl)-1H-indazole-5-sulfonic acid cyclopentyl(4-ethylphenyl)amide Compound 32 | A | ND |
| 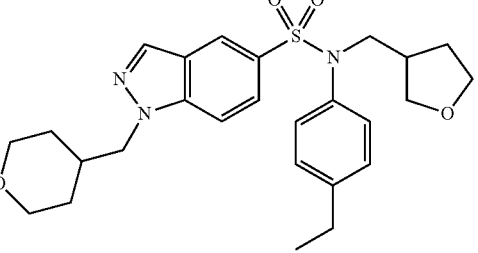 | 1-(tetrahydropyran-4-ylmethyl)-1H-indazole-5-sulfonic acid (4-ethylphenyl)(tetrahydrofuran-3-ylmethyl)amide Compound 33 | C | ND |
| 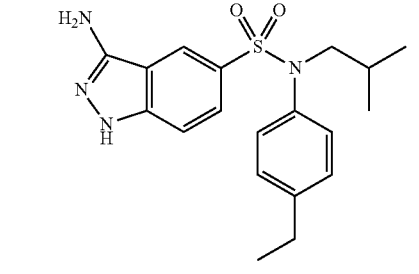 [SMILES: CCc1ccc(N(CC(C)C)S(=O)(=O)c2ccc3[nH]nc(N)c3c2)cc1] | 3-amino-1H-indazole-5-sulfonic acid (4-ethylphenyl) isobutylamide Compound 34 | C | ND |
| 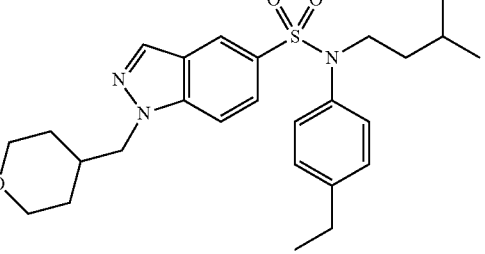 | N-(4-ethylphenyl)-N-isopentyl-1-((tetrahydro-2H-pyran-4-yl)methyl)-1H-indazole-5-sulfonamide Compound 35 | C | ND |

TABLE 1-continued

| Structure | Name | IC50 hRORg | IC50 hCD4/IL17 |
|---|---|---|---|
| | N-(4-ethylphenyl)-N-isobutyl-1-(pyridin-4-ylmethyl)-1H-indazole-5-sulfonamide Compound 36 | B | A |
| | N-(4-ethylphenyl)-N-isobutyl-1-(oxetan-3-ylmethyl)-1H-indazole-5-sulfonamide Compound 37 | B | A |
| | 1-(tetrahydropyran-4-yl)-1H-indazole-5-sulfonic acid (4-ethylphenyl) isobutylamide Compound 38 | C | ND |
| | N-(4-ethylphenyl)-N-isobutyl-1-((tetrahydro-2H-pyran-4-yl)methyl)-1H-indazole-5-sulfonamide Compound 39 | B | B |

TABLE 2

| Structure | Name | IC50 hRORg | IC50 hCD4/IL17 |
|---|---|---|---|
| | 1-(1-acetylpyrrolidin-3-yl)-1H-indazole-5-sulfonic acid (4-ethylphenyl)isobutylamide Compound 40 | C | ND |

TABLE 2-continued

| | | IC50 hRORg | IC50 hCD4/IL17 |
|---|---|---|---|
| 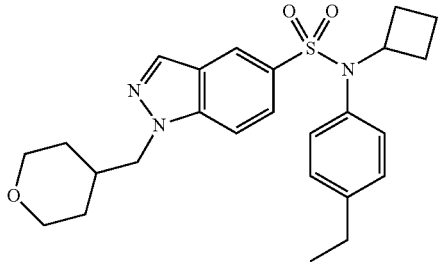 [SMILES: CCc1ccc(N(C2CCC2)S(=O)(=O)c2ccc3c(cnn3CC3CCOCC3)c2)cc1] | 1-(tetrahydropyran-4-ylmethyl)-1H-indazole-5-sulfonic acid cyclobutyl(4-ethylphenyl)amide<br>Compound 41 | C | ND |
| 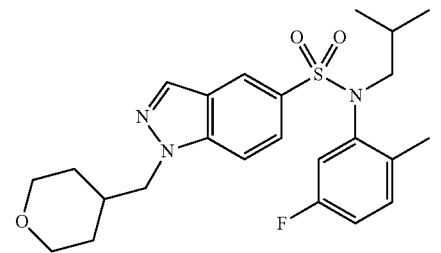 [SMILES: Cc1ccc(F)cc1N(CC(C)C)S(=O)(=O)c1ccc2c(cnn2CC2CCOCC2)c1] | 1-(tetrahydropyran-4-ylmethyl)-1H-indazole-5-sulfonic acid (5-fluoro-2-methylphenyl)isobutylamide<br>Compound 42 | B | ND |
| 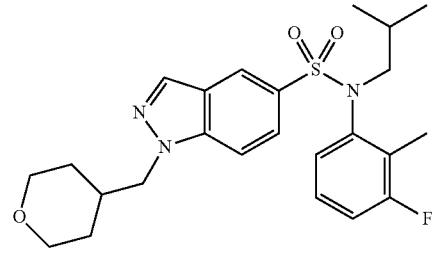 [SMILES: Cc1c(F)cccc1N(CC(C)C)S(=O)(=O)c1ccc2c(cnn2CC2CCOCC2)c1] | 1-(tetrahydropyran-4-ylmethyl)-2H-indazole-5-sulfonic acid (3-fluoro-2-methylphenyl)isobutylamide<br>Compound 43 | B | ND |
| 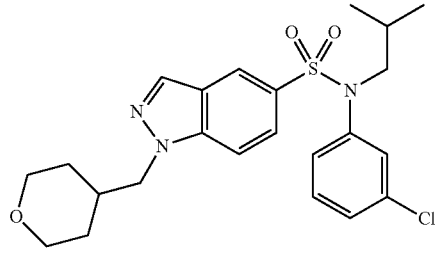 [SMILES: CC(C)CN(c1cccc(Cl)c1)S(=O)(=O)c1ccc2c(cnn2CC2CCOCC2)c1] | 1-(tetrahydropyran-4-ylmethyl)-1H-indazole-5-sulfonic acid (5-chlorophenyl)isobutylamide<br>Compound 44 | C | ND |
| 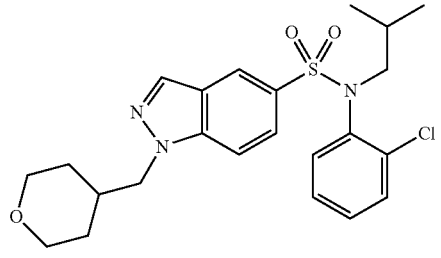 [SMILES: CC(C)CN(c1ccccc1Cl)S(=O)(=O)c1ccc2c(cnn2CC2CCOCC2)c1] | 1-(tetrahydropyran-4-ylmethyl)-1H-indazole-5-sulfonic acid (2-chlorophenyl)isobutylamide<br>Compound 45 | C | ND |
| 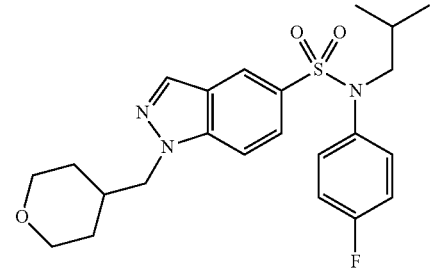 [SMILES: CC(C)CN(c1ccc(F)cc1)S(=O)(=O)c1ccc2c(cnn2CC2CCOCC2)c1] | 1-(tetrahydropyran-4-ylmethyl)-1H-indazole-5-sulfonic acid (4-fluorophenyl)isobutylamide<br>Compound 46 | C | ND |

TABLE 2-continued

| | | IC50 hRORg | IC50 hCD4/IL17 |
|---|---|---|---|
| 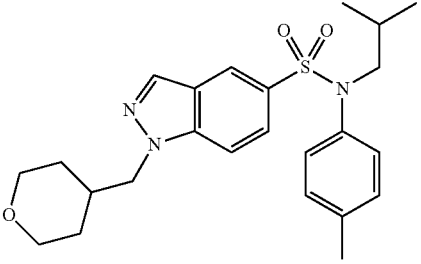 [SMILES: Cc1ccc(N(CC(C)C)S(=O)(=O)c2ccc3c(cnn3CC3CCOCC3)c2)cc1] | 1-(tetrahydropyran-4-ylmethyl)-1H-indazole-5-sulfonic acid isobutyl-p-tolylamide<br>Compound 47 | C | ND |
| 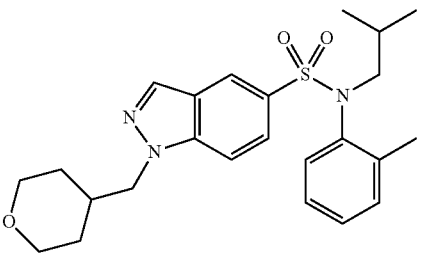 [SMILES: Cc1ccccc1N(CC(C)C)S(=O)(=O)c1ccc2c(cnn2CC2CCOCC2)c1] | 1-(tetrahydropyran-4-ylmethyl)-1H-indazole-5-sulfonic acid isobutyl-o-tolylamide<br>Compound 48 | C | ND |
| 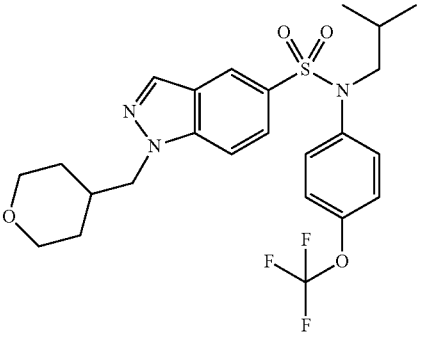 [SMILES: CC(C)CN(c1ccc(OC(F)(F)F)cc1)S(=O)(=O)c1ccc2c(cnn2CC2CCOCC2)c1] | 1-(tetrahydropyran-4-ylmethyl)-1H-indazole-5-sulfonic acid (4-trifluoromethoxyphenyl)isobutylamide<br>Compound 49 | C | ND |
| 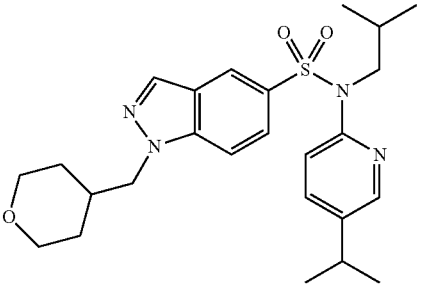 [SMILES: CC(C)CN(c1ccc(C(C)C)cn1)S(=O)(=O)c1ccc2c(cnn2CC2CCOCC2)c1] | 1-(tetrahydropyran-4-ylmethyl)-1H-indazole-5-sulfonic acid isobutyl(5-isopropylpyridin-2-yl)amide<br>Compound 50 | C | ND |
| 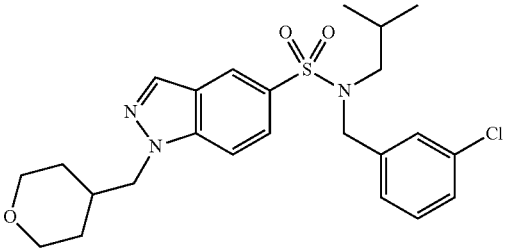 [SMILES: CC(C)CN(Cc1cccc(Cl)c1)S(=O)(=O)c1ccc2c(cnn2CC2CCOCC2)c1] | 1-(tetrahydropyran-4-ylmethyl)-1H-indazole-5-sulfonic acid (3-chlorobenzyl)isobutylamide<br>Compound 51 | C | ND |

TABLE 2-continued

| | | IC50 hRORg | IC50 hCD4/IL17 |
|---|---|---|---|
| 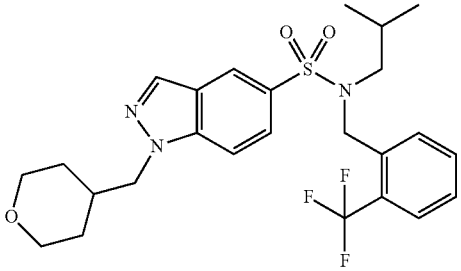 [SMILES: CC(C)CN(Cc1ccccc1C(F)(F)F)S(=O)(=O)c1ccc2c(cnn2CC2CCOCC2)c1] | 1-(tetrahydropyran-4-ylmethyl)-1H-indazole-5-sulfonic acid isobutyl(2-trifluoromethylbenzyl)amide Compound 52 | B | ND |
| 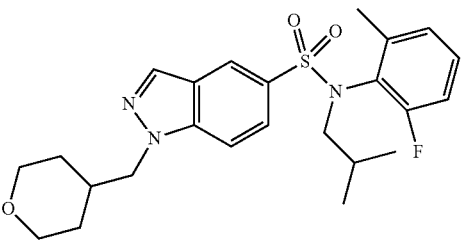 [SMILES: Cc1cccc(F)c1N(CC(C)C)S(=O)(=O)c1ccc2c(cnn2CC2CCOCC2)c1] | 1-(tetrahydropyran-4-ylmethyl)-1H-indazole-5-sulfonic acid (2-fluoro-6-methylphenyl)isobutylamide Compound 53 | C | ND |
| 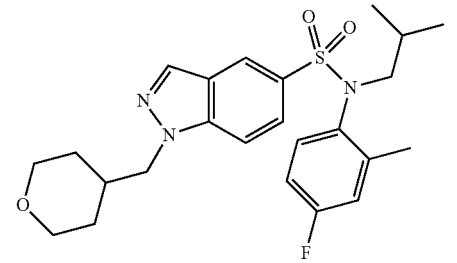 [SMILES: Cc1cc(F)ccc1N(CC(C)C)S(=O)(=O)c1ccc2c(cnn2CC2CCOCC2)c1] | 1-(tetrahydropyran-4-ylmethyl)-1H-indazole-5-sulfonic acid (4-fluoro-2-methylphenyl)isobutylamide Compound 54 | B | ND |
| 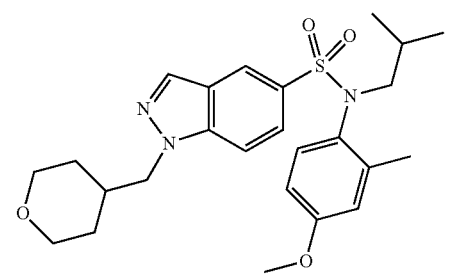 [SMILES: COc1ccc(N(CC(C)C)S(=O)(=O)c2ccc3c(cnn3CC3CCOCC3)c2)c(C)c1] | 1-(tetrahydropyran-4-ylmethyl)-1H-indazole-5-sulfonic acid isobutyl(4-methoxy-2-methylphenyl)amide Compound 55 | B | ND |
| 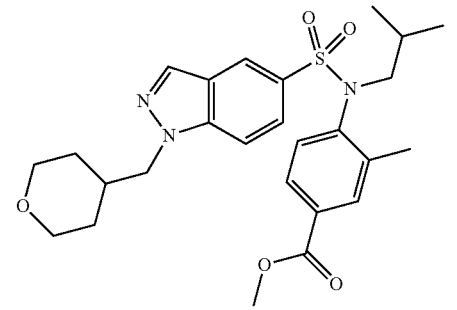 [SMILES: COC(=O)c1ccc(N(CC(C)C)S(=O)(=O)c2ccc3c(cnn3CC3CCOCC3)c2)c(C)c1] | methyl 4-{isobutyl[1-(tetrahydropyran-4-ylmethyl)-1H-indazole-5-sulfonyl]amino}-3-methylbenzoate Compound 56 | B | A |

TABLE 2-continued

| | | IC50 hRORg | IC50 hCD4/IL17 |
|---|---|---|---|
| | 1-(tetrahydropyran-4-ylmethyl)-1H-indazole-5-sulfonic acid (4-cyano-2-methylphenyl)isobutylamide Compound 57 | B | ND |
| | 1-(tetrahydropyran-4-ylmethyl)-1H-indazole-5-sulfonic acid isobutyl(2-trifluoromethylphenyl)amide Compound 58 | B | ND |
| | 1-(tetrahydropyran-4-ylmethyl)-1H-indazole-5-sulfonic acid isobutyl(4-trifluoromethylphenyl)amide Compound 59 | C | ND |
| | 1-(tetrahydropyran-4-ylmethyl)-1H-indazole-5-sulfonic acid (3-chloro-2-hydroxymethylpropyl)(4-ethylphenyl)amide Compound 60 | C | ND |
| | 3-(tetrahydropyran-4-ylmethoxy)-1H-indazole-5-sulfonic acid (4-ethylphenyl)isobutylamide Compound 61 | C | ND |

TABLE 2-continued

| | | IC50 hRORg | IC50 hCD4/IL17 |
|---|---|---|---|
| 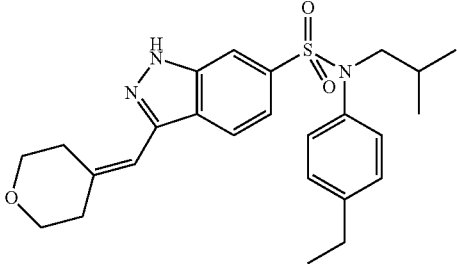 [SMILES: CCc1ccc(N(CC(C)C)S(=O)(=O)c2ccc3c(C=C4CCOCC4)n[nH]c3c2)cc1] | 3-(tetrahydropyran-4-ylidenemethyl)-1H-indazole-6-sulfonic acid (4-ethylphenyl)isobutylamide Compound 62 | A | ND |
| 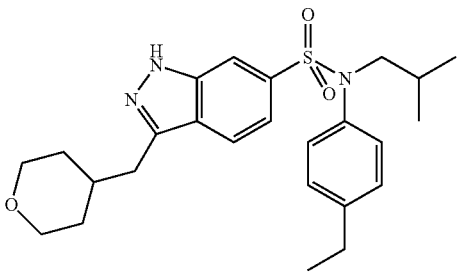 [SMILES: CCc1ccc(N(CC(C)C)S(=O)(=O)c2ccc3c(CC4CCOCC4)n[nH]c3c2)cc1] | 3-(tetrahydropyran-4-ylmethyl)-1H-indazole-6-sulfonic acid (4-ethylphenyl)isobutylamide Compound 63 | A | A |
| 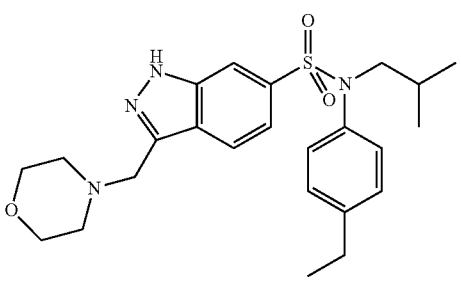 | 3-morpholin-4-ylmethyl-1H-indazole-6-sulfonic acid (4-ethylphenyl)isobutylamide Compound 64 | A | A |
| 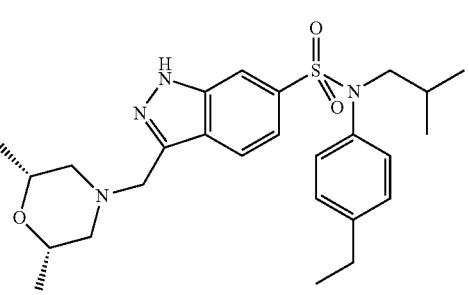 [SMILES: CCc1ccc(N(CC(C)C)S(=O)(=O)c2ccc3c(CN4C[C@@H](C)O[C@@H](C)C4)n[nH]c3c2)cc1] | 3-((cis)-2,6-dimethylmorpholin-4-ylmethyl)-1H-indazole-6-sulfonic acid (4-ethylphenyl)isobutylamide Compound 65 | C | ND |
| 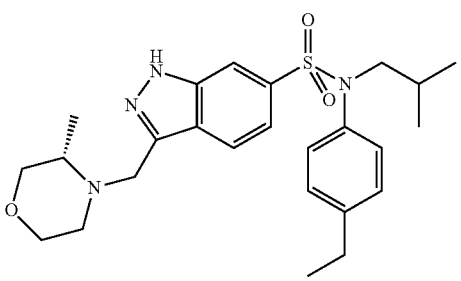 [SMILES: CCc1ccc(N(CC(C)C)S(=O)(=O)c2ccc3c(CN4CCOC[C@@H]4C)n[nH]c3c2)cc1] | 3-((S)-3-methylmorpholin-4-ylmethyl)-1H-indazole-6-sulfonic acid (4-ethylphenyl)isobutylamide Compound 66 | B | ND |

TABLE 2-continued

| | | | IC50 hRORg | IC50 hCD4/IL17 |
|---|---|---|---|---|
| 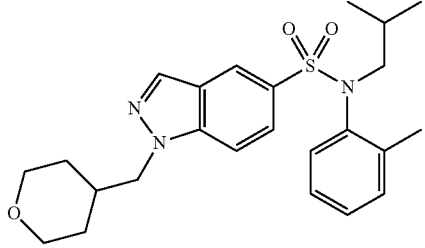 [SMILES: Cc1ccccc1N(CC(C)C)S(=O)(=O)c1ccc2c(cnn2CC2CCOCC2)c1] | 1-(tetrahydropyran-4-ylmethyl)-1H-indazole-5-sulfonic acid isobutyl-o-tolylamide Compound 69 | | C | ND |
| 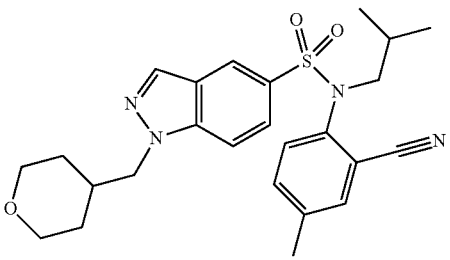 [SMILES: Cc1ccc(N(CC(C)C)S(=O)(=O)c2ccc3c(cnn3CC3CCOCC3)c2)c(C#N)c1] | 1-(tetrahydropyran-4-ylmethyl)-1H-indazole-5-sulfonic acid (2-cyano-4-methylphenyl)isobutylamide Compound 70 | | B | ND |
| 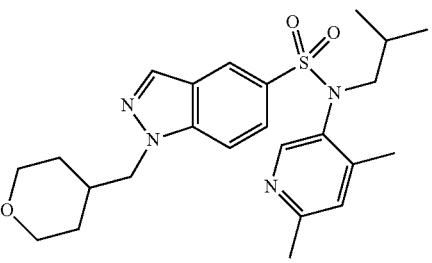 [SMILES: Cc1cc(C)c(N(CC(C)C)S(=O)(=O)c2ccc3c(cnn3CC3CCOCC3)c2)cn1] | 1-(tetrahydropyran-4-ylmethyl)-1H-indazole-5-sulfonic acid (4,6-dimethylpyridin-3-yl)isobutylamide Compound 71 | | C | C |
| 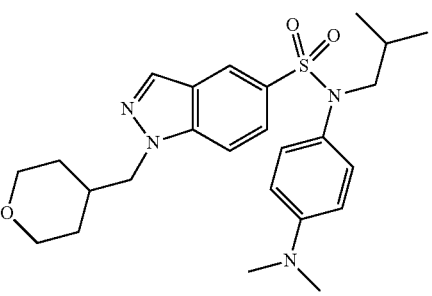 [SMILES: CC(C)CN(c1ccc(N(C)C)cc1)S(=O)(=O)c1ccc2c(cnn2CC2CCOCC2)c1] | 1-(tetrahydropyran-4-ylmethyl)-1H-indazole-5-sulfonic acid (4-dimethylaminophenyl)isobutylamide Compound 72 | | B | B |
| 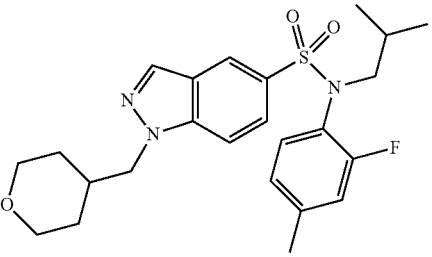 [SMILES: Cc1ccc(N(CC(C)C)S(=O)(=O)c2ccc3c(cnn3CC3CCOCC3)c2)c(F)c1] | 1-(tetrahydropyran-4-ylmethyl)-1H-indazole-5-sulfonic acid (2-fluoro-4-methylphenyl)isobutylamide Compound 73 | | ND | ND |

TABLE 2-continued

| | | IC50 hRORg | IC50 hCD4/IL17 |
|---|---|---|---|
| 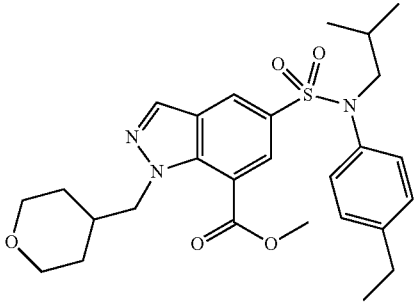 [SMILES: CCc1ccc(N(CC(C)C)S(=O)(=O)c2cc(C(=O)OC)c3c(cnn3CC3CCOCC3)c2)cc1] | methyl 5-[(4-ethylphenyl)isobutyl-sulfamoyl]-1-(tetrahydropyran-4-ylmethyl)-1H-indazole-7-carboxylate Compound 74 | C | ND |
| 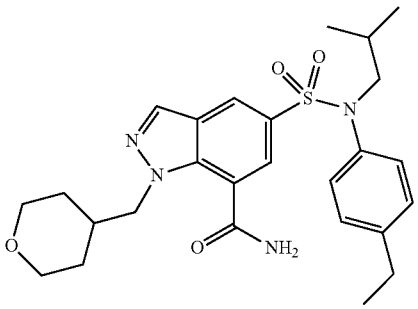 [SMILES: CCc1ccc(N(CC(C)C)S(=O)(=O)c2cc(C(N)=O)c3c(cnn3CC3CCOCC3)c2)cc1] | 5-[(4-ethylphenyl)isobutyl-sulfamoyl]-1-(tetrahydropyran-4-ylmethyl)-1H-indazole-7-carboxylic acid amide Compound 75 | ND | ND |

ND: not determined; A: IC50 <100 nM.; B: IC50 = 100 nM-1 µM; C: IC50 >1 µM

In the tables described above, the median inhibitory concentrations $IC_{50}$ for the compounds belonging to formula (I) according to the invention have been given according to the following models:

GAL4-RORγ Transactivation

The RORγ transactivation model was developed from the line HG5LN, which is a HeLa line that stably expresses a luciferase reporter gene controlled by a pentamer of the GAL4 recognition domain of yeast and of a β-globin promoter. The HG5LN line was stably transfected by the DNA-binding domain (DBD) of GAL4 fused to the ROR gamma ligand-binding domain (LBD). Molecules that inhibit the ROR gamma constitutive activity reduce the luciferase expression, thus leading to a reduction in the emitted luminescence.

The cells are seeded in 384-well plates (5000 cells in 45 µL/well of culture medium containing 10% fetal calf serum) and incubated for 4 hours at 37° C., 5% $CO_2$. 5 µL of the test molecules (compounds described in the tables described above) are then added to each well and the plates are incubated for 18 hours at a temperature of 37° C. under 5% of $CO_2$. 20 µL of luciferase substrate (Promega) are added to each well and the luminescence emitted is read by a microplate reader.

The luminescence units ("RLU") are normalized by positive controls ("POS" containing a saturated concentration of N-(2,2,2-trifluoroethyl)-N-[4-[2,2,2-trifluoro-1-hydroxy-1-(trifluoromethyl)ethyl]phenyl])benzenesulfonamide and negative controls ("NEG" containing DMSO): % inhibition=((RLU−NEG)*100)/(POS−NEG). The IC50 values are calculated from a 4-parameter logistic model using the XLFit software (IDBS).

IL-17A Secretion

This model allows measurement of the effect of inhibitors on IL-17A secretion by CD4+ cells. The cells are frozen CD4+ cells (STEMCELL, #70026), isolated from peripheral human blood and activated with anti-CD3 and anti-CD28 antibodies. The amount of IL-17a secreted is measured by the TR-FRET (kit HTRF® Human Interleukin 17A (Cisbio, #64H17PEC)) technology.

The cells are rapidly thawed, resuspended in their culture medium (RPMI inactivated 10% FCS) supplemented with soluble anti-CD28 antibodies and seeded (100 000 cells/well) in 96-well plates precoated with anti-CD3 antibodies. The cells are then treated with the ranges of inhibitors to be tested (from 1000 nM to 0.05 nM, 0.1% DMSO). After 4 days of incubation, the HTRF signal is measured using a microplate reader (λexcitation=337 nm, λemission=620/665 nm). The ratios obtained (665/620) are normalized relative to the positive control (cells activated with anti-CD3 and anti-CD28, 0.1% DMSO). The $IC_{50}$ values are calculated from a 4-parameter logistic model using the XLFit software (IDBS).

Preferentially, the compounds of formula (I) according to the invention are chosen from the following compounds:

TABLE 3

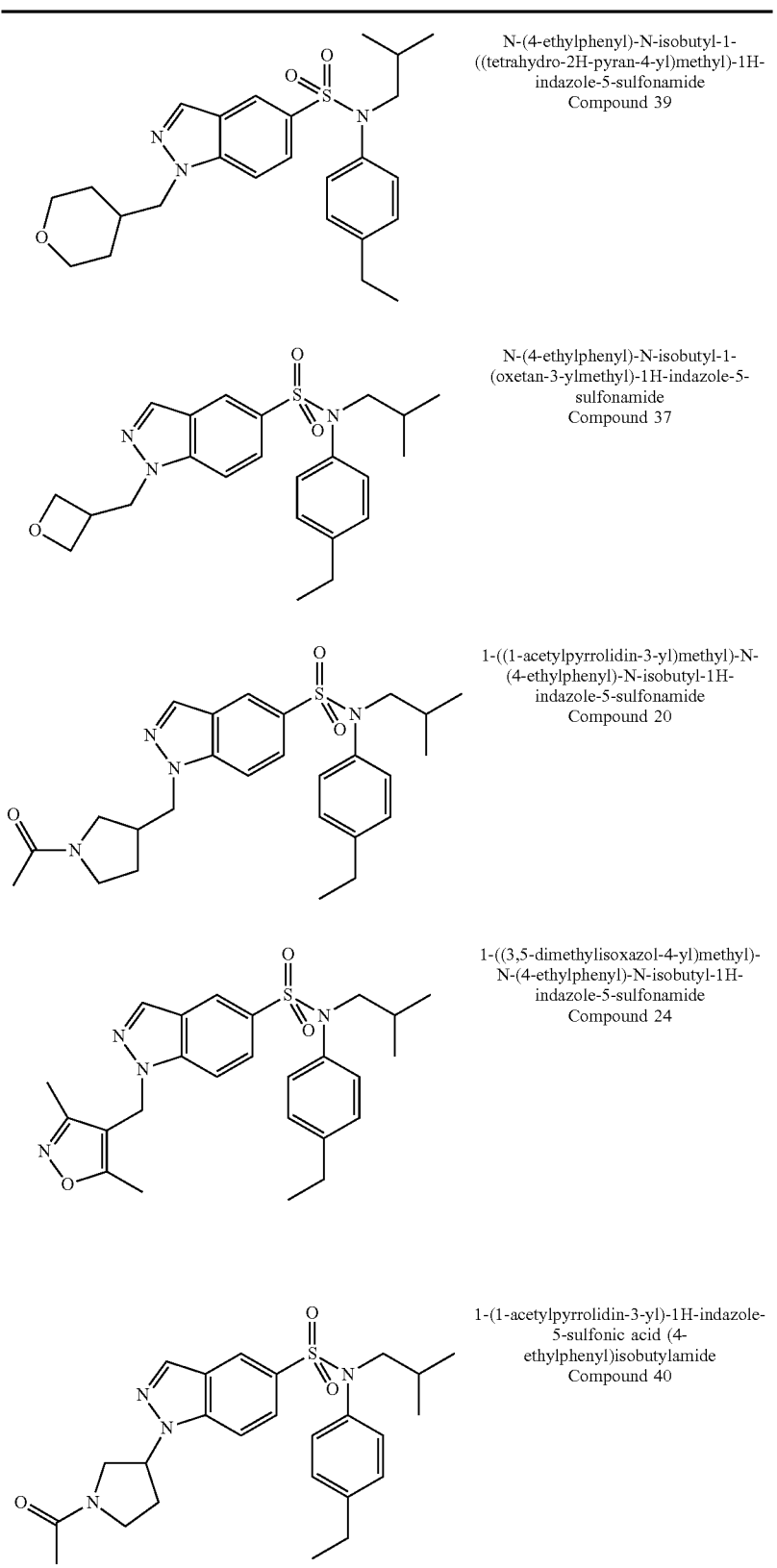

N-(4-ethylphenyl)-N-isobutyl-1-((tetrahydro-2H-pyran-4-yl)methyl)-1H-indazole-5-sulfonamide
Compound 39

N-(4-ethylphenyl)-N-isobutyl-1-(oxetan-3-ylmethyl)-1H-indazole-5-sulfonamide
Compound 37

1-((1-acetylpyrrolidin-3-yl)methyl)-N-(4-ethylphenyl)-N-isobutyl-1H-indazole-5-sulfonamide
Compound 20

1-((3,5-dimethylisoxazol-4-yl)methyl)-N-(4-ethylphenyl)-N-isobutyl-1H-indazole-5-sulfonamide
Compound 24

1-(1-acetylpyrrolidin-3-yl)-1H-indazole-5-sulfonic acid (4-ethylphenyl)isobutylamide
Compound 40

TABLE 3-continued

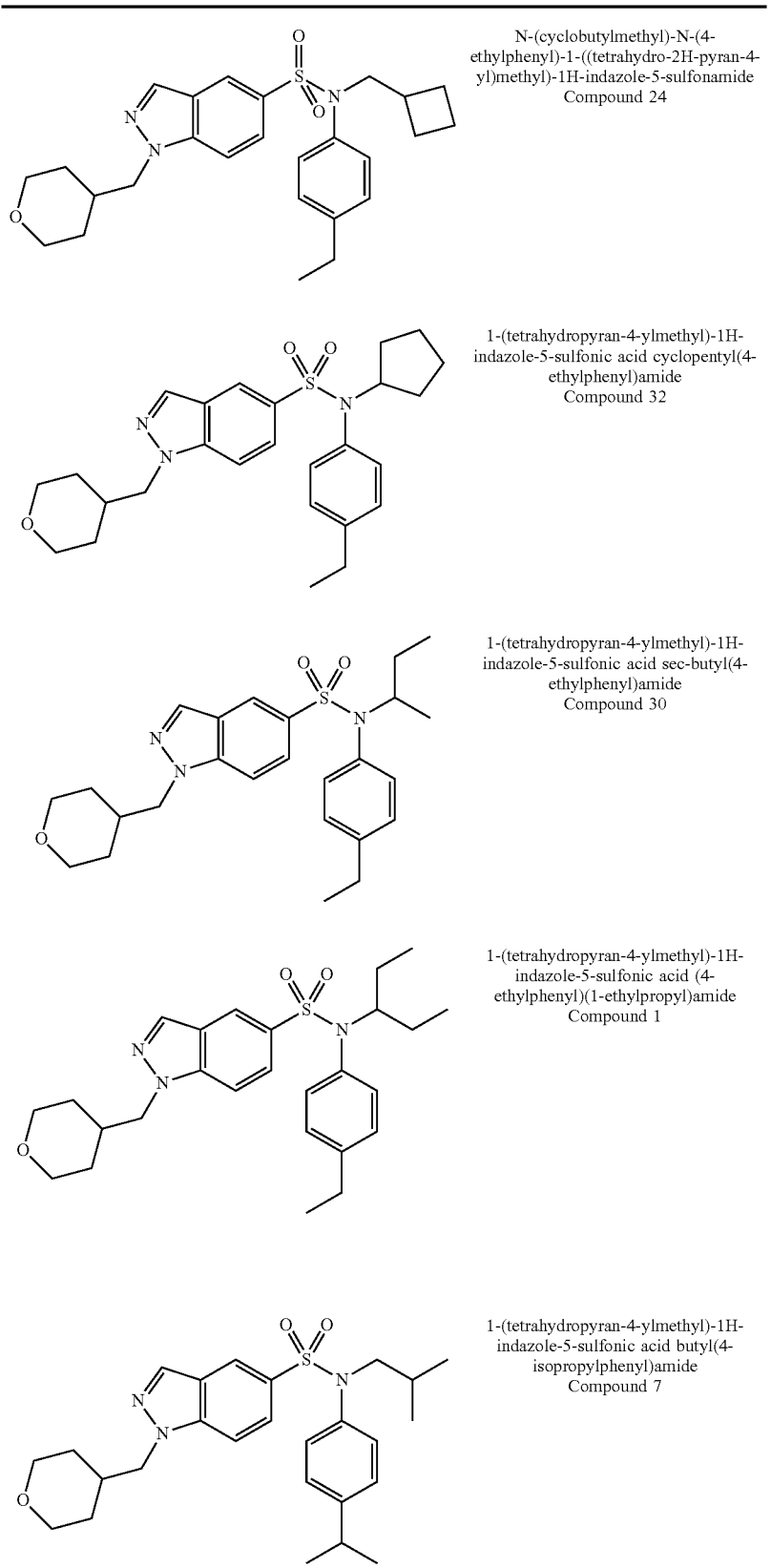

N-(cyclobutylmethyl)-N-(4-ethylphenyl)-1-((tetrahydro-2H-pyran-4-yl)methyl)-1H-indazole-5-sulfonamide
Compound 24

1-(tetrahydropyran-4-ylmethyl)-1H-indazole-5-sulfonic acid cyclopentyl(4-ethylphenyl)amide
Compound 32

1-(tetrahydropyran-4-ylmethyl)-1H-indazole-5-sulfonic acid sec-butyl(4-ethylphenyl)amide
Compound 30

1-(tetrahydropyran-4-ylmethyl)-1H-indazole-5-sulfonic acid (4-ethylphenyl)(1-ethylpropyl)amide
Compound 1

1-(tetrahydropyran-4-ylmethyl)-1H-indazole-5-sulfonic acid butyl(4-isopropylphenyl)amide
Compound 7

TABLE 3-continued

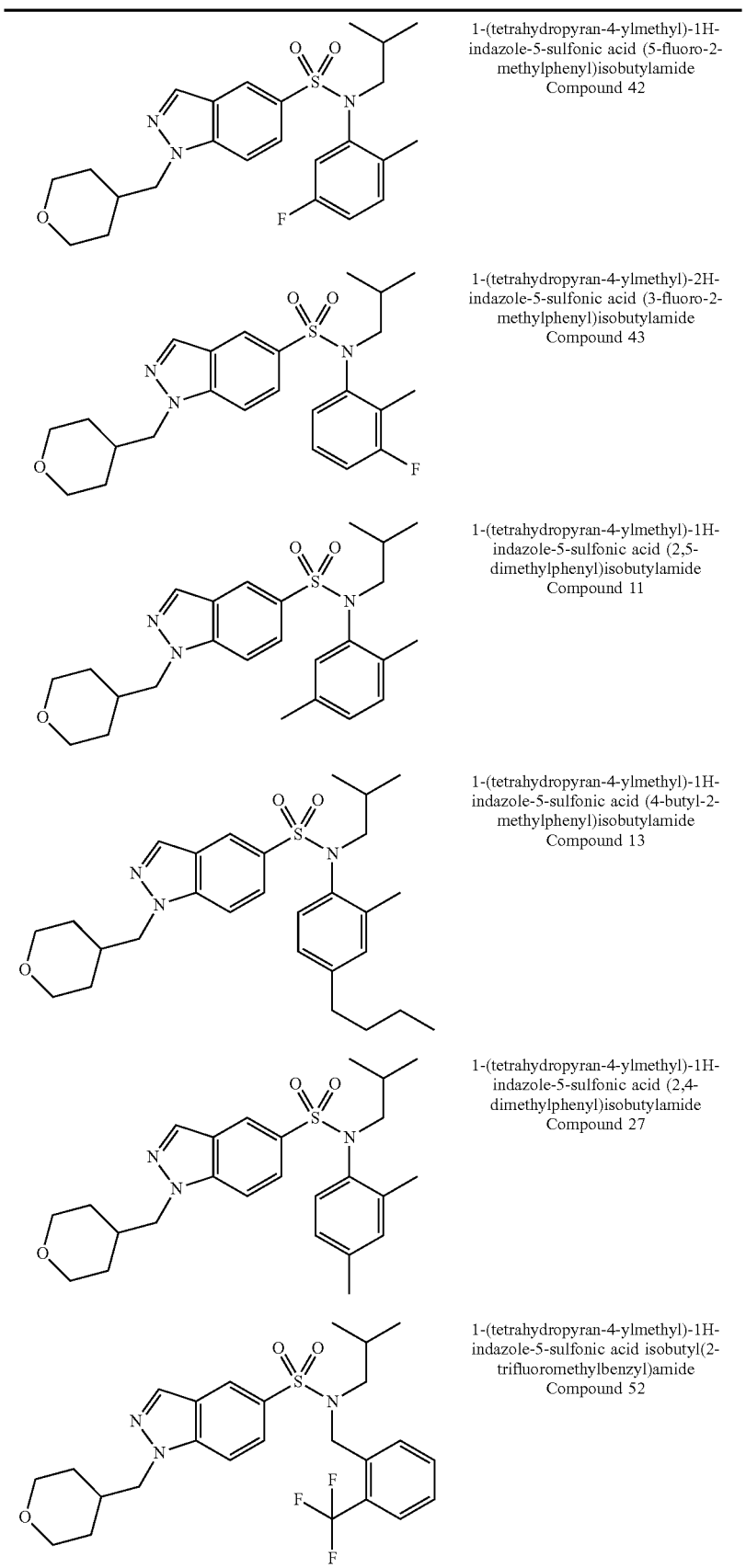

1-(tetrahydropyran-4-ylmethyl)-1H-indazole-5-sulfonic acid (5-fluoro-2-methylphenyl)isobutylamide
Compound 42

1-(tetrahydropyran-4-ylmethyl)-2H-indazole-5-sulfonic acid (3-fluoro-2-methylphenyl)isobutylamide
Compound 43

1-(tetrahydropyran-4-ylmethyl)-1H-indazole-5-sulfonic acid (2,5-dimethylphenyl)isobutylamide
Compound 11

1-(tetrahydropyran-4-ylmethyl)-1H-indazole-5-sulfonic acid (4-butyl-2-methylphenyl)isobutylamide
Compound 13

1-(tetrahydropyran-4-ylmethyl)-1H-indazole-5-sulfonic acid (2,4-dimethylphenyl)isobutylamide
Compound 27

1-(tetrahydropyran-4-ylmethyl)-1H-indazole-5-sulfonic acid isobutyl(2-trifluoromethylbenzyl)amide
Compound 52

TABLE 3-continued

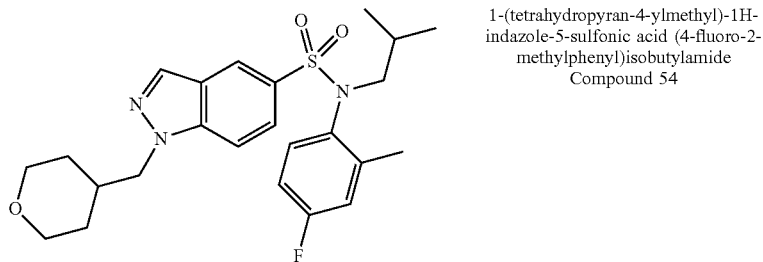

1-(tetrahydropyran-4-ylmethyl)-1H-indazole-5-sulfonic acid (4-fluoro-2-methylphenyl)isobutylamide
Compound 54

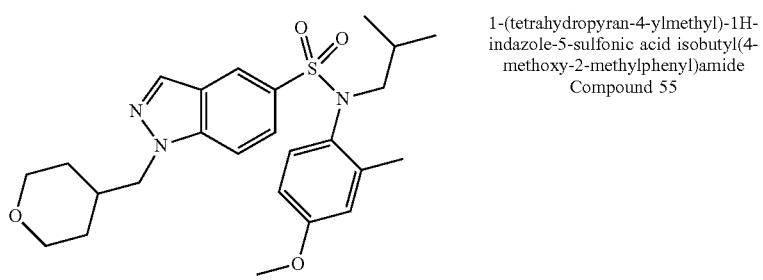

1-(tetrahydropyran-4-ylmethyl)-1H-indazole-5-sulfonic acid isobutyl(4-methoxy-2-methylphenyl)amide
Compound 55

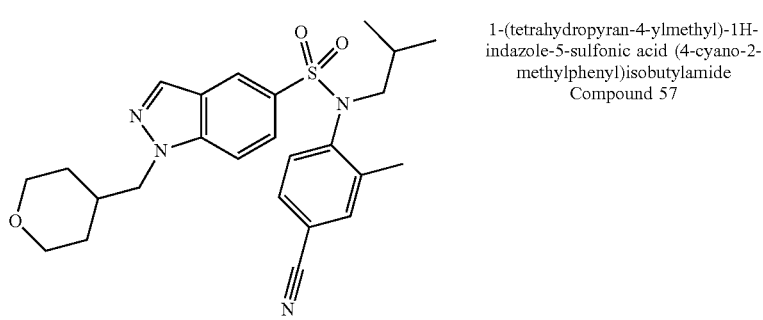

1-(tetrahydropyran-4-ylmethyl)-1H-indazole-5-sulfonic acid (4-cyano-2-methylphenyl)isobutylamide
Compound 57

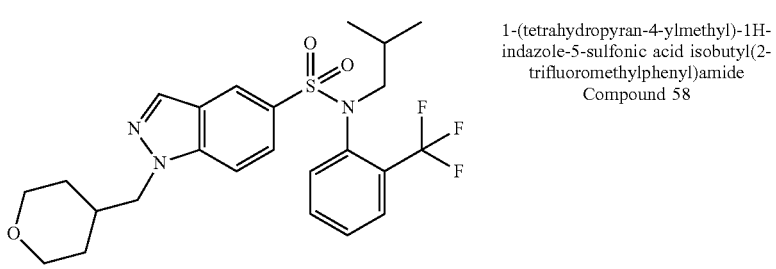

1-(tetrahydropyran-4-ylmethyl)-1H-indazole-5-sulfonic acid isobutyl(2-trifluoromethylphenyl)amide
Compound 58

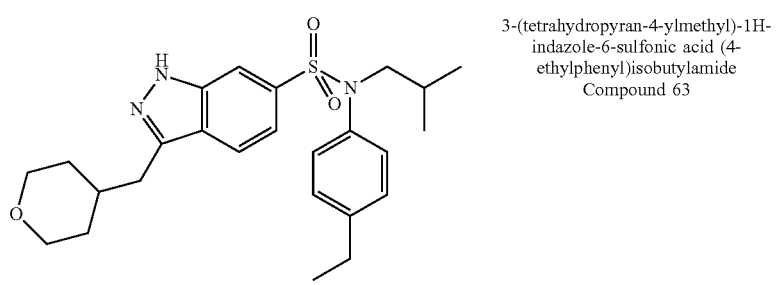

3-(tetrahydropyran-4-ylmethyl)-1H-indazole-6-sulfonic acid (4-ethylphenyl)isobutylamide
Compound 63

TABLE 3-continued

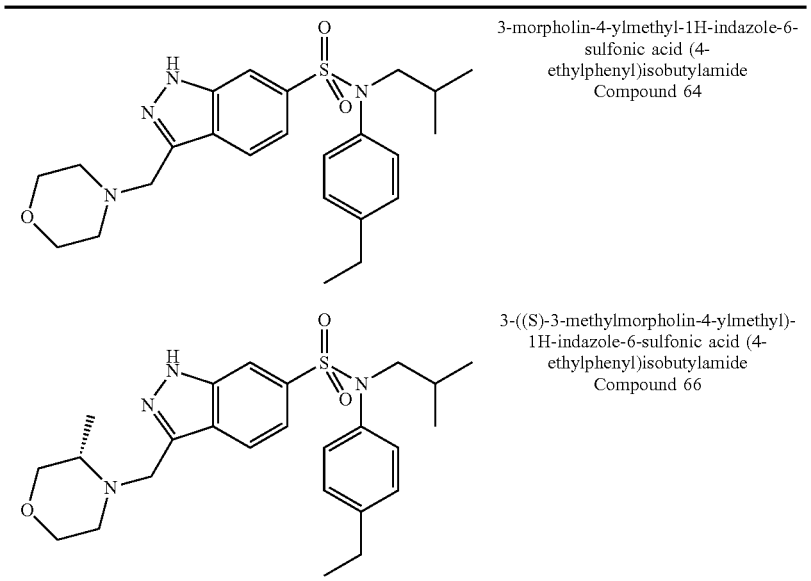

| | |
|---|---|
| | 3-morpholin-4-ylmethyl-1H-indazole-6-sulfonic acid (4-ethylphenyl)isobutylamide<br>Compound 64 |
| | 3-((S)-3-methylmorpholin-4-ylmethyl)-1H-indazole-6-sulfonic acid (4-ethylphenyl)isobutylamide<br>Compound 66 |

In particular, among the compounds of formula (II), compounds 1, 2, 7, 11, 21, 24, 27, 30, 32, 36, 37, 39, 40, 42, 43, 52, 54, 55, 57 and 58 are preferred.

Among the compounds of formula (III), compounds 63, 64 and 66 are preferred.

The invention also relates to the compound(s) as described previously, as medicament and cosmetic.

Preferably, the invention also relates to the compound(s) as described previously, as medicament.

Specifically, the compounds according to the invention have advantageous pharmacological properties, given that said compounds modulate, i.e. inhibit, the activity of the RORγt receptor.

Thus, these properties make the compound(s) of formula (I) as described previously usable as medicament in the treatment of diseases mediated by the RORγt receptor.

Preferably, the compound(s) according to the invention are used in the treatment of inflammatory disorders and/or autoimmune diseases mediated by the RORγt receptor.

More preferentially, the compound(s) according to the invention, preferably those chosen from the compounds corresponding to formulae (II) and (III), are used in the treatment of acne, psoriasis and/or atopic dermatitis.

According to another embodiment, the compounds according to the invention are used for cosmetic treatment of the skin.

As indicated above, the present invention also relates to a pharmaceutical composition comprising, in a pharmaceutically acceptable medium, one or more compounds of formula (I) as defined previously, pharmaceutically acceptable addition salts thereof, hydrates thereof and/or solvates thereof.

Preferably, the pharmaceutical composition comprises one or more compounds chosen from the compounds of formulae (II) and (III) as defined previously, the pharmaceutically acceptable addition salts thereof, hydrates thereof and/or solvates thereof.

More preferentially, the pharmaceutical composition comprises one or more compounds of formula (I) chosen from compounds (1) to (75) defined previously.

Even more preferentially, the pharmaceutical composition comprises one or more compounds of formula (I) chosen from compounds 1, 2, 7, 11, 21, 24, 27, 30, 32, 36, 37, 39, 40, 42, 43, 52, 54, 55, 57, 58, 63, 64 and 66.

The pharmaceutical composition according to the invention as described previously may be administered orally or topically.

Preferably, the pharmaceutical composition is conditioned in a form that is suitable for topical application.

Via the oral route, the composition may be in the form of tablets, gel capsules, coated tablets, syrups, suspensions, solutions, powders, granules, emulsions, suspensions of microspheres or nanospheres or lipid or polymeric vesicles allowing controlled release.

Via the topical route, the pharmaceutical composition according to the invention is more particularly intended for treating the skin and mucous membranes, and may be in liquid, pasty or solid form, and more particularly in the form of ointments, creams, milks, pomades, powders, impregnated pads, syndets, solutions, gels, sprays, mousses, suspensions, sticks, shampoos or washing bases. It may also be in the form of suspensions of microspheres or nanospheres or lipid or polymeric vesicles or of polymeric or gelled patches allowing controlled release.

The pharmaceutical composition is used for treating inflammatory disorders and/or autoimmune diseases mediated by the RORγt receptor.

More preferentially, the pharmaceutical composition is used in the treatment of acne and/or psoriasis.

The invention also relates to a process for treating diseases mediated by the RORγt receptor, comprising the administration, especially topically or orally, of a therapeutically effective amount of the pharmaceutical composition as defined above to a patient.

Preferably, the pharmaceutical composition is applied topically.

In accordance with another embodiment, a subject of the present invention is also one or more compounds of formula (II) as defined previously, the pharmaceutically acceptable addition salts thereof, hydrates thereof and/or solvates thereof:

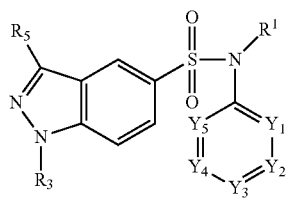

(II)

in which formula (II) $R^1$, $R^3$, $R^5$ and $Y^1$ to $Y^5$ have the same meanings as in formula (Ia) described previously.

Preferably, $R^3$ represents a group $(CHR^6)_n$—$(Z)_o$—$(CHR'^6)_p$—$R^7$ with $R^7$ representing a non-cationic heterocyclic radical, a non-cationic cycloalkyl radical or a non-cationic aromatic or heteroaromatic radical as defined previously.

Among the compounds of formula (II), compounds 1, 2, 7, 11, 21, 24, 27, 30, 32, 36, 37, 39, 40, 42, 43, 52, 54, 55, 57 and 58 are preferred.

According to this embodiment, the invention also relates to the compound(s) of formula (II), as medicament and cosmetic.

In particular, the invention relates to the compound(s) of formula (II), for their use in the treatment of inflammatory disorders and/or autoimmune diseases mediated by the RORγt receptor.

Preferentially, a subject of the invention is the compound(s) of formula (II) for their use in the treatment of acne.

As a variant, a subject of the invention is also the compound(s) of formula (II) for their use in the treatment of psoriasis.

Alternatively, the compound(s) of formula (II) according to the invention are used for cosmetic treatment of the skin.

Furthermore, the invention also relates to a pharmaceutical composition comprising, in a pharmaceutically acceptable medium, one or more compounds of formula (II) as defined previously, pharmaceutically acceptable addition salts thereof, hydrates thereof and/or solvates thereof.

The pharmaceutical composition is used for treating inflammatory disorders and/or autoimmune diseases mediated by the RORγt receptor.

In accordance with another embodiment, a subject of the present invention is also one or more compounds of formula (III) as defined previously, the pharmaceutically acceptable addition salts thereof, hydrates thereof and/or solvates thereof:

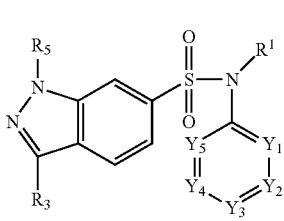

(III)

in which formula (III) $R^1$, $R^3$, $R^5$ and $Y^1$ to $Y^5$ have the same meanings as in formula (I) described previously.

Preferably, $R^3$ represents a group $(CHR^6)_n$—$(Z)_o$—$(CHR'^6)_p$—$R^7$ with $R^7$ representing a non-cationic heterocyclic radical, a non-cationic cycloalkyl radical or a non-cationic aromatic or heteroaromatic radical as defined previously.

Among the compounds of formula (III), compounds 63, 64 and 66 are preferred.

According to this embodiment, the invention also relates to the compound(s) of formula (III), as medicament and cosmetic.

In particular, the invention relates to the compound(s) of formula (III), for their use in the treatment of inflammatory disorders and/or autoimmune diseases mediated by the RORγt receptor.

Preferentially, a subject of the invention is the compound(s) of formula (III) for their use in the treatment of acne.

As a variant, a subject of the invention is also the compound(s) of formula (III) for their use in the treatment of psoriasis.

Alternatively, the compound(s) of formula (III) according to the invention are used for cosmetic treatment of the skin.

Furthermore, the invention also relates to a pharmaceutical composition comprising, in a pharmaceutically acceptable medium, one or more compounds of formula (III) as defined previously, pharmaceutically acceptable addition salts thereof, hydrates thereof and/or solvates thereof.

The pharmaceutical composition is used for treating inflammatory disorders and/or autoimmune diseases mediated by the RORγt receptor.

The examples that follow serve to illustrate the invention without, however, being limiting in nature.

EXAMPLES

The standard LCMS method for analyzing the products is as follows: BEH $C_{18}$ standard column (150×2.1 mm, 1.8 μm) solvent: water/acetonitrile 0.1% formic acid.

The preparative HPLC purifications were performed on a $C_{18}$ column using, as eluent: 85% acetonitrile in water/0.1% formic acid.

Part I: Synthesis of the Bicyclic Sulfonamides Via Reaction Scheme 1

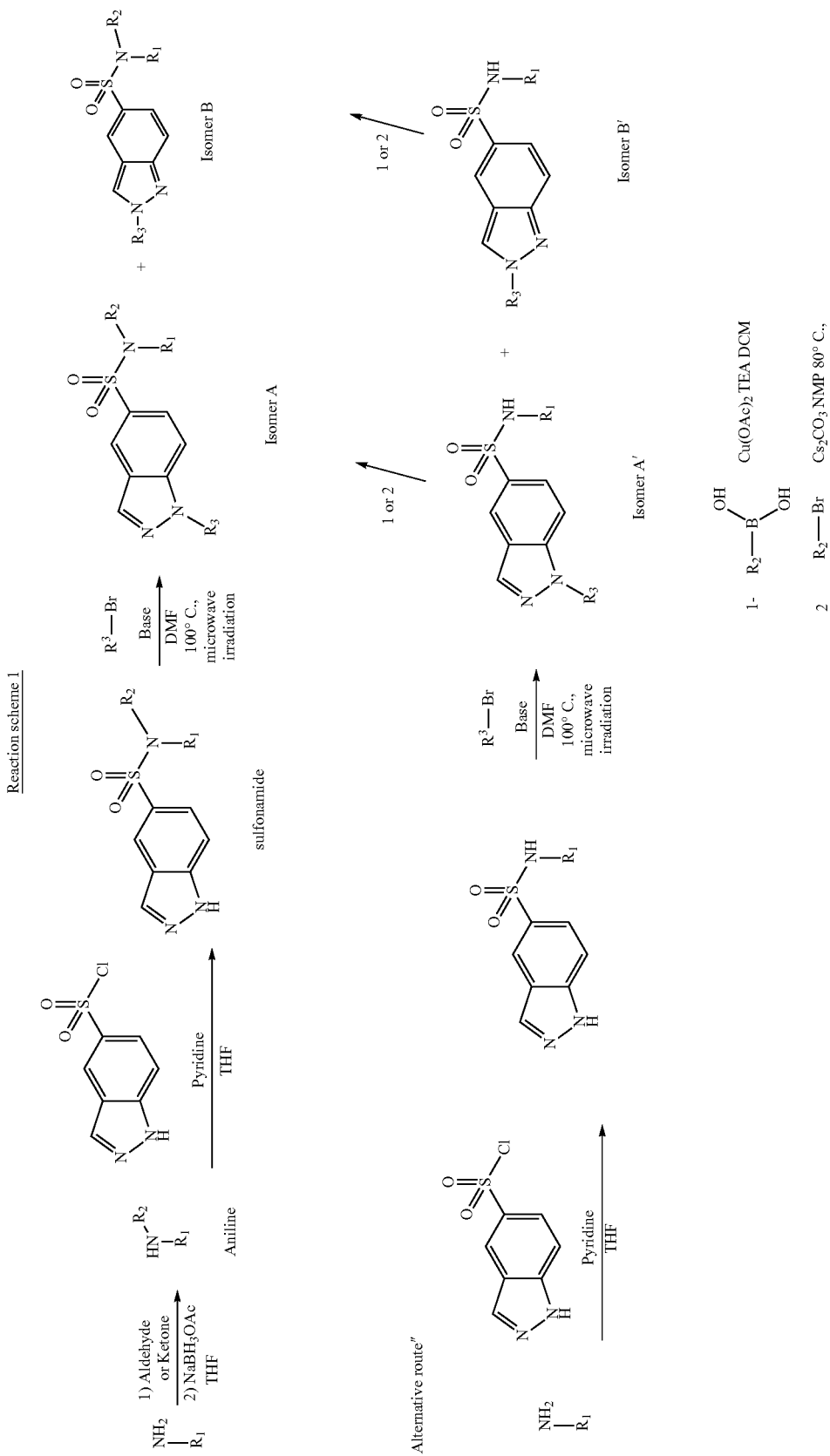

Example 1: Synthesis of N-(4-ethylphenyl)-N-isobutyl-1-((tetrahydro-2H-pyran-4-yl)methyl)-1H-indazole-5-sulfonamide

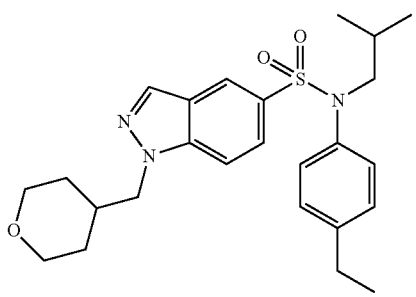

Compound 39

1. Synthesis of Intermediate 1.1

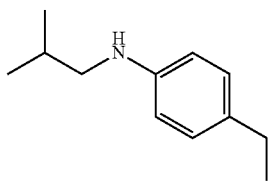

(4-ethylphenyl)isobutylamine

Isobutyraldehyde (6.33 ml; 0.07 mol) in tetrahydrofuran (100 ml) is added to 4-ethylaniline (9.48 ml; 0.08 mol). The mixture is stirred for 2 hours at room temperature. Sodium triacetoxyborohydride (22.04 g; 0.10 mol) is then added. The mixture is stirred overnight at room temperature, water (100 ml) are added and the resulting mixture is extracted with ethyl acetate (2×100 ml). The organic phases are combined, washed with brine (100 ml), dried ($Na_2SO_4$) and concentrated.

The crude product is chromatographed on silica gel (eluent: heptane/dichloromethane from 0 to 50% of dichloromethane). The (4-ethylphenyl)isobutylamine is obtained in the form of an orange oil with a compliant $^1$H NMR.

MS: [M+H]=179

2. Synthesis of Intermediate 1.2

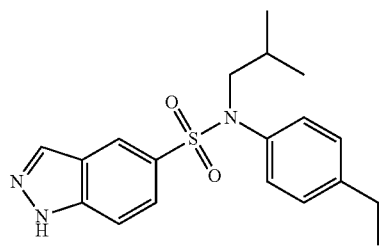

N-(4-ethylphenyl)-N-isobutyl-1H-indazole-5-sulfonamide

1H-Indazole-5-sulfonyl chloride (502 mg; 2.20 mmol) is added to (4-ethylphenyl)isobutylamine (300 mg; 1.69 mmol) and pyridine (820 µl; 10.15 mmol) in tetrahydrofuran (6 ml). The reaction medium is stirred for 7 hours at room temperature, hydrolyzed and extracted with ethyl acetate. The organic phases are combined, washed with brine, dried ($Na_2SO_4$) and concentrated.

The crude product is chromatographed on silica gel (eluent: heptane/ethyl acetate, from 20 to 50% of ethyl acetate). The N-(4-ethylphenyl)-N-isobutyl-1H-indazole-5-sulfonamide (357 mg; 59%) is obtained in the form of a cream-colored solid with a compliant $^1$H NMR.

MS: [M+H]=358

3. Synthesis of Compound 39 According to the Invention

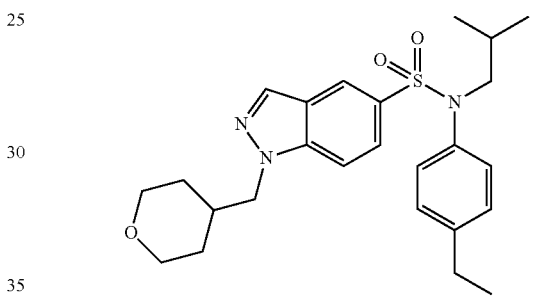

4-(Bromomethyl)tetrahydropyran (90 mg; 0.50 mmol) is added to N-(4-ethylphenyl)-N-isobutyl-1H-indazole-5-sulfonamide (150 mg; 0.42 mmol) and cesium carbonate (137 mg; 0.42 mmol) in N,N-dimethylformamide (12 ml). The reaction medium is stirred for 30 minutes at a temperature of 100° C. under microwave irradiation, hydrolyzed and extracted with ethyl acetate. The organic phases are combined, washed with brine, dried ($Na_2SO_4$) and concentrated.

The crude product is chromatographed on silica gel (eluent: heptane/ethyl acetate, 40% of ethyl acetate). The N-(4-ethylphenyl)-N-isobutyl-1-((tetrahydro-2H-pyran-4-yl)methyl)-1H-indazole-5-sulfonamide (97 mg; 50%) is obtained in the form of a white powder.

$^1$H NMR (400 MHz, DMSO-d6) δ 0.85 (d, J=6.6 Hz, 7H), 1.17 (t, J=7.6 Hz, 4H), 1.22-1.53 (m, 6H), 2.16-2.31 (m, 1H), 2.59 (q, J=7.6 Hz, 2H), 3.15-3.44 (m, 6H), 3.83 (ddd, J=11.5, 4.4, 2.0 Hz, 3H), 4.39 (d, J=7.2 Hz, 3H), 6.92-7.05 (m, 3H), 7.10-7.21 (m, 3H), 7.26 (dd, J=9.1, 1.8 Hz, 1H), 7.74 (d, J=9.3 Hz, 1H), 8.10 (d, J=1.7 Hz, 1H), 8.62 (s, 1H).

MS: [M+H]=456

With a procedure similar to that described for the synthesis of example 1, the compounds of the table below are obtained:

Example 2

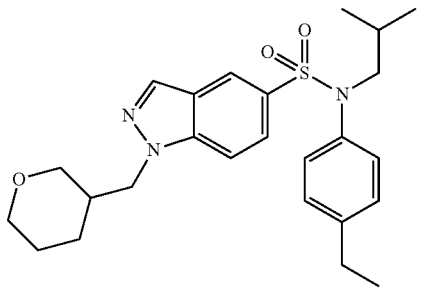

Compound 22

N-(4-ethylphenyl)-N-isobutyl-1-((tetrahydro-2H-pyran-3-yl)methyl)-1H-indazole-5-sulfonamide
1H NMR (DMSO-d6) δ: 0.85 (d, J = 6.6 Hz, 6H), 1.17 (t, J = 7.6 Hz, 3H), 1.23-1.35 (m, 1H), 1.35-1.53 (m, 2H), 1.54-1.72 (m, 2H), 2.08-2.23 (m, 1H), 2.59 (q, J = 7.6 Hz, 2H), 3.21 (dd, J = 11.2, 8.9 Hz, 1H), 3.32-3.40 (m, 3H), 3.57-3.65 (m, 1H), 3.70 (dt, J = 10.9, 3.9 Hz, 1H), 4.31-4.48 (m, 2H), 6.96 (d, J = 8.3 Hz, 2H), 7.16 (d, J = 8.4 Hz, 2H), 7.45 (dd, J = 9.0, 1.8 Hz, 1H), 7.84-7.89 (m, 1H), 8.09 (d, J = 1.8 Hz, 1H), 8.29 (d, J = 0.8 Hz, 1H)
MS: [M + H] = 456

Example 3

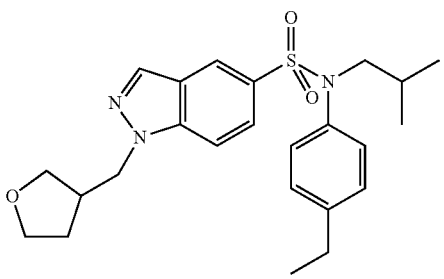

Compound 21

N-(4-ethylphenyl)-N-isobutyl-1-((tetrahydrofuran-3-yl)methyl)-1H-indazole-5-sulfonamide
1H NMR (DMSO-d6) δ: 0.85 (d, J = 6.7 Hz, 6H), 1.17 (t, J = 7.6 Hz, 3H), 1.42 (hept, J = 6.8 Hz, 1H), 1.57-1.73 (m, 1H), 1.83-2.00 (m, 1H), 2.60 (q, J = 7.6 Hz, 2H), 2.81 (hept, J = 7.1 Hz, 1H), 3.31-3.35 (m, 2H), 3.50 (dd, J = 8.6, 5.6 Hz, 1H), 3.60-3.71 (m, 2H), 3.81 (td, J = 8.1, 5.5 Hz, 1H), 4.36-4.55 (m, 2H), 6.96 (d, J = 8.4 Hz, 2H), 7.17 (d, J = 8.3 Hz, 2H), 7.46 (dd, J = 8.8, 1.8 Hz, 1H), 7.90 (d, J = 9.0 Hz, 1H), 8.09 (d, J = 1.7 Hz, 1H), 8.30 (d, J = 0.9 Hz, 1H)
MS: [M + H] = 442

Example 4

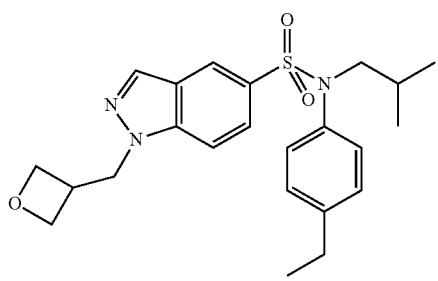 [SMILES: CCc1ccc(N(CC(C)C)S(=O)(=O)c2ccc3c(cnn3CC3COC3)c2)cc1]

Compound 37

N-(4-ethylphenyl)-N-isobutyl-1-(oxetan-3-ylmethyl)-1H-indazole-5-sulfonamide
1H NMR (DMSO-d6) δ: 0.85 (d, J = 6.6 Hz, 6H), 1.17 (t, J = 7.6 Hz, 3H), 1.41 (non, J = 6.8 Hz, 1H), 2.60 (q, J = 7.6 Hz, 2H), 3.32 (m, 2H), 3.52 (tt, J = 7.6, 6.1 Hz, 1H), 4.49 (t, J = 6.2 Hz, 2H), 4.67 (dd, J = 7.8, 6.1 Hz, 2H), 4.77 (d, J = 7.2 Hz, 2H), 6.96 (d, J = 8.3 Hz, 2H), 7.17 (d, J = 8.3 Hz, 2H), 7.47 (dd, J = 8.9, 1.7 Hz, 1H), 7.91 (d, J = 8.9 Hz, 1H), 8.09 (d, J = 1.8 Hz, 1H), 8.29 (d, J = 0.9 Hz, 1H)
MS: [M + H] = 428

Example 5

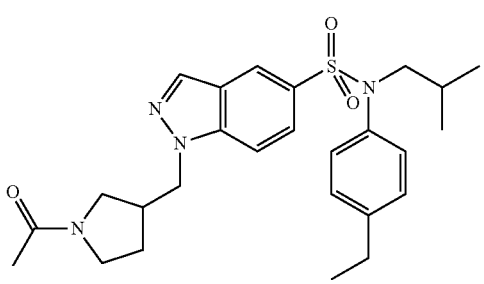 [SMILES: CCc1ccc(N(CC(C)C)S(=O)(=O)c2ccc3c(cnn3CC3CCN(C(C)=O)C3)c2)cc1]

Compound 20

1-((1-acetylpyrrolidin-3-yl)methyl)-N-(4-ethylphenyl)-N-isobutyl-1H-indazole-5-sulfonamide
1H NMR (DMSO-d6, 80° C.) δ: 0.86 (d, J = 6.6 Hz, 6H), 1.19 (t, J = 7.6 Hz, 3H), 1.44-1.60 (m, 1H), 1.60-1.83 (m, 1H), 1.83-2.07 (m, 4H), 2.61 (q, J = 7.6 Hz, 2H), 2.72-2.94 (m, 1H), 3.09-3.61 (m, 6H), 4.51 (d, J = 7.1 Hz, 2H), 6.99 (d, J = 8.5 Hz, 2H), 7.16 (d, J = 8.1 Hz, 2H), 7.49 (d, J = 8.7 Hz, 1H), 7.85 (d, J = 8.9 Hz, 1H), 8.10 (s, 1H), 8.28 (s, 1H)
MS: [M + H] = 483

Example 6

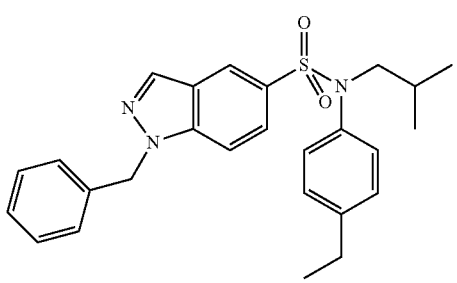

Compound 23

1-benzyl-N-(4-ethylphenyl)-N-isobutyl-1H-indazole-5-sulfonamide
1H NMR (DMSO-d6) δ: 0.84 (d, J = 6.7 Hz, 6H), 1.16 (t, J = 7.6 Hz, 3H), 1.41 (hept, J = 6.9 Hz, 1H), 2.59 (q, J = 7.6 Hz, 2H), 3.32 (m, 2H), 5.71 (s, 2H), 6.98 (d, J = 8.4 Hz, 2H), 7.16 (d, J = 8.4 Hz, 2H), 7.25 (dd, J = 9.2, 1.8 Hz, 1H), 7.31-7.43 (m, 5H), 7.73 (d, J = 9.1 Hz, 1H), 8.12 (dd, J = 1.9, 0.8 Hz, 1H), 8.75 (d, J = 1.0 Hz, 1H)
MS: [M + H] = 448

| Example | Structure | Name / NMR |
|---|---|---|
| Example 7 | 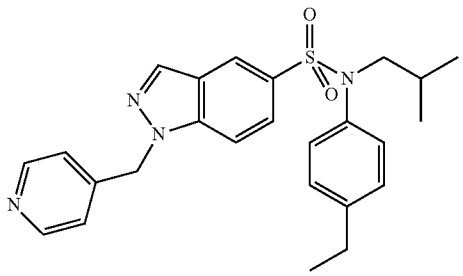<br>Compound 36 | N-(4-ethylphenyl)-N-isobutyl-1-(pyridin-4-ylmethyl)-1H-indazole-5-sulfonamide<br>1H NMR (DMSO-d6) δ: 0.85 (d, J = 6.6 Hz, 6H), 1.17 (t, J = 7.6 Hz, 3H), 1.32-1.48 (m, 1H), 2.59 (q, J = 7.7 Hz, 2H), 3.33 (m, 2H), 5.82 (s, 2H), 6.96 (d, J = 7.9 Hz, 2H), 7.15 (dd, J = 11.8, 6.5 Hz, 4H), 7.48 (d, J = 8.9 Hz, 1H), 7.90 (d, J = 8.9 Hz, 1H), 8.14 (s, 1H), 8.39 (s, 1H), 8.52 (d, J = 5.1 Hz, 2H)<br>MS: [M + H] = 449 |
| Example 8 | 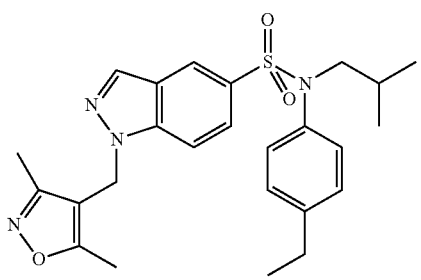 [SMILES: CCc1ccc(N(CC(C)C)S(=O)(=O)c2ccc3c(cnn3Cc3c(C)noc3C)c2)cc1]<br>Compound 6 | 1-((3,5-dimethylisoxazol-4-yl)methyl)-N-(4-ethylphenyl)-N-isobutyl-1H-indazole-5-sulfonamide<br>1H NMR (DMSO-d6) δ: 0.85 (d, J = 6.6 Hz, 6H), 1.17 (t, J = 7.6 Hz, 3H), 1.41 (hept, J = 6.8 Hz, 1H), 2.11 (s, 3H), 2.44 (s, 3H), 2.59 (q, J = 7.6 Hz, 2H), 3.33 (s, 2H), 5.54 (s, 2H), 6.88-7.00 (m, 2H), 7.12-7.20 (m, 2H), 7.50 (dd, J = 8.9, 1.8 Hz, 1H), 7.88-8.01 (m, 1H), 8.10 (d, J = 2.0 Hz, 1H), 8.30 (d, J = 0.9 Hz, 1H)<br>MS: [M + H] = 467 |

Example 9: Synthesis of 1-((1-acetylazetidin-3-yl)methyl)-1H-indazole-5-sulfonic acid (4-ethylphenyl)isobutylamide

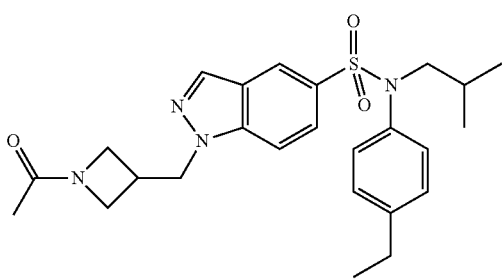

Compound 19

1-(3-Hydroxymethylazetidin-1-yl)ethanone (0.27 g; 2.09 mmol) in toluene (1 ml) is added to a mixture of N-(4-ethylphenyl)-N-isobutyl-1H-indazole-5-sulfonamide (0.20 g; 0.56 mmol) and (triphenyl-λ⁵-phosphanylidene)acetonitrile (0.51 g; 1.68 mmol) in anhydrous toluene (3 ml) under argon. The reaction medium is stirred for 3 days at a temperature of 95° C., hydrolyzed and extracted with ethyl acetate. The organic phase is washed, dried (Na$_2$SO$_4$), filtered and concentrated.

The crude product is purified by preparative HPLC (C18 column, eluent: acetonitrile in water/0.1% of formic acid). The 1-(1-acetylazetidin-3-ylmethyl)-1H-indazole-5-sulfonic acid (4-ethylphenyl)isobutylamide (136 mg; 51%) is obtained in the form of a pale yellow solid.

¹H NMR (DMSO-d6) δ: 0.85 (d, J=6.6 Hz, 6H), 1.17 (t, J=7.6 Hz, 3H), 1.42 (hept, J=6.8 Hz, 1H), 1.73 (s, 3H), 2.59 (q, J=7.6 Hz, 2H), 3.07-3.20 (m, 1H), 3.30-3.36 (m, 2H), 3.69 (dd, J=9.6, 5.6 Hz, 1H), 3.89 (t, J=9.0 Hz, 1H), 3.98 (dd, J=8.5, 5.5 Hz, 1H), 4.18 (t, J=8.4 Hz, 1H), 4.71 (d, J=7.3 Hz, 2H), 6.96 (d, J=8.4 Hz, 2H), 7.17 (d, J=8.4 Hz, 2H), 7.48 (dd, J=9.0, 1.7 Hz, 1H), 7.89-7.97 (m, 1H), 8.09 (d, J=1.7 Hz, 1H), 8.31 (d, J=0.9 Hz, 1H)

MS: [M+H]=469

Example 10: Synthesis of 1-(tetrahydropyran-4-yl)-1H-indazole-5-sulfonic acid (4-ethylphenyl)isobutylamide

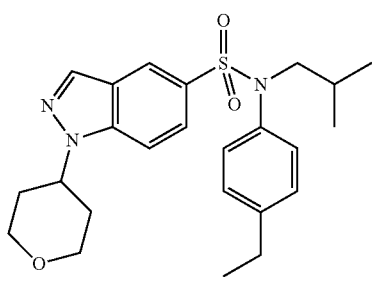

Compound 38

By following the same procedure as that for example 9, 1-(tetrahydropyran-4-yl)-1H-indazole-5-sulfonic acid (4-ethylphenyl)isobutylamide (22 mg; 36%) is obtained in the form of a white solid.

¹H NMR (DMSO-d6) δ: 0.85 (d, J=6.7 Hz, 6H), 1.18 (t, J=7.6 Hz, 3H), 1.41 (non, J=6.5 Hz, 1H), 1.85-1.97 (m, 2H), 2.15 (qd, J=12.3, 4.6 Hz, 2H), 2.60 (q, J=7.6 Hz, 2H), 3.30-3.32 (m, 2H), 3.58 (td, J=11.9, 2.0 Hz, 2H), 3.98-4.07 (m, 2H), 4.99 (td, J=11.3, 5.7 Hz, 1H), 6.98 (d, J=8.4 Hz, 2H), 7.18 (d, J=8.4 Hz, 2H), 7.44 (dd, J=8.9, 1.7 Hz, 1H), 7.94 (d, J=8.9 Hz, 1H), 8.11 (d, J=1.6 Hz, 1H), 8.32 (s, 1H)

MS: [M+H]=442

Example 11: Synthesis of 1-(1-acetylpyrrolidin-3-yl)-1H-indazole-5-sulfonic acid (4-ethylphenyl)isobutylamide Compound 17

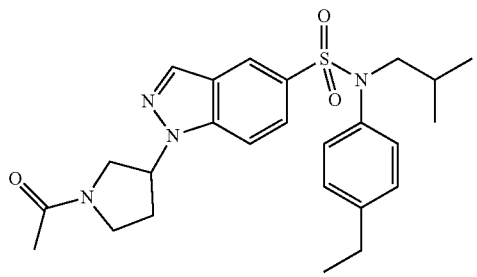

A mixture of N-(4-ethylphenyl)-N-isobutyl-1H-indazole-5-sulfonamide (0.20 g; 0.56 mmol), cesium carbonate (0.27 g; 0.84 mmol) and 1-(3-bromopyrrolidin-1-yl)ethanone (0.13 g; 0.67 mmol) in 1-methyl-2-pyrrolidone (3 ml) is stirred for 5 hours at a temperature of 80° C., hydrolyzed and extracted with ethyl acetate. The organic phase is washed with water, dried ($Na_2SO_4$), filtered and concentrated.

The crude product is purified by preparative HPLC (C18 column, eluent: acetonitrile in water/0.1% of formic acid). The 1-(1-acetylpyrrolidin-3-yl)-1H-indazole-5-sulfonic acid (4-ethylphenyl)isobutylamide (29 mg; 11%) is obtained in the form of a white solid.

Mixture of two conformers: $^1$H NMR (DMSO-d6) δ: 0.85 (dd, J=6.7, 1.1 Hz, 6H), 1.18 (t, J=7.6 Hz, 3H), 1.33-1.50 (m, 1H), 2.01 (s, 3H), 2.60 (q, J=7.6 Hz, 2H), 3.34 (d, J=2.4 Hz, 2H), 3.46-3.54 (m, 1H), 3.59-3.65 (m, 1H), 3.65-3.72 (m, 1H), 3.76-3.82 (m, 1H), 3.85 (dd, J=12.3, 6.8 Hz, 1H), 4.05 (dd, J=10.8, 7.0 Hz, 1H), 5.57 (ddt, J=27.8, 11.5, 6.2 Hz, 1H), 6.90-7.03 (m, 2H), 7.16-7.21 (m, 2H), 7.49 (ddd, J=8.8, 5.4, 1.7 Hz, 1H), 7.92 (t, J=9.0 Hz, 1H), 8.11 (dd, J=3.4, 1.6 Hz, 1H), 8.32-8.41 (m, 1H)

MS: [M+H]=469

With a procedure similar to that for intermediate 1.1, corresponding to a reductive amination between 1 equivalent of aldehyde and 1.15 equivalents of aniline in tetrahydrofuran in the presence of 1.45 equivalents of sodium triacetoxyborohydride, the anilines of the table below are obtained:

| Intermediate 12.1 | cyclopropylmethyl(4-ethylphenyl)amine (300 mg; 46%) obtained in the form of an orange oil with a compliant $^1$H NMR. MS: [M + H] = 176 |
| Intermediate 13.1 | cyclobutylmethyl(4-ethylphenyl)amine (400 mg; 56%) obtained in the form of an orange oil with a compliant $^1$H NMR. MS: [M + H] = 190 |
| Intermediate 14.1 | cyclopentylmethyl(4-ethylphenyl)amine (19.3 g; 56%) obtained in the form of an amber-colored oil with a compliant $^1$H NMR. MS: [M + H] = 190 |
| Intermediate 15.1 | cyclobutylmethyl(4-ethylphenyl)amine (700 mg; 97%) obtained in the form of an oil with a compliant $^1$H NMR. MS: [M + H] = 176 |
| Intermediate 16.1 | (tetrahydrofuran-3-ylmethyl)(4-ethylphenyl)amine (600 mg; 78%) obtained in the form of an orange oil with a compliant $^1$H NMR. MS: [M + H] = 206 |

| | | |
|---|---|---|
| Intermediate 17.1 | 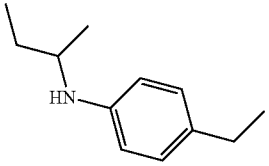 | sec-butyl(4-ethylphenyl)amine (600 mg; 90%) obtained in the form of an orange oil with a compliant $^1$H NMR.<br>MS: [M + H] = 178 |
| Intermediate 18.1 | 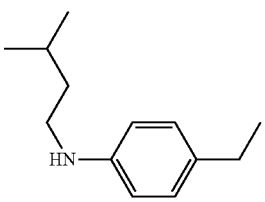 | (4-ethylphenyl)(3-methylbutyl)amine (250 mg; 32%) obtained in the form of an orange oil with a compliant $^1$H NMR.<br>MS: [M + H] = 192 |
| Intermediate 19.1 | 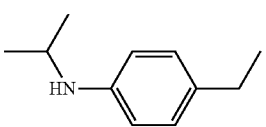 | 4-ethyl-N-isopropylaniline (300 mg; 49%) obtained in the form of an orange oil with a compliant $^1$H NMR.<br>MS: [M + H] = 165 |
| Intermediate 20.1 | 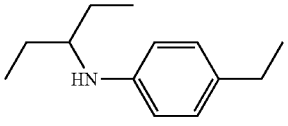 | (4-ethylphenyl)(1-ethylpropyl)amine (700 mg; 98%) obtained in the form of an oil with a compliant $^1$H NMR.<br>MS: [M + H] = 192 |
| Intermediate 21.1 | 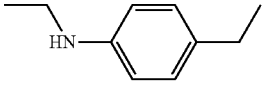 | ethyl(4-ethylphenyl)amine commercial |
| Intermediate 22.1 | 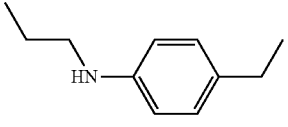 | propyl(4-ethylphenyl)amine (450 mg; 73%) obtained in the form of an oil with a compliant $^1$H NMR.<br>MS: [M + H] = 165 |
| Intermediate 23.1 | 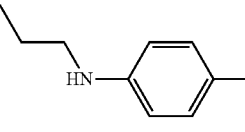 | butyl(4-ethylphenyl)amine (650 mg; 98%) obtained in the form of an oil with a compliant $^1$H NMR.<br>MS: [M + H] = 178 |
| Intermediate 24.1 | 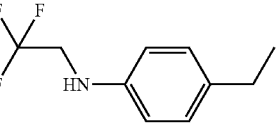 | (2,2,2-trifluoroethyl)(4-ethylphenyl)amine commercial |
| Intermediate 25.1 | 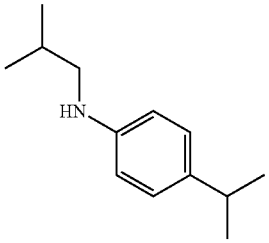 | isobutyl(4-isopropylphenyl)amine (600 mg; 93%) obtained in the form of an oil with a compliant $^1$H NMR.<br>MS: [M + H] = 193 |
| Intermediate 26.1 | 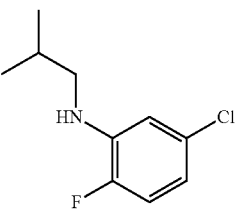 | (5-chloro-2-fluorophenyl)isobutylamine (350 mg; 56%) obtained in the form of an oil with a compliant $^1$H NMR.<br>MS: [M + H] = 202 |

-continued

| Intermediate 27.1 | 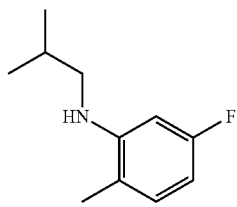 | (5-fluoro-2-methylphenyl)isobutylamine (802 mg; 61%) obtained in the form of an oil with a compliant $^1$H NMR. MS: [M + H] = 182 |
| Intermediate 28.1 | 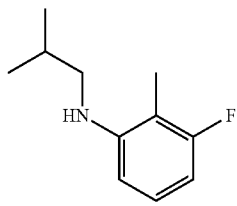 | (3-fluoro-2-methylphenyl)isobutylamine (408 mg; 31%) obtained in the form of an oil with a compliant $^1$H NMR. MS: [M + H] = 182 |
| Intermediate 29.1 | 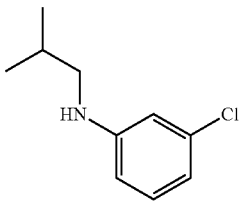 | (5-chlorophenyl)isobutylamine (655 mg; 100%) obtained in the form of an oil with a compliant $^1$H NMR. MS: [M + H] = 185 |
| Intermediate 30.1 | 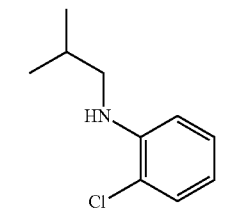 | (2-chlorophenyl)isobutylamine (655 mg; 100%) obtained in the form of an oil with a compliant $^1$H NMR. MS: [M + H] = 184 |
| Intermediate 31.1 | 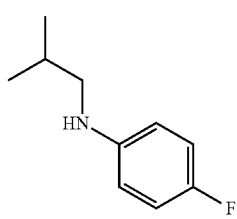 | (4-fluorophenyl)isobutylamine (684 mg; 100%) obtained in the form of an oil with a compliant $^1$H NMR. MS: [M + H] = 169 |
| Intermediate 32.1 | 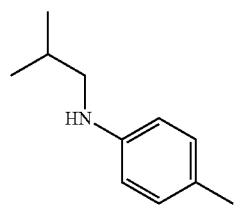 | (4-methylphenyl)isobutylamine (876 mg; 63%) obtained in the form of a colorless oil with a compliant $^1$H NMR. MS: [M + H] = 164 |
| Intermediate 33.1 | 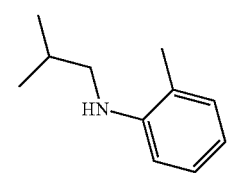 | isobutyl-o-tolylamine (972.8 mg; 70%) obtained in the form of an oil with a compliant $^1$H NMR. MS: [M + H] = 164 |

| | | |
|---|---|---|
| Intermediate 34.1 | 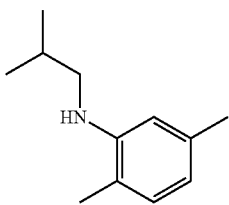 | (2,5-dimethylphenyl)isobutylamine (700 mg; 97%) obtained in the form of an oil with a compliant $^1$H NMR. MS: [M + H] = 179 |
| Intermediate 35.1 | 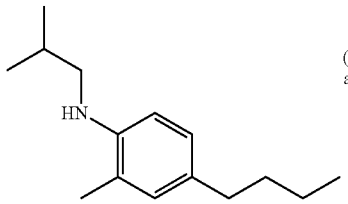 | (4-butyl-2-methylphenyl)isobutylamine (520 mg; 85%) obtained in the form of a clear yellow oil with a compliant $^1$H NMR. MS: [M + H] = 220 |
| Intermediate 36.1 | 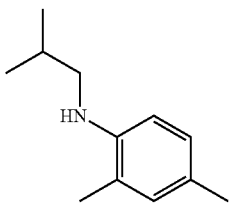 | (2,4-dimethylphenyl)isobutylamine (1.15 g; 83%) obtained in the form of an oil with a compliant $^1$H NMR. MS: [M + H] = 179 |
| Intermediate 37.1 | 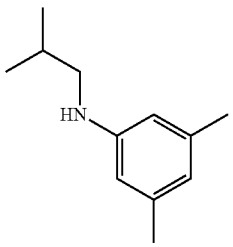 | (3.5-dimethylphenyl)isobutylamine (600 mg; 82%) obtained in the form of a colorless oil with a compliant $^1$H NMR. MS: [M + H] = 179 |
| Intermediate 38.1 | 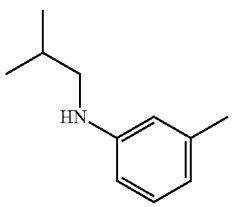 | (3-methylphenyl)isobutylamine (600 mg; 79%) obtained in the form of a colorless oil with a compliant $^1$H NMR. MS: [M + H] = 164 |
| Intermediate 39.1 | 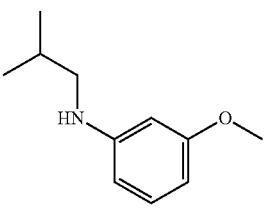 | (3-methoxyphenyl)isobutylamine (600 mg; 82%) obtained in the form of a colorless oil with a compliant $^1$H NMR. MS: [M + H] = 181 |
| Intermediate 40.1 | 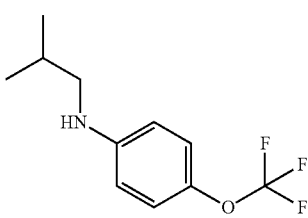 [SMILES: CC(C)CNc1ccc(OC(F)(F)F)cc1] | (4-trifluoromethoxyphenyl)isobutylamine (600 mg; 100%) obtained in the form of an oil with a compliant $^1$H NMR. MS: [M + H] = 235 |

| | | |
|---|---|---|
| Intermediate 41.1 | 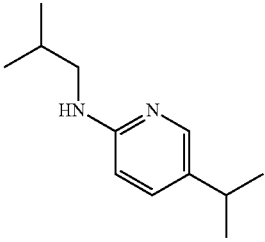 | isobutyl(5-isopropylpyridin-2-yl)amine (600 mg; 93%) obtained in the form of an oil with a compliant $^1$H NMR. MS: [M + H] = 193 |
| Intermediate 42.1 | 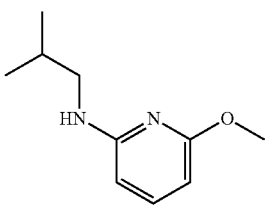 | (3-methoxypyridin-2-yl)isobutylamine (450 mg; 68%) obtained in the form of an oil with a compliant $^1$H NMR. MS: [M + H] = 181 |
| Intermediate 43.1 | 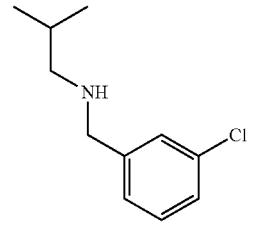 | (3-chlorobenzyl)isobutylamine (500 mg; 68%) obtained in the form of an oil with a compliant $^1$H NMR. MS: [M + H] = 198 |
| Intermediate 44.1 | 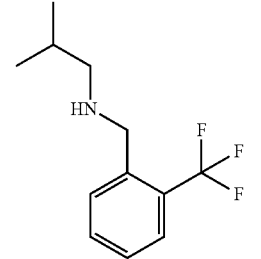 [SMILES: CC(C)CNCc1ccccc1C(F)(F)F] | (3-methoxypyridin-2-yl)isobutylamine (600 mg; 100%) obtained in the form of an oil with a compliant $^1$H NMR. MS: [M + H] = 232 |
| Intermediate 45.1 | 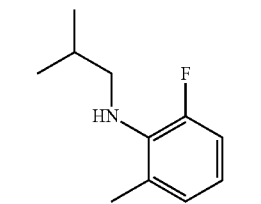 | (2-fluoro-6-methylphenyl)isobutylamine (560 mg; 44%) obtained in the form of an oil with a compliant $^1$H NMR. MS: [M + H] = 182 |
| Intermediate 46.1 | 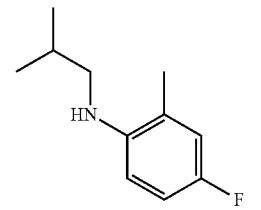 | (4-chloro-2-methylphenyl)isobutylamine (892 mg; 71%) obtained in the form of an oil with a compliant $^1$H NMR. MS: [M + H] = 182 |
| Intermediate 47.1 | 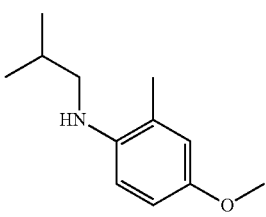 | isobutyl(4-methoxy-2-methylphenyl)amine (980 mg; 77%) obtained in the form of an oil with a compliant $^1$H NMR. MS: [M + H] = 193 |

With a procedure similar to that for intermediate 1.2, by reacting 1 equivalent of N-substituted anilines (derived from the above table or corresponding commercial products) with 1.3 equivalents of 1H-indazole-5-sulfonyl chloride in tetrahydrofuran (20 vol) in the presence of 6 equivalents of pyridine, the intermediates of the table below are obtained:

| Intermediate | Structure | Description |
|---|---|---|
| Intermediate 12.2 | 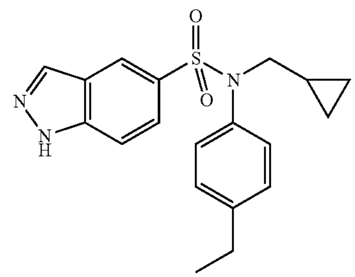 [SMILES: CCc1ccc(N(CC2CC2)S(=O)(=O)c2ccc3[nH]ncc3c2)cc1] | 1H-indazole-5-sulfonic acid cyclopropylmethyl(4-ethylphenyl)amide (450 mg; 81%) is obtained in the form of colorless oil with a compliant $^1$H NMR. MS: [M + H] = 356 |
| Intermediate 13.2 | 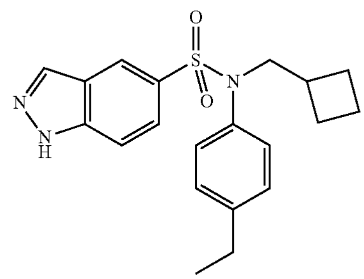 [SMILES: CCc1ccc(N(CC2CCC2)S(=O)(=O)c2ccc3[nH]ncc3c2)cc1] | 1H-indazole-5-sulfonic acid cyclobutylmethyl(4-ethylphenyl)amide (590 mg; 55%) obtained in the form of a colorless oil with a compliant $^1$H NMR. MS: [M + H] = 370 |
| Intermediate 14.2 | 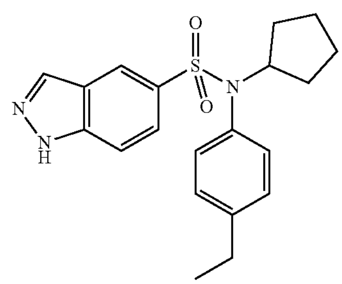 [SMILES: CCc1ccc(N(C2CCCC2)S(=O)(=O)c2ccc3[nH]ncc3c2)cc1] | 1H-indazole-5-sulfonic acid cyclopentyl(4-ethylphenyl)amide (250 mg; 47%) obtained in the form of a colorless oil with a compliant $^1$H NMR. MS: [M + H] = 370 |
| Intermediate 15.2 | 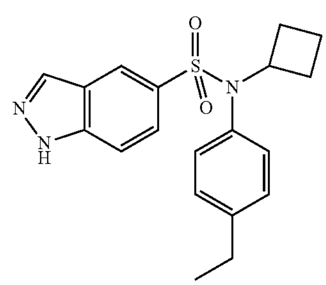 [SMILES: CCc1ccc(N(C2CCC2)S(=O)(=O)c2ccc3[nH]ncc3c2)cc1] | 1H-indazole-5-sulfonic acid cyclobutyl(4-ethylphenyl)amide (80 mg; 51%) obtained in the form of a colorless oil with a compliant $^1$H NMR. MS: [M + H] = 356 |
| Intermediate 16.2 | 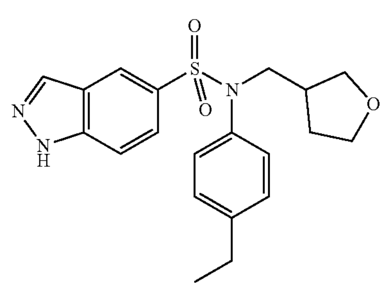 [SMILES: CCc1ccc(N(CC2CCOC2)S(=O)(=O)c2ccc3[nH]ncc3c2)cc1] | 1H-indazole-5-sulfonic acid (4-ethylphenyl)(tetrahydrofuran-3-ylmethyl)amide (800 mg; 78%) obtained in the form of a colorless oil with a compliant $^1$H NMR. MS: [M + H] = 386 |

| | | |
|---|---|---|
| Intermediate 17.2 | 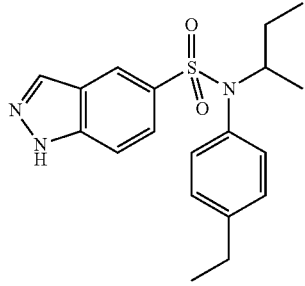 [SMILES: CCc1ccc(N(C(C)CC)S(=O)(=O)c2ccc3[nH]ncc3c2)cc1] | 1H-indazole-5-sulfonic acid sec-butyl(4-ethylphenyl)amide (310 mg; 56%) obtained in the form of a colorless oil with a compliant $^1$H NMR. MS: [M + H] = 358 |
| Intermediate 18.2 | 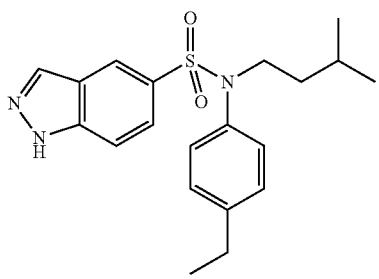 [SMILES: CCc1ccc(N(CCC(C)C)S(=O)(=O)c2ccc3[nH]ncc3c2)cc1] | 1H-indazole-5-sulfonic acid (4-ethylphenyl)(3-methylbutyl)amide (220 mg; 50%) obtained in the form of a colorless oil with a compliant $^1$H NMR. MS: [M + H] = 372 |
| Intermediate 19.2 | 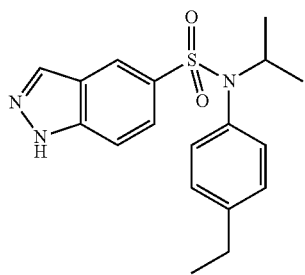 [SMILES: CCc1ccc(N(C(C)C)S(=O)(=O)c2ccc3[nH]ncc3c2)cc1] | 1H-indazole-5-sulfonic acid (4-ethylphenyl)isopropylamide (400 mg; 70%) obtained in the form of a colorless oil with a compliant $^1$H NMR MS: [M + H] = 344 |
| Intermediate 20.2 | 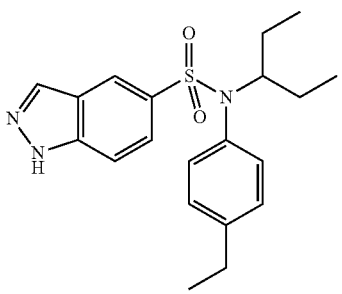 [SMILES: CCc1ccc(N(C(CC)CC)S(=O)(=O)c2ccc3[nH]ncc3c2)cc1] | 1H-indazole-5-sulfonic acid (4-ethylphenyl)(1-ethylpropyl)amide (40 mg; 25%) obtained in the form of a colorless oil with a compliant $^1$H NMR. MS: [M + H] = 372 |
| Intermediate 21.2 | 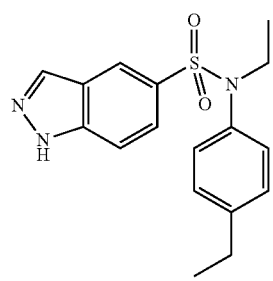 [SMILES: CCc1ccc(N(CC)S(=O)(=O)c2ccc3[nH]ncc3c2)cc1] | 1H-indazole-5-sulfonic acid ethyl(4-ethylphenyl)amide (160 mg; 55%) obtained in the form of a colorless oil with a compliant $^1$H NMR. MS: [M + H] = 330 |

| Intermediate | Structure | Description |
|---|---|---|
| Intermediate 22.2 | 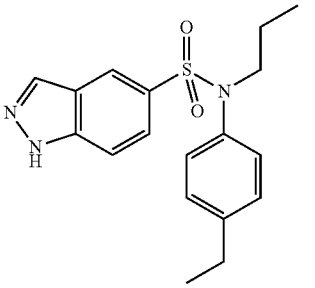 [SMILES: CCCN(c1ccc(CC)cc1)S(=O)(=O)c1ccc2[nH]ncc2c1] | 1H-indazole-5-sulfonic acid (4-ethylphenyl)propylamide (400 mg; 46%) obtained in the form of a colorless oil with a compliant ¹H NMR.<br>MS: [M + H] = 344 |
| Intermediate 23.2 | 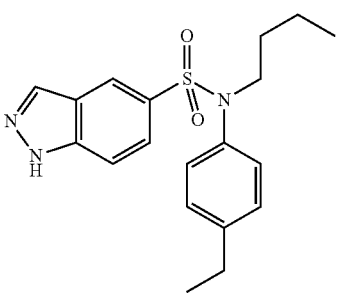 [SMILES: CCCCN(c1ccc(CC)cc1)S(=O)(=O)c1ccc2[nH]ncc2c1] | 1H-indazole-5-sulfonic acid (4-ethylphenyl)butylamide (800 mg; 67%) obtained in the form of a colorless oil with a compliant ¹H NMR.<br>MS: [M + H] = 358 |
| Intermediate 25.2 | 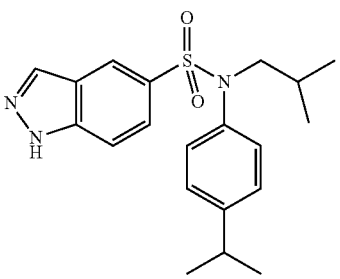 [SMILES: CC(C)CN(c1ccc(C(C)C)cc1)S(=O)(=O)c1ccc2[nH]ncc2c1] | 1H-indazole-5-sulfonic acid isobutyl(4-isopropylphenyl)amide (800 mg; 76%) obtained in the form of a colorless oil with a compliant ¹H NMR.<br>MS: [M + H] = 372 |
| Intermediate 26.2 | 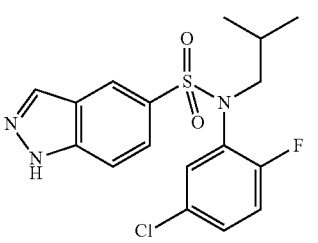 [SMILES: CC(C)CN(c1cc(Cl)ccc1F)S(=O)(=O)c1ccc2[nH]ncc2c1] | 1H-indazole-5-sulfonic acid (5-chloro-2-fluorophenyl)isobutylamide (120 mg; 20%) obtained in the form of a colorless oil with a compliant ¹H NMR.<br>MS: [M + H] = 381 |
| Intermediate 27.2 | 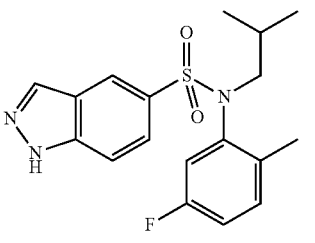 [SMILES: Cc1ccc(F)cc1N(CC(C)C)S(=O)(=O)c1ccc2[nH]ncc2c1] | 1H-indazole-5-sulfonic acid (5-fluoro-2-methylphenyl)isobutylamide (267 mg; 53%) obtained in the form of a colorless oil with a compliant ¹H NMR.<br>MS: [M + H] = 362 |
| Intermediate 28.2 | 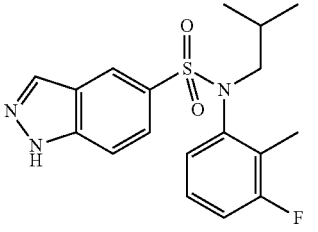 [SMILES: Cc1c(F)cccc1N(CC(C)C)S(=O)(=O)c1ccc2[nH]ncc2c1] | 1H-indazole-5-sulfonic acid (3-fluoro-2-methylphenyl)isobutylamide (137 mg; 38%) obtained in the form of a colorless oil with a compliant ¹H NMR.<br>MS: [M + H] = 362 |

| Intermediate | Structure | Description |
|---|---|---|
| Intermediate 29.2 | 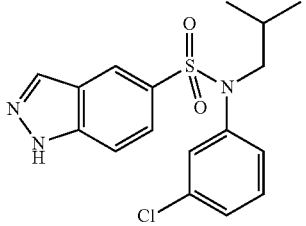 [SMILES: CC(C)CN(c1cccc(Cl)c1)S(=O)(=O)c1ccc2[nH]ncc2c1] | 1H-indazole-5-sulfonic acid (5-chlorophenyl)isobutylamide (90 mg; 56%) obtained in the form of a white solid with a compliant $^1$H NMR.<br>MS: [M + H] = 364 |
| Intermediate 31.2 | 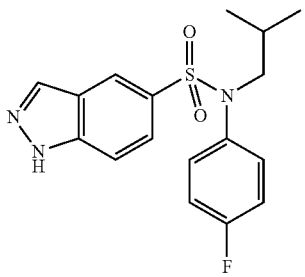 [SMILES: CC(C)CN(c1ccc(F)cc1)S(=O)(=O)c1ccc2[nH]ncc2c1] | 1H-indazole-5-sulfonic acid (4-fluorophenyl)isobutylamide (100 mg; 66%) obtained in the form of a colorless oil with a compliant $^1$H NMR.<br>MS: [M + H] = 348 |
| Intermediate 32.2 | 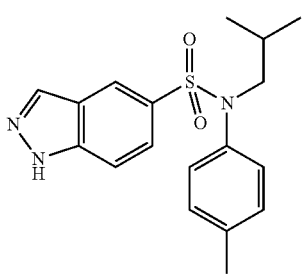 [SMILES: Cc1ccc(N(CC(C)C)S(=O)(=O)c2ccc3[nH]ncc3c2)cc1] | 1H-indazole-5-sulfonic acid isobutyl-p-tolylamide (770 mg; 81%) obtained in the form of a colorless oil with a compliant $^1$H NMR<br>MS: [M + H] = 344 |
| Intermediate 33.2 | 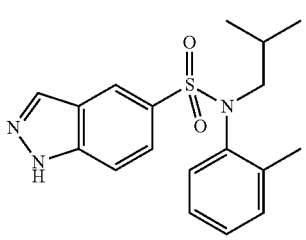 [SMILES: Cc1ccccc1N(CC(C)C)S(=O)(=O)c1ccc2[nH]ncc2c1] | 1H-indazole-5-sulfonic acid isobutyl-o-tolylamide (481 mg; 46%) obtained in the form of a white solid with compliant $^1$H NMR.<br>MS: [M + H] = 344 |
| Intermediate 34.2 | 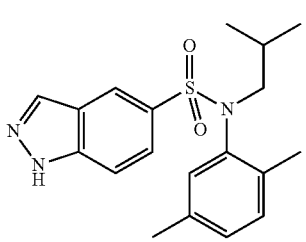 [SMILES: Cc1ccc(C)c(N(CC(C)C)S(=O)(=O)c2ccc3[nH]ncc3c2)c1] | 1H-indazole-5-sulfonic acid (2,5-dimethylphenyl)isobutylamide (540 mg; 59%) obtained in the form of a colorless oil with a compliant $^1$H NMR.<br>MS: [M + H] = 358 |
| Intermediate 35.2 | 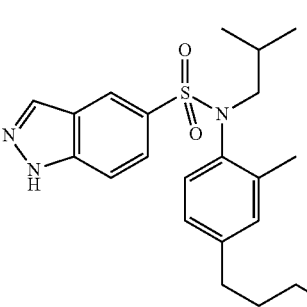 | 1H-indazole-5-sulfonic acid (4-butyl-2-methylphenyl)isobutylamide (650 mg; 75%) obtained in the form of a colorless oil with a compliant $^1$H NMR.<br>MS: [M + H] = 400 |

| Intermediate | | Description |
|---|---|---|
| Intermediate 36.2 | (structure) | 1H-indazole-5-sulfonic acid (2,4-dimethylphenyl)isobutylamide (500 mg; 55%) obtained in the form of a colorless oil with a compliant $^1$H NMR.<br>MS: [M + H] = 381 |
| Intermediate 37.2 | (structure) | 1H-indazole-5-sulfonic acid (3,5-dimethylphenyl)isobutylamide (140 mg; 13%) obtained in the form of a colorless oil with a compliant $^1$H NMR.<br>MS: [M + H] = 358 |
| Intermediate 38.2 | (structure) | 1H-indazole-5-sulfonic acid (3-methylphenyl)isobutylamide (310 mg; 27%) obtained in the form of a colorless oil with a compliant $^1$H NMR.<br>MS: [M + H] = 344 |
| Intermediate 39.2 | (structure) | 1H-indazole-5-sulfonic acid (3-methoxyphenyl)isobutylamide (450 mg; 62%) obtained in the form of a colorless oil with a compliant $^1$H NMR.<br>MS: [M + H] = 360 |
| Intermediate 40.2 | (structure) | 1H-indazole-5-sulfonic acid (4-trifluoromethoxyphenyl)isobutylamide (100 mg; 55%) obtained in the form of a colorless oil with a compliant $^1$H NMR.<br>MS: [M + H] = 414 |
| Intermediate 42.2 | (structure) | 1H-indazole-5-sulfonic acid (3-methoxypyridin-2-yl)isobutylamide (300 mg; 37%) obtained in the form of a colorless oil with a compliant $^1$H NMR.<br>MS: [M + H] = 361 |

| | | |
|---|---|---|
| Intermediate 43.2 | (structure) | 1H-indazole-5-sulfonic acid (3-chlorobenzyl)isobutylamide (50 mg; 30%) obtained in the form of a colorless oil with a compliant $^1$H NMR.<br>MS: [M + H] = 378 |
| Intermediate 44.2 | (structure) | 1H-indazole-5-sulfonic acid isobutyl(2-trifluoromethylbenzyl)amide (70 mg; 39%) obtained in the form of a colorless oil with a compliant $^1$H NMR.<br>MS: [M + H] = 412 |
| Intermediate 45.2 | (structure) | 1H-indazole-5-sulfonic acid (2-fluoro-6-methylphenyl)isobutylamide (305 mg; 65%) obtained in the form of a white solid with a compliant $^1$H NMR.<br>MS: [M + H] = 362 |
| Intermediate 46.2 | (structure) | 1H-indazole-5-sulfonic acid (4-fluoro-2-methylphenyl)isobutylamide (307 mg; 65%) is obtained in the form of a yellowish solid with a compliant $^1$H NMR.<br>MS: [M − H] = 360 |
| Intermediate 47.2 | (structure) | 1H-indazole-5-sulfonic acid isobutyl(4-methoxy-2-methylphenyl)amide (437 mg; 89%) obtained in the form of a colorless oil with a compliant $^1$H NMR.<br>MS: [M + H] = 374 |
| Intermediate 48.1 | (structure) | methyl 4-(1H-indazole-5-sulfonylamino)-3-methylbenzoate Obtained from the commercial amine. (480 mg; 63%) obtained in the form of a white solid with a compliant $^1$H NMR.<br>MS: [M − H] = 346 |

| Intermediate 49.1 | 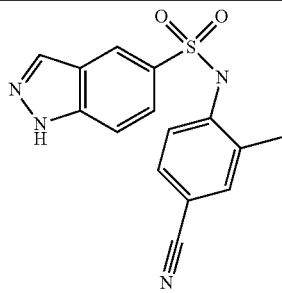 | 1H-indazole-5-sulfonic acid (4-cyano-2-methylphenyl)amide Obtained from the commercial amine. (330 mg; 80%) obtained in the form of a beige-colored solid with a compliant ¹H NMR. MS: [M − H] = 313 |
|---|---|---|

1. Synthesis of Intermediate 24.2

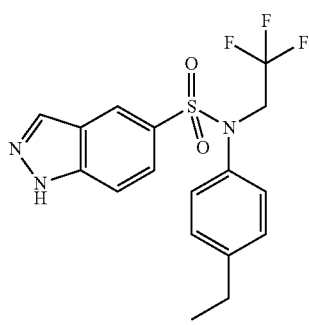 [SMILES: CCc1ccc(N(CC(F)(F)F)S(=O)(=O)c2ccc3[nH]ncc3c2)cc1]

1H-indazole-5-sulfonic acid (4-ethylphenyl)(2,2,2-trifluoroethyl)amide

A mixture of 1H-indazole-5-sulfonyl chloride (200 mg; 0.88 mmol), pyridine (3 ml), potassium iodide (7.3 mg; 0.04 mmol), 4-dimethylaminopyridine (5.4 mg; 0.04 mmol) and N-(4-ethylphenyl)-N-(2,2,2-trifluoroethyl)amine hydrochloride (231 mg; 0.96 mmol) is stirred for 16 hours at a temperature of 100° C.

Silver(I) fluoride (5.6 mg; 0.04 mmol) is added to the reaction medium, which is stirred for 3 days at a temperature of 80° C.

The crude product is purified by preparative HPLC (C18 column, eluent: acetonitrile in water/0.1% of formic acid). The 1H-indazole-5-sulfonic acid (4-ethylphenyl)(2,2,2-trifluoroethyl)amide (20 mg; 6%) is obtained in the form of a clear yellow oil.
MS: [M+H]=384

2. Synthesis of Intermediate 30.2

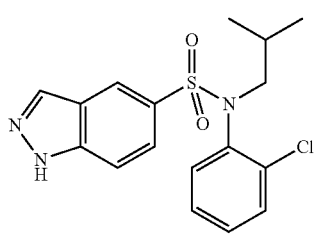 [SMILES: CC(C)CN(c1ccccc1Cl)S(=O)(=O)c1ccc2[nH]ncc2c1]

1H-indazole-5-sulfonic acid (2-chlorophenyl)isobutylamide

A mixture of 1H-indazole-5-sulfonyl chloride (200 mg; 0.88 mmol), pyridine (3.0 ml), potassium iodide (14 mg; 0.08 mmol), 4-dimethylaminopyridine (5.4 mg; 0.04 mmol) and (2-chlorophenyl)isobutylamine (600 mg; 3.27 mmol) is stirred for 3 days at a temperature of 100° C.

The crude product is purified by preparative HPLC (C18 column, eluent: acetonitrile in water/0.1% of formic acid). The 1H-indazole-5-sulfonic acid (2-chlorophenyl)isobutylamide (10 mg; 3%) is obtained in the form of a yellow oil with a compliant ¹H NMR.
MS: [M+H]=364

3. Synthesis of Intermediate 41.2

1H-indazole-5-sulfonic acid cyclopropylmethyl(4-ethylphenyl)amide

With the same procedure as that used for intermediate 30.2, 1H-indazole-5-sulfonic acid cyclopropylmethyl(4-ethylphenyl)amide (40 mg; 12%) is obtained in the form of a yellow oil with a compliant ¹H NMR.
MS: [M+H]=373

4. Synthesis of Intermediate 45.2

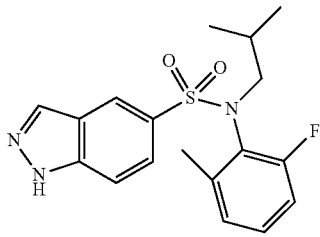 [SMILES: Cc1cccc(F)c1N(CC(C)C)S(=O)(=O)c1ccc2[nH]ncc2c1]

1H-indazole-5-sulfonic acid (2-fluoro-6-methylphenyl)isobutylamide (2-Fluoro-6-methylphenyl)isobutylamine (520 mg; 2.87 mmol) is added to a solution of 1H-indazole-5-sulfonyl chloride (297.4 mg; 1.30 mmol) in acetonitrile (1.25 ml) and the reaction medium is stirred for 40 minutes with microwave irradiation at a temperature of 100° C. The reaction medium is treated with 1N hydrochloric acid solution and extracted with ethyl acetate. The organic phases are combined, washed with water, dried (MgSO₄), filtered and concentrated.

The crude product is chromatographed on silica gel (eluent: heptane/ethyl acetate, from 0 to 60% of ethyl acetate). The 1H-indazole-5-sulfonic acid (2-fluoro-6-methylphenyl)isobutylamide (305 mg; 65%) is obtained in the form of a white solid with a compliant ¹H NMR.

MS: [M+H]=362

With a procedure similar to that described for the synthesis of example 1, the addition of 1.2 equivalents of 4-(bromomethyl)tetrahydropyran to 1 equivalent of N-substituted 1H-indazole-5-sulfonamide (prepared previously) in N,N-dimethylformamide in the presence of 1 equivalent of cesium carbonate under microwave irradiation at 100° C. leads to the compounds in the table below:

| Example 12 | 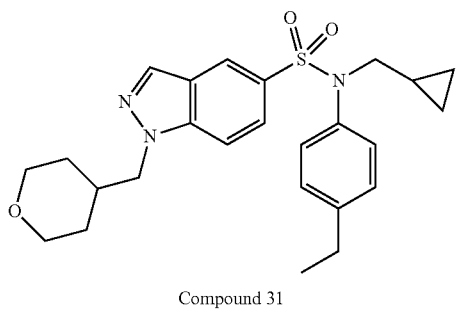 [SMILES: CCc1ccc(N(CC2CC2)S(=O)(=O)c2ccc3c(cnn3CC3CCOCC3)c2)cc1]<br>Compound 31 | N-(cyclopropylmethyl)-N-(4-ethylphenyl)-1-((tetrahydro-2H-pyran-4-yl)methyl)-1H-indazole-5-sulfonamide<br>¹H NMR (DMSO-d6) δ: 0.23-0.35 (m, 2H), 0.64-0.77 (m, 1H), 1.12 (t, J = 7.6 Hz, 3H), 1.19-1.37 (m, 4H), 2.10 (dtd, J = 11.1, 6.9, 3.4 Hz, 1H), 2.54 (q, J = 7.6 Hz, 2H), 3.17 (td, J = 11.3, 3.0 Hz, 2H), 3.38 (d, J = 7.0 Hz, 2H), 3.76 (ddd, J = 11.5, 4.4, 2.2 Hz, 2H), 4.32 (d, J = 7.1 Hz, 2H), 6.89-6.97 (m, 2H), 7.11 (d, J = 8.3 Hz, 2H), 7.45 (dd, J = 8.9, 1.7 Hz, 1H), 7.85 (dt, J = 8.8, 0.9 Hz, 1H), 8.06 (d, J = 1.6 Hz, 1H), 8.23 (d, J = 0.9 Hz, 1H).<br>MS: [M + H] = 454 |
| --- | --- | --- |
| Example 13 | 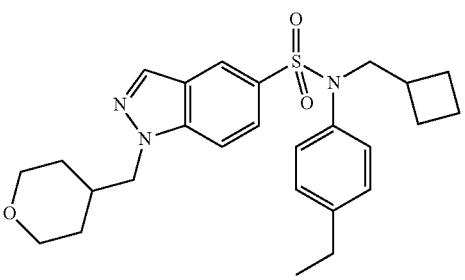<br>Compound 24 | N-(cyclobutylmethyl)-N-(4-ethylphenyl)-1-((tetrahydro-2H-pyran-4-yl)methyl)-1H-indazole-5-sulfonamide<br>¹H NMR (DMSO-d6) δ: 1.17 (t, J = 7.6 Hz, 3H), 1.24-1.45 (m, 4H), 1.54-1.66 (m, 2H), 1.69-1.89 (m, 4H), 2.10-2.30 (m, 2H), 2.59 (q, J = 7.6 Hz, 2H), 3.27 (td, J = 11.6, 2.4 Hz, 2H), 3.56 (d, J = 7.5 Hz, 2H), 3.83 (ddd, 2H), 4.40 (d, J = 7.1 Hz, 2H), 6.88-6.96 (m, 2H), 7.15 (d, J = 8.3 Hz, 2H), 7.31 (dd, J = 9.1, 1.8 Hz, 1H), 7.75 (d, J = 9.1 Hz, 1H), 8.12-8.14 (m, 1H), 8.63 (d, J = 0.9 Hz, 1H)<br>MS: [M + H] = 468 |
| Example 14 | 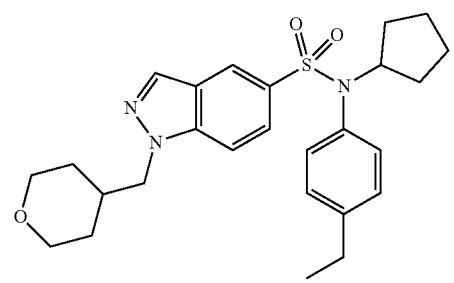<br>Compound 32 | 1-(tetrahydropyran-4-ylmethyl)-1H-indazole-5-sulfonic acid cyclopentyl(4-ethylphenyl)amide<br>¹H NMR (DMSO-d6) δ: 1.12-1.26 (m, 5H), 1.26-1.49 (m, 9H), 1.74 (dd, J = 12.2, 6.9 Hz, 2H), 2.61 (q, J = 7.6 Hz, 2H), 3.24 (td, J = 11.3, 2.9 Hz, 2H), 3.82 (ddd, J = 11.5, 4.3, 2.2 Hz, 2H), 4.39 (d, J = 7.0 Hz, 2H), 4.46-4.57 (m, 1H), 6.87-6.92 (m, 2H), 7.17-7.23 (m, 2H), 7.69 (dd, J = 9.0, 1.8 Hz, 1H), 7.91-7.96 (m, 1H), 8.21 (d, J = 1.6 Hz, 1H), 8.30 (d, J = 0.9 Hz, 1H)<br>MS: [M + H] = 468 |

| | | |
|---|---|---|
| Example 15 | 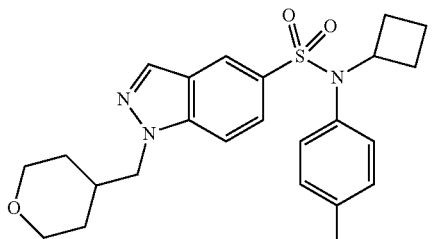<br>Compound 41 | 1-(tetrahydropyran-4-ylmethyl)-1H-indazole-5-sulfonic acid cyclobutyl(4-ethylphenyl)amide<br>¹H NMR (DMSO-d6) δ: 1.18 (t, J = 7.6 Hz, 3H), 1.23-1.62 (m, 6H), 1.76 (dq, J = 12.0, 9.7 Hz, 2H), 2.05 (dddd, J = 9.4, 7.4, 5.1, 2.5 Hz, 2H), 2.10-2.26 (m, 1H), 2.61 (q, J = 7.6 Hz, 2H), 3.24 (td, J = 11.3, 2.9 Hz, 2H), 3.82 (ddd, J = 11.5, 4.3, 2.1 Hz, 2H), 4.38 (dd, J = 8.5, 6.5 Hz, 3H), 6.80 (d, J = 8.3 Hz, 2H), 7.17 (d, J = 8.3 Hz, 2H), 7.48 (dd, J = 9.0, 1.8 Hz, 1H), 7.90 (d, J = 9.1 Hz, 1H), 8.11 (d, J = 1.6 Hz, 1H), 8.31 (s, 1H)<br>MS: [M + H] = 454 |
| Example 16 | 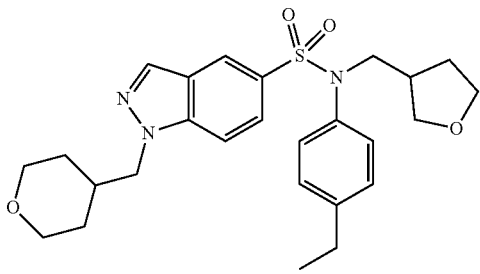<br>Compound 33 | 1-(tetrahydropyran-4-ylmethyl)-1H-indazole-5-sulfonic acid (4-ethylphenyl)(tetrahydrofuran-3-ylmethyl)amide<br>¹H NMR (DMSO-d6) δ: 1.18 (t, J = 7.6 Hz, 3H), 1.25-1.43 (m, 4H), 1.58 (dq, J = 13.2, 6.8 Hz, 1H), 1.76-1.90 (m, 1H), 2.06 (p, J = 5.9 Hz, 1H), 2.11-2.22 (m, 1H), 2.61 (q, J = 7.6 Hz, 2H), 3.24 (td, J = 11.3, 3.0 Hz, 2H), 3.42 (dd, J = 8.6, 5.2 Hz, 1H), 3.48-3.62 (m, 4H), 3.71 (td, J = 8.1, 5.4 Hz, 1H), 3.76-3.89 (m, 2H), 4.39 (d, J = 7.0 Hz, 2H), 6.91-7.00 (m, 2H), 7.14 -7.24 (m, 2H), 7.48 (dd, J = 9.0, 1.7 Hz, 1H), 7.87-7.95 (m, 1H), 8.12 (d, J = 1.6 Hz, 1H), 8.30 (d, J = 1.0 Hz, 1H)<br>MS: [M + H] = 484 |
| Example 17 | 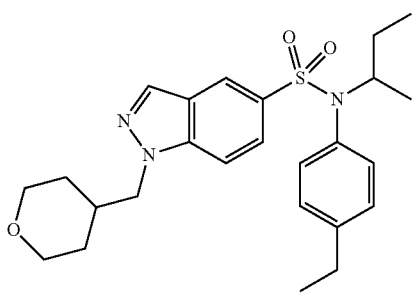<br>Compound 30 | 1-(tetrahydropyran-4-ylmethyl)-1H-indazole-5-sulfonic acid sec-butyl(4-ethylphenyl)amide<br>¹H NMR (DMSO-d6) δ: 0.85 (t, J = 7.3 Hz, 3H), 0.93 (d, J = 6.7 Hz, 3H), 1.12-1.25 (m, 5H), 1.26-1.44 (m, 4H), 2.62 (q, J = 7.6 Hz, 2H), 3.24 (td, J = 11.3, 3.2 Hz, 2H), 3.82 (ddd, J = 11.5, 4.3, 2.3 Hz, 2H), 4.19 (dt, J = 7.8, 6.4 Hz, 1H), 4.39 (d, J = 7.1 Hz, 2H), 6.91 (d, J = 8.3 Hz, 2H), 7.21 (d, J = 8.3 Hz, 2H), 7.68 (dd, J = 8.9, 1.8 Hz, 1H), 7.94 (dt, J = 9.0, 0.9 Hz, 1H), 8.20 (d, J = 1.6 Hz, 1H), 8.30 (d, J = 0.9 Hz, 1H)<br>MS: [M + H] = 456 |
| Example 18 | 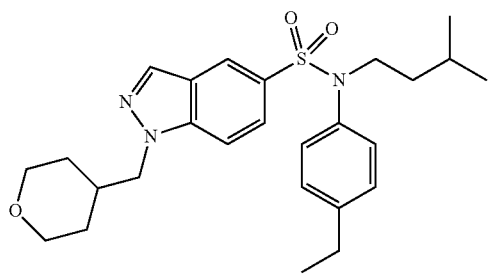<br>Compound 35 | N-(4-ethylphenyl)-N-isopentyl-1-((tetrahydro-2H-pyran-4-yl)methyl)-1H-indazole-5-sulfonamide<br>¹H NMR (DMSO-d6) δ: 0.80 (d, J = 6.6 Hz, 6H), 1.17 (t, J = 7.6 Hz, 5H), 1.25-1.42 (m, 4H), 1.61 (hept, J = 6.7 Hz, 1H), 2.09-2.24 (m, 1H), 2.60 (q, J = 7.6 Hz, 2H), 3.23 (td, J = 11.2, 3.1 Hz, 2H), 3.55 (t, J = 7.1 Hz, 2H), 3.81 (dt, J = 11.5, 3.3 Hz, 2H), 4.38 (d, J = 7.1 Hz, 2H), 6.90-6.99 (m, 2H), 7.12-7.22 (m, 2H), 7.47 (dd, J = 9.0, 1.7 Hz, 1H), 7.87-7.96 (m, 1H), 8.11 (d, J = 2.0 Hz, 1H), 8.30 (d, J = 1.1 Hz, 1H)<br>MS: [M + H] = 470 |

-continued

| | | |
|---|---|---|
| Example 19 | 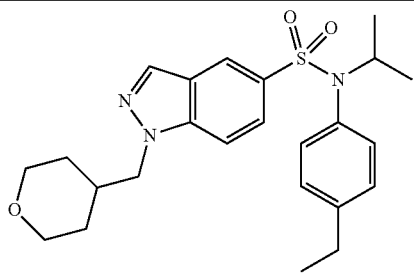<br>Compound 29 | N-(4-ethylphenyl)-N-isopropyl-1-((tetrahydro-2H-pyran-4-yl)methyl)-1H-indazole-5-sulfonamide<br>$^1$H NMR (DMSO-d6) δ: 0.95 (d, J = 6.7 Hz, 6H), 1.19 (t, J = 7.6 Hz, 3H), 1.26-1.45 (m, 4H), 2.63 (q, J = 7.6 Hz, 2H), 3.24 (td, J = 11.3, 3.0 Hz, 2H), 3.82 (ddd, J = 11.5, 4.3, 2.2 Hz, 2H), 4.39 (d, J = 7.1 Hz, 2H), 4.47 (p, J = 6.7 Hz, 1H), 6.90-6.98 (m, 2H), 7.22 (d, J = 8.3 Hz, 2H), 7.70 (dd, J = 8.9, 1.8 Hz, 1H), 7.90-7.99 (m, 1H), 8.22 (d, J = 1.6 Hz, 1H), 8.30 (d, J = 0.9 Hz, 1H).<br>MS: [M + H] = 442 |
| Example 20 | 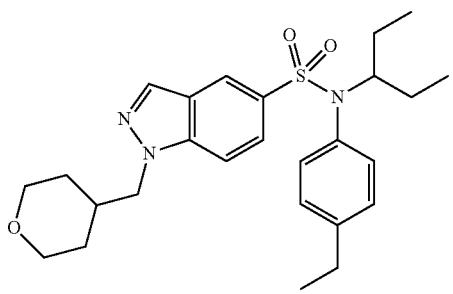<br>Compound 1 | 1-(tetrahydropyran-4-ylmethyl)-1H-indazole-5-sulfonic acid (4-ethylphenyl)(1-ethylpropyl)amide<br>$^1$H NMR (DMSO-d6) δ: 0.85 (t, J = 7.3 Hz, 6H), 1.07-1.22 (m, 5H), 1.30 (ddd, J = 20.0, 9.0, 5.7 Hz, 6H), 2.16 (s, 1H), 2.61 (q, J = 7.6 Hz, 2H), 3.23 (td, J = 11.2, 3.4 Hz, 2H), 3.81 (d, J = 11.1 Hz, 2H), 3.91 (q, J = 6.5 Hz, 1H), 4.39 (d, J = 7.2 Hz, 2H), 6.86-6.93 (m, 2H), 7.21 (d, J = 8.3 Hz, 2H), 7.93 (d, J = 9.0 Hz, 1H), 8.15 (d, J = 1.5 Hz, 1H), 8.29 (d, J = 0.9 Hz, 1H).<br>MS: [M + H] = 470 |
| Example 22 | 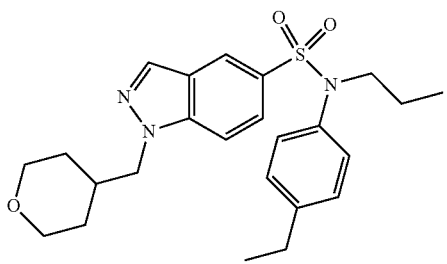<br>Compound 8 | 1-(tetrahydropyran-4-ylmethyl)-1H-indazole-5-sulfonic acid (4-ethylphenyl)propylamide<br>$^1$H NMR (DMSO-d6) δ: 0.83 (t, J = 7.3 Hz, 3H), 1.17 (t, J = 7.6 Hz, 3H), 1.25-1.44 (m, 6H), 2.24 (ddt, J = 10.9, 7.5, 3.8 Hz, 1H), 2.60 (q, J = 7.5 Hz, 2H), 3.26 (td, J = 11.6, 2.5 Hz, 2H), 3.50 (t, J = 6.9 Hz, 2H), 3.83 (ddd, J = 11.5, 4.5, 2.0 Hz, 2H), 4.40 (d, J = 7.1 Hz, 2H), 6.93-7.02 (m, 2H), 7.17 (d, J = 8.3 Hz, 2H), 7.29 (dd, J = 9.1, 1.8 Hz, 1H), 7.70-7.80 (m, 1H), 8.12 (dd, J = 1.9, 0.8 Hz, 1H), 8.62 (d, J = 11.0 Hz, 1H)<br>MS: [M + H] = 442 |
| Example 23 | 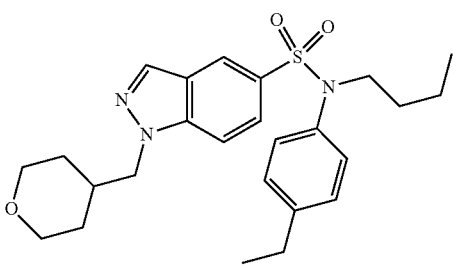<br>Compound 9 | 1-(tetrahydropyran-4-ylmethyl)-1H-indazole-5-sulfonic acid butyl(4-ethylphenyl)amide<br>$^1$H NMR (DMSO-d6) δ: 0.74-0.88 (m, 3H), 1.17 (t, J = 7.6 Hz, 3H), 1.23-1.45 (m, 8H), 2.24 (ddt, J = 11.0, 7.6, 3.8 Hz, 1H), 2.60 (q, J = 7.6 Hz, 2H), 3.26 (td, J = 11.5, 2.5 Hz, 2H), 3.54 (q, J = 4.4 Hz, 2H), 3.83 (ddd, J = 11.5, 4.3, 2.0 Hz, 2H), 4.40 (d, J = 7.2 Hz, 2H), 6.93-7.01 (m, 2H), 7.17 (d, J = 8.3 Hz, 2H), 7.28 (dd, J = 9.1, 1.8 Hz, 1H), 7.74 (dd, J = 9.0, 1.0 Hz, 1H), 8.11-8.14 (m, 1H), 8.62 (d, J = 0.9 Hz, 1H).<br>MS: [M + H] = 456 |
| Example 25 | 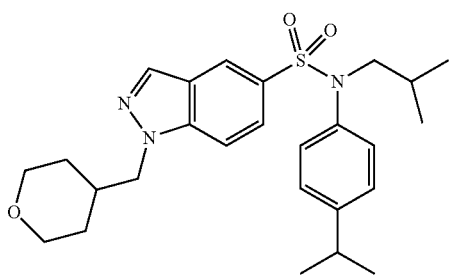<br>Compound 7 | 1-(tetrahydropyran-4-ylmethyl)-1H-indazole-5-sulfonic acid butyl(4-isopropylphenyl)amide<br>$^1$H NMR (DMSO-d6) δ: 0.85 (d, J = 6.7 Hz, 6H), 1.19 (d, J = 6.9 Hz, 6H), 1.25-1.50 (m, 5H), 2.11-2.22 (m, 1H), 2.88 (hept, J = 6.8 Hz, 1H), 3.23 (td, J = 11.3, 2.9 Hz, 2H), 3.82 (ddd, J = 11.6, 4.4, 2.2 Hz, 2H), 4.38 (d, J = 7.1 Hz, 2H), 6.94-7.03 (m, 2H), 7.20 (d, J = 8.4 Hz, 2H), 7.44 (dd, J = 8.9, 1.8 Hz, 1H), 7.85-7.94 (m, 1H), 8.09 (d, J = 1.7 Hz, 1H), 8.29 (d, J = 0.9 Hz, 1H)<br>MS: [M + H] = 470 |

| | | |
|---|---|---|
| Example 26 | 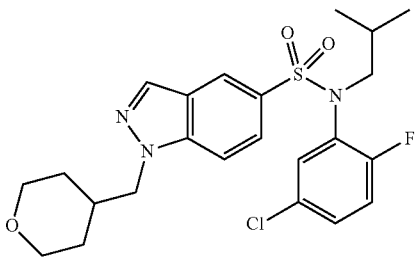
Compound 10 | 1-(tetrahydropyran-4-ylmethyl)-1H-indazole-5-sulfonic acid (5-chloro-2-fluorophenyl)isobutylamide
$^1$H NMR (DMSO-d6) δ: 0.85 (d, J = 6.6 6H), 1.21-1.49 (m, 5H), 2.17 (dd, J = 10.5, 5.9 Hz, 1H), 3.23 (td, J = 11.1, 3.3 Hz, 2H), 3.76-3.87 (m, 2H), 4.40 (d, J = 7.0 Hz, 2H), 7.15 (dd, J = 6.5, 2.7 Hz, 1H), 7.35 (dd, J = 10.1, 8.9 Hz, 1H), 7.50 (ddd, J = 8.8, 4.1, 2.6 Hz, 1H), 7.56 (dd, J = 9.0, 1.8 Hz, 1H), 7.92-7.99 (m, 1H), 8.20 (d, J = 1.7 Hz, 1H), 8.33 (d, J = 1.0 Hz, 1H).
MS: [M + H] = 480 |
| Example 27 | 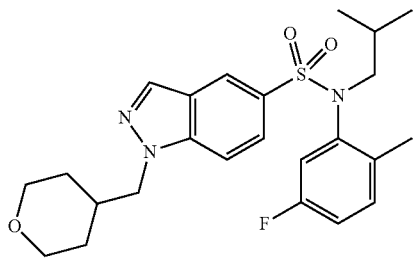
Compound 42 | 1-(tetrahydropyran-4-ylmethyl)-1H-indazole-5-sulfonic acid (5-fluoro-2-methylphenyl)isobutylamide
$^1$H NMR (DMSO-d6) δ: 0.77 (d, J = 6.7 Hz, 3H), 0.95 (d, J = 6.6 Hz, 3H), 1.22-1.49 (m, 5H), 2.07-2.25 (m, 1H), 2.27 (s, 3H), 3.13 (dd, J = 13.2, 4.7 Hz, 1H), 3.23 (td, J = 11.2, 3.4 Hz, 2H), 3.43 (dd, J = 13.2, 9.1 Hz, 1H), 3.81 (dt, J = 11.5, 3.2 Hz, 2H), 4.40 (d, J = 7.1 Hz, 2H), 6.45 (dd, J = 10.1, 2.7 Hz, 1H), 7.12 (td, J = 8.3, 2.7 Hz, 1H), 7.35 (dd, J = 8.6, 6.6 Hz, 1H), 7.51 (dd, J = 8.9, 1.8 Hz, 1H), 7.91-7.99 (m, 1H), 8.16 (d, J = 1.6 Hz, 1H), 8.34 (d, J = 0.9 Hz, 1H).
MS: [M + H] = 460 |
| Example 28 | 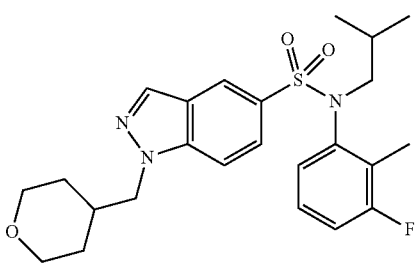
Compound 43 | 1-(tetrahydropyran-4-ylmethyl)-2H-indazole-5-sulfonic acid (3-fluoro-2-methylphenyl)isobutylamide
$^1$H NMR (DMSO-d6) δ: 0.77 (d, J = 6.7 Hz, 3H), 0.94 (d, J = 6.5 Hz, 3H), 1.18-1.52 (m, 5H), 2.08-2.27 (m, 4H), 3.13 (dd, J = 13.1, 4.8 Hz, 1H), 3.23 (td, J = 11.2, 3.1 Hz, 2H), 3.46 (dd, J = 13.2, 9.0 Hz, 1H), 3.73-3.88 (m, 2H), 4.39 (d, J = 7.1 Hz, 2H), 6.52 (d, J = 8.1 Hz, 1H), 7.06-7.26 (m, 2H), 7.52 (dd, J = 8.9, 1.8 Hz, 1H), 7.93 (d, J = 8.8 Hz, 1H), 8.14 (d, J = 1.7 Hz, 1H), 8.32 (d, J = 1.0 Hz, 1H).
MS: [M + H] = 460 |
| Example 29 | 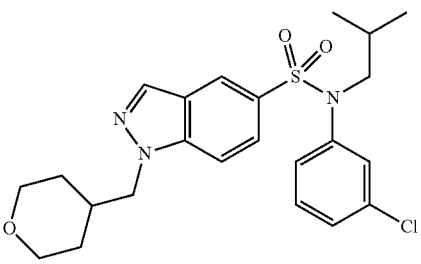
Compound 44 | 1-tetrahydropyran-4-ylmethyl)-1H-indazole-5-sulfonic acid (5-chlorophenyl)isobutylamide
$^1$H NMR (DMSO-d6) δ: 0.85 (d, J = 6.6 Hz, 6H), 1.21-1.50 (m, 5H), 3.23 (td, J = 11.2, 3.2 Hz, 2H), 3.38 (d, J = 7.3 Hz, 2H), 3.80 (s, 2H), 4.38 (d, J = 7.1 Hz, 2H), 7.08 (dt, J = 7.0, 2.0 Hz, 1H), 7.13 (t, J = 1.9 Hz, 1H), 7.34-7.40 (m, 2H), 7.41-7.44 (m, 1H), 7.91 (d, J = 8.9 Hz, 1H), 8.11 (d, J = 1.7 Hz, 1H), 8.31 (d, J = 1.0 Hz, 1H).
MS: [M + H] = 462 |
| Example 30 | 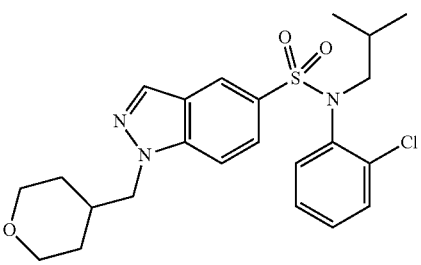
Compound 45 | 1-(tetrahydropyran-4-ylmethyl)-1H-indazole-5-sulfonic acid (2-chlorophenyl)isobutylamide
$^1$H NMR (400 MHz, CDCl3) δ 0.86 (t, J = 6.2 Hz, 6H), 1.37 (td, J = 10.9, 9.9, 4.0 Hz, 4H), 1.55 (dt, J = 13.5, 6.8 Hz, 2H), 2.22 (s, 1H), 3.28 (td, J = 11.1, 4.0 Hz, 2H), 3.36 (dd, J = 7.2, 1.8 Hz, 2H), 3.89 (dt, J = 11.6, 3.3 Hz, 2H), 4.22 (d, J = 7.1 Hz, 2H), 7.19 (m, 3H), 7.25-7.30 (m, 1H), 7.36 (d, J = 8.8 Hz, 1H), 7.61 (dd, J = 8.9, 1.7 Hz, 1H), 8.03 (s, 1H), 8.07 (d, J = 1.6 Hz, 1H).
MS: [M + H] = 462 |

| Example 31 | 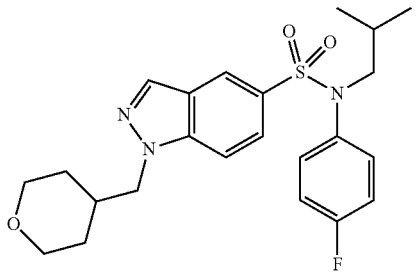
Compound 46 | 1-(tetrahydrouyran-4-ylmethyl)-1H-indazole-5-sulfonic acid (4-fluorophenyl)isobutylamide
$^1$H NMR (DMSO-d6) δ: 0.85 (d, J = 6.6 Hz, 6H), 1.23-1.48 (m, 5H), 2.16 (ddd, J = 11.0, 6.9, 4.2 Hz, 1H), 3.23 (td, J = 11.3, 2.9 Hz, 2H), 3.35 (s, 2H), 3.82 (ddd, J = 11.5, 4.5, 2.2 Hz, 2H), 4.38 (d, J = 7.0 Hz, 2H), 7.05-7.22 (m, 4H), 7.45 (dd, J = 8.9, 1.7 Hz, 1H), 7.90 (d, J = 8.9 Hz, 1H), 8.07 (d, J = 1.7 Hz, 1H), 8.30 (s, 1H).
MS: [M + H] = 446 |
| Example 32 | 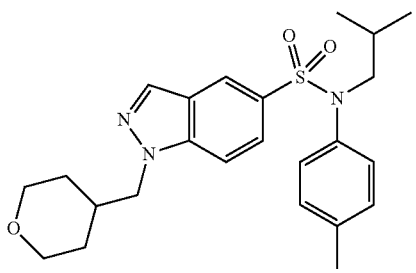
Compound 47 | 1-(tetrahydropyran-4-ylmethyl)-1H-indazole-5-sulfonic acid isobutyl-p-tolylamide
$^1$H NMR (DMSO-d6) δ: 0.85 (d, J = 6.7 Hz, 6H), 1.23-1.48 (m, 5H), 2.05-2.25 (m, 1H), 2.29 (s, 3H), 3.24 (td, J = 11.3, 2.8 Hz, 3H), 3.32 (td, 2H), 3.82 (dd, J = 11.3, 3.7 Hz, 2H), 4.38 (d, J = 7.1 Hz, 2H), 6.89-6.95 (m, 2H), 7.13 (d, J = 8.1 Hz, 2H), 7.45 (dd, J = 8.9, 1.8 Hz, 1H), 7.89 (d, J = 8.8 Hz, 1H), 8.07 (d, J = 1.6 Hz, 1H), 8.30 (s, 1H).
MS: [M + H] = 442 |
| Example 33 | 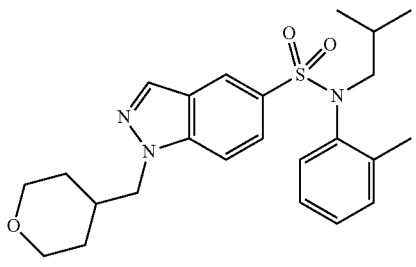
Compound 48 | 1-(tetrahydropyran-4-ylmethyl)-1H-indazole-5-sulfonic acid isobutyl-o-tolylamide
$^1$H NMR (DMSO-d6) δ: 0.76 (d, J = 6.7 Hz, 3H), 0.96 (d, J = 6.6 Hz, 3H), 1.24-1.50 (m, 5H), 2.07-2.26 (m, 1H), 2.30 (s, 3H), 3.13 (dd, J = 13.2, 4.9 Hz, 1H), 3.24 (td, J = 11.0, 2.9 Hz, 2H), 3.45 (dd, J = 13.1, 8.9 Hz, 1H), 3.82 (dd, J = 13.4, 2.4 Hz, 2H), 4.40 (d, J = 7.1 Hz, 2H), 6.62 (dd, J = 8.1, 1.3 Hz, 1H), 7.08 (td, J = 7.7, 1.7 Hz, 1H), 7.24 (td, J = 7.5, 1.3 Hz, 1H), 7.31 (dd, J = 7.8, 1.6 Hz, 1H), 7.53 (dd, J = 8.9, 1.8 Hz, 1H), 7.93 (d, J = 8.9 Hz, 1H), 8.13 (s, 1H), 8.32 (s, 1H).
MS: [M + H] = 442 |
| Example 34 | 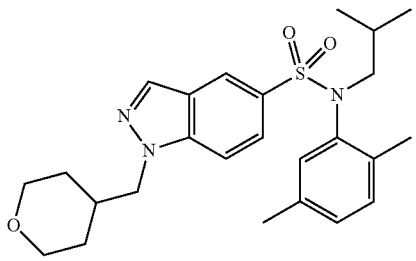
Compound 11 | 1-(tetrahydropyran-4-ylmethyl)-1H-indazole-5-sulfonic acid (2,5-dimethylphenyl)isobutylamide
$^1$H NMR (DMSO-d6) δ: 0.77 (d, J = 6.7 Hz, 3H), 0.96 (d, J = 6.6 Hz, 3H), 1.26-1.38 (m, 4H), 1.44 (dtd, J = 8.9, 6.7, 4.8 Hz, 1H), 2.03 (s, 3H), 2.12-2.22 (m, 1H), 2.23 (s, 3H), 3.07 (dd, J = 13.1, 4.8 Hz, 1H), 3.19-3.27 (m, 2H), 3.43 (dd, J = 13.1, 8.9 Hz, 1H), 3.81 (dq, J = 10.8, 3.4 Hz, 2H), 4.41 (d, J = 7.0 Hz, 2H), 6.29 (d, J = 1.7 Hz, 1H), 7.04 (dd, J = 7.8, 1.8 Hz, 1H), 7.17 (d, J = 7.7 Hz, 1H), 7.49 (dd, J = 9.0, 1.7 Hz, 1H), 7.93 (dt, J = 9.0, 0.9 Hz, 1H), 8.13 (d, J = 1.6 Hz, 1H), 8.32 (d, J = 0.9 Hz, 1H)
MS: [M + H] = 456 |

| | | |
|---|---|---|
| Example 35 | 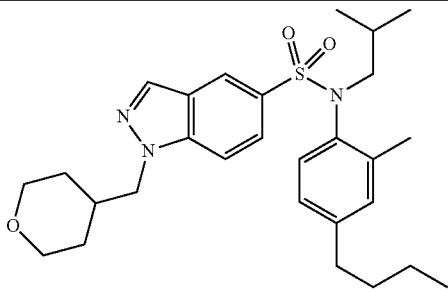<br>Compound 13 | 1-(tetrahydropyran-4-ylmethyl)-1H-indazole-5-sulfonic acid (4-butyl-2-methylphenyl)isobutylamide<br>$^1$H NMR (DMSO-d6) δ: 0.75 (d, J = 6.6 Hz, 3H), 0.90 (t, J = 7.3 Hz, 3H), 0.95 (d, J = 6.6 Hz, 3H), 1.24-1.47 (m, 8H), 1.48-1.59 (m, 2H), 2.16 (s, 1H), 2.25 (s, 3H), 3.09 (dd, J = 13.1, 4.9 Hz, 1H), 3.24 (td, J = 11.1, 3.2 Hz, 2H), 3.37-3.46 (m, 1H), 3.77-3.88 (m, 2H), 4.39 (d, J = 7.0 Hz, 2H), 6.52 (d, J = 8.2 Hz, 1H), 6.88 (dd, J = 8.2, 2.2 Hz, 1H), 7.11 (d, J = 2.1 Hz, 1H), 7.52 (dd, J = 9.0, 1.7 Hz, 1H), 7.85-7.98 (m, 1H), 8.13 (d, J = 1.6 Hz, 1H), 8.31 (d, J = 0.9 Hz, 1H)<br>MS: [M + H] = 498 |
| Example 36 | 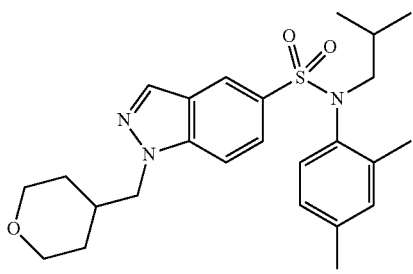<br>Compound 27 | 1-(tetrahydropyran-4-ylmethyl)-1H-indazole-5-sulfonic acid (2,4-dimethylphenyl)isobutylamide<br>$^1$H NMR (DMSO-d6) δ: 0.76 (d, J = 6.7 Hz, 3H), 0.96 (d, J = 6.5 Hz, 3H), 1.22-1.48 (m, 5H), 2.09 (d, J = 4.8 Hz, 1H), 2.11-2.21 (m, 1H), 2.25 (d, J = 4.1 Hz, 6H), 3.08 (dd, J = 13.1, 4.8 Hz, 1H), 3.24 (td, J = 11.2, 3.2 Hz, 2H), 3.43 (dd, J = 13.1, 8.9 Hz, 1H), 3.76-3.87 (m, 2H), 4.40 (d, J = 7.0 Hz, 2H), 6.48 (d, J = 8.1 Hz, 1H), 6.87 (dd, J = 8.1, 2.1 Hz, 1H), 7.11 (d, J = 2.1 Hz, 1H), 7.53 (dd, J = 9.0, 1.7 Hz, 1H), 7.90-7.96 (m, 1H), 8.13 (d, J = 1.7 Hz, 1H), 8.32 (d, J = 0.9 Hz, 1H)<br>MS: [M + H] = 456 |
| Example 37 | 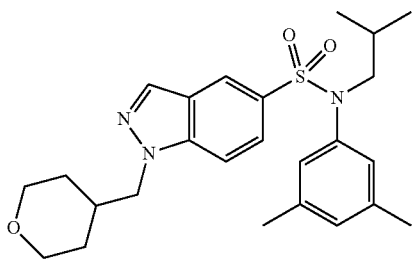<br>Compound 28 | 1-(tetrahydropyran-4-ylmethyl)-1H-indazole-5-sulfonic acid (3,5-dimethylphenyl)isobutylamide<br>$^1$H NMR (DMSO-d6) δ: 0.85 (d, J = 6.6 Hz, 6H), 1.22-1.38 (m, 4H), 1.44 (hept, J = 6.8 Hz, 1H), 2.16 (s, 7H), 3.23 (td, J = 11.1, 3.6 Hz, 2H), 3.29 (d, J = 7.3 Hz, 2H), 3.76-3.85 (m, 2H), 4.39 (d, J = 7.0 Hz, 2H), 6.58-6.63 (m, 2H), 6.94 (s, 1H), 7.42 (dd, J = 8.8, 1.7 Hz, 1H), 7.87-7.92 (m, 1H), 8.09 (d, J = 1.6 Hz, 1H), 8.31 (d, J = 0.9 Hz, 1H)<br>MS: [M + H] = 456 |
| Example 38 | 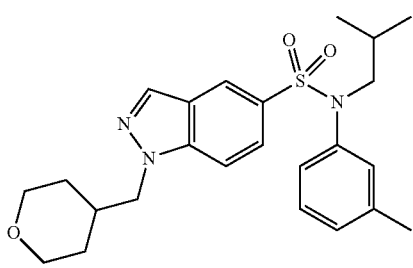<br>Compound 26 | 1-(tetrahydropyran-4-ylmethyl)-1H-indazole-5-sulfonic acid (3-methylphenyl)isobutylamide<br>$^1$H NMR (DMSO-d6) δ: 0.85 (d, J = 6.6 Hz, 6H), 1.23-1.52 (m, 5H), 2.22 (s, 4H), 3.23 (td, J = 11.3, 3.2 Hz, 2H), 3.77-3.87 (m, 2H), 4.38 (d, J = 7.1 Hz, 2H), 6.78-6.89 (m, 2H), 7.10-7.15 (m, 1H), 7.20 (t, J = 7.7 Hz, 1H), 7.85-7.93 (m, 1H), 8.08 (d, J = 1.6 Hz, 1H), 8.30 (d, J = 0.9 Hz, 1H)<br>MS: [M + H] = 442 |
| Example 39 | 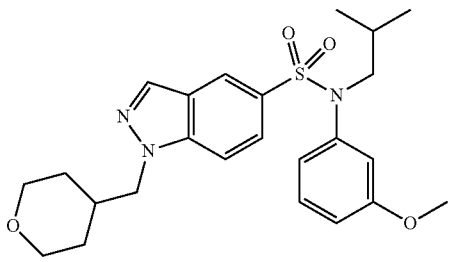<br>Compound 25 | 1-(tetrahydropyran-4-ylmethyl)-1H-indazole-5-sulfonic acid (3-methoxyphenyl)isobutylamide<br>$^1$H NMR (DMSO-d6) δ: 0.86 (d, J = 6.6 Hz, 6H), 1.21-1.38 (m, 4H), 1.45 (hept, J = 6.8 Hz, 1H), 3.23 (td, J = 11.3, 3.2 Hz, 2H), 3.61 (s, 3H), 3.81 (dt, J = 11.7, 2.7 Hz, 2H), 4.38 (d, J = 7.0 Hz, 2H), 6.53 (t, J = 2.3 Hz, 1H), 6.66 (ddd, J = 7.9, 2.0, 0.9 Hz, 1H), 6.89 (ddd, J = 8.3, 2.5, 0.9 Hz, 1H), 7.24 (t, J = 8.1 Hz, 1H), 7.46 (dd, J = 8.9, 1.7 Hz, 1H), 7.88-7.94 (m, 1H), 8.10 (d, J = 1.6 Hz, 1H), 8.30 (d, J = 0.8 Hz, 1H)<br>MS: [M + H] = 458 |

| Example 40 | 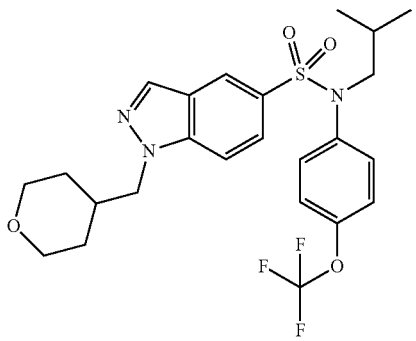<br>Compound 49 | 1-(tetrahydropyran-4-ylmethyl)-1H-indazole-5-sulfonic acid (4-trifluoromethoxyphenyl)isobutylamide<br>$^1$H NMR (DMSO-d6) δ: 0.85 (d, J = 6.6 Hz, 6H), 1.24-1.47 (m, 5H), 2.10-2.20 (m, 1H), 3.23 (td, J = 11.3, 2.9 Hz, 2H), 3.37 (d, J = 7.4 Hz, 2H), 3.80 (s, 2H), 4.38 (d, J = 7.1 Hz, 2H), 7.20-7.26 (m, 2H), 7.32-7.37 (m, 2H), 7.43 (dd, J = 9.0, 1.8 Hz, 1H), 7.91 (d, J = 9.0 Hz, 1H), 8.10 (d, J = 1.7 Hz, 1H), 8.30 (d, J = 0.9 Hz, 1H);<br>MS: [M + H] = 512 |
|---|---|---|
| Example 41 | 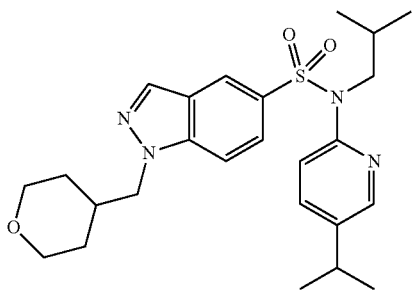<br>Compound 50 | 1-(tetrahydropyran-4-ylmethyl)-1H-indazole-5-sulfonic acid isobutyl(5-isopropylpyridin-2-yl)amide<br>$^1$H NMR (Chloroform-d) δ: 0.82 (d, J = 6.7 Hz, 6H), 1.20 (s, 6H), 1.30-1.44 (m, 4H), 2.15-2.28 (m, 1H), 2.87 (p, J = 7.0 Hz, 1H), 3.28 (td, J = 11.5, 3.0 Hz, 2H), 3.42 (d, J = 7.3 Hz, 2H), 3.86-3.93 (m, 2H), 4.18 (d, J = 7.2 Hz, 2H), 7.29-7.33 (m, 1H), 7.40 (dd, J = 9.0, 1.7 Hz, 1H), 7.49 (d, J = 8.1 Hz, 1H), 7.55 (dd, J = 8.3, 2.5 Hz, 1H), 8.01 (d, J = 0.8 Hz, 1H), 8.04 (d, J = 1.8 Hz, 1H), 8.08 (d, J = 2.5 Hz, 1H).<br>MS: [M + H] = 471 |
| Example 42 | 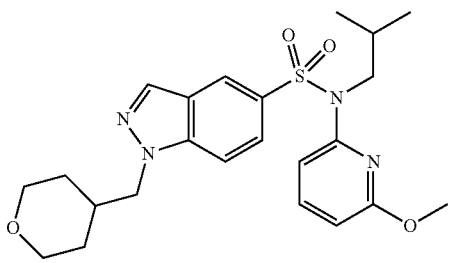<br>Compound 12 | 1-(tetrahydropyran-4-ylmethyl)-1H-indazole-5-sulfonic acid (3-methoxypyridin-2-yl)isobutylamide<br>$^1$H NMR (DMSO-d6) δ: 0.86 (d, J = 6.6 Hz, 6H), 1.20-1.37 (m, 4H), 1.57 (hept, J = 6.9 Hz, 1H), 2.03-2.24 (m, 1H), 3.12-3.26 (m, 3H), 3.42 (s, 3H), 3.53 (d, J = 7.1 Hz, 2H), 3.71-3.87 (m, 2H), 4.37 (d, J = 7.1 Hz, 2H), 6.69 (d, J = 8.1 Hz, 1H), 7.12 (d, J = 7.5 Hz, 1H), 7.46 (dd, J = 9.0, 1.8 Hz, 1H), 7.73-7.82 (m, 1H), 7.88 (dd, J = 9.0, 1.0 Hz, 1H), 8.19 (d, J = 1.6 Hz, 1H), 8.29 (d, J = 0.9 Hz, 1H)<br>MS: [M + H] = 459 |
| Example 43 | 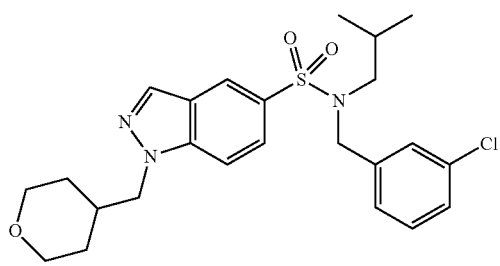<br>Compound 51 | 1-(tetrahydropyran-4-ylmethyl)-1H-indazole-5-sulfonic acid (3-chlorobenzyl)isobutylamide<br>$^1$H NMR (DMSO-d6) δ: 0.70 (d, J = 6.6 Hz, 6H), 1.25-1.42 (m, 4H), 1.58 (dt, J = 13.6, 6.9 Hz, 1H), 2.92 (d, J = 7.6 Hz, 2H), 3.24 (td, J = 11.3, 3.2 Hz, 2H), 3.82 (d, J = 11.2 Hz, 2H), 4.40 (d, J = 7.1 Hz, 2H), 7.24-7.37 (m, 4H), 7.80 (dd, J = 9.0, 1.7 Hz, 1H), 7.96 (d, J = 8.9 Hz, 1H), 8.31 (d, J = 0.9 Hz, 1H), 8.37 (d, J = 1.7 Hz, 1H)<br>MS: [M + H] = 476 |

| Example 44 | 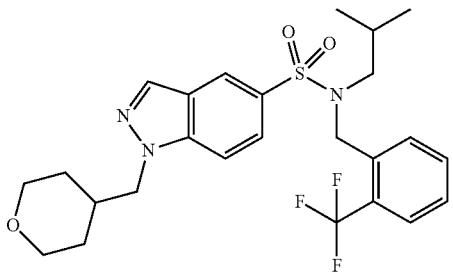<br>Compound 52 | 1-(tetrahydropyran-4-ylmethyl)-1H-indazole-5-sulfonic acid isobutyl(2-trifluoromethylbenzyl)amide<br>$^1$H NMR (DMSO-d6) δ: 0.70 (d, J = 6.6 Hz, 6H), 1.23-1.43 (m, 5H), 2.97 (d, J = 7.2 Hz, 2H), 3.24 (td, J = 11.3, 3.0 Hz, 2H), 3.82 (d, J = 10.7 Hz, 2H), 4.40 (d, J = 7.1 Hz, 2H), 4.48 (s, 2H), 7.50 (t, J = 7.6 Hz, 1H), 7.70 (q, J = 7.6 Hz, 2H), 7.78 (d, J = 7.9 Hz, 1H), 7.83 (dd, J = 8.9, 1.8 Hz, 1H), 7.98 (d, J = 8.9 Hz, 1H), 8.39 (d, J = 1.7 Hz, 1H)<br>MS: [M + H] = 510 |
|---|---|---|
| Example 45 | 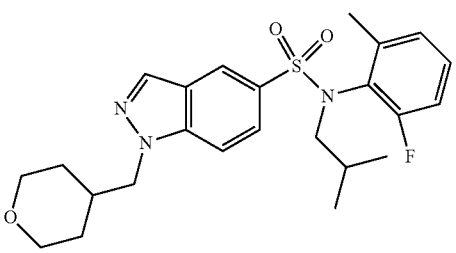<br>Compound 53 | 1-(tetrahydropyran-4-ylmethyl)-1H-indazole-5-sulfonic acid (2-fluoro-6-methylphenyl)isobutylamide<br>$^1$H NMR (DMSO-d6) δ: 0.77 (d, J = 6.7 Hz, 3H), 0.93 (d, J = 6.6 Hz, 3H), 1.21-1.39 (m, 4H), 1.41-1.57 (m, 1H), 2.08-2.25 (m, 1H), 2.28 (s, 3H), 3.15 (dd, J = 13.7, 5.8 Hz, 1H), 3.23 (td, J = 11.0, 3.7 Hz, 2H), 3.45 (dd, J = 13.6, 7.9 Hz, 1H), 3.81 (dt, J = 11.4, 3.3 Hz, 2H), 4.39 (d, J = 7.0 Hz, 2H), 7.00 (ddd, J = 10.2, 8.3, 1.6 Hz, 1H), 7.15 (d, J = 7.6 Hz, 1H), 7.23-7.36 (m, 1H), 7.63 (dd, J = 8.9, 1.8 Hz, 1H), 7.93 (d, J = 9.1 Hz, 1H), 8.21 (d, J = 1.6 Hz, 1H), 8.31 (d, J = 1.0 Hz, 1H)<br>MS: [M + H] = 460 |
| Example 46 | 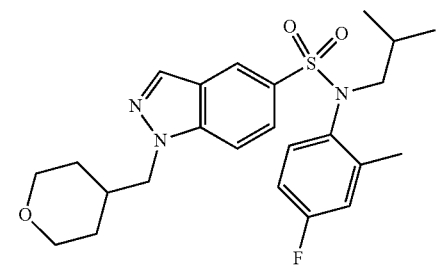<br>Compound 54 | 1-(tetrahyropyran-4-ylmethyl)-1H-indazole-5-sulfonic acid (4-fluoro-2-methylphenyl)isobutylamide<br>$^1$H NMR (DMSO-d6) δ: 0.77 (d, J = 6.7 Hz, 3H), 0.95 (d, J = 6.5 Hz, 3H), 1.24-1.50 (m, 5H), 2.11-2.24 (m, 1H), 2.29 (s, 3H), 3.10 (dd, J = 13.1, 4.8 Hz, 1H), 3.23 (td, J = 11.2, 3.2 Hz, 2H), 3.45 (dd, J = 13.2, 8.9 Hz, 1H), 3.82 (dt, J = 11.6, 2.7 Hz, 2H), 4.39 (d, J = 7.1 Hz, 2H), 6.66 (dd, J = 8.9, 5.5 Hz, 1H), 6.92 (td, J = 8.4, 3.1 Hz, 1H), 7.18 (dd, J = 9.8, 3.0 Hz, 1H), 7.53 (dd, J = 8.9, 1.7 Hz, 1H), 7.93 (dd, J = 9.0, 0.9 Hz, 1H), 8.13 (d, J = 1.6 Hz, 1H), 8.32 (d, J = 0.9 Hz, 1H)<br>MS: [M + H] = 460 |
| Example 47 | 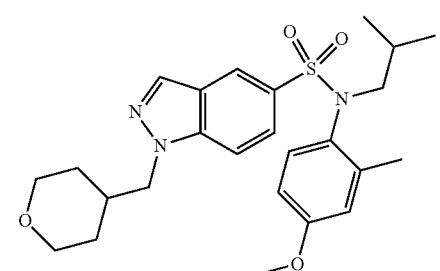<br>Compound 55 | 1-(tetrahydropyran-4-ylmethyl)-1H-indazole-5-sulfonic acid isobutyl(4-methoxy-2-methylphenyl)amide<br>1H NMR (DMSO-d6) δ: 0.76 (d, J = 6.7 Hz, 3H), 0.96 (d, J = 6.6 Hz, 3H), 1.23-1.53 (m, 5H), 2.08-2.21 (m, 1H), 2.24 (s, 3H), 3.07 (dd, J = 13.0, 4.8 Hz, 1H), 3.24 (td, J = 11.2, 3.2 Hz, 2H), 3.43 (dd, J = 13.1, 8.9 Hz, 1H), 3.73 (s, 3H), 3.82 (dt, J = 11.4, 3.3 Hz, 2H), 4.39 (d, J = 7.1 Hz, 2H), 6.51 (d, J = 8.8 Hz, 1H), 6.61 (dd, J = 8.8, 3.0 Hz, 1H), 6.85 (d, J = 2.9 Hz, 1H), 7.53 (dd, J = 8.9, 1.7 Hz, 1H), 7.87-7.96 (m, 1H), 8.12 (d, J = 1.6 Hz, 1H), 8.31 (d, J = 0.9 Hz, 1H)<br>MS: [M + H] = 472 |

| | | |
|---|---|---|
| Example 48 | 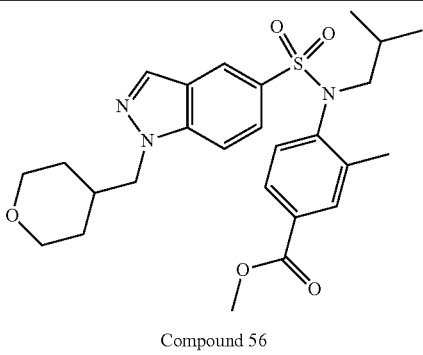br>Compound 56 | methyl 4-{isobutyl[1-(tetrahydropyran-4-ylmethyl)-1H-indazole-5-sulfonyl]amino}-3-methylbenzoate<br>$^1$H NMR (DMSO-d6) δ: 0.76 (d, J = 6.7 Hz, 3H), 0.94 (d, J = 6.6 Hz, 3H), 1.23-1.49 (m, 5H), 2.09-2.23 (m, 1H), 2.37 (s, 3H), 3.15 (dd, J = 13.2, 4.8 Hz, 1H), 3.24 (td, J = 11.2, 3.0 Hz, 2H), 3.46 (dd, J = 13.3, 8.9 Hz, 1H), 3.75-3.88 (m, 5H), 4.40 (d, J = 7.1 Hz, 2H), 6.80 (d, J = 8.3 Hz, 1H), 7.51 (dd, J = 8.9, 1.7 Hz, 1H), 7.65 (dd, J = 8.3, 2.2 Hz, 1H), 7.91 (d, J = 2.2 Hz, 1H), 7.93 (d, J = 8.9 Hz, 1H), 8.15 (d, J = 1.7 Hz, 1H), 8.32 (d, J = 0.9 Hz, 1H)<br>MS: [M + H] = 500 |
| Example 49 | 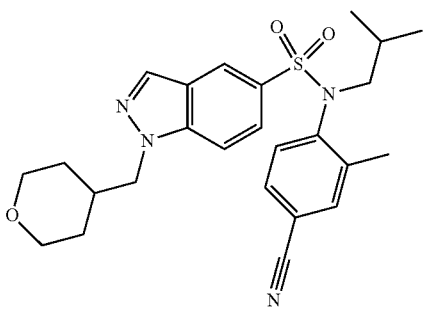<br>Compound 57 | 1-(tetrahydropyran-4-ylmethyl)-1H-indazole-5-sulfonic acid (4-cyano-2-methylphenyl)isobutylamide<br>$^1$H NMR (DMSO-d6) δ: 0.76 (d, J = 6.6 Hz, 3H), 0.93 (d, J = 6.5 Hz, 3H), 1.21-1.48 (m, 5H), 2.06-2.25 (m, 1H), 2.35 (s, 3H), 3.07-3.29 (m, 3H), 3.45 (dd, J = 13.3, 9.0 Hz, 1H), 3.82 (dd, J = 10.1, 3.2 Hz, 2H), 4.40 (d, J = 7.0 Hz, 2H), 6.88 (d, J = 8.3 Hz, 1H), 7.52 (dd, J = 9.0, 1.8 Hz, 1H), 7.59 (dd, J = 8.2, 2.1 Hz, 1H), 7.86 (d, J = 2.0 Hz, 1H), 7.94 (dd, J = 9.0, 0.9 Hz, 1H), 8.15 (d, J = 1.6 Hz, 1H), 8.33 (d, J = 1.0 Hz, 1H).<br>MS: [M + H] = 467 |

Example 50: Synthesis of 1-(tetrahydropyran-4-ylmethyl)-1H-indazole-5-sulfonic acid (4-ethylphenyl)(tetrahydropyran-4-ylmethyl)amide

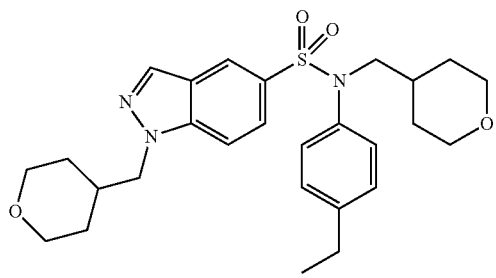

Compound 5

1. Synthesis of Intermediate 50.1

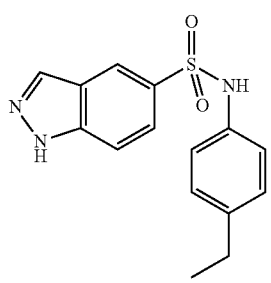 [SMILES: CCc1ccc(NS(=O)(=O)c2ccc3[nH]ncc3c2)cc1]

1H-indazole-5-sulfonic acid (4-ethylphenyl)amide

A mixture of 1H-indazole-5-sulfonyl chloride (1.00 g; 4.39 mmol), pyridine (5.0 ml) and 4-ethylaniline (603 μl; 4.82 mmol) is stirred for 4 hours at 50° C. The reaction medium is diluted with ethyl acetate and extracted. The organic phase is washed with saturated ammonium chloride solution, with saturated sodium hydrogen carbonate solution and with water. It is dried (MgSO$_4$), filtered and concentrated to dryness.

The crude product is chromatographed on silica gel (eluent: heptane/ethyl acetate, from 0 to 40% of ethyl acetate). The 1H-indazole-5-sulfonic acid (4-ethylphenyl)amide (1.32 g; 100%) is obtained in the form of an orange oil with a compliant $^1$H NMR.

MS: [M+H]=302

2. Synthesis of Compound 5 According to the Invention

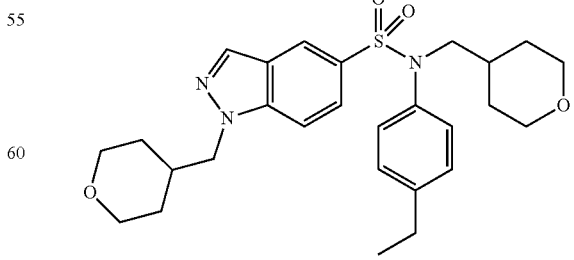

A mixture of 1H-indazole-5-sulfonic acid (4-ethylphenyl) amide (1.30 g; 4.31 mmol), cesium carbonate (2.11 g; 6.47 mmol) and 4-(bromomethyl)tetrahydropyran (680 µl; 5.18 mmol; 1.20 eq.) in N-methyl-2-pyrrolidone (10 ml) is stirred for 16 hours at a temperature of 50° C. The reaction medium is diluted with ethyl acetate (30 ml). The organic phase is washed with saturated NH₄Cl solution (20 ml), with saturated NaHCO₃ solution (20 ml) and with water (20 ml). The organic phase is dried (MgSO₄), filtered and concentrated.

The crude product is purified by preparative HPLC (C18 column, eluent: acetonitrile in water/0.1% of formic acid). The 1-(tetrahydropyran-4-ylmethyl)-1H-indazole-5-sulfonic acid (4-ethylphenyl)(tetrahydropyran-4-ylmethyl)amide (360 mg; 17%) is obtained in the form of a white solid.

¹H NMR (DMSO-d6) δ: 1.08-1.23 (m, 5H), 1.25-1.47 (m, 5H), 1.52-1.62 (m, 2H), 2.60 (q, J=7.5 Hz, 2H), 3.13 (td, J=11.6, 2.2 Hz, 2H), 3.23 (td, J=11.3, 3.0 Hz, 2H), 3.43 (d, J=7.2 Hz, 2H), 3.72-3.87 (m, 4H), 4.38 (d, J=7.1 Hz, 2H), 6.97 (d, J=8.4 Hz, 2H), 7.17 (d, J=8.4 Hz, 2H), 7.46 (dd, J=9.0, 1.7 Hz, 1H), 7.84-7.98 (m, 1H), 8.10 (d, J=1.7 Hz, 1H), 8.29 (d, J=0.9 Hz, 1H)

MS: [M+H]=498

Another fraction is obtained corresponding to the mixture below:

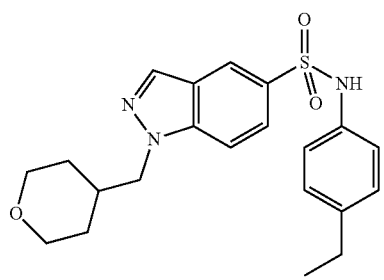

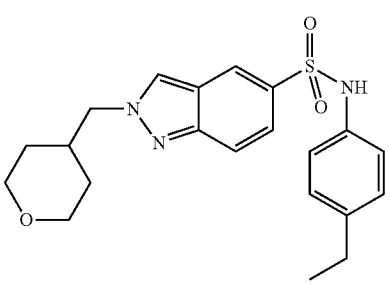

Intermediate 51.1: Mixture of N-(4-ethylphenyl)-1-((tetrahydro-2H-pyran-4-yl)methyl)-1H-indazole-5-sulfonamide and N-(4-ethylphenyl)-2-((tetrahydro-2H-pyran-4-yl)methyl)-2H-indazole-5-sulfonamide.

The mixture of N-(4-ethylphenyl)-1-((tetrahydro-2H-pyran-4-yl)methyl)-1H-indazole-5-sulfonamide and N-(4-ethylphenyl)-2-((tetrahydro-2H-pyran-4-yl)methyl)-2H-indazole-5-sulfonamide (170.00 mg; 10%) is obtained in the form of a solid with a compliant ¹H NMR.

MS: [M+H]=400

Example 51: Synthesis of 1-(tetrahydropyran-4-ylmethyl)-1H-indazole-5-sulfonic acid cyclopropyl (4-ethylphenyl)amide

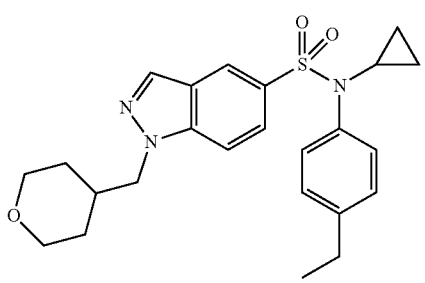

Compound 3

A spatulaful of molecular sieves is added to a mixture of N-(4-ethylphenyl)-1-((tetrahydro-2H-pyran-4-yl)methyl)-1H-indazole-5-sulfonamide and N-(4-ethylphenyl)-2-((tetrahydro-2H-pyran-4-yl)methyl)-2H-indazole-5-sulfonamide (170 mg; 0.43 mmol), triethylamine (180 µl; 1.28 mmol), copper(II) acetate (232 mg; 1.28 mmol) and cyclopropylboronic acid (220 mg; 2.55 mmol) in dichloromethane (3 ml).

The reaction medium is stirred for 16 hours at room temperature under 1 atmosphere of oxygen and filtered through Celite, which is rinsed with dichloromethane (50 ml) and with water (20 ml). The organic phase is extracted, washed with a mixture (1/1) of aqueous ammonia and saturated NH₄Cl solution (2×50 ml) and then with water (50 ml), dried (MgSO₄), filtered and concentrated.

The crude product is purified by preparative HPLC (C18 column, eluent: acetonitrile in water/0.1% of formic acid). The 1-(tetrahydropyran-4-ylmethyl)-1H-indazole-5-sulfonic acid cyclopropyl(4-ethylphenyl)amide 002 (40 mg; 21%) is obtained in the form of a white solid.

¹H NMR (DMSO-d6) δ: 0.62 (t, J=3.2 Hz, 2H), 0.76 (dt, J=7.1, 3.6 Hz, 2H), 1.14-1.22 (m, 4H), 1.23-1.42 (m, 4H), 2.16 (dd, J=10.8, 5.1 Hz, 1H), 2.58-2.71 (m, 3H), 3.17-3.29 (m, 3H), 3.76-3.89 (m, 2H), 4.38 (d, J=7.1 Hz, 2H), 6.87-7.02 (m, 2H), 7.15 (d, J=8.4 Hz, 2H), 7.46 (dd, J=8.8, 1.7 Hz, 1H), 7.91 (d, J=8.9 Hz, 1H), 8.15 (d, J=1.6 Hz, 1H), 8.33 (d, J=0.9 Hz, 1H)

MS: [M+H]=440

Example 52: Synthesis of 1-(tetrahydropyran-4-ylmethyl)-1H-indazole-5-sulfonic acid isobutyl(2-trifluoromethylphenyl)amide

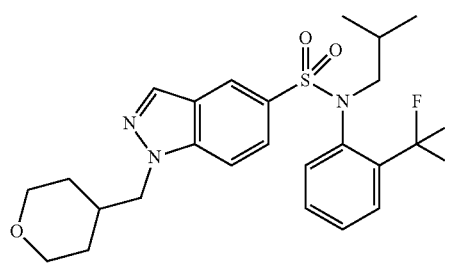

Compound 58

1. Synthesis of Intermediate 52.1

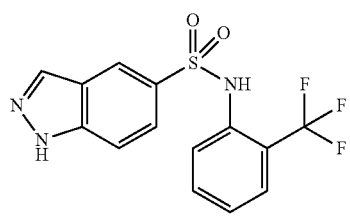 [SMILES: O=S(=O)(Nc1ccccc1C(F)(F)F)c1ccc2[nH]ncc2c1]

1H-indazole-5-sulfonic acid (2-trifluoromethylphenyl)amide

A mixture of 1H-indazole-5-sulfonyl chloride (500.0 mg; 2.19 mmol), pyridine (3.0 ml) and 2-(trifluoromethyl)aniline (306.18 µl; 2.41 mmol) is stirred for 16 hours at a temperature of 40° C. The reaction medium is diluted with ethyl acetate and extracted. The organic phase is washed with saturated ammonium chloride solution, with saturated sodium hydrogen carbonate solution and with water. It is dried (MgSO$_4$), filtered and concentrated to dryness.

The crude product is chromatographed on silica gel (eluent: heptane/ethyl acetate, from 0 to 40% of ethyl acetate).

The 1H-indazole-5-sulfonic acid (2-trifluoromethylphenyl)amide (300 mg; 40%) is obtained in the form of a white solid with a compliant $^1$H NMR.

MS: [M+H]=342

2. Synthesis of Compound 58 According to the Invention

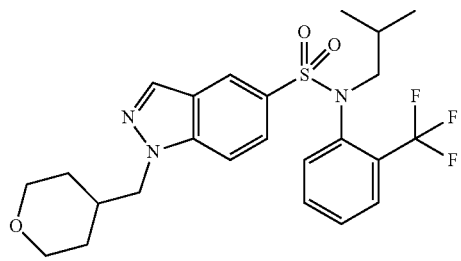 [SMILES: CC(C)CN(c1ccccc1C(F)(F)F)S(=O)(=O)c1ccc2c(cnn2CC2CCOCC2)c1]

Cesium carbonate (30 mg; 1.32 mmol) and 4-(bromomethyl)tetrahydropyran (127 µl; 0.97 mmol) are added to a solution of 1H-indazole-5-sulfonic acid (2-trifluoromethylphenyl)amide (300 mg; 0.88 mmol) in 1-methyl-2-pyrrolidone (3 ml). The reaction medium is stirred for 16 hours at room temperature. 1-Bromo-2-methylpropane (287 µl; 2.64 mmol) is added and the reaction medium is stirred for 6 hours at 80° C. The reaction medium is diluted with ethyl acetate, washed with saturated ammonium chloride solution and then with saturated sodium hydrogen carbonate solution and with water. The organic phase is dried (MgSO$_4$), filtered and concentrated to dryness.

The crude product is purified by preparative HPLC (C18 column, eluent: acetonitrile in water/0.1% of formic acid). The 1-(tetrahydropyran-4-ylmethyl)-1H-indazole-5-sulfonic acid isobutyl(2-trifluoromethylphenyl)amide (80 mg; 16%) is obtained in the form of a beige-colored solid.

$^1$H NMR (DMSO-d6) δ: 0.71 (d, J=6.7 Hz, 3H), 0.85-0.93 (m, 3H), 1.25-1.43 (m, 4H), 1.48 (dtd, J=8.8, 6.6, 4.6 Hz, 1H), 2.12-2.25 (m, 1H), 3.15 (dd, J=13.4, 4.6 Hz, 1H), 3.24 (td, J=10.8, 10.4, 2.2 Hz, 2H), 3.46 (dd, J=13.4, 8.8 Hz, 1H), 3.78-3.86 (m, 2H), 4.41 (d, J=7.1 Hz, 2H), 6.99 (dd, J=5.7, 3.7 Hz, 1H), 7.56 (dd, J=9.0, 1.7 Hz, 1H), 7.58-7.64 (m, 2H), 7.85 (dt, J=5.6, 3.7 Hz, 1H), 7.96 (d, J=8.9 Hz, 1H), 8.18-8.24 (m, 1H), 8.35 (s, 1H).

MS: [M+H]=496

Example 53: Synthesis of 1-(tetrahydropyran-4-ylmethyl)-1H-indazole-5-sulfonic acid isobutyl(4-trifluoromethylphenyl)amide

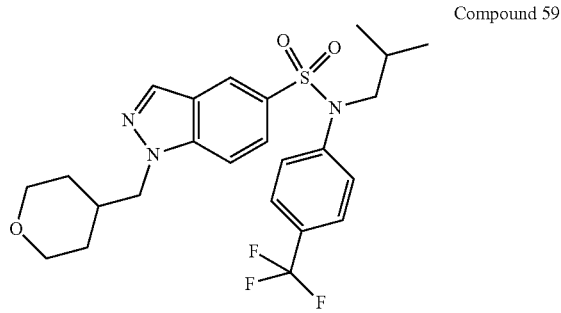 [SMILES: CC(C)CN(c1ccc(C(F)(F)F)cc1)S(=O)(=O)c1ccc2c(cnn2CC2CCOCC2)c1]

Compound 59

1. Synthesis of Intermediate 53.1

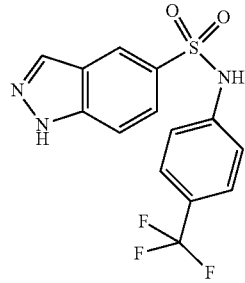 [SMILES: O=S(=O)(Nc1ccc(C(F)(F)F)cc1)c1ccc2[nH]ncc2c1]

1H-indazole-5-sulfonic acid (4-trifluoromethylphenyl)amide

A mixture of 1H-indazole-5-sulfonyl chloride (250.0 mg; 1.10 mmol) and 4-(trifluoromethyl)aniline (388.6 µl; 2.41 mmol) in acetonitrile (1.7 ml) is stirred for 40 minutes at a temperature of 100° C. under microwave irradiation. The reaction medium is diluted with ethyl acetate and extracted.

The organic phase is washed with saturated ammonium chloride solution, with saturated sodium hydrogen carbonate solution and with water. It is dried (MgSO$_4$), filtered and concentrated to dryness.

The 1H-indazole-5-sulfonic acid (4-trifluoromethylphenyl)amide (297 mg; 79%) is obtained in the form of a yellowish solid with a compliant $^1$H NMR.

MS: [M+H]=342

2. Synthesis of Compound 59 According to the Invention

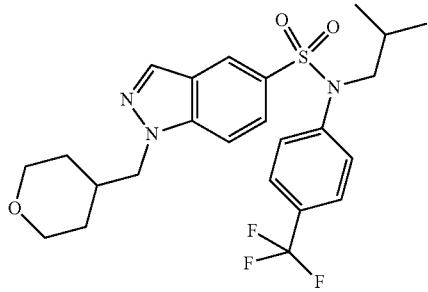 [SMILES: CC(C)CN(c1ccc(C(F)(F)F)cc1)S(=O)(=O)c1ccc2c(cnn2CC2CCOCC2)c1]

With a procedure similar to that described for example 52, 1-(tetrahydropyran-4-ylmethyl)-1H-indazole-5-sulfonic acid isobutyl(4-trifluoromethylphenyl)amide (178 mg; 40%) is obtained in the form of a white solid.

$^1$H NMR (DMSO-d6) δ: 0.84 (d, J=6.6 Hz, 6H), 1.22-1.51 (m, 5H), 2.07-2.24 (m, 1H), 3.23 (td, J=11.4, 2.9 Hz, 2H), 3.42 (d, J=7.3 Hz, 2H), 3.81 (ddd, J=11.6, 4.2, 2.1 Hz, 2H), 4.37 (d, J=7.1 Hz, 2H), 7.37 (d, J=8.2 Hz, 2H), 7.43 (dd, J=8.9, 1.8 Hz, 1H), 7.73 (d, J=8.6 Hz, 2H), 7.91 (d, 1H), 8.13 (d, J=1.6 Hz, 1H), 8.31 (d, J=1.0 Hz, 1H).

MS: [M+H]=496

Example 54: Synthesis of 1-(tetrahydropyran-4-ylmethyl)-1H-indazole-5-sulfonic acid (2-cyano-4-methylphenyl)isobutylamide Compound 70

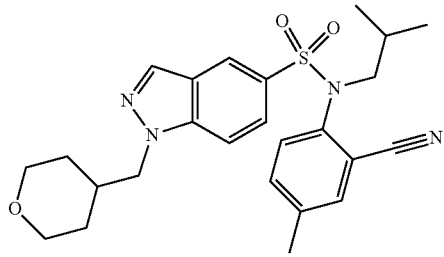

1. Synthesis of Intermediate 54.1

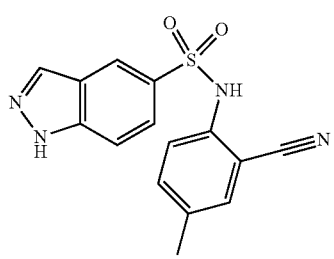 [SMILES: Cc1ccc(NS(=O)(=O)c2ccc3[nH]ncc3c2)c(C#N)c1]

1H-indazole-5-sulfonic acid (2-cyano-4-methylphenyl)amide

With a procedure similar to that described for intermediate 53.1, 1H-indazole-5-sulfonic acid (2-cyano-4-methylphenyl)amide (342.4 mg; 100%) is obtained in the form of a yellowish solid with a compliant $^1$H NMR.

MS: [M+H]=313

2. Synthesis of 1-(tetrahydropyran-4-ylmethyl)-1H-indazole-5-sulfonic acid (2-cyano-4-methylphenyl) isobutylamide (compound 70)

With a procedure similar to that described for example 52, 1-(tetrahydropyran-4-ylmethyl)-2H-indazole-5-sulfonic acid (2-cyano-4-methylphenyl)isobutylamide (129.7 mg; 20%) is obtained in the form of a white solid.

$^1$H NMR (Chloroform-d) δ: 0.93 (d, J=6.7 Hz, 6H), 1.42-1.53 (m, 4H), 1.54-1.67 (m, 1H), 2.21-2.39 (m, 1H), 2.42 (s, 3H), 3.37 (td, J=11.3, 3.5 Hz, 2H), 3.45 (d, J=7.2 Hz, 2H), 3.98 (dt, J=11.7, 2.6 Hz, 2H), 4.32 (d, J=7.2 Hz, 2H), 7.25 (d, J=8.2 Hz, 1H), 7.41 (dd, J=8.2, 2.1 Hz, 1H), 7.45 (d, J=2.1 Hz, 1H), 7.52 (d, J=8.9 Hz, 1H), 7.78 (dd, J=8.9, 1.6 Hz, 1H), 8.15 (d, J=1.0 Hz, 1H), 8.18 (d, J=1.6 Hz, 1H).

MS: [M+H]=467

Example 55: Synthesis of 1-(tetrahydropyran-4-ylmethyl)-1H-indazole-5-sulfonic acid (4,6-dimethylpyridin-3-yl)isobutylamide Compound 71

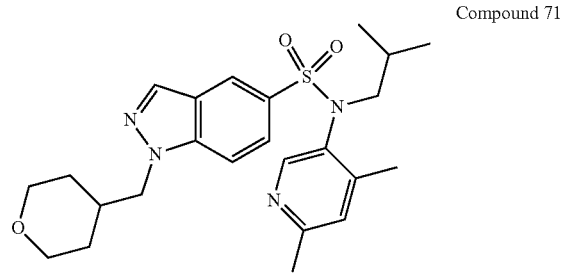 [SMILES: Cc1cc(C)c(N(CC(C)C)S(=O)(=O)c2ccc3c(cnn3CC3CCOCC3)c2)cn1]

1. Synthesis of Intermediate 55.1

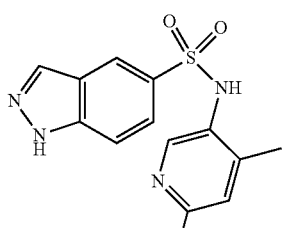

1H-indazole-5-sulfonic acid (4,6-dimethylpyridin-3-yl)amide

With a procedure similar to that described for intermediate 53.1, 1H-indazole-5-sulfonic acid (4,6-dimethylpyridin- 3-yl)amide (151 mg; 46%) is obtained in the form of a yellowish solid with a compliant ¹H NMR.
MS: [M+H]=303

2. Synthesis of 1-(tetrahydropyran-4-ylmethyl)-1H-indazole-5-sulfonic acid (4,6-dimethylpyridin-3-yl)isobutylamide With a procedure similar to that described for example 52, 1-(tetrahydropyran-4-ylmethyl)-1H-indazole-5-sulfonic acid (4,6-dimethylpyridin-3-yl)isobutylamide (17 mg; 7%) is obtained in the form of a white solid.
¹H NMR (DMSO-d6) δ: 0.78 (d, J=6.7 Hz, 3H), 0.95 (d, J=6.6 Hz, 3H), 1.18-1.56 (m, 5H), 2.13-2.27 (m, 4H), 2.41 (s, 3H), 3.19-3.29 (m, 3H), 3.44 (dd, J=13.3, 8.6 Hz, 1H), 3.78-3.89 (m, 2H), 4.40 (d, J=7.0 Hz, 2H), 7.21 (s, 1H), 7.56 (dd, J=8.9, 1.8 Hz, 1H), 7.68 (s, 1H), 7.96 (d, J=8.8 Hz, 1H), 8.16 (d, J=1.7 Hz, 1H), 8.33 (s, 1H).
MS: [M+H]=457

Example 56: Synthesis of 1-(tetrahydropyran-4-ylmethyl)-1H-indazole-5-sulfonic acid (4-dimethylaminophenyl)isobutylamide

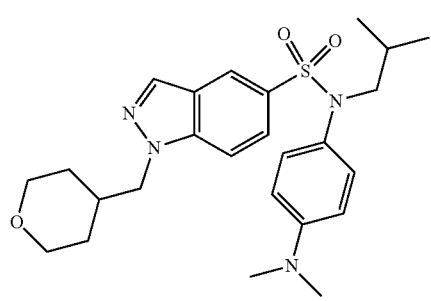

Compound 72

1. Synthesis of Intermediate 56.1

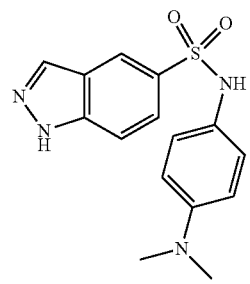 [SMILES: CN(C)c1ccc(NS(=O)(=O)c2ccc3[nH]ncc3c2)cc1]

1H-indazole-5-sulfonic acid (4-dimethylaminophenyl)amide

With a procedure similar to that described for intermediate 53.1, 1H-indazole-5-sulfonic acid (4-dimethylaminophenyl)amide (281 mg; 81%) is obtained in the form of a fluffy white solid with a compliant ¹H NMR.
MS: [M+H]=317

2. Synthesis of 1-(tetrahydropyran-4-ylmethyl)-1H-indazole-5-sulfonic acid (4-dimethylaminophenyl)isobutylamide (compound 72)

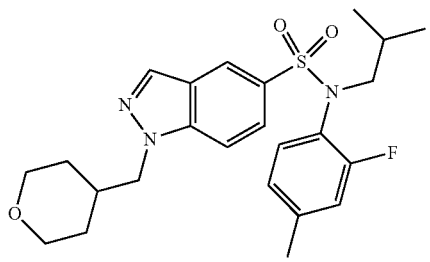

With a procedure similar to that described for example 52, 1-(tetrahydropyran-4-ylmethyl)-1H-indazole-5-sulfonic acid (4-dimethylaminophenyl)isobutylamide (19 mg; 4%) is obtained in the form of a white solid.
¹H 1H NMR (Chloroform-d) δ: 0.94 (d, J=6.7 Hz, 6H), 1.38-1.55 (m, 3H), 1.62 (dd, J=13.2, 6.3 Hz, 2H), 2.31 (dt, J=11.0, 5.6 Hz, 1H), 2.97 (s, 6H), 3.30 (d, J=7.3 Hz, 2H), 3.38 (td, J=11.3, 3.1 Hz, 2H), 3.99 (ddd, J=11.7, 4.4, 2.1 Hz, 2H), 4.31 (d, J=7.1 Hz, 2H), 6.60 (d, J=8.4 Hz, 2H), 6.84-6.91 (m, 2H), 7.41-7.46 (m, 1H), 7.60 (dd, J=8.9, 1.6 Hz, 1H), 8.08 (d, J=1.7 Hz, 1H), 8.11 (d, J=0.9 Hz, 1H).
MS: [M+H]=471

Example 57: Synthesis of 1-(tetrahydropyran-4-ylmethyl)-1H-indazole-5-sulfonic acid (2-fluoro-4-methylphenyl)isobutylamide Compound 73

1. Synthesis of Intermediate 57.1

1H-indazole-5-sulfonic acid (2-fluoro-4-methylphenyl)amide

With a procedure similar to that described for intermediate 53.1, 1H-indazole-5-sulfonic acid (2-fluoro-4-methylphenyl)amide (189 mg; 94%) is obtained in the form of a yellowish solid with a compliant $^1$H NMR.

MS: [M+H]=306

2. Synthesis of 1-(tetrahydropyran-4-ylmethyl)-1H-indazole-5-sulfonic acid (2-fluoro-4-methylphenyl) isobutylamide With a procedure similar to that described for example 52, 1-(tetrahydropyran-4-ylmethyl)-1H-indazole-5-sulfonic acid (2-fluoro-4-methylphenyl)isobutylamide (19 mg; 4%) is obtained in the form of a white solid.

$^1$H 1H NMR (Chloroform-d) δ: 0.93 (d, J=6.6 Hz, 6H), 1.47 (td, J=11.2, 10.7, 4.2 Hz, 3H), 1.54-1.69 (m, 2H), 2.30 (dd, J=10.7, 4.6 Hz, 1H), 2.36 (s, 3H), 3.24-3.47 (m, 5H), 3.95-4.03 (m, 2H), 4.31 (d, J=7.1 Hz, 2H), 6.82 (dd, J=11.5, 1.8 Hz, 1H), 6.94 (dd, J=8.2, 1.8 Hz, 1H), 7.16 (t, J=8.1 Hz, 1H), 7.45 (dt, J=9.0, 0.9 Hz, 1H), 7.67 (dd, J=8.9, 1.6 Hz, 1H), 8.13 (dd, J=9.3, 1.2 Hz, 2H).

MS: [M+H]=460

Part II: Synthesis of the Bicyclic Sulfonamides Via Reaction Scheme 2

Reaction scheme 2

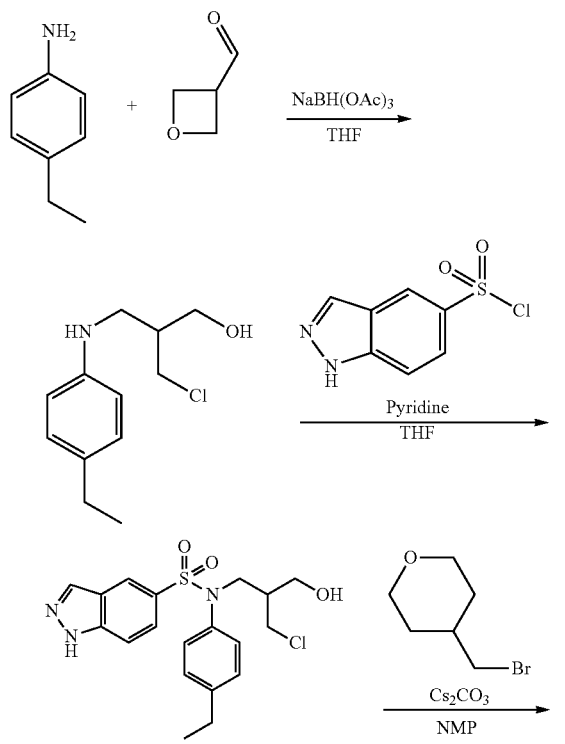

Example 58: Synthesis of 1-(tetrahydropyran-4-ylmethyl)-1H-indazole-5-sulfonic acid (4-ethylphenyl)oxetan-3-ylmethylamide

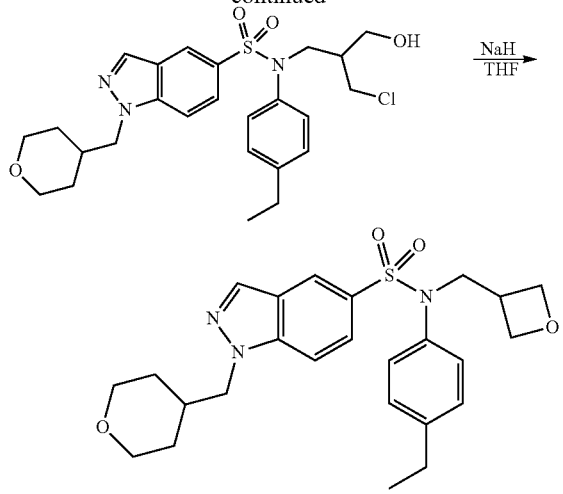

Compound 16

1. Synthesis of Intermediate 58.1

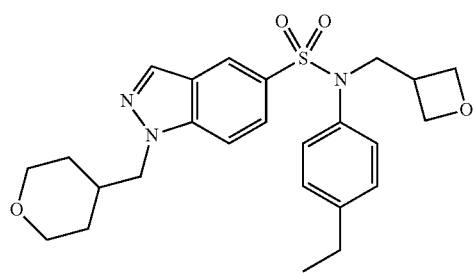

2-chloromethyl-3-(4-ethylphenylamino)propan-1-ol

A mixture of 4-ethylaniline (513 μl; 4.13 mmol), oxetane-3-carbaldehyde (807.3 mg; 3.75 mmol) and tetrahydrofuran (2.5 ml) is stirred for 2 hours at room temperature. Sodium triacetoxyborohydride (1.19 g; 5.63 mmol) is added and the reaction medium is stirred for 16 hours at room temperature, hydrolyzed and extracted with ethyl acetate.

The organic phases are combined, washed with brine, dried (Na$_2$SO$_4$) and concentrated.

The crude product is chromatographed on silica gel (eluent: heptane/ethyl acetate, from 0 to 40% of ethyl acetate). The 2-chloromethyl-3-(4-ethylphenylamino)propan-1-ol (340 mg; 40%) is obtained in the form of an orange oil with a $^1$H NMR showing the opening of the oxetane.

MS: [M+H]=228

2. Synthesis of Intermediate 58.2

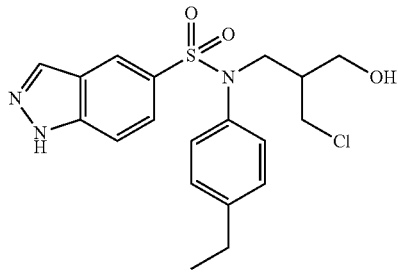 [SMILES: CCc1ccc(N(CC(CO)CCl)S(=O)(=O)c2ccc3[nH]ncc3c2)cc1]

2-chloromethyl-3-(4-ethylphenylamino)propan-1-ol

A mixture of 1H-indazole-5-sulfonyl chloride (368.5 mg; 1.62 mmol), pyridine (3.0 ml; 37.17 mmol) and (4-ethylphenyl)oxetan-3-ylmethylamine (340 mg; 1.78 mmol) is stirred for 30 minutes at a temperature of 100° C. under microwave irradiation.

The reaction medium is diluted with ethyl acetate. The organic phase is washed with saturated ammonium chloride solution, with saturated sodium hydrogen carbonate solution and with water. It is dried (MgSO$_4$), filtered and concentrated to dryness.

The crude product is chromatographed on silica gel (eluent: heptane/ethyl acetate, from 0 to 40% of ethyl acetate). The 1H-indazole-5-sulfonic acid (2-chloromethyl-3-hydroxypropyl)(4-ethylphenyl)amide (260 mg; 39%) is obtained in the form of a colorless oil with a compliant $^1$H NMR.

MS: [M+H]=408

3. Synthesis of Intermediate 58.3

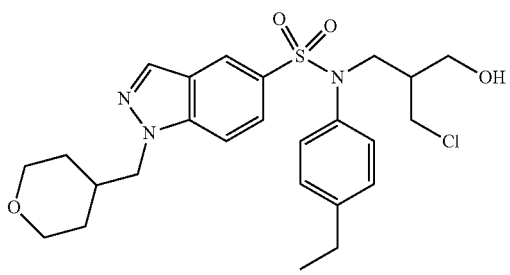 [SMILES: CCc1ccc(N(CC(CO)CCl)S(=O)(=O)c2ccc3c(cnn3CC3CCOCC3)c2)cc1]

1-(tetrahydropyran-4-ylmethyl)-1H-indazole-5-sulfonic acid (3-chloro-2-hydroxymethylpropyl)(4-ethylphenyl)amide A mixture of 1H-indazole-5-sulfonic acid (2-chloromethyl-3-hydroxypropyl)(4-ethylphenyl)amide (1.26 g; 0.64 mmol), cesium carbonate (0.31 mg; 0.96 mmol) and 4-(bromomethyl)tetrahydropyran (100 μl; 0.76 mmol) in N-methyl-2-pyrrolidone (4 ml) is stirred for 1 hour at a temperature of 80° C. The reaction medium is diluted with ethyl acetate (20 ml).

The organic phase is washed with saturated NH$_4$Cl solution, with saturated NaHCO$_3$ solution and with water. The organic phase is dried (MgSO$_4$), filtered and concentrated.

The crude product is purified by preparative HPLC (C18 column, eluent: acetonitrile in water/0.1% of formic acid). The 1-(tetrahydropyran-4-ylmethyl)-1H-indazole-5-sulfonic acid (3-chloro-2-hydroxymethylpropyl)(4-ethylphenyl)amide (100 mg; 31%) is obtained in the form of a colorless oil. $^1$H NMR (DMSO-d6) δ: 1.18 (t, J=7.6 Hz, 3H), 1.25-1.43 (m, 4H), 1.73 (p, J=6.4 Hz, 1H), 2.61 (q, J=7.6 Hz, 2H), 3.23 (td, J=11.3, 3.0 Hz, 2H), 3.35-3.41 (m, 1H), 3.46-3.52 (m, 1H), 3.52-3.63 (m, 2H), 3.69 (qd, J=10.8, 4.9 Hz, 2H), 3.82 (ddd, J=11.4, 4.3, 2.2 Hz, 2H), 4.39 (d, J=7.0 Hz, 2H), 4.69 (t, J=5.1 Hz, 1H), 6.95-7.02 (m, 2H), 7.16-7.22 (m, 2H), 7.44 (dd, J=9.0, 1.8 Hz, 1H), 7.92 (d, J=8.9 Hz, 1H), 8.10 (d, J=1.6 Hz, 1H), 8.31 (s, 1H)

MS: [M+H]=506

4. Synthesis of Compound 16 According to the Invention

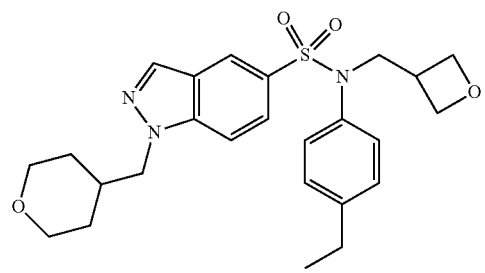 [SMILES: CCc1ccc(N(CC2COC2)S(=O)(=O)c2ccc3c(cnn3CC3CCOCC3)c2)cc1]

60% sodium hydride (17.4 mg; 0.43 mmol) is added to a solution of 1-(tetrahydropyran-4-ylmethyl)-1H-indazole-5-sulfonic acid (3-chloro-2-hydroxymethylpropyl)(4-ethylphenyl)amide (100 mg; 0.20 mmol) in tetrahydrofuran (3 ml). The reaction medium is stirred for 1 hour at a temperature of 80° C. and then for 16 hours at a temperature of 30° C.

The reaction medium is diluted with ethyl acetate (20 ml). The organic phase is washed with saturated NH$_4$Cl solution (20 ml), with saturated NaHCO$_3$ solution (20 ml) and with water (20 ml). The organic phase is dried (MgSO$_4$), filtered and concentrated.

The crude product is purified by preparative HPLC (C18 column, eluent: acetonitrile in water/0.1% of formic acid). The 1-(tetrahydropyran-4-ylmethyl)-1H-indazole-5-sulfonic acid (4-ethylphenyl)oxetan-3-ylmethylamide (35.0 mg; 33%) is obtained in the form of a white solid.

$^1$H NMR (Methanol-d4) δ: 1.20 (t, J=7.6 Hz, 3H), 1.31-1.51 (m, 5H), 2.27 (tq, J=10.6, 6.2, 5.6 Hz, 1H), 2.62 (q, J=7.6 Hz, 2H), 3.01 (hept, J=7.3 Hz, 1H), 3.31-3.43 (m, 2H), 3.92 (d, J=7.7 Hz, 3H), 4.33-4.42 (m, 3H), 4.56-4.66 (m, 2H), 6.88 (d, J=8.2 Hz, 2H), 6.93-7.03 (m, 1H), 7.13 (d, J=8.1 Hz, 2H), 7.58 (dd, J=8.9, 1.7 Hz, 1H), 7.74 (d, J=8.8 Hz, 1H), 8.13 (s, 1H)

MS: [M+H]=470

Part III: Synthesis of the Bicyclic Sulfonamides Via Reaction Scheme 3

Reaction scheme 3

Example 59: Synthesis of methyl 5-[(4-ethylphenyl)isobutylsulfamoyl]-1-(tetrahydropyran-4-ylmethyl)-1H-indazole-7-carboxylate Compound 74

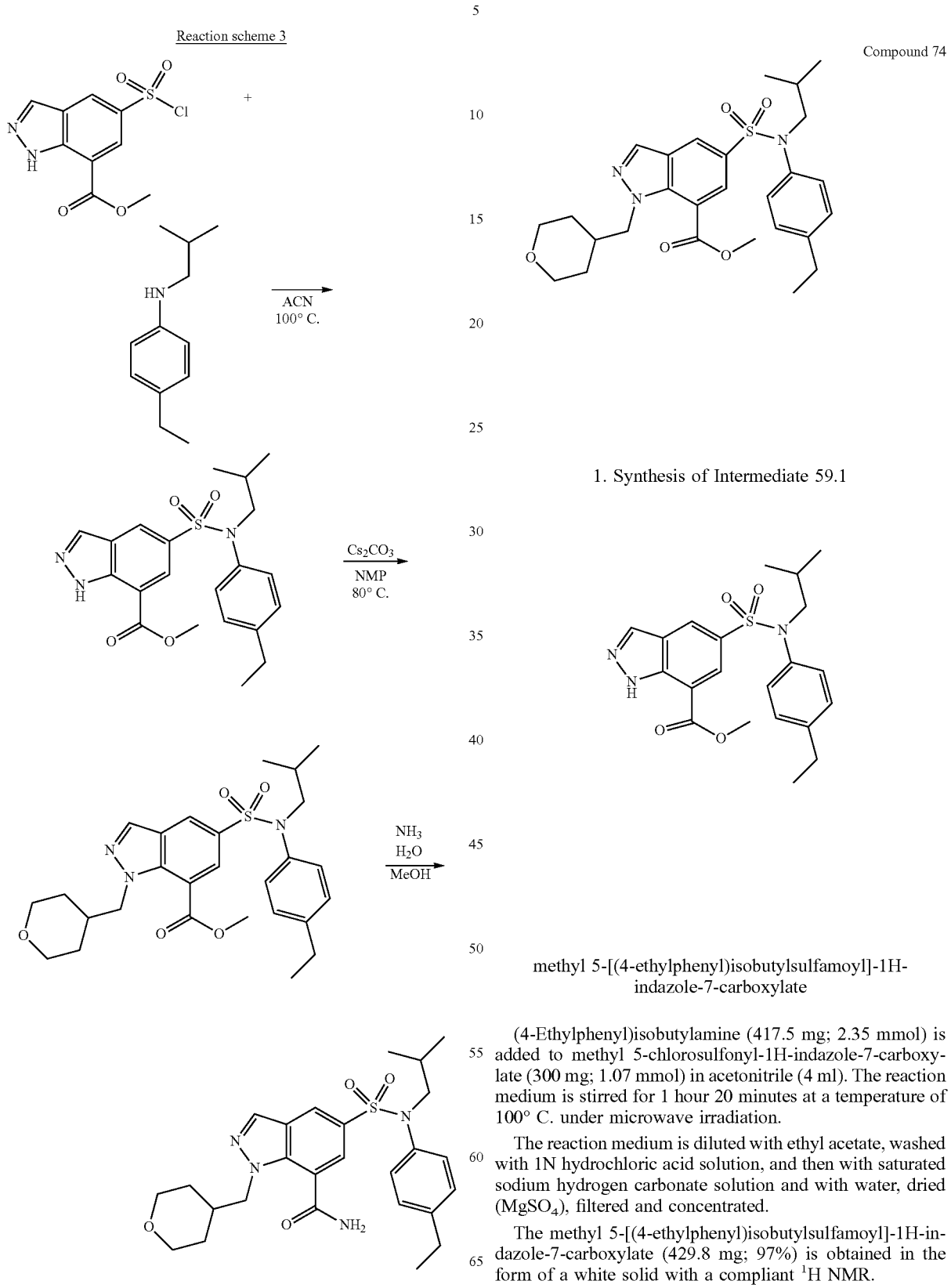

1. Synthesis of Intermediate 59.1 methyl 5-[(4-ethylphenyl)isobutylsulfamoyl]-1H-indazole-7-carboxylate (4-Ethylphenyl)isobutylamine (417.5 mg; 2.35 mmol) is added to methyl 5-chlorosulfonyl-1H-indazole-7-carboxylate (300 mg; 1.07 mmol) in acetonitrile (4 ml). The reaction medium is stirred for 1 hour 20 minutes at a temperature of 100° C. under microwave irradiation.

The reaction medium is diluted with ethyl acetate, washed with 1N hydrochloric acid solution, and then with saturated sodium hydrogen carbonate solution and with water, dried ($MgSO_4$), filtered and concentrated.

The methyl 5-[(4-ethylphenyl)isobutylsulfamoyl]-1H-indazole-7-carboxylate (429.8 mg; 97%) is obtained in the form of a white solid with a compliant $^1$H NMR.

MS: [M+H]=416

2. Synthesis of methyl 5-[(4-ethylphenyl)isobutyl-sulfamoyl]-1-(tetrahydropyran-4-ylmethyl)-1H-indazole-7-carboxylate (compound 74)

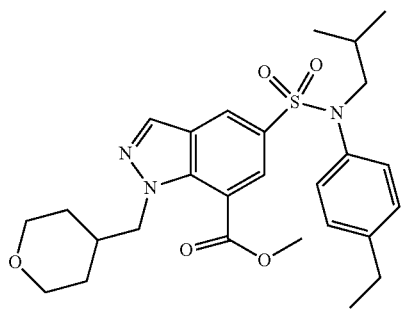 [SMILES: CCc1ccc(N(CC(C)C)S(=O)(=O)c2cc(C(=O)OC)c3c(cnn3CC3CCOCC3)c2)cc1]

4-(Bromomethyl)tetrahydropyran (97.6 µl; 0.74 mmol) is added to a mixture of methyl 5-[(4-ethylphenyl)isobutylsulfamoyl]-1H-indazole-7-carboxylate (280.0 mg; 0.67 mmol) and cesium carbonate (329 mg; 1 mmol) in 1-methyl-2-pyrrolidone (2.8 ml). The reaction medium is stirred at a temperature of 80° C. overnight.

The crude product is filtered and then purified by preparative HPLC (C18 column, eluent: acetonitrile in water/ 0.1% of formic acid). The methyl 5-[(4-ethylphenyl)isobutylsulfamoyl]-1-(tetrahydropyran-4-ylmethyl)-1H-indazole-7-carboxylate (223.4 mg; 63%) is obtained in the form of a white solid.

NMR (DMSO-d6) δ: 0.85 (d, J=6.6 Hz, 6H), 1.18 (t, J=7.6 Hz, 3H), 1.25 (dt, J=11.1, 5.3 Hz, 4H), 1.33-1.55 (m, 1H), 1.86-2.12 (m, 1H), 2.60 (q, J=7.6 Hz, 2H), 3.18 (td, J=11.1, 3.6 Hz, 2H), 3.35 (s, 2H), 3.79 (dt, J=11.4, 3.3 Hz, 2H), 3.93 (s, 3H), 4.57 (d, J=7.2 Hz, 2H), 6.93-7.06 (m, 2H), 7.12-7.23 (m, 2H), 7.80 (d, J=1.7 Hz, 1H), 8.37 (d, J=1.9 Hz, 1H), 8.48 (s, 1H)

MS: [M+H]=514

Example 60: Synthesis of 5-[(4-ethylphenyl)isobutylsulfamoyl]-1-(tetrahydropyran-4-ylmethyl)-1H-indazole-7-carboxylic acid amide Compound 75

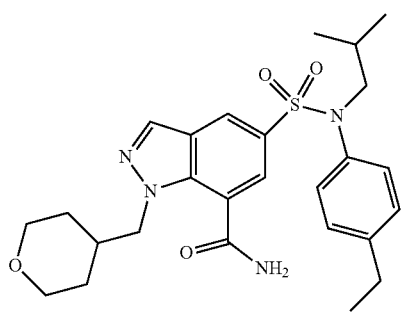

Aqueous ammonia (1.05 ml) is added to a solution of methyl 5-[(4-ethylphenyl)isobutylsulfamoyl]-1-(tetrahydropyran-4-ylmethyl)-1H-indazole-7-carboxylate (210.0 mg; 0.41 mmol) in N,N-dimethylformamide (1.05 ml).

The reaction medium is stirred for 3 days at room temperature and for 2 days at a temperature of 60° C. The reaction medium is diluted and extracted with dichloromethane. The organic phases are combined, dried (MgSO₄), filtered and concentrated to dryness.

The crude product is filtered and then purified by preparative HPLC (C18 column, eluent: acetonitrile in water/ 0.2% of ammonium carbonate). The 5-[(4-ethylphenyl) isobutylsulfamoyl]-1-(tetrahydropyran-4-ylmethyl)-1H-indazole-7-carboxylic amide is obtained in the form of a white solid.

¹H NMR (Chloroform-d) δ: 0.94 (d, J=6.7 Hz, 6H), 1.25 (t, J=7.6 Hz, 3H), 1.38-1.51 (m, 4H), 1.59-1.69 (m, 1H), 2.08-2.21 (m, 1H), 2.67 (q, J=7.6 Hz, 2H), 3.25-3.39 (m, 4H), 3.90-4.01 (m, 2H), 4.59 (d, J=7.2 Hz, 2H), 5.75 (s, 1H), 6.00 (s, 1H), 6.94-7.00 (m, 2H), 7.11-7.18 (m, 2H), 7.62 (d, J=1.7 Hz, 1H), 8.15 (d, J=1.6 Hz, 1H), 8.19 (s, 1H) MS: [M+H]=499

Part IV: Synthesis of the Bicyclic Sulfonamides Via Reaction Scheme 4

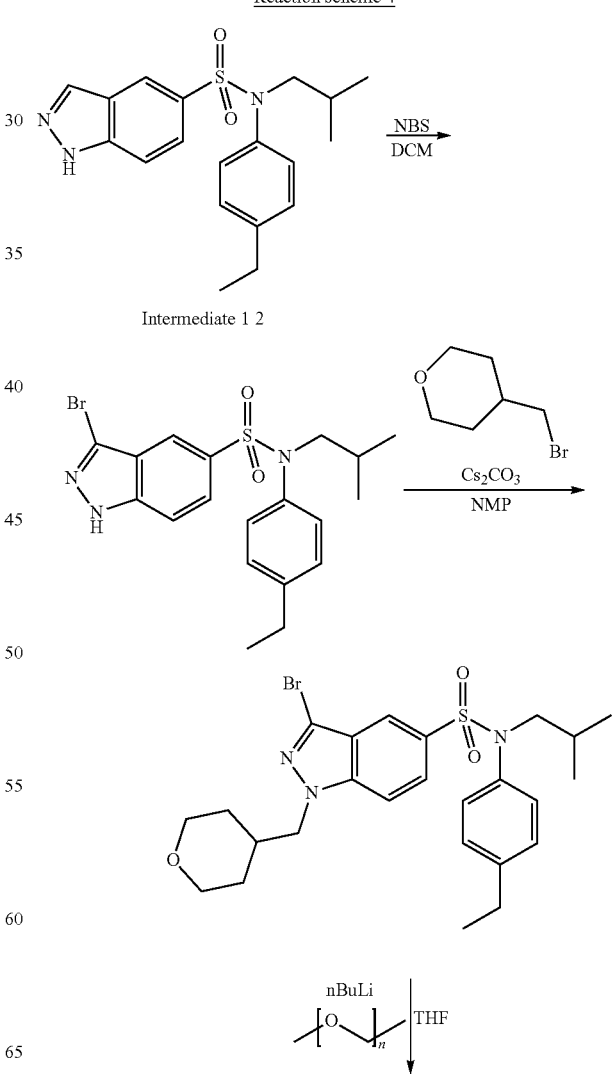

-continued

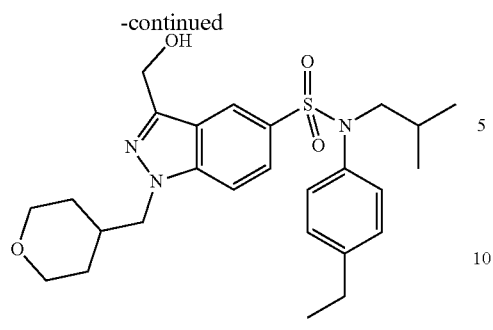

Example 61: Synthesis of N-(4-ethylphenyl)-N-isobutyl-1-((tetrahydro-2H-pyran-4-yl)methyl)-1H-indazole-5-sulfonamide Compound 14

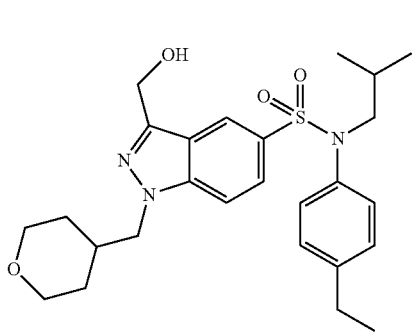

1. Synthesis of Intermediate 60.1

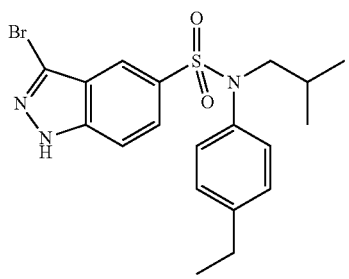 [SMILES: CCc1ccc(N(CC(C)C)S(=O)(=O)c2ccc3[nH]nc(Br)c3c2)cc1]

3-bromo-1H-indazole-5-sulfonic acid (4-ethylphenyl)isobutylamide

N-Bromosuccinimide (120 mg; 0.67 mmol) is added to a solution of 1H-indazole-5-sulfonic acid (4-ethylphenyl)isobutylamide (200 mg; 0.56 mmol) in dichloromethane (5 ml). The reaction medium is stirred for 16 hours at room temperature, diluted with dichloromethane and extracted.

The organic phase is washed with saturated NH$_4$Cl solution, with saturated NaHCO$_3$ solution and with water, dried (MgSO$_4$), filtered and concentrated to dryness.

The 3-bromo-1H-indazole-5-sulfonic acid (4-ethylphenyl)isobutylamide (260 mg; 100%) is obtained in the form of a pale yellow solid with a compliant $^1$H NMR.

MS: [M+H]=436

2. Synthesis of Intermediate 60.2

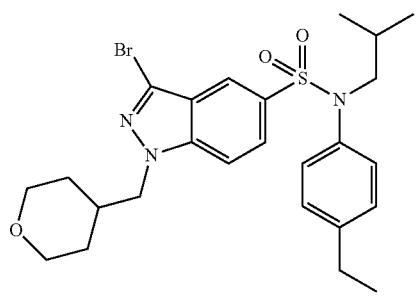 [SMILES: CCc1ccc(N(CC(C)C)S(=O)(=O)c2ccc3c(c2)c(Br)nn3CC2CCOCC2)cc1]

3-bromo-1-(tetrahydropyran-4-ylmethyl)-1H-indazole-5-sulfonic acid (4-ethylphenyl)isobutylamide A mixture of 3-bromo-1H-indazole-5-sulfonic acid (4-ethylphenyl)isobutylamide (260 mg; 0.60 mmol), cesium carbonate (388 mg; 1.19 mmol) and 4-(bromomethyl)tetrahydropyran (160 mg; 0.89 mmol) in N-methyl-2-pyrrolidone (3 ml) is stirred for 1 hour at a temperature of 80° C.

The reaction medium is diluted with ethyl acetate (30 ml). The organic phase is washed with saturated NH$_4$Cl solution (20 ml), with saturated NaHCO$_3$ solution (20 ml) and with water (20 ml), dried (MgSO$_4$), filtered and concentrated to dryness.

The 3-bromo-1-(tetrahydropyran-4-ylmethyl)-1H-indazole-5-sulfonic acid (4-ethylphenyl)isobutylamide (350 mg; 100%) is obtained in the form of a clear yellow oil with a compliant $^1$H NMR.

MS: [M+H]=534

3. Synthesis of Compound 14 According to the Invention

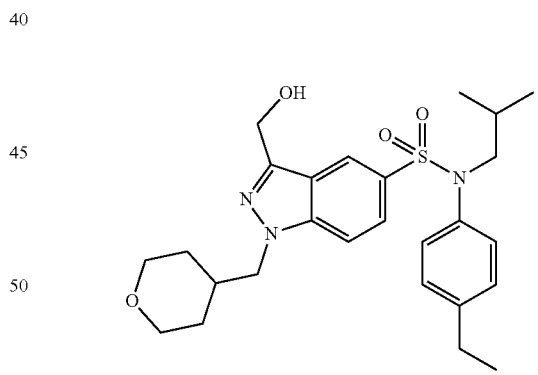

2.5 M n-Butyllithium (900 µl; 2.24 mmol) is added, under argon, to a solution of 3-bromo-1-(tetrahydropyran-4-ylmethyl)-1H-indazole-5-sulfonic acid (4-ethylphenyl)isobutylamide (200 mg; 0.37 mmol) in tetrahydrofuran (3 ml) at a temperature of −78° C. The reaction medium is stirred for 30 minutes, paraformaldehyde (980 mg; 2.24 mmol) is then added, the temperature is allowed to return to room temperature and the medium is then stirred for 3 hours at a temperature of 60° C.

The reaction medium is hydrolyzed with 1M hydrochloric acid solution (5 ml) at room temperature for 10 days, and diluted with ethyl acetate (50 ml).

The organic phase is washed with saturated NH₄Cl solution (20 ml), with saturated NaHCO₃ solution (20 ml) and with water (20 ml), dried (MgSO₄), filtered and concentrated to dryness.

The crude product is purified by preparative HPLC (C18 column, eluent: acetonitrile in water/0.1% of formic acid). The 3-hydroxymethyl-1-(tetrahydropyran-4-ylmethyl)-1H-indazole-5-sulfonic acid (4-ethylphenyl)isobutylamide (20 mg; 11%) is obtained in the form of a colorless oil.

¹H NMR (CD3OD-d4) δ: 0.90 (d, J=6.7 Hz, 7H), 1.22 (t, J=7.6 Hz, 3H), 1.27-1.58 (m, 4H), 1.71 (d, J=12.7 Hz, 2H), 2.16 (s, 1H), 2.64 (q, J=7.7 Hz, 2H), 3.35 (s, 2H), 3.41 (t, J=11.6 Hz, 2H), 3.96 (dd, J=11.9, 4.1 Hz, 2H), 4.66 (s, 2H), 6.92 (d, J=9.0 Hz, 1H), 7.00 (d, J=7.9 Hz, 2H), 7.16 (d, J=8.0 Hz, 2H), 7.44 (d, J=8.6 Hz, 1H), 8.03 (d, J=2.4 Hz, 1H)
MS: [M+H]=486

Part V: Synthesis of the Bicyclic Sulfonamides Via Reaction Scheme 5

1. Synthesis of Intermediate 61.1

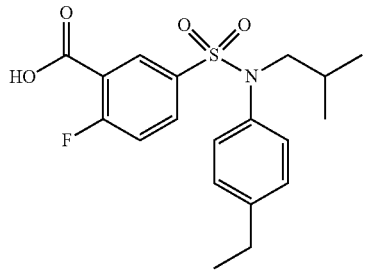 [SMILES: CCc1ccc(N(CC(C)C)S(=O)(=O)c2ccc(F)c(C(=O)O)c2)cc1]

Reaction scheme 5

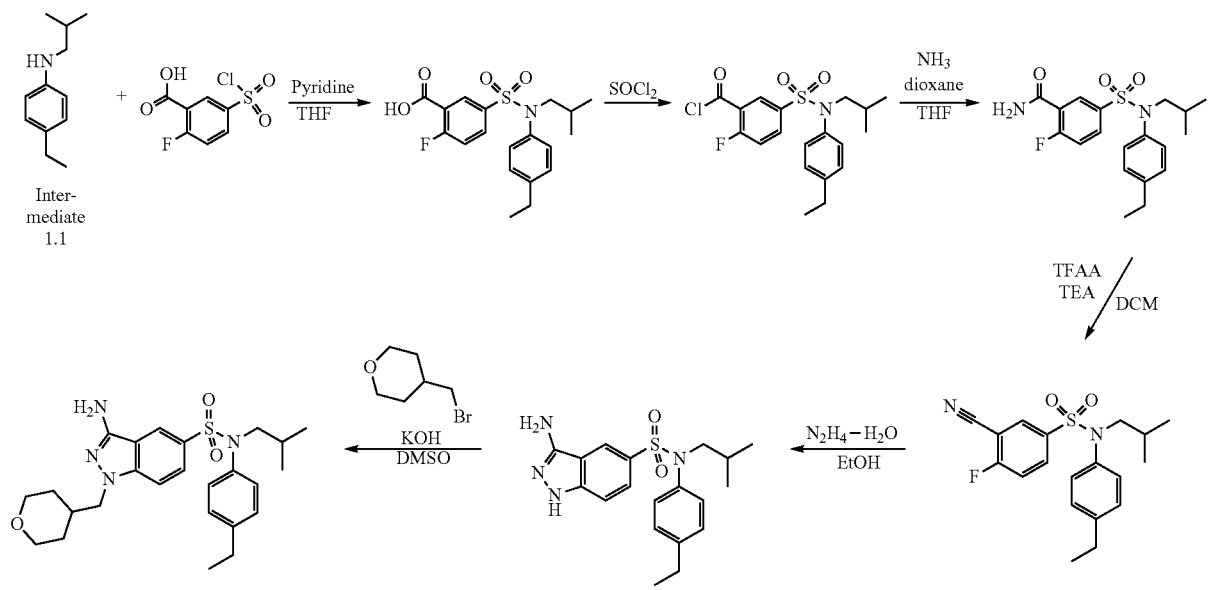

Example 62: Synthesis of 3-amino-1H-indazole-5-sulfonic acid (4-ethylphenyl)isobutylamide

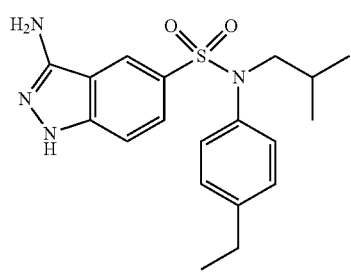

Compound 34

5-[(4-ethylphenyl)isobutylsulfamoyl]-2-fluorobenzoic acid

A solution of (4-ethylphenyl)isobutylamine (0.80 g; 4.51 mmol) and pyridine (0.36 ml; 4.51 mmol) in tetrahydrofuran (8 ml) is added to a solution of 5-chlorosulfonyl-2-fluorobenzoic acid (1.44 g; 5.87 mmol) in tetrahydrofuran (8 ml).

The reaction medium is stirred for 19 hours at room temperature, hydrolyzed with aqueous 1N HCl solution and diluted with ethyl acetate.

The organic phase is washed with aqueous 1N HCl solution. The organic phase is dried (Na₂SO₄), filtered and concentrated.

The crude product is chromatographed on silica gel (eluent: dichloromethane/methanol, from 0 to 10% of methanol) and then by preparative HPLC (C18 column, eluent: from 60% to 70% of acetonitrile in water/0.1% of formic acid). The 5-[(4-ethylphenyl)isobutylsulfamoyl]-2- fluorobenzoic acid (0.56 g; 33%) is obtained in the form of an off-white solid with a compliant ¹H NMR.

MS: [M−H]=378

2. Synthesis of Intermediate 61.2

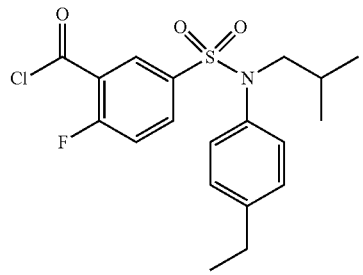 [SMILES: CCc1ccc(N(CC(C)C)S(=O)(=O)c2ccc(F)c(C(=O)Cl)c2)cc1]

5-[(4-ethylphenyl)isobutylsulfamoyl]-2-fluorobenzoic

A solution of 5-[(4-ethylphenyl)isobutylsulfamoyl]-2-fluorobenzoic acid (0.59 g; 1.55 mmol) in thionyl chloride (5.0 ml) is stirred for 3 hours at reflux and then concentrated to dryness. The 5-[(4-ethylphenyl)isobutylsulfamoyl]-2-fluorobenzoyl chloride (0.62 g; 100%) is obtained in the form of a brown oil.

MS: [M−H]=397

3. Synthesis of Intermediate 61.3

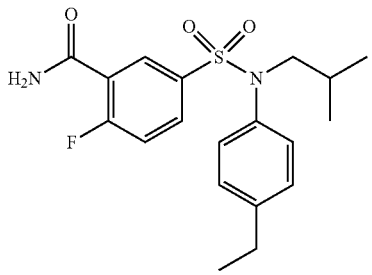 [SMILES: CCc1ccc(N(CC(C)C)S(=O)(=O)c2ccc(F)c(C(N)=O)c2)cc1]

5-[(4-ethylphenyl)isobutylsulfamoyl]-2-fluorobenzamide

A 0.5M solution of ammonia in dioxane (8.4 ml; 4.2 mmol) is added portionwise over a period of 43 hours to a solution of 5-[(4-ethylphenyl)isobutylsulfamoyl]-2-fluorobenzoyl chloride (0.31 g; 0.78 mmol) in tetrahydrofuran (3 ml). The reaction medium is hydrolyzed with aqueous NaHCO₃ solution and extracted with ethyl acetate.

The extracted organic phase is washed with 1N sodium hydroxide, dried (Na₂SO₄), filtered and concentrated. The crude product is chromatographed on silica gel (eluent: heptane/ethyl acetate, from 20 to 50% of ethyl acetate). The 5-[(4-ethylphenyl)isobutylsulfamoyl]-2-fluorobenzamide (0.17 g; 58%) is obtained in the form of a white solid with a compliant ¹H NMR.

MS: [M−H]=379

4. Synthesis of Intermediate 61.4

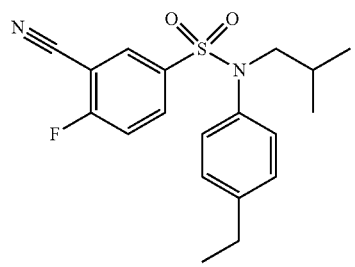 [SMILES: CCc1ccc(N(CC(C)C)S(=O)(=O)c2ccc(F)c(C#N)c2)cc1]

3-cyano-N-(4-ethylphenyl)-4-fluoro-N-isobutylbenzenesulfonamide

Triethylamine (0.19 ml; 1.35 mmol) and then trifluoroacetic anhydride (93 μl; 0.67 mmol) are added to a solution of 5-[(4-ethylphenyl)isobutylsulfamoyl]-2-fluorobenzamide (0.17 g; 0.45 mmol) at 0° C. The reaction medium is stirred for 1 hour, hydrolyzed for 15 minutes and extracted with ethyl acetate. The organic phases are combined, dried (Na₂SO₄), filtered and concentrated.

The 3-cyano-N-(4-ethylphenyl)-4-fluoro-N-isobutylbenzenesulfonamide (0.17 g; 89%) is obtained in the form of a white solid (HPLC purity=85%) with a compliant ¹H NMR.

MS: [M−H]=361

5. Synthesis of Compound 34 According to the Invention

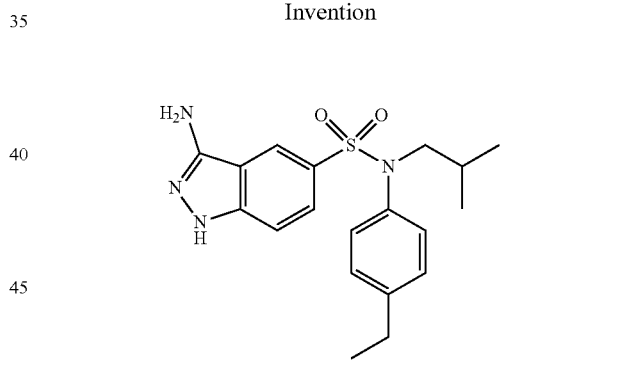

Hydrazine hydrate (1.25 ml; 25.7 mmol) is added to a suspension of 3-cyano-N-(4-ethylphenyl)-4-fluoro-N-isobutylbenzenesulfonamide (0.19 g; 0.45 mmol) in ethanol (2.5 ml). The reaction medium is stirred for 50 minutes at a temperature of 100° C. in a tube. The reaction medium is concentrated.

The crude product is purified by preparative HPLC (C18 column, eluent: acetonitrile in water/0.2% of ammonium carbonate). The 3-amino-1H-indazole-5-sulfonic acid (4-ethylphenyl)isobutylamide (78 mg; 53%) is obtained in the form of a solid.

¹H NMR (DMSO-d6) δ: 0.85 (d, J=6.6 Hz, 6H), 1.17 (t, J=7.5 Hz, 3H), 1.34-1.48 (m, 1H), 2.59 (q, J=7.7 Hz, 2H), 3.28-3.32 (m, 2H), 5.73 (s, 2H), 6.96 (d, J=7.8 Hz, 2H), 7.16 (d, J=7.8 Hz, 2H), 7.26 (d, J=8.8 Hz, 1H), 7.32 (d, J=8.8 Hz, 1H), 8.19 (s, 1H), 11.91 (s, 1H).

MS: [M−H]=373

Example 63: Synthesis of 3-amino-1H-indazole-5-sulfonic acid (4-ethylphenyl)isobutylamide

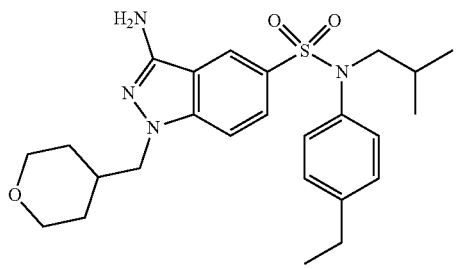

Compound 15

3-Amino-1H-indazole-5-sulfonic acid (4-ethylphenyl)isobutylamide (54 mg; 0.14 mmol) in dimethyl sulfoxide (0.80 ml) is added to potassium hydroxide (29 mg; 0.44 mmol) at 85% in dimethyl sulfoxide (0.20 ml). The reaction medium is stirred for 5 minutes and 4-(bromomethyl)tetrahydropyran (27 mg; 0.15 mmol) in dimethyl sulfoxide (0.50 ml) is then added. Stirring is continued for 3 hours 20 minutes, followed by hydrolysis with a few drops of water and filtration through a filter syringe. The filtrate is purified by preparative HPLC (C18 column, eluent: acetonitrile in water/0.1% of formic acid).

The 3-amino-1-(tetrahydropyran-4-ylmethyl)-1H-indazole-5-sulfonic acid (4-ethylphenyl)isobutylamide (30 mg; 44%) is obtained in the form of a colorless oil.

$^1$H NMR (DMSO-d6) δ: 0.85 (d, J=6.6 Hz, 6H), 1.17 (t, J=7.6 Hz, 3H), 1.21-1.47 (m, 5H), 2.59 (q, J=7.6 Hz, 2H), 3.23 (td, J=11.5, 2.4 Hz, 2H), 3.77-3.88 (m, 2H), 4.03 (d, J=7.0 Hz, 2H), 6.92-7.01 (m, 2H), 7.16 (d, J=8.3 Hz, 2H), 7.26 (dd, J=8.9, 1.8 Hz, 1H), 7.51 (d, J=8.9 Hz, 1H), 8.17 (d, J=1.7 Hz, 1H).

MS: [M−H]=471

Part VI: Synthesis of the Bicyclic Sulfonamides Via Reaction Scheme 6

Reaction scheme 6

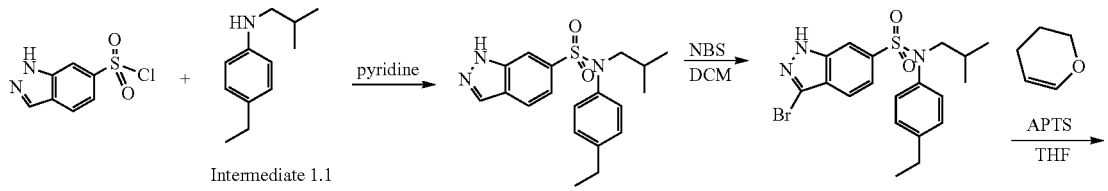

Intermediate 1.1

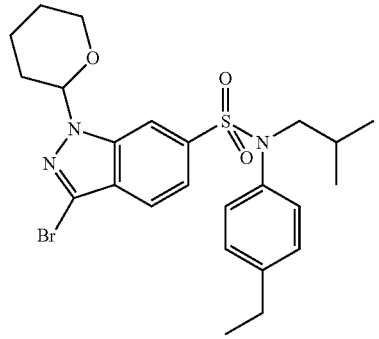

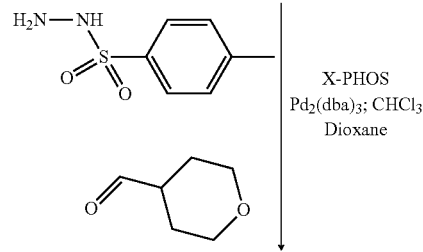

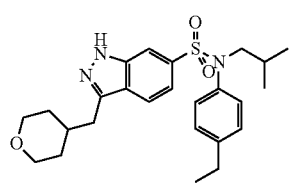 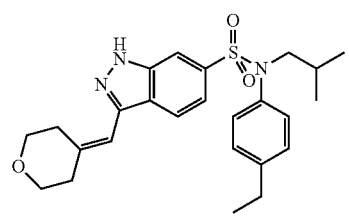 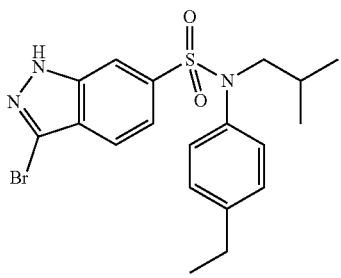

Example 64: Synthesis of 3-(tetrahydropyran-4-ylidenemethyl)-1H-indazole-6-sulfonic acid (4-ethylphenyl)isobutylamide Compound 62

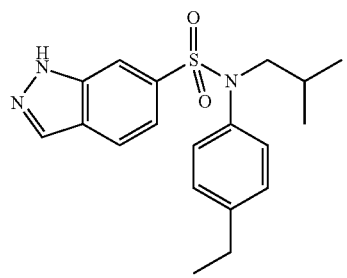 [SMILES: CCc1ccc(N(CC(C)C)S(=O)(=O)c2ccc3cn[nH]c3c2)cc1]

1. Synthesis of Intermediate 63.1

1H-Indazole-6-sulfonic acid (4-ethylphenyl)isobutylamide

A mixture of 1H-indazole-6-sulfonyl chloride (500 mg; 2.31 mmol), pyridine (3 ml) and (4-ethylphenyl)oxetan-3-ylmethylamine (491 mg; 2.77 mmol) is stirred for 30 minutes at a temperature of 50° C. The reaction medium is diluted with ethyl acetate.

The organic phase is washed with saturated NH₄Cl solution, with saturated NaHCO₃ solution and with water. It is dried over magnesium sulfate, filtered and concentrated to dryness.

The crude product is chromatographed on silica gel (eluent: heptane/ethyl acetate, from 0 to 40% of ethyl acetate). The 1H-Indazole-6-sulfonic acid (4-ethylphenyl)isobutylamide (640 mg; 78%) is obtained in the form of a colorless oil and is obtained with a compliant ¹H NMR.

MS: [M+H]=358

2. Synthesis of Intermediate 63.2

3-bromo-1H-indazole-6-sulfonic acid (4-ethylphenyl)isobutylamide

N-Bromosuccinimide (956 mg; 5.37 mmol) is added to a solution of 1H-indazole-6-sulfonic acid (4-ethylphenyl)isobutylamide (1.60 g; 4.48 mmol) in dichloromethane (10 ml). The reaction medium is stirred for 16 hours at room temperature and diluted with dichloromethane.

The organic phase is extracted and washed with saturated ammonium chloride solution, with saturated sodium hydrogen carbonate solution and with water. It is dried (MgSO₄), filtered and concentrated to dryness. The 3-bromo-1H-indazole-6-sulfonic acid (4-ethylphenyl)isobutylamide (1.9 g; 97%) is obtained in the form of a pale yellow solid with a compliant ¹H NMR.

MS: [M+H]=436

3. Synthesis of Intermediate 63.3

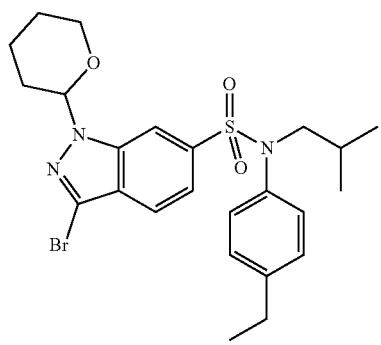 [SMILES: CCc1ccc(N(CC(C)C)S(=O)(=O)c2ccc3c(Br)nn(C4CCCCO4)c3c2)cc1]

3-bromo-1-(tetrahydropyran-2-yl)-1H-indazole-6-sulfonic acid (4-ethylphenyl)isobutylamide A mixture of 3-bromo-1H-indazole-6-sulfonic acid (4-ethylphenyl)isobutylamide (700 mg; 1.60 mmol), pyridinium p-toluenesulfonate (202 mg; 0.80 mmol) and 3,4-dihydro-2H-pyran (0.58 ml; 6.42 mmol) in tetrahydrofuran (10 ml) is stirred for 16 hours at 80° C. The reaction medium is diluted with ethyl acetate (20 ml) and extracted.

The organic phase is washed with saturated $NH_4Cl$ solution, with saturated $NaHCO_3$ solution and with water, dried ($MgSO_4$), filtered and concentrated to dryness.

The crude product is purified by preparative HPLC (C18 column, eluent: acetonitrile in water/0.1% of formic acid). The 3-bromo-1-(tetrahydropyran-2-yl)-1H-indazole-6-sulfonic acid (4-ethylphenyl)isobutylamide (500 mg; 57%) is obtained in the form of a white solid.

$^1$H NMR (DMSO-d6) δ: 0.86 (dd, J=13.3, 6.7 Hz, 6H), 1.18 (t, J=7.6 Hz, 3H), 1.38-1.63 (m, 3H), 1.68-1.81 (m, 1H), 1.98 (d, J=10.7 Hz, 2H), 2.60 (q, J=7.6 Hz, 2H), 3.36-3.41 (m, 2H), 3.67-3.76 (m, 1H), 6.00 (dd, J=9.3, 2.4 Hz, 1H), 6.95-7.02 (m, 2H), 7.16-7.21 (m, 2H), 7.41 (dd, J=8.5, 1.4 Hz, 1H), 7.83 (d, J=8.8 Hz, 1H), 7.99 (s, 1H)

MS: [M+H]=520

4. Synthesis of Intermediate 63.4

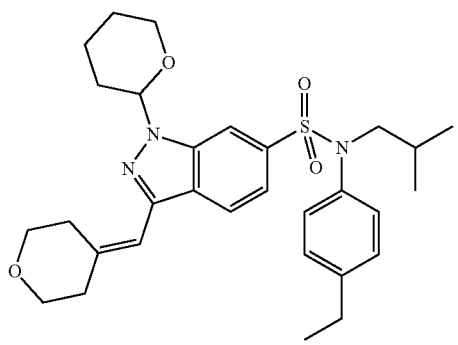 [SMILES: CCc1ccc(N(CC(C)C)S(=O)(=O)c2ccc3c(C=C4CCOCC4)nn(C4CCCCO4)c3c2)cc1]

1-(tetrahydropyran-2-yl)-3-(tetrahydropyran-4-ylidenemethyl)-1H-indazole-6-sulfonic acid (4-ethylphenyl)isobutylamide A mixture of p-toluenesulfonyl hydrazide (286 mg; 1.54 mmol), 4-formyltetrahydropyran (175 mg; 1.54 mmol) and 1,4-dioxane (2 ml) is stirred for 1 hour under argon. Lithium tert-butoxide (125 mg; 1.54 mmol), X-PHOS (18 mg; 0.04 mmol), tris(dibenzylideneacetone)dipalladium(0)-chloroform adduct (40 mg; 0.04 mmol) and 3-bromo-1-(tetrahydropyran-2-yl)-1H-indazole-6-sulfonic acid (4-ethylphenyl)isobutylamide (200 mg; 0.38 mmol) are added under argon, and the reaction medium is stirred for 5 hours at 100° C.

The reaction medium is diluted with 20 ml of ethyl acetate and extracted. The organic phase is washed with saturated $NH_4Cl$ solution (20 ml), with saturated $NaHCO_3$ solution (20 ml) and with water (20 ml), dried ($MgSO_4$), filtered and concentrated.

The crude product is chromatographed on silica gel (eluent: heptane/ethyl acetate, from 0 to 100% of ethyl acetate). The 1-(tetrahydropyran-2-yl)-3-(tetrahydropyran-4-ylidenemethyl)-1H-indazole-6-sulfonic acid (4-ethylphenyl) isobutylamide (100 mg; 48%) is obtained in the form of a yellow oil with a compliant $^1$H NMR.

MS: [M+H]=538

5. Synthesis of Compound 62 According to the Invention

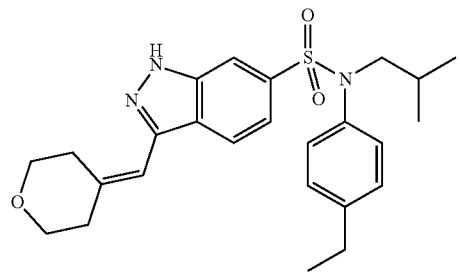 [SMILES: CCc1ccc(N(CC(C)C)S(=O)(=O)c2ccc3c(C=C4CCOCC4)n[nH]c3c2)cc1]

A mixture of 1-(tetrahydropyran-2-yl)-3-(tetrahydropyran-4-ylidenemethyl)-1H-indazole-6-sulfonic acid (4-ethylphenyl)isobutylamide (100 mg; 0.19 mmol), acetic acid (6 ml) and water (2 ml) is stirred for 5 hours at a temperature of 80° C. The reaction medium is diluted with 20 ml of ethyl acetate and extracted. The organic phase is washed with saturated $NH_4Cl$ solution (20 ml), with saturated $NaHCO_3$ solution (20 ml) and with water (20 ml), dried ($MgSO_4$), filtered and concentrated.

The crude product is chromatographed on silica gel (eluent: heptane/ethyl acetate, from 0 to 100% of ethyl acetate). The 3-(tetrahydropyran-4-ylidenemethyl)-1H-indazole-6-sulfonic acid (4-ethylphenyl)isobutylamide (80 mg; 93%) is obtained in the form of a white solid.

$^1$H NMR (DMSO-d6) δ: 0.85 (d, J=6.7 Hz, 7H), 1.17 (t, J=7.6 Hz, 3H), 1.41 (dt, J=13.6, 6.8 Hz, 1H), 2.60 (q, J=7.3 Hz, 2H), 2.93 (t, J=5.4 Hz, 2H), 3.65 (t, J=5.5 Hz, 2H), 3.73 (t, J=5.4 Hz, 2H), 6.61 (s, 1H), 6.95 (d, J=8.3 Hz, 2H), 7.13-7.21 (m, 2H), 7.22 (dd, J=8.5, 1.5 Hz, 1H), 7.63-7.67 (m, 1H), 7.98 (d, J=8.5 Hz, 1H).

MS: [M+H]=454

Example 65: Synthesis of 3-(tetrahydropyran-4-ylmethyl)-1H-indazole-6-sulfonic acid (4-ethylphenyl)isobutylamide

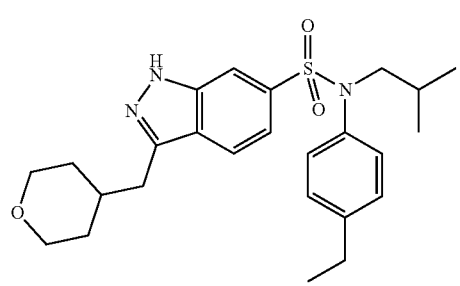

Compound 63

3-(Tetrahydropyran-4-ylidenemethyl)-1H-indazole-6-sulfonic acid (4-ethylphenyl)isobutylamide (60 mg; 0.13 mmol) in methanol (3 ml) in the presence of palladium (5% Pd on activated charcoal: Degussa type) (14 mg) is placed for 16 hours under hydrogen (1 atm). The reaction medium is filtered through Celite. The filtrate is concentrated to dryness. The crude product is chromatographed on silica gel (eluent: heptane/ethyl acetate, from 0 to 100% of ethyl acetate). The 3-(tetrahydropyran-4-ylmethyl)-1H-indazole-6-sulfonic acid (4-ethylphenyl)isobutylamide (30 mg; 50%) is obtained in the form of a white solid.

$^1$H NMR (DMSO-d6) δ: 0.85 (d, J=6.4 Hz, 6H), 1.17 (t, J=7.6 Hz, 3H), 1.23-1.48 (m, 3H), 1.56 (d, J=13.4 Hz, 2H), 1.97 (d, J=11.7 Hz, 1H), 2.56-2.65 (m, 2H), 2.90 (d, J=7.0 Hz, 2H), 3.26 (t, J=11.3 Hz, 2H), 3.82 (dd, J=11.6, 3.8 Hz, 2H), 6.97 (d, J=8.1 Hz, 2H), 7.19 (dd, J=14.2, 8.2 Hz, 3H), 7.62 (s, 1H), 7.95 (d, J=8.3 Hz, 1H), 13.15 (s, 1H).

MS: [M+H]=456

Part VII: Synthesis of the Bicyclic Sulfonamides Via Reaction Scheme 7

1. Synthesis of Intermediate 65.1

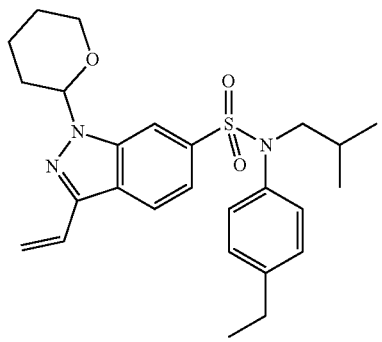 [SMILES: C=Cc1nn(C2CCCCO2)c2cc(S(=O)(=O)N(CC(C)C)c3ccc(CC)cc3)ccc12]

Reaction scheme 7

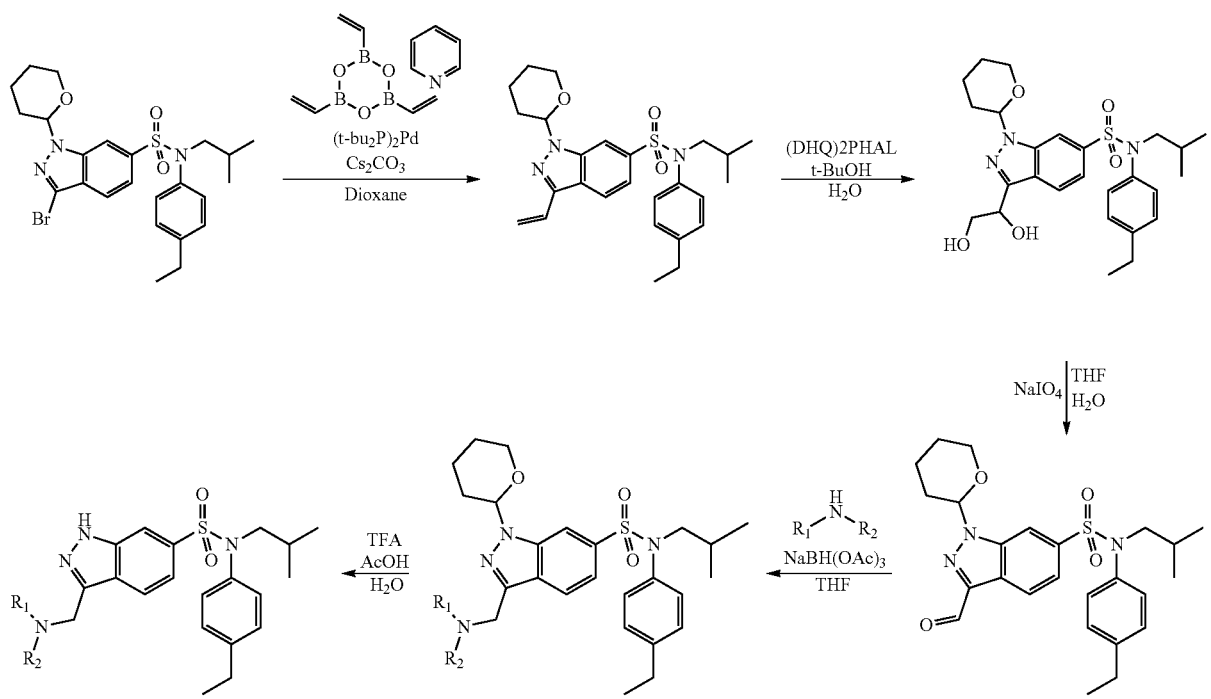

Example 65: Synthesis of 3-morpholin-4-ylmethyl-1H-indazole-6-sulfonic acid (4-ethylphenyl)isobutylamide Compound 64

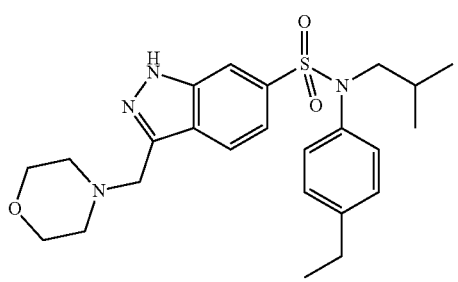

1-(tetrahydropyran-2-yl)-3-vinyl-1H-indazole-6-sulfonic acid (4-ethylphenyl)isobutylamide Bis(tri-t-butylphosphine)palladium(0) (49 mg; 0.10 mmol) is added to a mixture, degassed under argon, of 3-bromo-1-(tetrahydropyran-2-yl)-1H-indazole-6-sulfonic acid (4-ethylphenyl)isobutylamide (500 mg; 0.96 mmol), cesium carbonate (940 mg; 2.88 mmol) and vinylboronic anhydride-pyridine complex (462 mg; 1.92 mmol) in 1,4-dioxane (3 ml) and water (1 ml).

The reaction medium is stirred for 3 hours at a temperature of 90° C. and filtered through Celite. The filtrate is diluted with ethyl acetate and extracted.

The organic phase is washed with 20 ml of saturated sodium hydrogen carbonate solution and with 20 ml of water. The organic phase is washed with saturated NH$_4$Cl solution (20 ml), with saturated NaHCO$_3$ solution (20 ml) and with water (20 ml), dried (MgSO$_4$), filtered and concentrated.

The crude product is chromatographed on silica gel (eluent: heptane/ethyl acetate, from 0 to 100% of ethyl acetate). The 1-(tetrahydropyran-2-yl)-3-vinyl-1H-indazole-6-sulfonic acid (4-ethylphenyl)isobutylamide (400 mg; 89%) is obtained in the form of a beige-colored solid with a compliant ¹H NMR.

MS: [M+H]=468

2. Synthesis of Intermediate 65.2

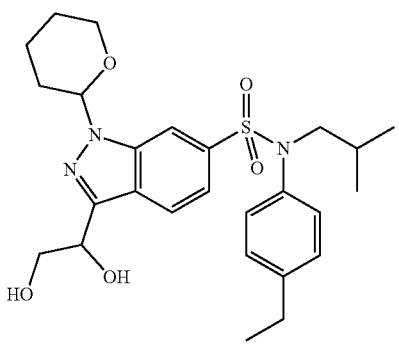 [SMILES: CCc1ccc(N(CC(C)C)S(=O)(=O)c2ccc3c(C(O)CO)nn(C4CCCCO4)c3c2)cc1]

3-(1,2-dihydroxyethyl)-1-(tetrahydropyran-2-yl)-1H-indazole-6-sulfonic acid (4-ethylphenyl)isobutylamide 1-(Tetrahydropyran-2-yl)-3-vinyl-1H-indazole-6-sulfonic acid (4-ethylphenyl)isobutylamide (400 mg; 0.86 mmol) is added to a mixture of (DHQ)₂PHAL (1.20 g; 1.46 mmol), tert-butyl alcohol (10 ml) and water (10 ml) cooled to a temperature of 0° C. The reaction medium is stirred for 16 hours at a temperature of 40° C. Sodium sulfite (5 g) is added.

The reaction medium is stirred for 45 minutes, diluted with ethyl acetate (30 ml) and extracted. The organic phases are combined, washed with saturated Na₂SO₃ solution (20 ml) and with water (20 ml), dried (MgSO₄), filtered and concentrated. The crude product is chromatographed on silica gel (eluent: heptane/ethyl acetate, from 0 to 100% of ethyl acetate).

The 3-(1,2-dihydroxyethyl)-1-(tetrahydropyran-2-yl)-1H-indazole-6-sulfonic acid (4-ethylphenyl)isobutylamide (380 mg; 89%) is obtained in the form of a clear oil with a compliant ¹H NMR.

MS: [M+H]=502

3. Synthesis of Intermediate 65.3

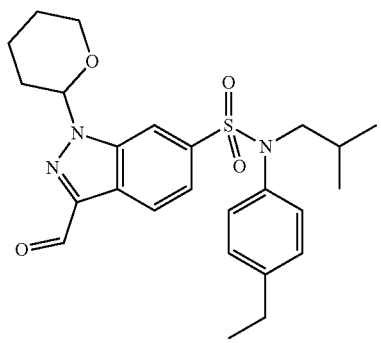 [SMILES: CCc1ccc(N(CC(C)C)S(=O)(=O)c2ccc3c(C=O)nn(C4CCCCO4)c3c2)cc1]

3-formyl-1-(tetrahydropyran-2-yl)-1H-indazole-6-sulfonic acid (4-ethylphenyl)isobutylamide Sodium metaperiodate (1.62 g; 7.58 mmol) is added to a mixture of 3-(1,2-dihydroxyethyl)-1-(tetrahydropyran-2-yl)-1H-indazole-6-sulfonic acid (4-ethylphenyl)isobutylamide (380 mg; 0.76 mmol), acetone (2 ml), tetrahydrofuran (2 ml) and water (2 ml).

The reaction medium is stirred for 2 hours 30 minutes at a temperature of 35° C., diluted with ethyl acetate (30 ml) and water (20 ml) and extracted.

The organic phases are combined, washed with saturated Na₂SO₃ solution (20 ml) and with water (20 ml), dried (MgSO₄), filtered and concentrated. The 3-formyl-1-(tetrahydropyran-2-yl)-1H-indazole-6-sulfonic acid (4-ethylphenyl)isobutylamide (120 mg; 34%) is obtained in the form of a white solid with a compliant ¹H NMR.

MS: [M+H]=470

4. Synthesis of Intermediate 65.4

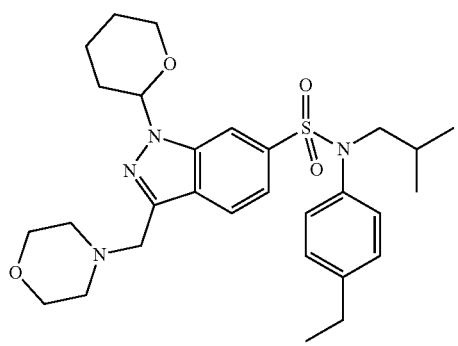 [SMILES: CCc1ccc(N(CC(C)C)S(=O)(=O)c2ccc3c(CN4CCOCC4)nn(C4CCCCO4)c3c2)cc1]

3-morpholin-4-ylmethyl-1-(tetrahydropyran-2-yl)-1H-indazole-6-sulfonic acid (4-ethylphenyl)isobutylamide Morpholine (45 µl; 0.51 mmol) and sodium triacetoxyborohydride (119 mg; 0.56 mmol) are added to a solution of 3-formyl-1-(tetrahydropyran-2-yl)-1H-indazole-6-sulfonic acid (4-ethylphenyl)isobutylamide (120 mg; 0.26 mmol) in tetrahydrofuran (3 ml). The reaction medium is stirred for 2 hours at room temperature. The reaction medium is diluted with ethyl acetate (20 ml) and water (10 ml) and extracted.

The organic phase is washed with saturated NH₄Cl solution (20 ml), with saturated NaHCO₃ solution (20 ml) and with water (20 ml), dried (MgSO₄) and concentrated.

The 3-morpholin-4-ylmethyl-1-(tetrahydropyran-2-yl)-1H-indazole-6-sulfonic acid (4-ethylphenyl)isobutylamide (130 mg; 94%) is obtained in the form of an oil with a compliant ¹H NMR.

MS: [M+H]=541

5. Synthesis of Compound 64 According to the Invention

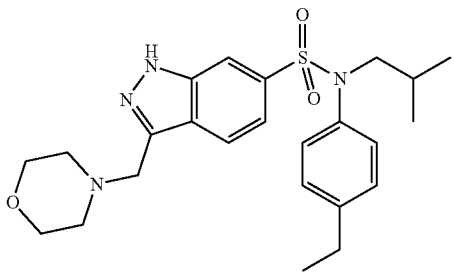 [SMILES: CCc1ccc(N(CC(C)C)S(=O)(=O)c2ccc3c(CN4CCOCC4)n[nH]c3c2)cc1]

A mixture of 3-morpholin-4-ylmethyl-1-(tetrahydropyran-2-yl)-1H-indazole-6-sulfonic acid (4-ethylphenyl)isobutylamide (130 mg; 0.24 mmol), acetic acid (30 ml) and water (10 ml) and a few drops of trifluoroacetic acid is stirred for 4 days at a temperature of 80° C. The reaction medium is diluted with 50 ml of ethyl acetate and extracted.

The organic phase is washed with saturated NH$_4$Cl solution (20 ml), with saturated NaHCO$_3$ solution (20 ml) and with water (20 ml), dried (MgSO$_4$), filtered and concentrated.

The crude product is purified by preparative HPLC (C18 column, eluent: acetonitrile in water/0.1% of formic acid). The 3-morpholin-4-ylmethyl-1H-indazole-6-sulfonic acid (4-ethylphenyl)isobutylamide (70 mg; 64%) is obtained in the form of a white solid after recrystallization from an acetone/water mixture.

1H NMR (DMSO-d6) δ: 0.85 (d, J=6.7 Hz, 6H), 1.18 (t, J=7.6 Hz, 3H), 2.44 (t, J=4.5 Hz, 4H), 2.61 (t, J=7.6 Hz, 2H), 3.33-3.37 (m, 2H), 3.87 (s, 2H), 6.95-7.00 (m, 2H), 7.15-7.21 (m, 2H), 7.25 (dd, J=8.5, 1.5 Hz, 1H), 8.06 (d, J=8.5 Hz, 1H), 13.27 (s, 1H).

MS: [M+H]=457

Example 66: Synthesis of 3-((cis)-2,6-dimethylmorpholin-4-ylmethyl)-1H-indazole-6-sulfonic acid (4-ethylphenyl)isobutylamide Compound 65

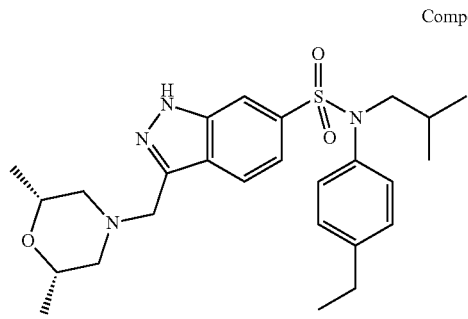

1. Synthesis of Intermediate 66.1

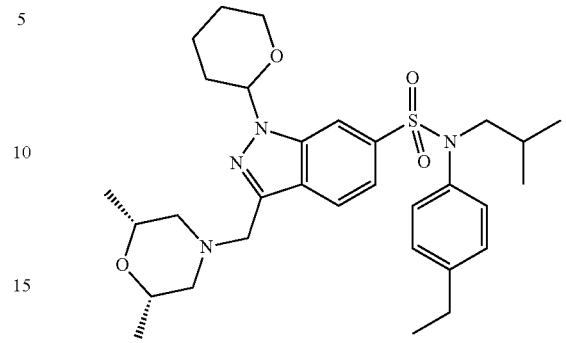

3-((2S,6R)-2,6-dimethylmorpholin-4-ylmethyl)-1-(tetrahydropyran-2-yl)-1H-indazole-6-sulfonic acid (4-ethylphenyl)isobutylamide cis-2,6-Dimethylmorpholine (50 µl; 0.38 mmol) and sodium triacetoxyborohydride (122 mg; 0.57 mmol) are added to a solution of 3-formyl-1-(tetrahydropyran-2-yl)-1H-indazole-6-sulfonic acid (4-ethylphenyl)isobutylamide (90 mg; 0.19 mmol) in tetrahydrofuran (2 ml).

The reaction medium is stirred for 16 hours at room temperature. The reaction medium is diluted with ethyl acetate (20 ml) and water (10 ml) and extracted. The organic phase is washed with saturated NH$_4$Cl solution (20 ml), with saturated NaHCO$_3$ solution (20 ml) and with water (20 ml), dried (MgSO$_4$) and concentrated. The 3-((2S,6R)-2,6-dimethylmorpholin-4-ylmethyl)-1-(tetrahydropyran-2-yl)-1H-indazole-6-sulfonic acid (4-ethylphenyl)isobutylamide (90 mg; 83%) is obtained in the form of an oil with a compliant $^1$H NMR.

MS: [M+H]=570

2. Synthesis of Compound 65 According to the Invention

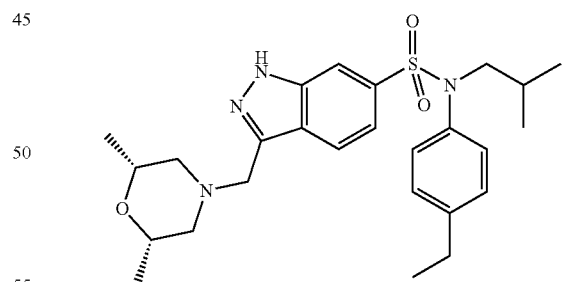

A mixture of 3-((2S,6R)-2,6-dimethylmorpholin-4-ylmethyl)-1-(tetrahydropyran-2-yl)-1H-indazole-6-sulfonic acid (4-ethylphenyl)isobutylamide (90 mg; 0.16 mmol), acetic acid (10 ml) and water (10 ml) and one drop of trifluoroacetic acid is stirred for 16 hours at a temperature of 80° C. The reaction medium is diluted with 50 ml of ethyl acetate and extracted.

The organic phase is washed with saturated NH$_4$Cl solution (20 ml), with saturated NaHCO$_3$ solution (20 ml) and with water (20 ml), dried (MgSO$_4$), filtered and concentrated.

The crude product is purified by preparative HPLC (C18 column, eluent: acetonitrile in water/0.1% of formic acid). The 3-((cis)-2,6-dimethylmorpholin-4-ylmethyl)-1H-indazole-6-sulfonic acid (4-ethylphenyl)isobutylamide (52 mg; 67%) is obtained in the form of a colorless oil.

1H NMR (DMSO-d6) δ: 0.85 (d, J=6.5 Hz, 6H), 1.02 (d, J=6.1 Hz, 6H), 1.18 (t, J=7.5 Hz, 3H), 1.42 (dt, J=13.3, 7.1 Hz, 1H), 1.74 (t, J=10.7 Hz, 2H), 2.55-2.65 (m, 2H), 2.70-2.80 (m, 2H), 3.33-3.44 (m, 2H), 3.55 (t, J=7.8 Hz, 2H), 3.85 (s, 2H), 6.98 (d, J=8.0 Hz, 2H), 7.17 (d, J=8.3 Hz, 2H), 7.23 (d, J=8.6 Hz, 1H), 7.66 (s, 1H), 8.03 (d, J=8.6 Hz, 1H), 8.20 (s, 1H), 13.25 (s, 1H).

MS: [M+H]=485

Example 67: Synthesis of 3-((S)-3-methylmorpholin-4-ylmethyl)-1H-indazole-6-sulfonic acid (4-ethylphenyl)isobutylamide Compound 66

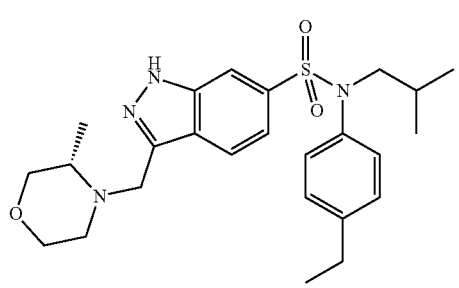

1. Synthesis of Intermediate 67.1

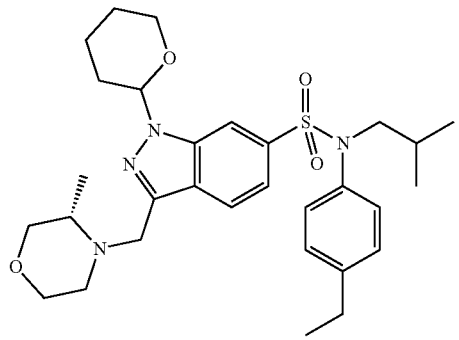 [SMILES: CCc1ccc(N(CC(C)C)S(=O)(=O)c2ccc3c(CN4CCOC[C@@H]4C)nn(C4CCCCO4)c3c2)cc1]

3-((S)-3-methylmorpholin-4-ylmethyl)-1-(tetrahydropyran-2-yl)-1H-indazole-6-sulfonic acid (4-ethylphenyl)isobutylamide With a procedure similar to that described for intermediate 67.1, 3-((S)-3-methylmorpholin-4-ylmethyl)-1-(tetrahydropyran-2-yl)-1H-indazole-6-sulfonic acid (4-ethylphenyl)isobutylamide (90 mg; 85%) is obtained in the form of an oil with a compliant $^1$H NMR.

MS: [M+H]=555

2. Synthesis of Compound 66 According to the Invention

With a procedure similar to that described for example 66, 3-((S)-3-methylmorpholin-4-ylmethyl)-1H-indazole-6-sulfonic acid (4-ethylphenyl)isobutylamide (42 mg; 54%) is obtained in the form of a colorless oil.

1H NMR (DMSO-d6) δ: 0.86 (d, J=6.8 Hz, 6H), 1.09-1.22 (m, 7H), 1.42 (dt, J=13.9, 6.9 Hz, 1H), 2.16-2.27 (m, 1H), 2.61 (t, J=7.6 Hz, 2H), 3.38 (d, J=19.0 Hz, 5H), 3.58-3.72 (m, 3H), 6.98 (d, J=7.9 Hz, 2H), 7.18 (d, J=7.9 Hz, 2H), 7.26 (d, J=8.5 Hz, 1H), 7.65 (s, 1H), 8.04 (d, J=8.6 Hz, 1H), 8.24 (s, 1H), 13.24 (s, 1H).

MS: [M+H]=471

The invention claimed is:

1. A compound of formula (II), or a pharmaceutically acceptable salt thereof, a hydrate thereof, or a solvate thereof:

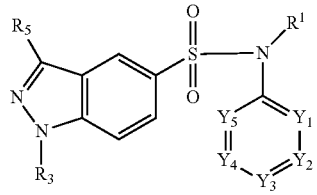

(II)

wherein:
one or two of the elements $Y^1$, $Y^2$, $Y^3$, $Y^4$ and $Y^5$ represent(s) a nitrogen atom and the other elements correspond to a group —$CR^2$, or each of the elements $Y^1$, $Y^2$, $Y^3$, $Y^4$ and $Y^5$ corresponds to a group —$CR^2$, $R^1$ represents a linear or branched $C_3$-$C_5$ alkyl radical, optionally substituted with a hydroxyl group and/or a halogen atom, a $C_3$-$C_5$ cycloalkyl radical, a —$CH_2$—$(C_3$-$C_5)$cycloalkyl radical, or a —$CH_2$—$(C_4$-$C_6)$heterocycloalkyl radical, $R^2$ represents a hydrogen atom or a halogen atom, a linear or branched $C_1$-$C_5$ alkyl radical, a $C_1$-$C_4$ alkoxy radical, a cyano group —CN, or a radical —C(=O)$R'^2$ with $R'^2$ denoting a $C_1$-$C_3$ alkoxy radical, or a —$CF_3$ radical; said alkyl, alkenyl and alkoxy radicals optionally being substituted with one or more halogen atoms, $R^3$ represents a hydrogen atom, a halogen atom, or a group $(CHR^6)_n$—$(Z)_o$—$(CHR'^6)_p$—$R^7$ or a group CH=$R^7$, n and o are zero,
p is zero or 1,
$R'^6$ represent a hydrogen atom,
$R^7$ represents:
  a heterocycloalkyl radical, wherein the heterocycloalkyl radical is optionally substituted with one or more halogen atoms, one or more linear or branched $C_1$-$C_3$ alkyl groups, one or more —OH groups, one or more carbonyl functions, one or more linear or branched $C_1$-$C_4$ hydroxyalkyl groups, one or more amino groups, one or more groups —C(=O)$R^{7a}$, or one or more groups S(=O)$_2R^{7a}$; $R^{7a}$ representing a linear or branched $C_1$-$C_3$ alkyl radical, a linear or branched $C_1$-$C_3$ alkoxy radical, or an amino radical N($R^{8a}$)($R^{8b}$),
  an aromatic radical, wherein the aromatic radical is optionally substituted with one or more halogen atoms, one or more linear or branched $C_1$-$C_3$ alkyl groups optionally substituted with one or more halogen atoms, one or more $C_1$-$C_3$ alkoxy groups, one or more amino groups —$NR^{11}R^{12}$, one or more groups —COR$^{11}$, one or more groups —COOR$^{11}$, one or more amido groups CONR$^{11}$R$^{12}$, one or more groups —SOR$^{11}$, one or more groups —SO$_2$R$^{11}$, one or more groups —NHCOR$^{11}$, one or more groups —NHCOOR$^{11}$, one or more groups —SO$_2$NR$^{11}$R$^{12}$ or one or more CN groups; R$^{11}$ and R$^{12}$, which are identical or different, representing a hydrogen atom, a hydroxyl radical —OH, or a linear or branched C$_1$-C$_3$ alkyl radical optionally substituted with one or more halogen atoms; or a heteroaromatic radical, wherein the heteroaromatic radical is optionally substituted with one or more halogen atoms, one or more linear or branched C$_1$-C$_3$ alkyl groups optionally substituted with one or more halogen atoms, one or more C$_1$-C$_3$ alkoxy groups, one or more amino groups —NR$^{11}$R$^{12}$, one or more groups —COR$^{11}$, one or more groups —COOR$^{11}$, one or more amido groups CONR$^{11}$R$^{12}$, one or more groups —SOR$^{11}$, one or more groups —SO$_2$R$^{11}$, one or more groups —NHCOR$^{11}$, one or more groups —NHCOOR$^{11}$, one or more groups —SO$_2$NR$^{11}$R$^{12}$ or one or more CN groups; R$^{11}$ and R$^{12}$, which are identical or different, representing a hydrogen atom, a hydroxyl radical —OH, or a linear or branched C$_1$-C$_3$ alkyl radical optionally substituted with one or more halogen atoms;

R$^5$ represents a hydrogen atom, a linear or branched C$_1$-C$_3$ alkyl radical optionally substituted with one or more halogen atoms; an amino radical —NH$_2$, an OCH$_2$—(C$_4$-C$_5$) heterocyclic radical, or a radical CH$_2$R$^{\prime7a}$ with R$^{\prime7a}$ denoting a hydroxyl group —OH function, and R$^{8a}$ and R$^{8b}$, which are identical or different, denote a hydrogen atom, a linear or branched C$_1$-C$_3$ alkyl radical or a cyclopropyl radical.

2. A compound of formula (III), or a pharmaceutically acceptable salt thereof, a hydrate thereof, or a solvate thereof:

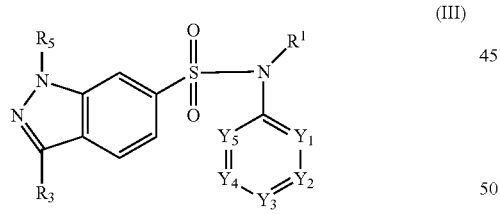

(III)

wherein:
one or two of the elements Y$^1$, Y$^2$, Y$^3$, Y$^4$ and Y$^5$ represent(s) a nitrogen atom and the other elements correspond to a group —CR$^2$, or each of the elements Y$^1$, Y$^2$, Y$^3$, Y$^4$ and Y$^5$ corresponds to a group —CR$^2$, R$^1$ represents a linear or branched C$_3$-C$_5$ alkyl radical, optionally substituted with a hydroxyl group and/or a halogen atom, a C$_3$-C$_5$ cycloalkyl radical, a linear or branched C$_2$-C$_5$ alkenyl radical, a —CH$_2$—(C$_3$-C$_5$)cycloalkyl radical, a C$_4$-C$_5$ heterocycloalkyl radical, or a —CH$_2$—(C$_4$-C$_6$)heterocycloalkyl radical, R$^2$ represents a hydrogen atom or a halogen atom, a linear or branched C$_1$-C$_5$ alkyl radical, a linear or branched C$_2$-C$_4$ alkenyl radical, a C$_1$-C$_4$ alkoxy radical, a cyano group —CN, a radical —C(=O)R$^{\prime2}$ with R$^{\prime2}$ denoting a C$_1$-C$_3$ alkoxy radical, or a —CF$_3$ radical; said alkyl, alkenyl and alkoxy radicals optionally being substituted with one or more halogen atoms, R$^3$ represents a hydrogen atom, a halogen atom, a group (CHR$^6$)$_n$—(Z)$_o$—(CHR$^{\prime6}$)$_p$—R$^7$ or a group CH=R$^7$, n, o and p, which are identical or different, represent zero or a natural integer ranging from 1 to 3, Z represents a divalent group selected from the group consisting of a methylene group —CH$_2$—, an amino group —NH— and an oxygen atom —O—, R$^6$ and R$^{\prime6}$, which are identical or different, represent a hydrogen atom, a methyl group —CH$_3$, a group —OH, a hydroxymethyl group, or a carboxylic function COOH, R$^7$ represents:
a hydrogen or a halogen atom,
a group COOR$^{\prime7}$ with R$^{\prime7}$ denoting (C$_1$)alkyl(C$_6$) heterocycle,
a heterocycloalkyl radical, wherein the heterocycloalkyl radical is optionally substituted with one or more halogen atoms, one or more linear or branched C$_1$-C$_3$ alkyl groups, one or more —OH groups, one or more carbonyl functions, one or more linear or branched C$_1$-C$_4$ hydroxyalkyl groups, one or more amino groups, one or more groups —C(=O)R$^{7a}$, or one or more groups S(=O)$_2$R$^{7a}$; R$^{7a}$ representing a linear or branched C$_1$-C$_3$ alkyl radical, a linear or branched C$_1$-C$_3$ alkoxy radical, or an amino radical N(R$^{8a}$)(R$^{8b}$),
a C$_3$-C$_6$ cycloalkyl radical, wherein the cycloalkyl radical is optionally substituted with one or more methyl radicals, one or more halogen atoms, a cyano group —CN or one or more groups —COR$^{13}$; R$^{13}$ denoting a linear or branched C$_1$-C$_3$ alkoxy radical, or a hydroxyl group,
an aromatic radical, wherein the aromatic radical is optionally substituted with one or more halogen atoms, one or more linear or branched C$_1$-C$_3$ alkyl groups optionally substituted with one or more halogen atoms, one or more C$_1$-C$_3$ alkoxy groups, one or more amino groups —NR$^{11}$R$^{12}$, one or more groups —COR$^{11}$, one or more groups —COOR$^{11}$, one or more amido groups CONR$^{12}$, one or more groups —SOR$^{11}$, one or more groups —SO$_2$R$^{11}$, one or more groups —NHCOR$^{11}$, one or more groups —NHCOOR$^{11}$, one or more groups —SO$_2$NR$^{11}$R$^{12}$ or one or more CN groups; R$^{11}$ and R$^{12}$, which are identical or different, representing a hydrogen atom, a hydroxyl radical —OH, or a linear or branched C$_1$-C$_3$ alkyl radical optionally substituted with one or more halogen atoms; or
a heteroaromatic radical, wherein the heteroaromatic radical is optionally substituted with one or more halogen atoms, one or more linear or branched C$_1$-C$_3$ alkyl groups optionally substituted with one or more halogen atoms, one or more C$_1$-C$_3$ alkoxy groups, one or more amino groups —NR$^{11}$R$^{12}$, one or more groups —COR$^{11}$, one or more groups —COOR$^{11}$, one or more amido groups CONR$^{11}$R$^{12}$, one or more groups —SOR$^{11}$, one or more groups —SO$_2$R$^{11}$, one or more groups —NHCOR$^{11}$, one or more groups —NHCOOR$^{11}$, one or more groups —SO$_2$NR$^{11}$R$^{12}$ or one or more CN groups; R$^{11}$ and R$^{12}$, which are identical or different, representing a hydrogen atom, a hydroxyl radical —OH, a linear or branched C$_1$-C$_3$ alkyl radical optionally substituted with one or more halogen atoms;

R⁵ represents a hydrogen atom, a linear or branched $C_1$-$C_3$ alkyl radical optionally substituted with one or more halogen atoms; an amino radical —$NH_2$, a $C_4$-$C_5$ heterocyclic radical, an $OCH_2$—($C_4$-$C_5$) heterocyclic radical, a radical $CH_2R'^{7a}$ with $R'^{7a}$ denoting a methoxy radical, a hydroxyl group —OH, a —$CH_2COOH$ group, a group —$CH(R^{5b})OH$, a carboxylic group —COOH, a —CN group, or a thioxo function, $R^{5b}$ represents a hydrogen atom, a linear or branched $C_1$-$C_3$ alkyl radical optionally substituted with one or more carboxylic functions, or a cyclopropyl radical, and $R^{8a}$ and $R^{8b}$, which are identical or different, denote a hydrogen atom, a linear or branched $C_1$-$C_3$ alkyl radical or a cyclopropyl radical.

3. The compound of formula (II) as defined by claim 1, wherein the compound is selected from the group consisting of:

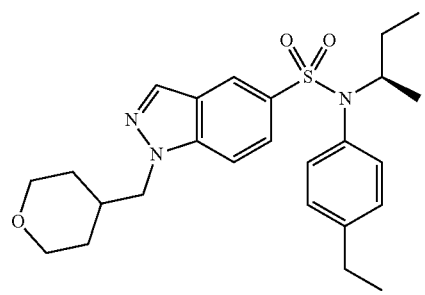 [SMILES: CCc1ccc(N([C@H](C)CC)S(=O)(=O)c2ccc3c(cnn3CC3CCOCC3)c2)cc1]

1-(tetrahydropyran-4-ylmethyl)-1H-indazole-5-sulfonic acid (4 ethylphenyl)(1 ethylpropyl)amide Compound 1, 1-(tetrahydropyran-4-ylmethyl)-1H-indazole-5-sulfonic acid ((R)-sec-butyl)(4-ethylphenyl)amide Compound 2,

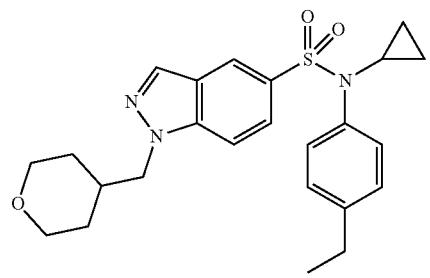 [SMILES: CCc1ccc(N(C2CC2)S(=O)(=O)c2ccc3c(cnn3CC3CCOCC3)c2)cc1]

1-(tetrahydropyran-4-ylmethyl)-1H-indazole-5-sulfonic acid cyclopropyl(4-ethylphenyl)amide Compound 3,

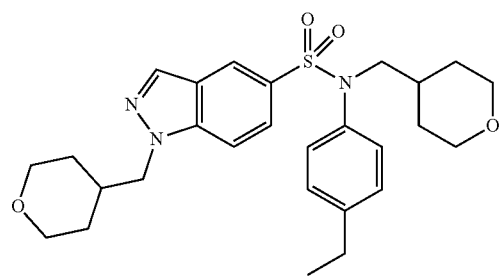 [SMILES: CCc1ccc(N(CC2CCOCC2)S(=O)(=O)c2ccc3c(cnn3CC3CCOCC3)c2)cc1]

1-(tetrahydropyran-4-ylmethyl)-1H-indazole-5-sulfonic acid (4-ethylphenyl)(tetrahydropyran-4-ylmethyl)amide Compound 5,

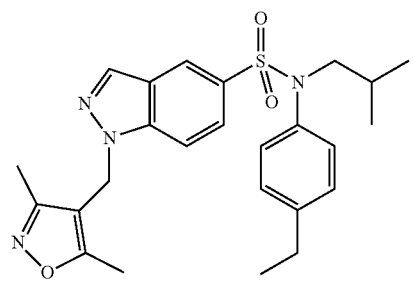 [SMILES: CCc1ccc(N(CC(C)C)S(=O)(=O)c2ccc3c(cnn3Cc3c(C)noc3C)c2)cc1]

1-((3,5-dimethylisoxazol-4-yl)methyl)-N-(4-ethylphenyl)-N-isobutyl-1H-indazole-5-sulfonamide Compound 6,

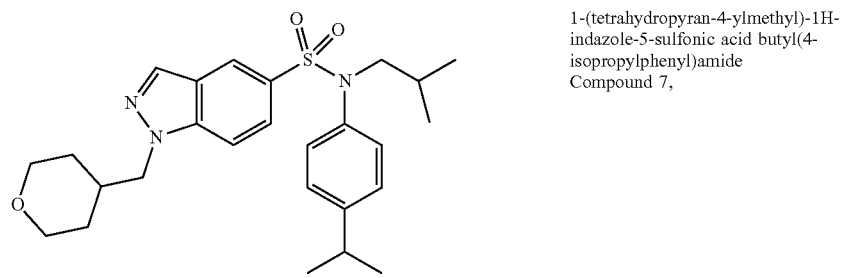

1-(tetrahydropyran-4-ylmethyl)-1H-indazole-5-sulfonic acid butyl(4-isopropylphenyl)amide
Compound 7,

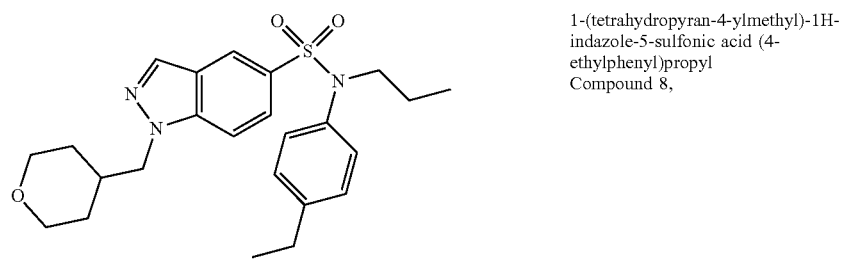

1-(tetrahydropyran-4-ylmethyl)-1H-indazole-5-sulfonic acid (4-ethylphenyl)propyl
Compound 8,

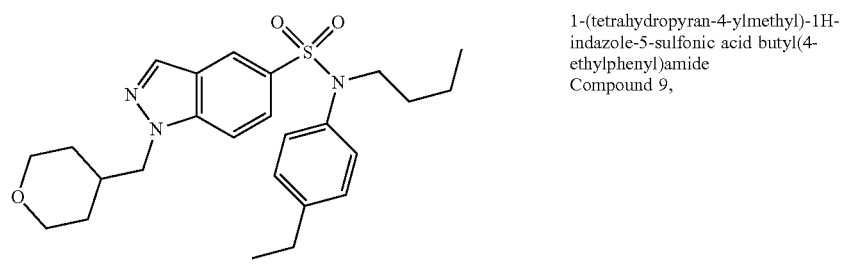

1-(tetrahydropyran-4-ylmethyl)-1H-indazole-5-sulfonic acid butyl(4-ethylphenyl)amide
Compound 9,

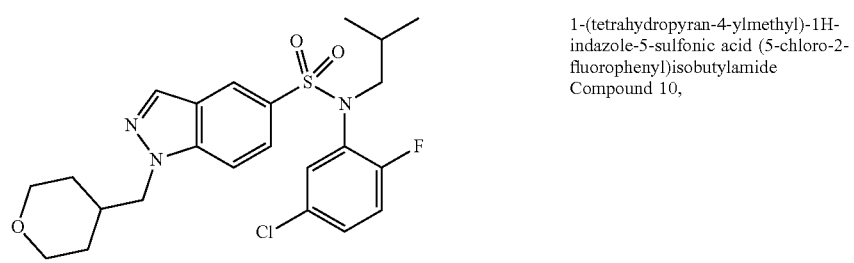

1-(tetrahydropyran-4-ylmethyl)-1H-indazole-5-sulfonic acid (5-chloro-2-fluorophenyl)isobutylamide
Compound 10,

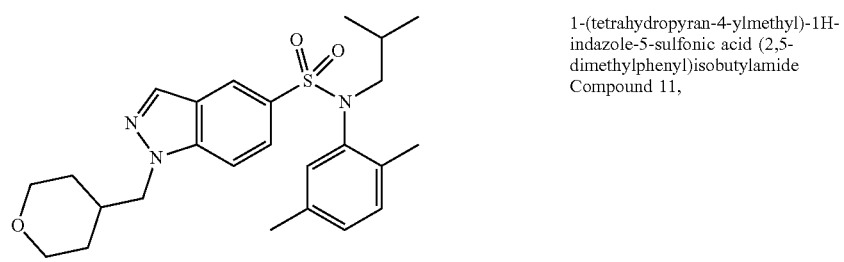

1-(tetrahydropyran-4-ylmethyl)-1H-indazole-5-sulfonic acid (2,5-dimethylphenyl)isobutylamide
Compound 11,

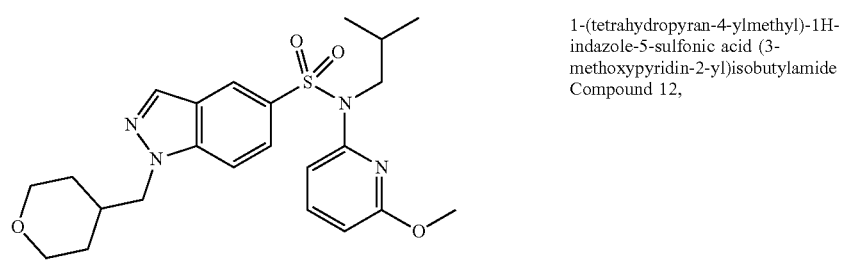

1-(tetrahydropyran-4-ylmethyl)-1H-indazole-5-sulfonic acid (3-methoxypyridin-2-yl)isobutylamide
Compound 12, -continued

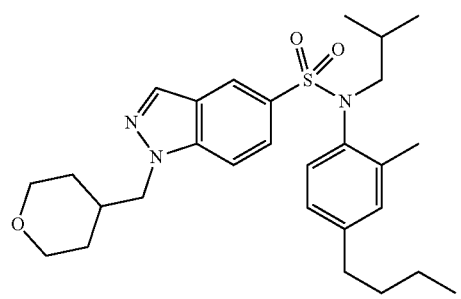 [SMILES: CCCCc1ccc(N(CC(C)C)S(=O)(=O)c2ccc3c(cnn3CC3CCOCC3)c2)c(C)c1]

1-(tetrahydropyran-4-ylmethyl)-1H-indazole-5-sulfonic acid (4-butyl-2-methylphenyl)isobutylamide Compound 13,

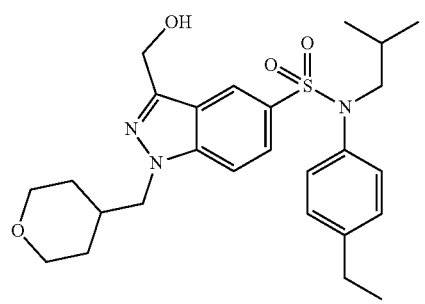 [SMILES: CCc1ccc(N(CC(C)C)S(=O)(=O)c2ccc3c(c2)c(CO)nn3CC2CCOCC2)cc1]

N-(4-ethylphenyl)-N-isobutyl-1-((tetrahydro-2H-pyran-4-yl)methyl)-1H-indazole-5-sulfonamide Compound 14,

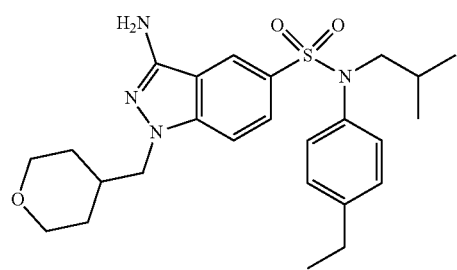 [SMILES: CCc1ccc(N(CC(C)C)S(=O)(=O)c2ccc3c(c2)c(N)nn3CC2CCOCC2)cc1]

3-amino-1H-indazole-5-sulfonic acid (4-ethylphenyl)isobutylamide Compound 15,

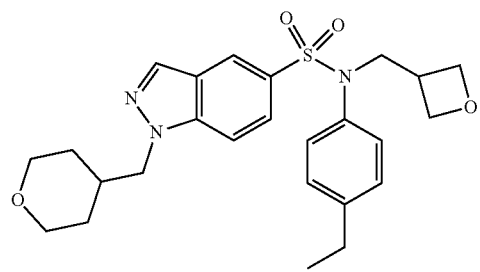 [SMILES: CCc1ccc(N(CC2COC2)S(=O)(=O)c2ccc3c(cnn3CC3CCOCC3)c2)cc1]

1-(tetrahydropyran-4-ylmethyl)-1H-indazole-5-sulfonic acid (4-ethylphenyl)oxetan-3-ylmethylamide Compound 16,

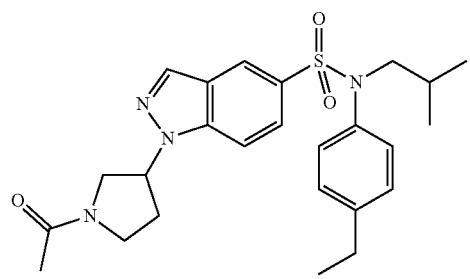 [SMILES: CCc1ccc(N(CC(C)C)S(=O)(=O)c2ccc3c(cnn3C3CCN(C(C)=O)C3)c2)cc1]

1-(1-acetylpyrrolidin-3-yl)-1H-indazole-5-sulfonic acid (4-ethylphenyl)isobutylamide Compound 17,

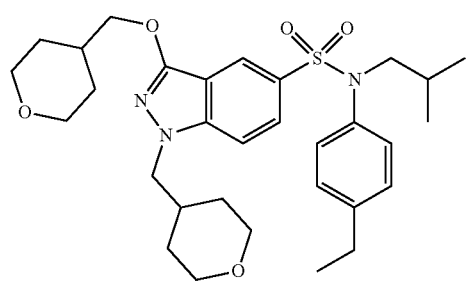 [SMILES: CCc1ccc(N(CC(C)C)S(=O)(=O)c2ccc3c(c2)c(OCC2CCOCC2)nn3CC2CCOCC2)cc1]

3-(tetrahydropyran-4-ylmethoxy)-1-(tetrahydropyran-4-ylmethyl)-1H-indazole-5-sulfonic acid (4-ehtlyphenyl)isobutylamide
Compound 18,

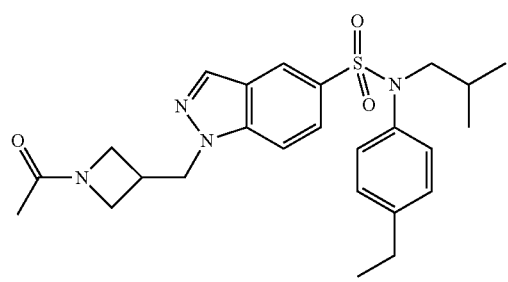 [SMILES: CCc1ccc(N(CC(C)C)S(=O)(=O)c2ccc3c(cnn3CC3CN(C(C)=O)C3)c2)cc1]

1-(3,5-dimethylisoxazol-4-ylmethyl)-1H-indazole-5-sulfonic acid (4-ethylphenyl)isobutylamide
Compound 19,

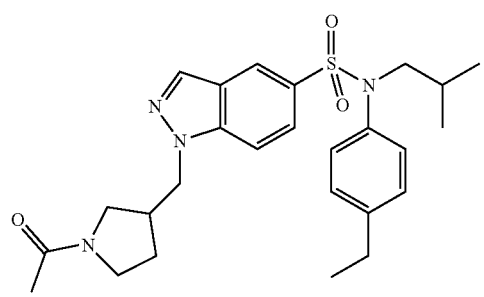 [SMILES: CCc1ccc(N(CC(C)C)S(=O)(=O)c2ccc3c(cnn3CC3CCN(C(C)=O)C3)c2)cc1]

1-((1-acetylpyrrolidin-3-yl)methyl)-N-(4-ethylphenyl)-N-isobutyl-1H-indazole-5-sulfonamide
Compound 20,

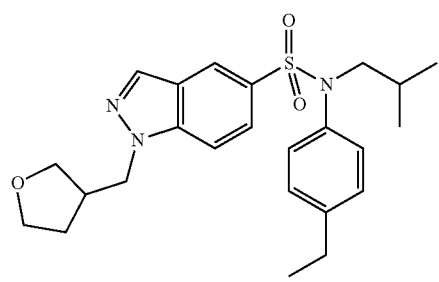 [SMILES: CCc1ccc(N(CC(C)C)S(=O)(=O)c2ccc3c(cnn3CC3CCOC3)c2)cc1]

N-(4-ethylphenyl)-N-isobutyl-1-((tetrahydrofuran-3-yl)methyl)-1H-indazole-5-sulfonamide
Compound 21,

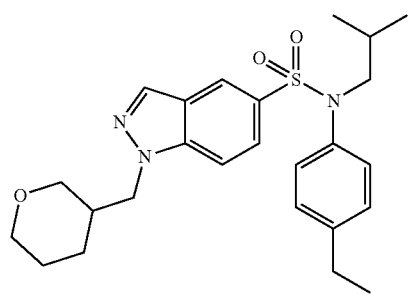 [SMILES: CCc1ccc(N(CC(C)C)S(=O)(=O)c2ccc3c(cnn3CC3CCCOC3)c2)cc1]

N-(4-ethylphenyl)-N-isobutyl-1-((tetrahydro-2H-pyran-3-yl)methyl)-1H-indazole-5-sulfonamide
Compound 22,

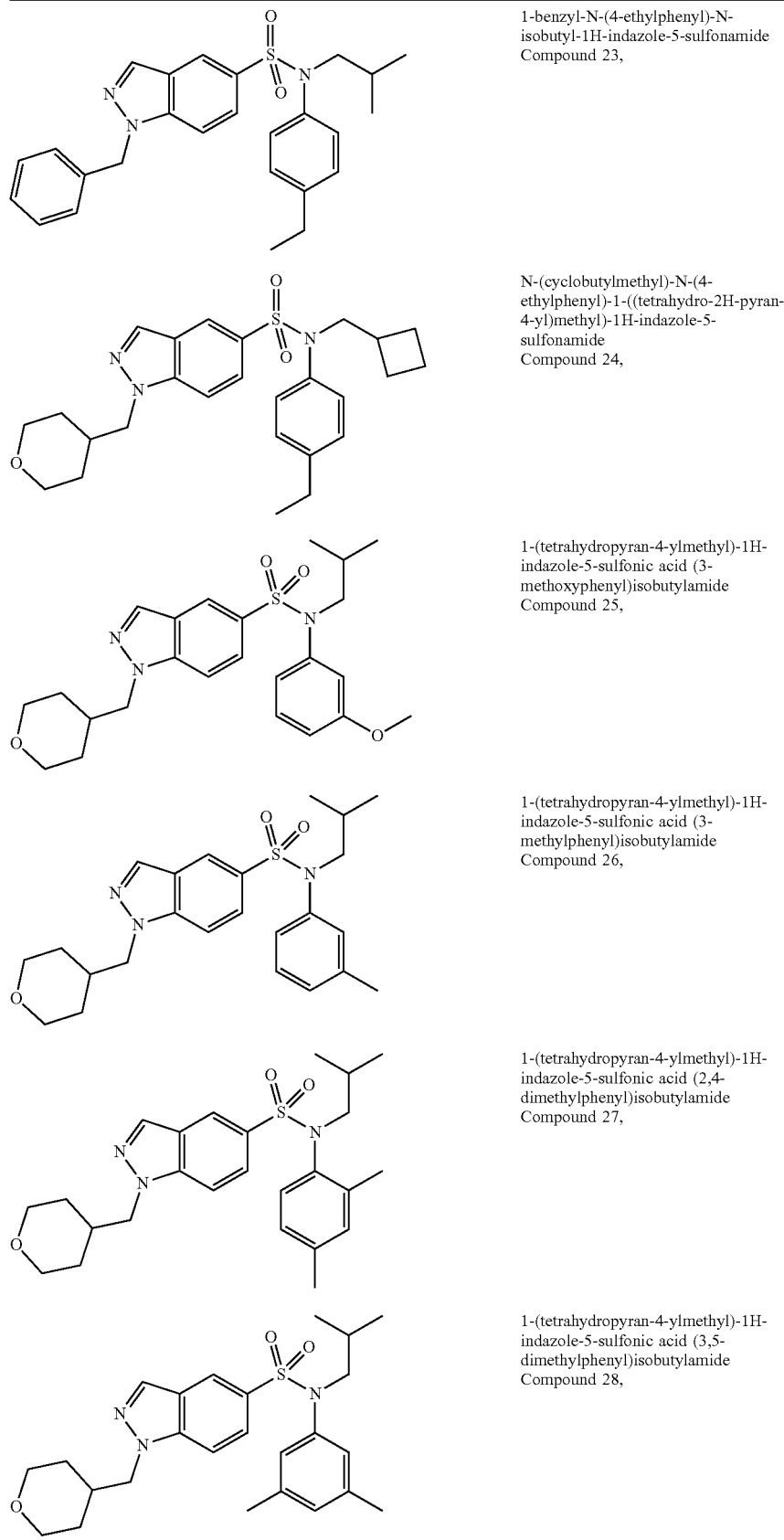

1-benzyl-N-(4-ethylphenyl)-N-isobutyl-1H-indazole-5-sulfonamide
Compound 23,

N-(cyclobutylmethyl)-N-(4-ethylphenyl)-1-((tetrahydro-2H-pyran-4-yl)methyl)-1H-indazole-5-sulfonamide
Compound 24, 1-(tetrahydropyran-4-ylmethyl)-1H-indazole-5-sulfonic acid (3-methoxyphenyl)isobutylamide
Compound 25, 1-(tetrahydropyran-4-ylmethyl)-1H-indazole-5-sulfonic acid (3-methylphenyl)isobutylamide
Compound 26, 1-(tetrahydropyran-4-ylmethyl)-1H-indazole-5-sulfonic acid (2,4-dimethylphenyl)isobutylamide
Compound 27, 1-(tetrahydropyran-4-ylmethyl)-1H-indazole-5-sulfonic acid (3,5-dimethylphenyl)isobutylamide
Compound 28,

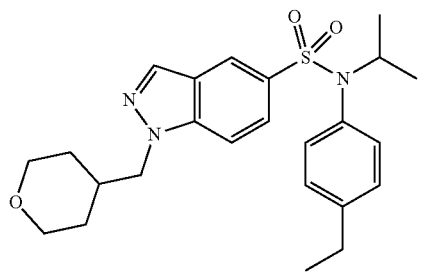 [SMILES: CCc1ccc(N(C(C)C)S(=O)(=O)c2ccc3c(cnn3CC3CCOCC3)c2)cc1]

N-(4-ethylphenyl)-N-isopropyl-1-((tetrahydro-2H-pyran-4-yl)methyl)-1H-indazole-5-sulfonamide
Compound 29,

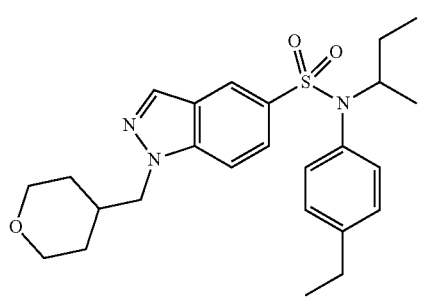 [SMILES: CCc1ccc(N(C(C)CC)S(=O)(=O)c2ccc3c(cnn3CC3CCOCC3)c2)cc1]

1-(tetrahydropyran-4-ylmethyl)-1H-indazole-5-sulfonic acid sec-butyl(4-ethylphenyl)amide
Compound 30,

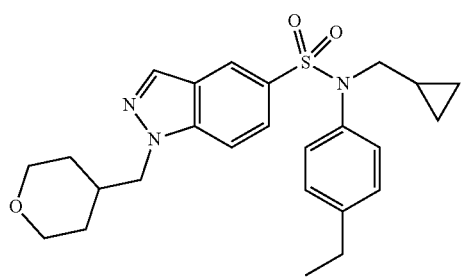 [SMILES: CCc1ccc(N(CC2CC2)S(=O)(=O)c2ccc3c(cnn3CC3CCOCC3)c2)cc1]

N-(cyclopropylmethyl)-N-(4-ethylphenyl)-1-((tetrahydro-2H-pyran-4-yl)methyl)-1H-indazole-5-sulfonamide
Compound 31,

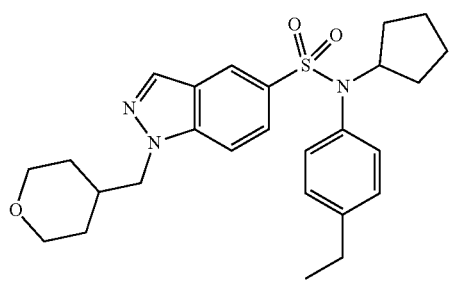 [SMILES: CCc1ccc(N(C2CCCC2)S(=O)(=O)c2ccc3c(cnn3CC3CCOCC3)c2)cc1]

1-(tetrahydropyran-4-ylmethyl)-1H-indazole-5-sulfonic acid cyclopentyl(4-ethylphenyl)amide
Compound 32,

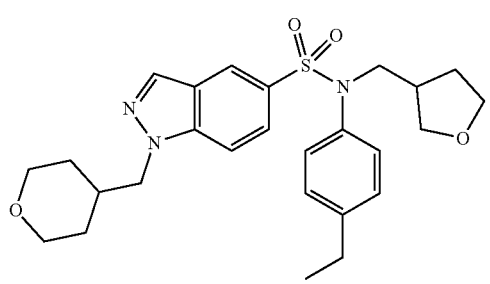 [SMILES: CCc1ccc(N(CC2CCOC2)S(=O)(=O)c2ccc3c(cnn3CC3CCOCC3)c2)cc1]

1-(tetrahydropyran-4-ylmethyl)-1H-indazole-5-sulfonic acid (4-ethylphenyl)(tetrahydrofuran-3-ylmethyl)amide
Compound 33,

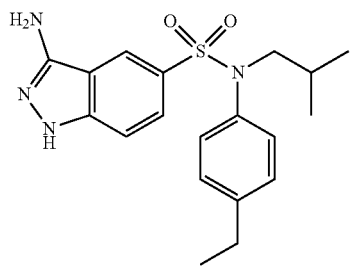 [SMILES: CCc1ccc(N(CC(C)C)S(=O)(=O)c2ccc3[nH]nc(N)c3c2)cc1]

3-amino-1H-indazole-5-sulfonic acid (4-ethylphenyl)isobutylamide
Compound 34,

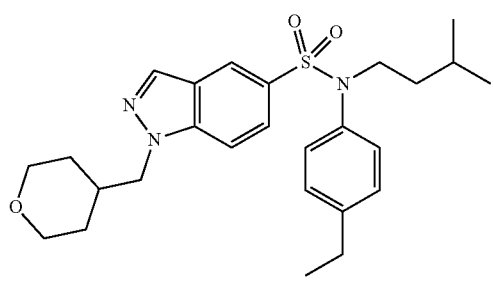 [SMILES: CCc1ccc(N(CCC(C)C)S(=O)(=O)c2ccc3c(cnn3CC3CCOCC3)c2)cc1]

N-(4-ethylphenyl)-N-isopentyl-1-((tetrahydro-2H-pyran-4-yl)methyl)-1H-indazole-5-sulfonamide
Compound 35,

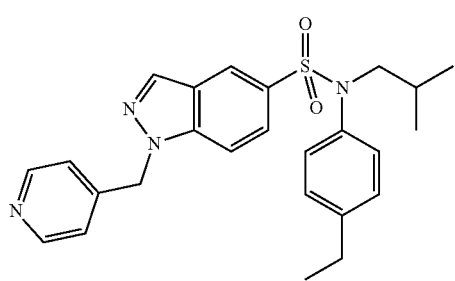 [SMILES: CCc1ccc(N(CC(C)C)S(=O)(=O)c2ccc3c(cnn3Cc3ccncc3)c2)cc1]

N-(4-ethylphenyl)-N-isobutyl-1-(pyridin-4-ylmethyl)-1H-indazole-5-sulfonamide
Compound 36,

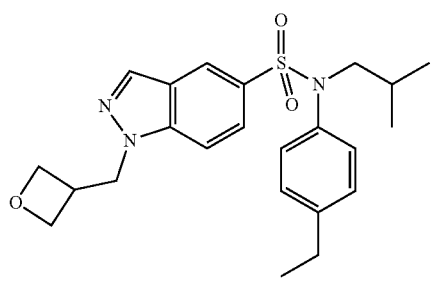 [SMILES: CCc1ccc(N(CC(C)C)S(=O)(=O)c2ccc3c(cnn3CC3COC3)c2)cc1]

N-(4-ethylphenyl)-N-isopentyl-1-(oxetan-3-ylmethyl)-1H-indazole-5-sulfonamide
Compound 37

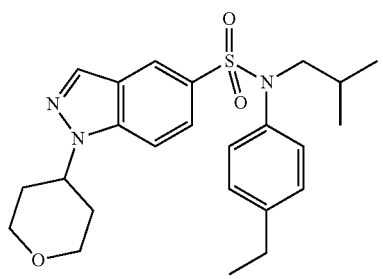 [SMILES: CCc1ccc(N(CC(C)C)S(=O)(=O)c2ccc3c(cnn3C3CCOCC3)c2)cc1]

1-(tetrahydropyran-4-yl)-1H-indazole-5-sulfonic acid (4-ethylphenyl)isobutylamide
Compound 38,

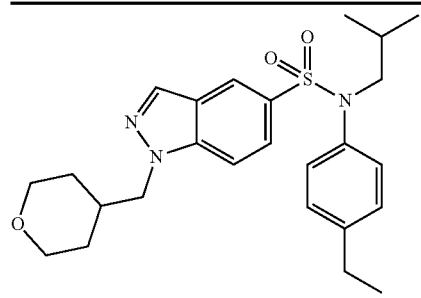
N-(4-ethylphenyl)-N-isopentyl-1-((tetrahydro-2H-pyran-4-yl)methyl)-1H-indazole-5-sulfonamide
Compound 39,

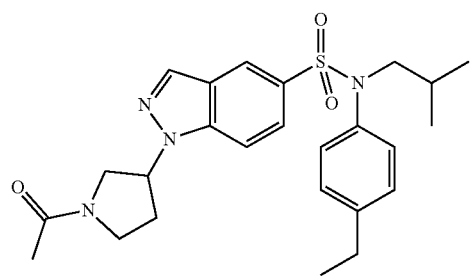 [SMILES: CCc1ccc(N(CC(C)C)S(=O)(=O)c2ccc3c(cnn3C3CCN(C(C)=O)C3)c2)cc1]
1-(1-acetylpyrrolidin-3-yl)-1H-indazole-5-sulfonic acid (4-ethylphenyl)isobutylamide
Compound 40,

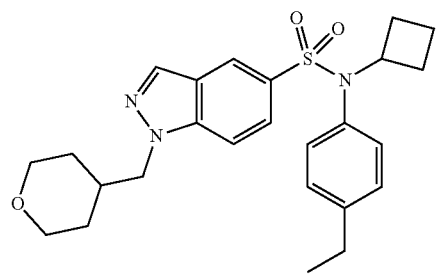 [SMILES: CCc1ccc(N(C2CCC2)S(=O)(=O)c2ccc3c(cnn3CC3CCOCC3)c2)cc1]
1-(tetrahydropyran-4-ylmethyl)-1H-indazole-5-sulfonic acid cyclobutyl(4-ethylphenyl)amide
Compound 41,

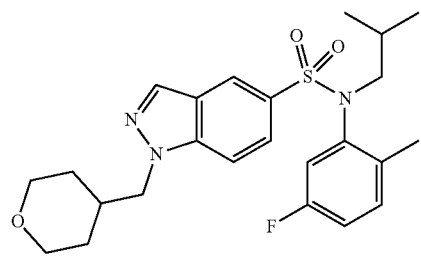 [SMILES: Cc1ccc(F)cc1N(CC(C)C)S(=O)(=O)c1ccc2c(cnn2CC2CCOCC2)c1]
1-(tetrahydropyran-4-ylmethyl)-1H-indazole-5-sulfonic acid (5-fluoro-2-methylphenyl)isobutylamide
Compound 42,

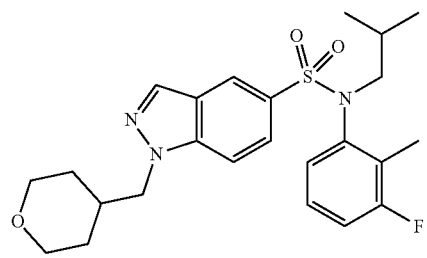 [SMILES: Cc1c(F)cccc1N(CC(C)C)S(=O)(=O)c1ccc2c(cnn2CC2CCOCC2)c1]
1-(tetrahydropyran-4-ylmethyl)-2H-indazole-5-sulfonic acid (3-fluoro-2-methylphenyl)isobutylamide
Compound 43,

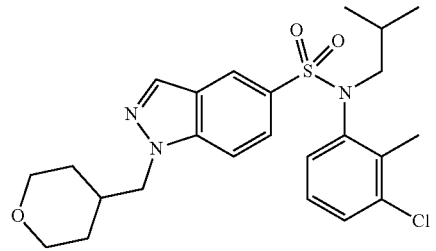 [SMILES: Cc1c(Cl)cccc1N(CC(C)C)S(=O)(=O)c1ccc2c(cnn2CC2CCOCC2)c1]
1-(tetrahydropyran-4-ylmethyl)-1H-indazole-5-sulfonic acid (5-chlorophenyl)isobutylamide
Compound 44, -continued

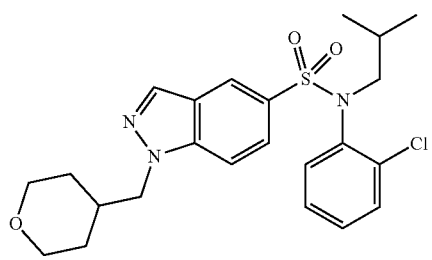 [SMILES: CC(C)CN(c1ccccc1Cl)S(=O)(=O)c1ccc2c(cnn2CC2CCOCC2)c1]

1-(tetrahydropyran-4-ylmethyl)-1H-indazole-5-sulfonic acid (2-chlorophenyl)isobutylamide
Compound 45,

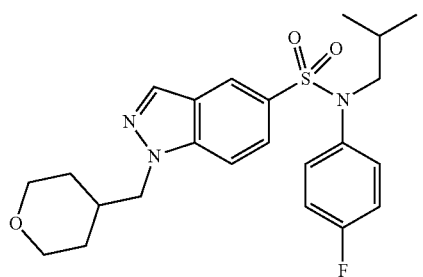 [SMILES: CC(C)CN(c1ccc(F)cc1)S(=O)(=O)c1ccc2c(cnn2CC2CCOCC2)c1]

1-(tetrahydropyran-4-ylmethyl)-1H-indazole-5-sulfonic acid (4-fluorophenyl)isobutylamide
Compound 46,

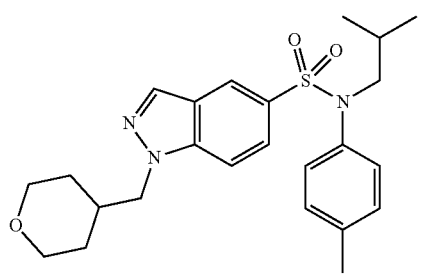 [SMILES: Cc1ccc(N(CC(C)C)S(=O)(=O)c2ccc3c(cnn3CC3CCOCC3)c2)cc1]

1-(tetrahydropyran-4-ylmethyl)-1H-indazole-5-sulfonic acid isobutyl-p-tolylamide
Compound 47,

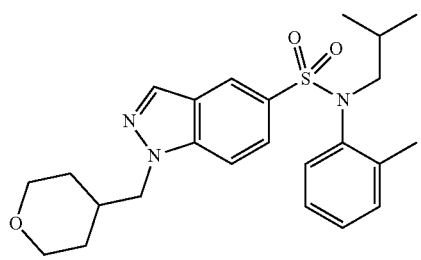 [SMILES: Cc1ccccc1N(CC(C)C)S(=O)(=O)c1ccc2c(cnn2CC2CCOCC2)c1]

1-(tetrahydropyran-4-ylmethyl)-1H-indazole-5-sulfonic acid isobutyl-o-tolylamide
Compound 48,

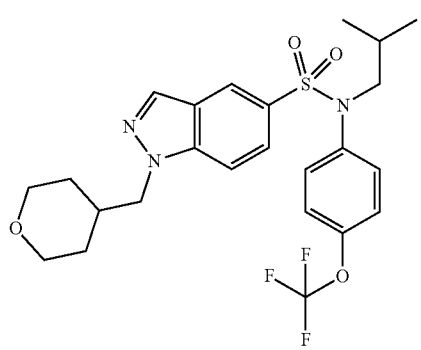 [SMILES: CC(C)CN(c1ccc(OC(F)(F)F)cc1)S(=O)(=O)c1ccc2c(cnn2CC2CCOCC2)c1]

1-(tetrahydropyran-4-ylmethyl)-1H-indazole-5-sulfonic acid (4-trifluoromethoxyphenyl)isobutylamide
Compound 49,

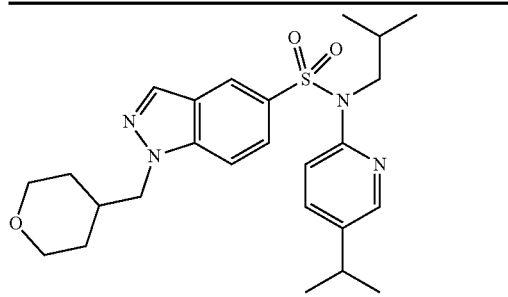

1-(tetrahydropyran-4-ylmethyl)-1H-indazole-5-sulfonic acid isobutyl(5-isopropylpyridin-2-yl)amide
Compound 50,

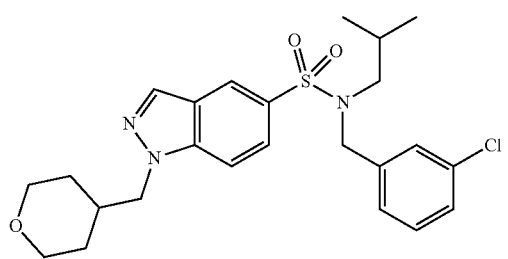 [SMILES: CC(C)CN(Cc1cccc(Cl)c1)S(=O)(=O)c1ccc2c(cnn2CC2CCOCC2)c1]

1-(tetrahydropyran-4-ylmethyl)-1H-indazole-5-sulfonic acid (3-chloro-benzyl)isobutylamide
Compound 51,

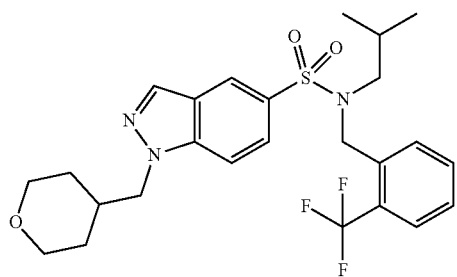 [SMILES: CC(C)CN(Cc1ccccc1C(F)(F)F)S(=O)(=O)c1ccc2c(cnn2CC2CCOCC2)c1]

1-(tetrahydropyran-4-ylmethyl)-1H-indazole-5-sulfonic acid isobutyl(2-trifluoromethylbenzyl)amide
Compound 52,

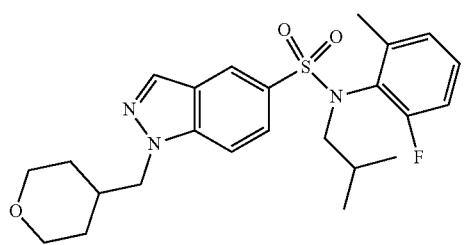 [SMILES: Cc1cccc(F)c1N(CC(C)C)S(=O)(=O)c1ccc2c(cnn2CC2CCOCC2)c1]

1-(tetrahydropyran-4-ylmethyl)-1H-indazole-5-sulfonic acid (2-fluoro-6-methylphenyl)isobutylamide
Compound 53,

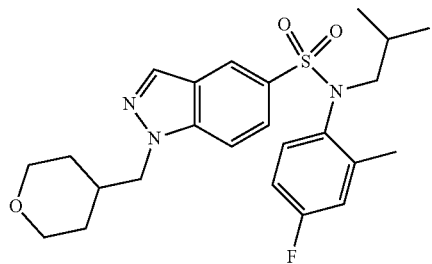 [SMILES: Cc1cc(F)ccc1N(CC(C)C)S(=O)(=O)c1ccc2c(cnn2CC2CCOCC2)c1]

1-(tetrahydropyran-4-ylmethyl)-1H-indazole-5-sulfonic acid (4-fluoro-2-methylphenyl)isobutylamide
Compound 54,

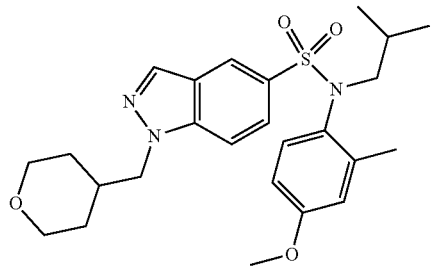 [SMILES: COc1ccc(N(CC(C)C)S(=O)(=O)c2ccc3c(cnn3CC3CCOCC3)c2)c(C)c1]

1-(tetrahydropyran-4-ylmethyl)-1H-indazole-5-sulfonic acid isobutyl(4-methoxy-2-methylphenyl)amide
Compound 55,

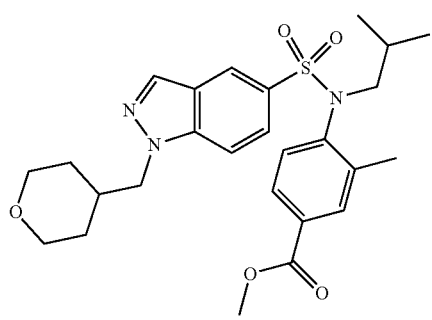 [SMILES: COC(=O)c1ccc(N(CC(C)C)S(=O)(=O)c2ccc3c(cnn3CC3CCOCC3)c2)c(C)c1]

methyl 4-{isobutyl[1-(tetrahydropyran-4-ylmethyl)-1H-indazole-5-sulfonyl]amino}-3-methylbenzoate
Compound 56,

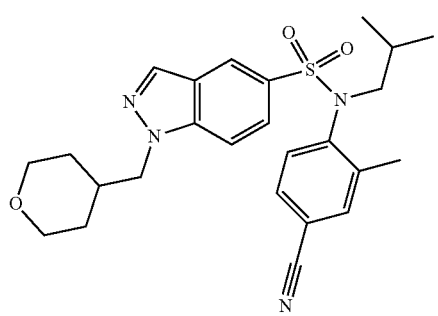 [SMILES: Cc1cc(C#N)ccc1N(CC(C)C)S(=O)(=O)c1ccc2c(cnn2CC2CCOCC2)c1]

1-(tetrahydropyran-4-ylmethyl)-1H-indazole-5-sulfonic acid (4-cyano-2-methylphenyl)isobutylamide
Compound 57,

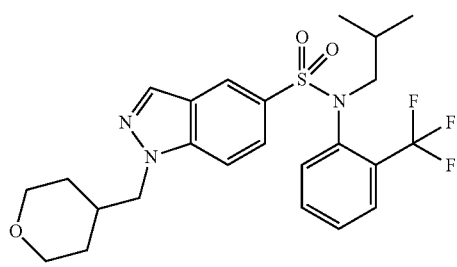 [SMILES: CC(C)CN(c1ccccc1C(F)(F)F)S(=O)(=O)c1ccc2c(cnn2CC2CCOCC2)c1]

1-(tetrahydropyran-4-ylmethyl)-1H-indazole-5-sulfonic acid isobutyl(2-trifluoromethylphenyl)amide
Compound 58,

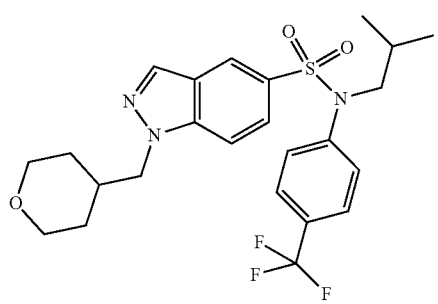 [SMILES: CC(C)CN(c1ccc(C(F)(F)F)cc1)S(=O)(=O)c1ccc2c(cnn2CC2CCOCC2)c1]

1-(tetrahydropyran-4-ylmethyl)-1H-indazole-5-sulfonic acid isobutyl(4-trifluoromethylphenyl)amide
Compound 59,

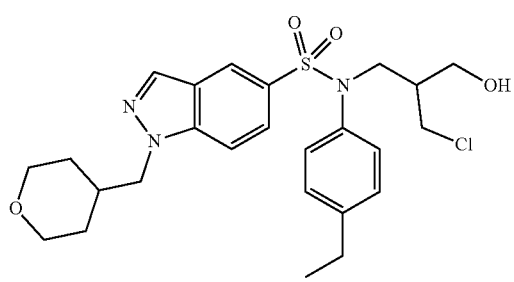 [SMILES: CCc1ccc(N(CC(CO)CCl)S(=O)(=O)c2ccc3c(cnn3CC3CCOCC3)c2)cc1]

1-(tetrahydropyran-4-ylmethyl)-1H-indazole-5-sulfonic acid (3-chloro-2-hydroxymethylpropyl)(4-ethylphenyl)amide
Compound 60,

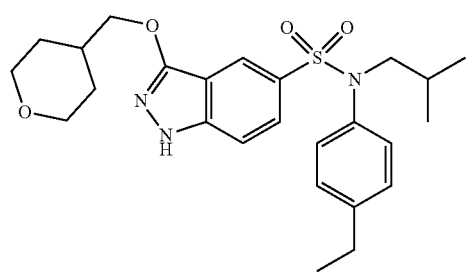 [SMILES: CCc1ccc(N(CC(C)C)S(=O)(=O)c2ccc3[nH]nc(OCC4CCOCC4)c3c2)cc1]

3-(tetrahydropyran-4-ylmethoxy)-1H-indazole-5-sulfonic acid (4-ethylphenyl)isobutylamide
Compound 61,

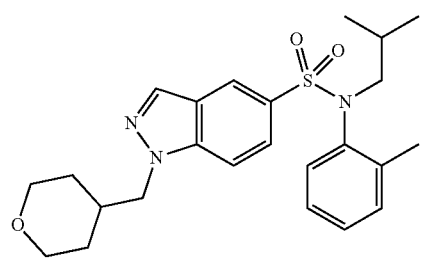 [SMILES: Cc1ccccc1N(CC(C)C)S(=O)(=O)c1ccc2c(cnn2CC2CCOCC2)c1]

1-(tetrahydropyran-4-ylmethyl)-1H-indazole-5-sulfonic acid isobutyl-o-tolylamide
Compound 69,

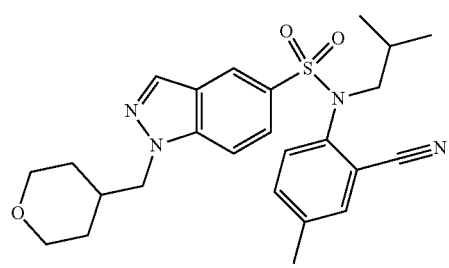 [SMILES: Cc1ccc(N(CC(C)C)S(=O)(=O)c2ccc3c(cnn3CC3CCOCC3)c2)c(C#N)c1]

1-(tetrahydropyran-4-ylmethyl)-1H-indazole-5-sulfonic acid (2-cyano-4-methylphenyl)isobutylamide
Compound 70,

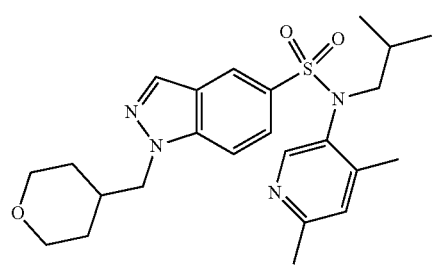 [SMILES: Cc1cc(C)c(N(CC(C)C)S(=O)(=O)c2ccc3c(cnn3CC3CCOCC3)c2)cn1]

1-(tetrahydropyran-4-ylmethyl)-1H-indazole-5-sulfonic acid (4,6-dimethylpyridin-3-yl)isobutylamide
Compound 71, and

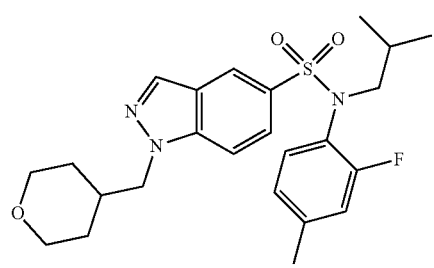 [SMILES: Cc1ccc(N(CC(C)C)S(=O)(=O)c2ccc3c(cnn3CC3CCOCC3)c2)c(F)c1]

1-(tetrahydropyran-4-ylmethyl)-1H-indazole-5-sulfonic acid (2-fluoro-4-methylphenyl)isobutylamide
Compound 73.

4. A pharmaceutical composition comprising at least one compound of formula (II) according to claim 1, or a pharmaceutically acceptable salt thereof, a hydrate thereof, or a solvate thereof.

5. The pharmaceutical composition as defined by claim 4, wherein the composition is formulated for topical or oral administration.

6. The pharmaceutical composition as defined by claim 4, wherein the composition is formulated for treating acne, atopic dermatitis and/or psoriasis.

7. The pharmaceutical composition as defined by claim 5, wherein the composition is formulated for oral administration in the form of a table, a gel capsule, a coated tablet, a syrup, a suspension, a solution, a powder, a granule, an emulsion, a suspension comprising a microsphere, a suspension comprising a nanosphere, a lipid vesical, or a polymeric vesicle.

8. The pharmaceutical composition as defined by claim 5, wherein the composition is formulated for topical administration in the form of an ointment, a cream, a milk, a pomade, a powder, an impregnated pad, a syndet, a solution, a gel, a spray, a mousse, a suspension, a stick, a shampoo, or a washing base.

9. The compound of formula (II) as defined by claim 1, wherein $R^7$ represents a heterocyclic radical selected from the group consisting of:

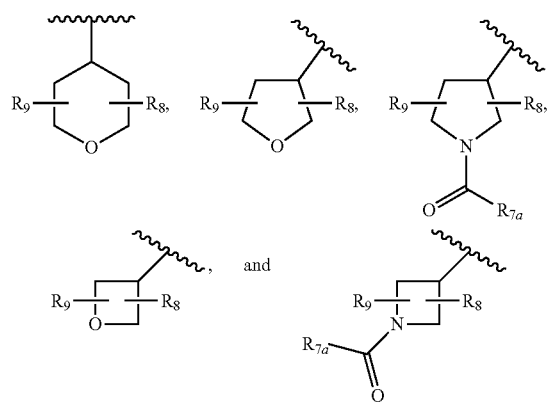

and

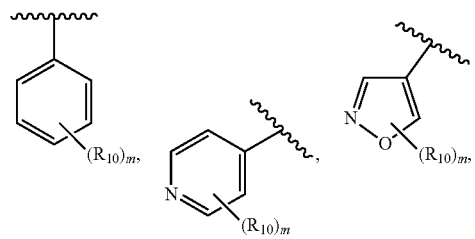

in which:
$R^{7a}$ represents a linear or branched $C_1$-$C_3$ alkyl radical, and
$R^8$ and $R^9$ represent a hydrogen atom.

10. The compound of formula (II) as defined by claim 1, wherein $R^7$ represents an aromatic or heteroaromatic radical selected from the group consisting of:

in which:
$R_{10}$ represents a hydrogen atom or a linear or branched $C_1$-$C_3$ alkyl group, and
m denotes zero or a natural integer ranging from 1 to 3.

11. The compound of formula (III) as defined by claim 2, wherein $R^7$ represents a heterocyclic radical selected from the group consisting of:

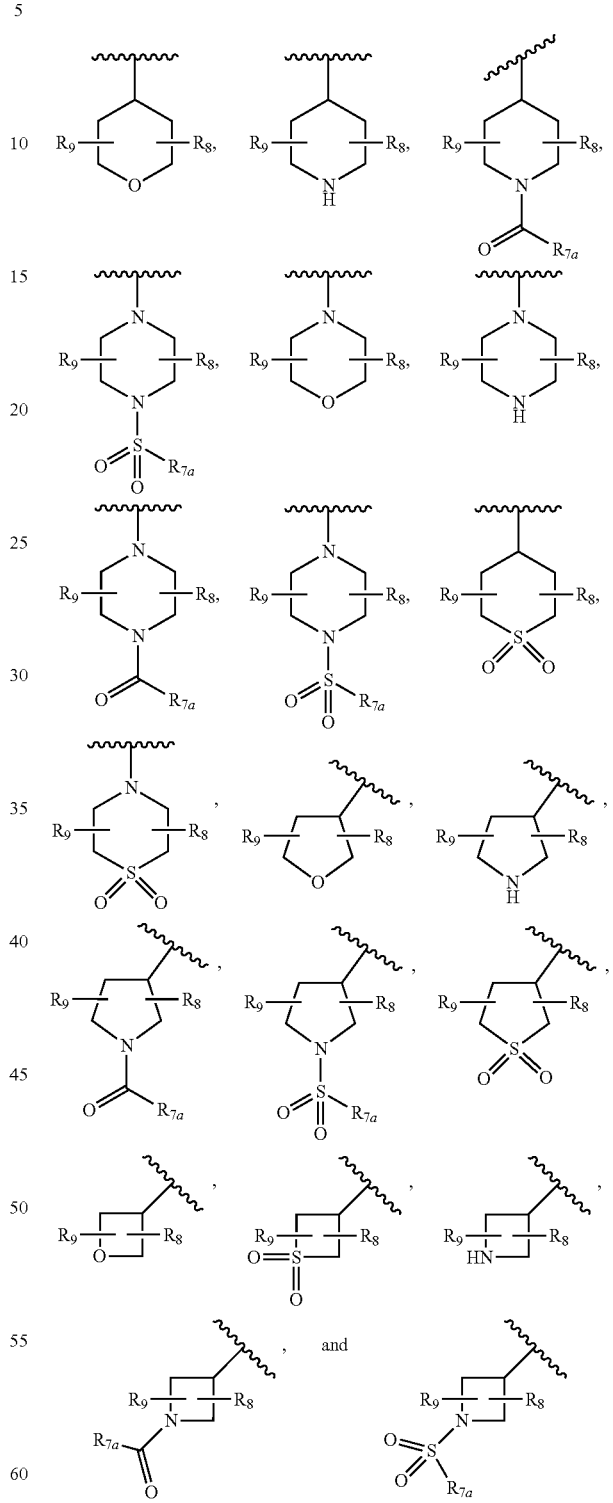

in which:
$R^{7a}$ represents a linear or branched $C_1$-$C_3$ alkyl radical, a linear or branched $C_1$-$C_3$ alkoxy radical or an amino radical $N(R^{8a})(R^{8b})$, R$^{8a}$ and R$^{8b}$, which may be identical or different, denote a hydrogen atom, a linear or branched C$_1$-C$_3$ alkyl radical or a cyclopropyl radical, R$_8$ and R$_9$, which are identical or different, represent a hydrogen atom, a linear or branched C$_1$-C$_3$ alkyl radical, a hydroxyl group —OH, a carbonyl function =O, a C$_1$ hydroxyalkyl radical (—CH$_2$OH), or an amino group NH$_2$, and R$_8$ and R$_9$ can form, together with the carbon atoms to which they are attached, a 5- to 7-membered carbocyclic ring.

12. The compound of formula (III) as defined by claim 2, wherein R$^7$ represents an aromatic or heteroaromatic radical selected from the group consisting of:

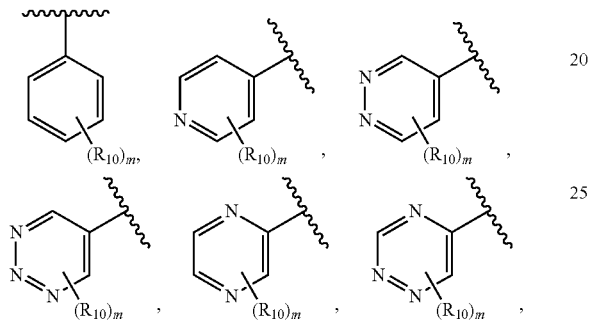

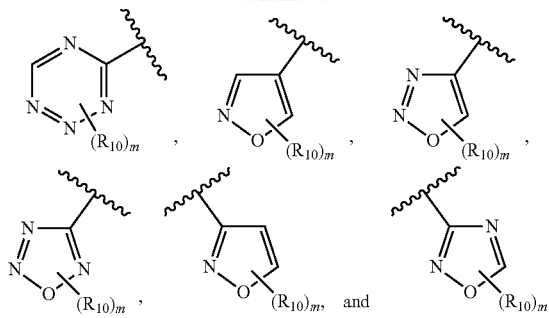

in which:
R$_{10}$ represents a hydrogen atom or a halogen atom, one linear or branched C$_1$-C$_3$ alkyl group optionally substituted with one or more halogen atoms, one C$_1$-C$_3$ alkoxy group, one amino group —NR$^{11}$R$^{12}$, one group —COR$^{11}$, one group —COOR$^{11}$, one amido group —CONR$^{11}$R$^{12}$, one group —SOR$^{11}$, one group —SO$_2$R$^{11}$, one group —NHCOR$^{11}$, one group —NHCOOR$^{11}$, one group —SO$_2$NR$^{11}$R$^{12}$ or one —CN group; R$^{11}$ and R$^{12}$, which are identical or different, representing a hydrogen atom or a linear or branched C$_1$-C$_3$ alkyl radical optionally substituted with one or more halogen atoms, and m denotes zero or a natural integer ranging from 1 to 3.

13. The compound of formula (III) as defined by claim 2, wherein the compound is selected from the group consisting of:

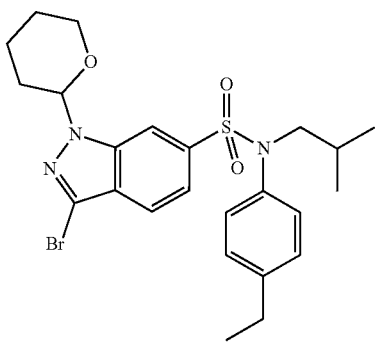 [SMILES: CCc1ccc(N(CC(C)C)S(=O)(=O)c2ccc3c(Br)nn(C4CCCCO4)c3c2)cc1]

3-bromo-1-(tetrahydropyran-2-yl)-1H-indazole-6-sulfonic acid (4-ethylphenyl)isobutylamide Compound 4,

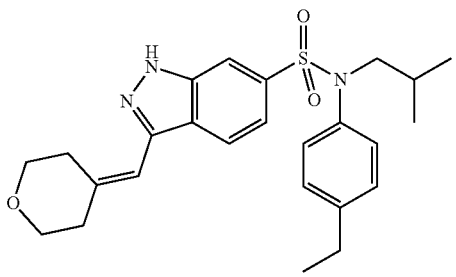

3-(tetrahydropyran-4-ylidenemethyl)-1H-indazole-6-sulfonic acid (4-ethylphenyl)isobutylamide Compound 62,

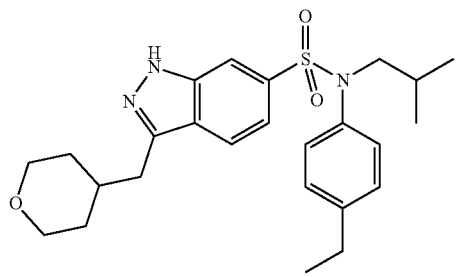 [SMILES: CCc1ccc(N(CC(C)C)S(=O)(=O)c2ccc3c(CN4CCOCC4)n[nH]c3c2)cc1]

3-(tetrahydropyran-4-ylmethyl)-1H-indazole-6-sulfonic acid (4-ethylphenyl)isobutylamide
Compound 63,

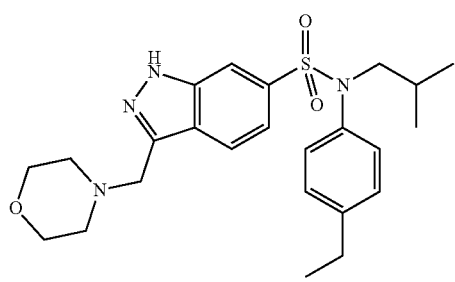

3-morpholin-4-ylmethyl-1H-indazole-6-sulfonic acid (4-ethylphenyl)isobutylamide
Compound 64,

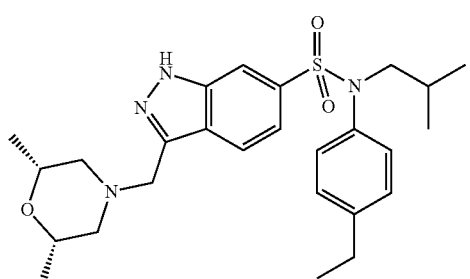

3-((cis)-2,6-dimethylmorpholin-4-ylmethyl)-1H-indazole-6-sulfonic acid (4-ethylphenyl)isobutylamide
Compound 65, and

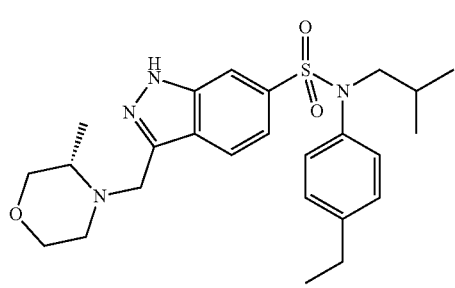 [SMILES: CCc1ccc(N(CC(C)C)S(=O)(=O)c2ccc3c(CN4CCOC[C@@H]4C)n[nH]c3c2)cc1]

3-((S)-3-methylmorpholin-4-ylmethyl)-1H-indazole-6-sulfonic acid (4-ethylphenyl)isobutylamide
Compound 66.

14. A pharmaceutical composition comprising at least one compound of formula (III) according to claim 2, or a pharmaceutically acceptable salt thereof, a hydrate thereof, or a solvate thereof.

15. The pharmaceutical composition as defined by claim 14, wherein the composition is formulated for topical or oral administration.

16. The pharmaceutical composition as defined by claim 14, wherein the composition is formulated for treating acne, atopic dermatitis and/or psoriasis.

17. The pharmaceutical composition as defined by claim 15, wherein the composition is formulated for oral administration in the form of a table, a gel capsule, a coated tablet, a syrup, a suspension, a solution, a powder, a granule, an emulsion, a suspension comprising a microsphere, a suspension comprising a nanosphere, a lipid vesical, or a polymeric vesicle.

18. The pharmaceutical composition as defined by claim 15, wherein the composition is formulated for topical administration in the form of an ointment, a cream, a milk, a pomade, a powder, an impregnated pad, a syndet, a solution, a gel, a spray, a mousse, a suspension, a stick, a shampoo, or a washing base.

19. A compound selected from the group consisting of:

Compound 1
1-(tetrahydropyran-4-ylmethyl)-1H-indazole-5-sulfonic acid (4-ethylphenyl)(1-ethylpropyl)amide, Compound 2

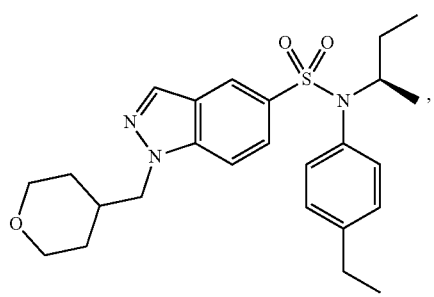

1-(tetrahydropyran-4-ylmethyl)-1H-indazole-5-
sulfonic acid ((R)-sec-butyl)(4-ethylphenyl)amide Compound 3

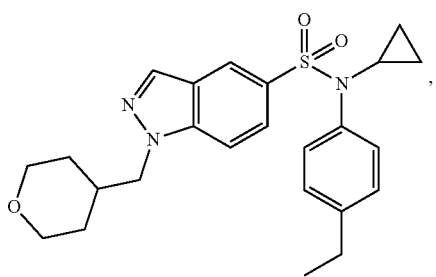

1-(tetrahydropyran-4-ylmethyl)-1H-indazole-5-
sulfonic acid cyclopropyl(4-ethylphenyl)amide Compound 4

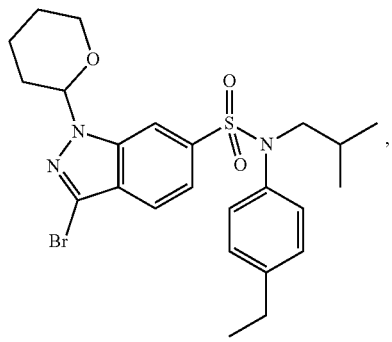

3-bromo-1-(tetrahydropyran-2-yl)-1H-indazole-6-
sulfonic acid (4-ethylphenyl)isobutylamide Compound 5

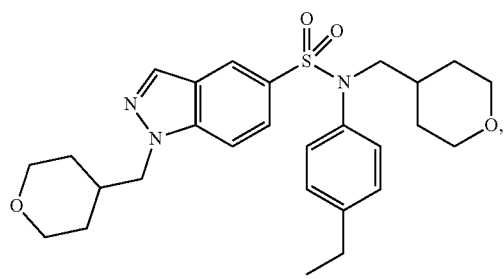

1-(tetrahydropyran-4-ylmethyl)-1H-indazole-5-sulfonic
acid (4-ethylphenyl)(tetrahydropyran-4-ylmethyl)amide Compound 6

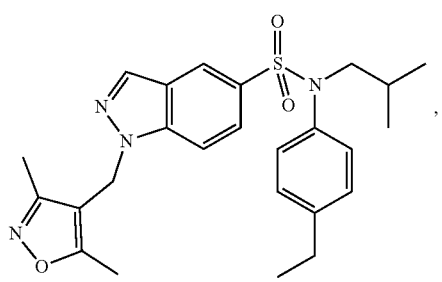

1-((3,5-dimethylisoxazol-4-yl)methyl)-N-(4-
ethylphenyl)-N-isobutyl-1H-indazole-5-sulfonamide Compound 7

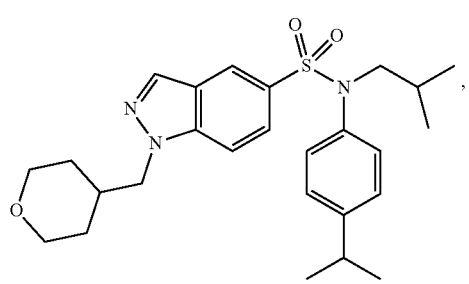

1-(tetrahydropyran-4-ylmethyl)-1H-indazole-5-
sulfonic acid butyl(4-isopropylphenyl)amide Compound 8

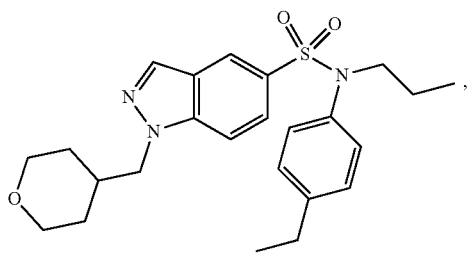

1-(tetrahydropyran-4-ylmethyl)-1H-indazole-5-
sulfonic acid (4-ethylphenyl)propyl Compound 9

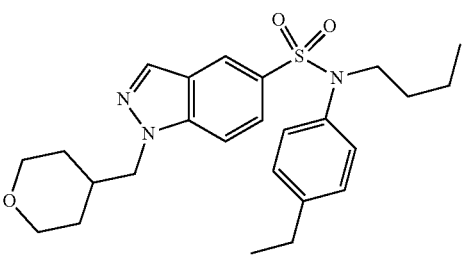

1-(tetrahydropyran-4-ylmethyl)-1H-indazole-5-
sulfonic acid butyl(4-ethylphenyl)amide Compound 10

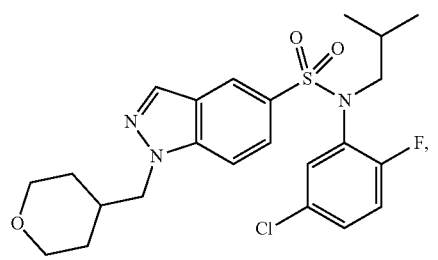

1-(tetrahydropyran-4-ylmethyl)-1H-indazole-5-
sulfonic acid (5-chloro-2-fluorophenyl)isobutylamide Compound 11

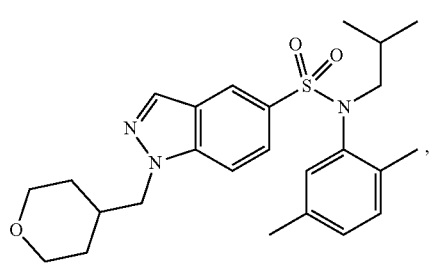

1-(tetrahydropyran-4-ylmethyl)-1H-indazole-5-
sulfonic acid (2,5-dimethylphenyl)isobutylamide Compound 12

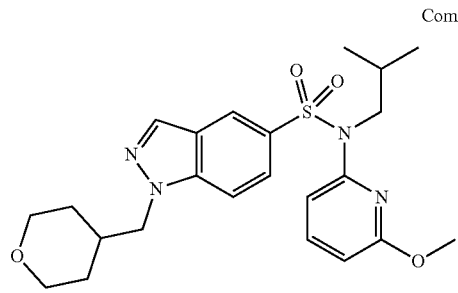

1-(tetrahydropyran-4-ylmethyl)-1H-indazole-5-
sulfonic acid (3-methoxypyridine-2-yl)isobutylamide Compound 13

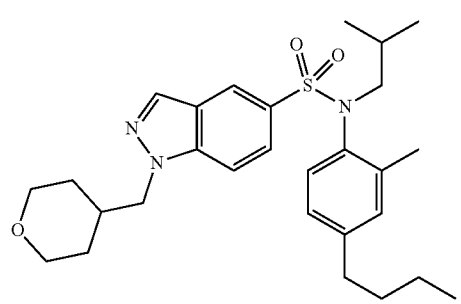

1-(tetrahydropyran-4-ylmethyl)-1H-indazole-5-
sulfonic acid (4-butyl-2-methylphenyl)isobutylamide Compound 14

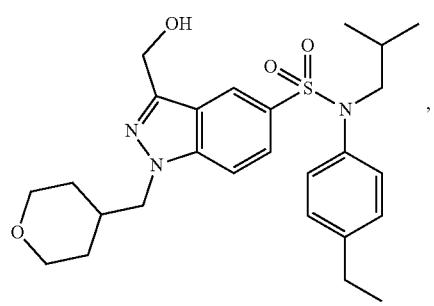

N-(4-ethylphenyl)-N-isobutyl-1-((tetrahydro-2H-
pyran-4-yl)methyl)-1H-indazole-5-sulfonamide Compound 15

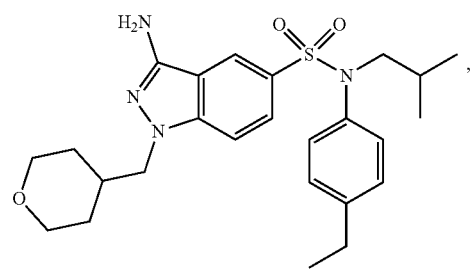

3-amino-1H-indazole-5-sulfonic acid (4-ethylphenyl)
isobutylamide

Compound 16

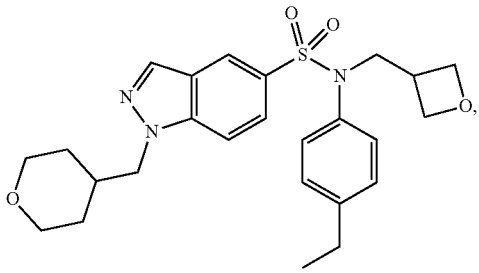

1-(tetrahydropyran-4-ylmethyl)-1H-indazole-5-sulfonic
acid (4-ethylphenyl)oxetan-3-ylmethylamide Compound 17

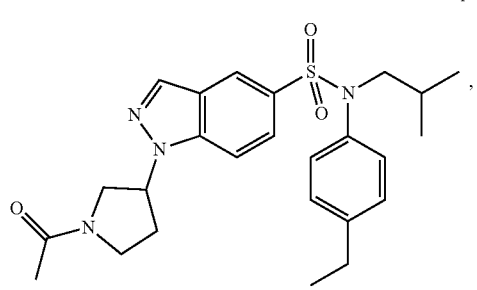

1-(1-acetylpyrrolidin-3-yl)-1H-indazole-5-sulfonic acid (4-
ethylphenyl)isobutylamide Compound 18

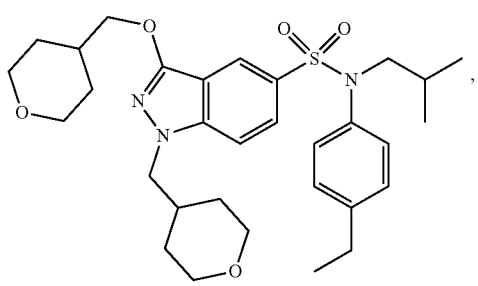

3-(tetrahydropyran-4-ylmethoxy)-1-(tetrahydropyran-4-ylmethyl)-1H-indazole-5-sulfonic acid (4-ethylphenyl)isobutylamide Compound 19

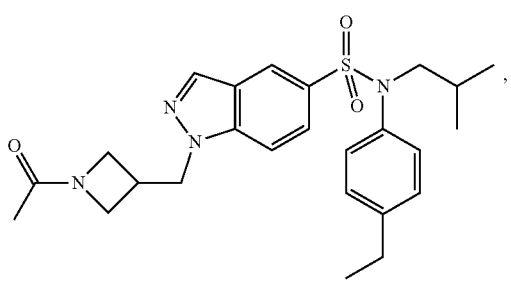

1-(3,5-dimethylisoxazol-4-ylmethyl)-1H-indazole-5-sulfonic acid (4-ethylphenyl)isobutylamide Compound 20

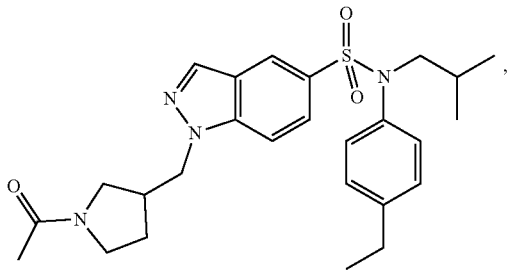

1-((1-acetylpyrrolidin-3-yl)methyl)-N-(4-ethylphenyl)-N-isobutyl-1H-indazole-5-sulfonamide Compound 21

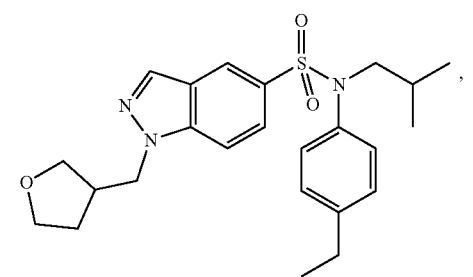

N-(4-ethylphenyl)-N-isobutyl-1-((tetrahydrofuran-3-yl)methyl)-1H-indazole-5-sulfonamide Compound 22

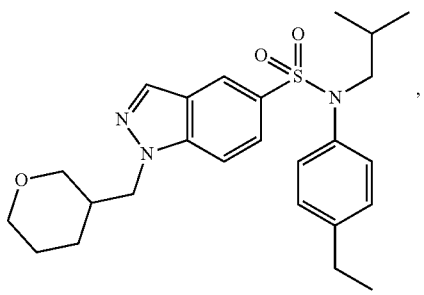

N-(4-ethylphenyl)-N-isobutyl-1-((tetrahydro-2H-pyran-3-yl)methyl)-1H-indazole-5-sulfonamide Compound 23

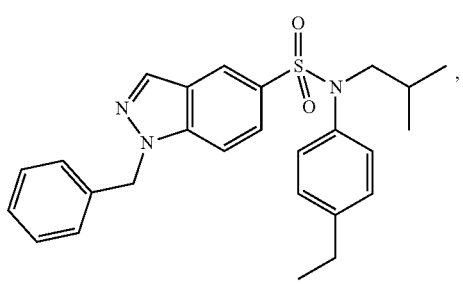

1-benzyl-N-(4-ethylphenyl)-N-isobutyl-1H-indazole-5-sulfonamide

Compound 24

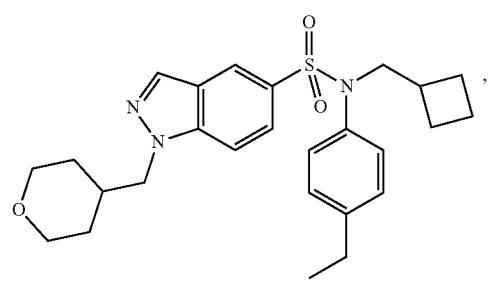

N-(cyclobutylmethyl)-N-(4-ethylphenyl)-1-((tetrahydro-2H-pryan-4-yl)methyl)-1H-indazole-5-sulfonamide Compound 25

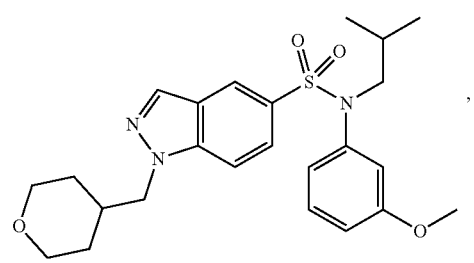

1-(tetrahydropyran-4-ylmethyl)-1H-indazole-5-sulfonic acid (3-methoxyphenyl)isobutylamide Compound 26

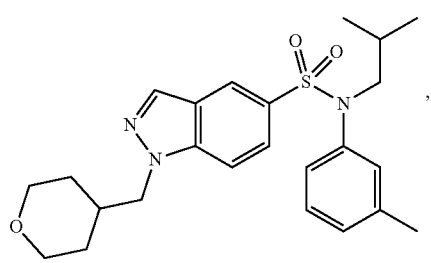

1-(tetrahydropyran-4-ylmethyl)-1H-indazole-5-sulfonic acid (3-methylphenyl)isobutylamide Compound 27

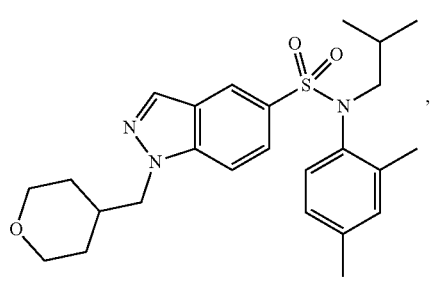

1-(tetrahydropyran-4-ylmethyl)-1H-indazole-5-sulfonic acid (2,4-dimethylphenyl)isobutylamide Compound 28

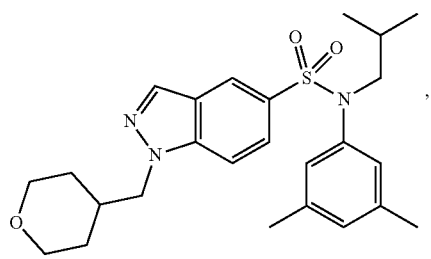

1-(tetrahydropyran-4-ylmethyl)-1H-indazole-5-sulfonic acid (3,5-dimethylphenyl)isobutylamide Compound 29

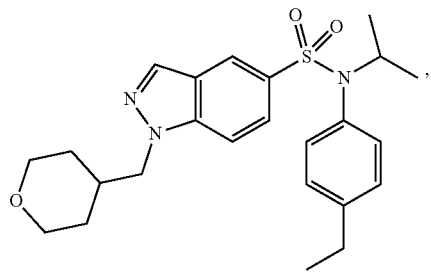

N-(4-ethylphenyl)-N-isopropyl-1-((tetrahydro-2H-pyran-4-yl)methyl)-1H-indazole-5-sulfonamide Compound 30

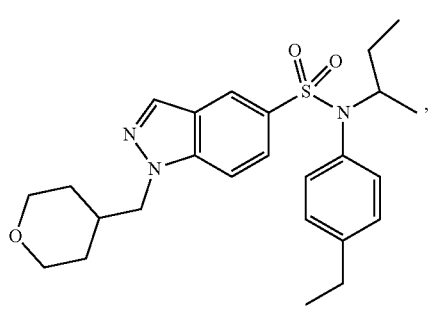

1-(tetrahydropyran-4-ylmethyl)-1H-indazole-5-sulfonic acid sec-butyl(4-ethylphenyl)amide Compound 31

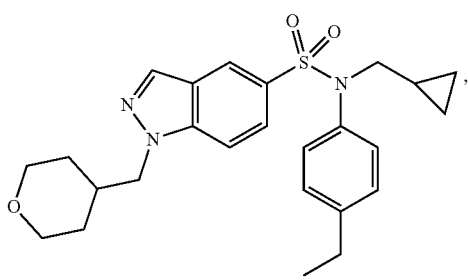

N-(cyclopropylmethyl)-N-(4-ethylphenyl)-1-((tetrahydro-2H-pyran-4-yl)methyl)-1H-indazole-5-sulfonamide Compound 32

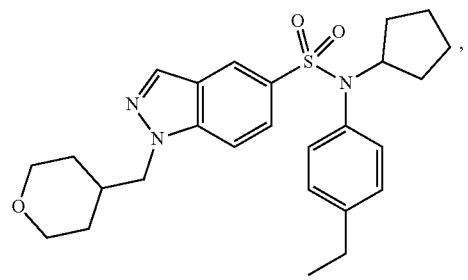

1-(tetrahydropyran-4-ylmethyl)-1H-indazole-5-sulfonic acid cyclopentyl(4-ethylphenyl)amide Compound 33

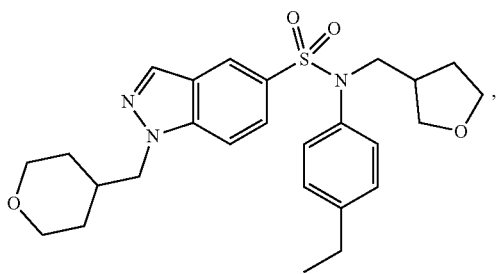

1-(tetrahydropyran-4-ylmethyl)-1H-indazole-5-sulfonic acid (4-ethylphenyl)(tetrahydrofuran-3-ylmethyl)amide Compound 34

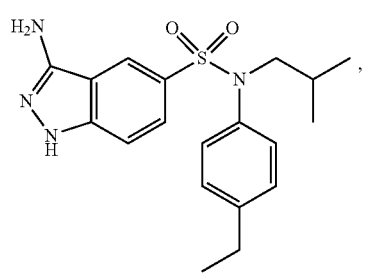

3-amino-IH-indazole-5-sulfonic acid (4-ethylphenyl)isobutylamide

Compound 38

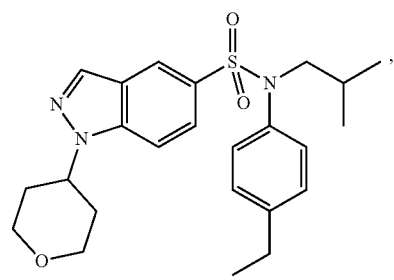

1-(tetrahydropyran-4-yl)-1H-indazole-5-sulfonic acid (4-ethylphenyl)isobutylamide Compound 35

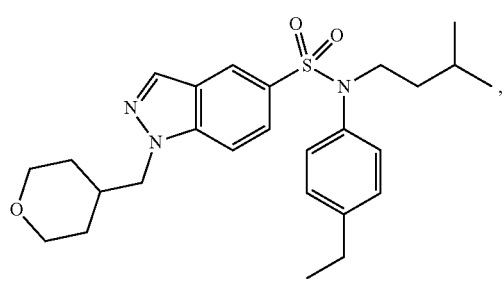

N-(4-ethylphenyl)-N-isopentyl-1-((tetrahydro-2H-pyran-4-yl)methyl)-1H-indazole-5-sulfonamide Compound 39

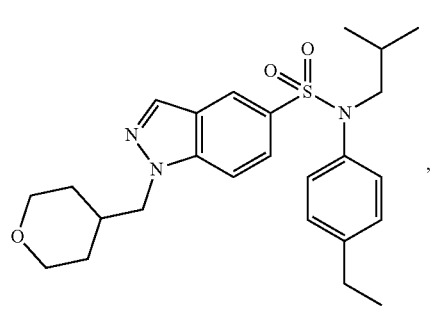

N-(4-ethylphenyl)-N-isobutyl-1-((tetrahydro-2H-pyran-4-yl)methyl)-1H-indazole-5-sulfonamide Compound 36

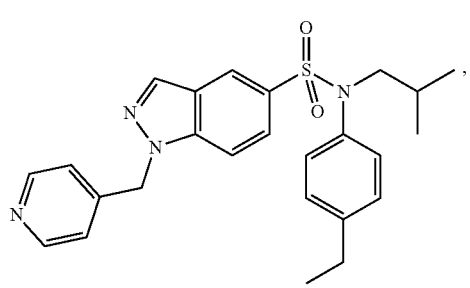

N-(4-ethylphenyl)-N-isobutyl-1-(pyridin-4-ylmethyl)-1H-indazole-5-sulfonamide

Compound 40

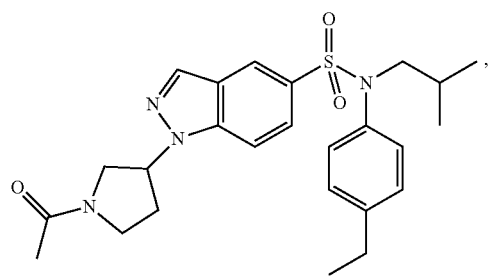

1-(1-acetylpyrrolidin-3-yl)-1H-indazole-5-sulfonic acid (4-ethylphenyl)isobutylamide Compound 37

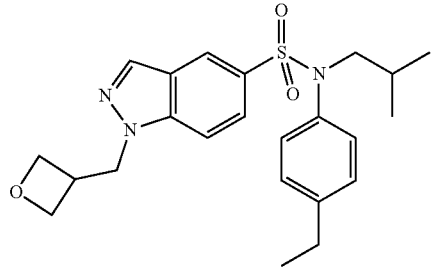

N-(4-ethylphenyl)-N-isobutyl-1-(oxetan-3-ylmethyl)-1H-indazole-5-sulfonamide

Compound 41

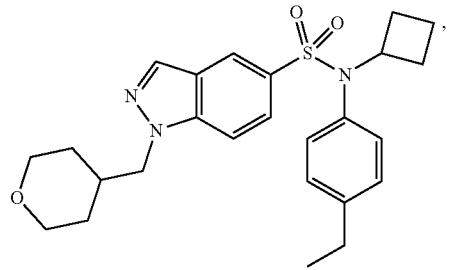

1-(tetrahydropyran-4-ylmethyl)-1H-indazole-5-sulfonic acid cyclobutyl(4-ethylphenyl)amide -continued Compound 42

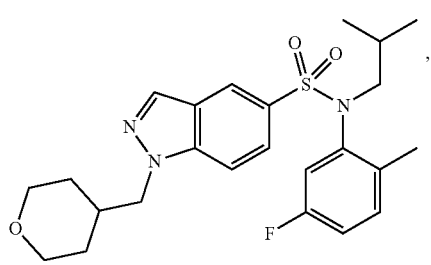

1-(tetrahydropyran-4-ylmethyl)-1H-indazole-5-
sulfonic acid (5-fluoro-2-methylphenyl)
isobutylamide Compound 43

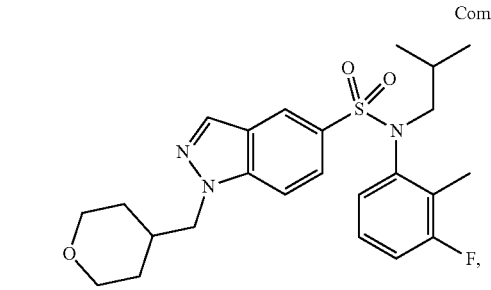

1-(tetrahydropyran-4-ylmethyl)-2H-indazole-5-sulfonic acid
(3-fluoro-2-methylphenyl)isobutylamide Compound 44

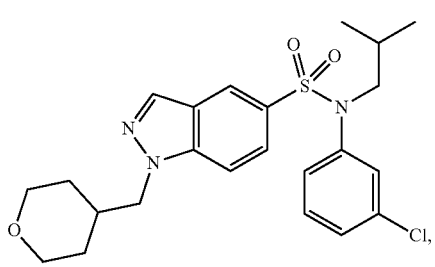

1-(tetrahydropyran-4-ylmethyl)-1H-indazole-5-
sulfonic acid (5-chlorophenyl)isobutylamide Compound 45

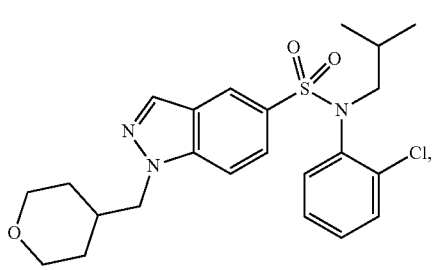

1-(tetrahydropyran-4-ylmethyl)-1H-indazole-5-
sulfonic acid (2-chlorophenyl)isobutylamide Compound 46

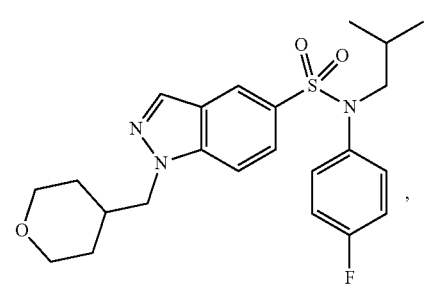

1-(tetrahydropyran-4-ylmethyl)-1H-indazole-5-
sulfonic acid (4-fluorophenyl)isobutylamide Compound 47

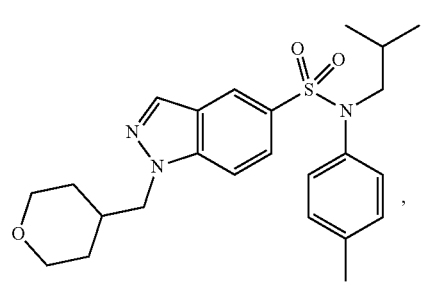

1-(tetrahydropyran-4-ylmethyl)-1H-indazole-5-
sulfonic acid isobutyl-p-tolylamide Compound 48

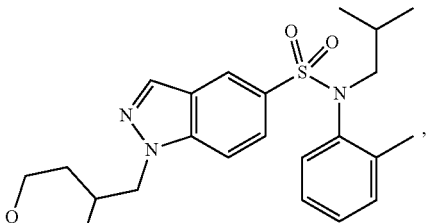

1-(tetrahydropyran-4-ylmethyl)-1H-indazole-5-
sulfonic acid isobutyl-o-tolylamide Compound 49

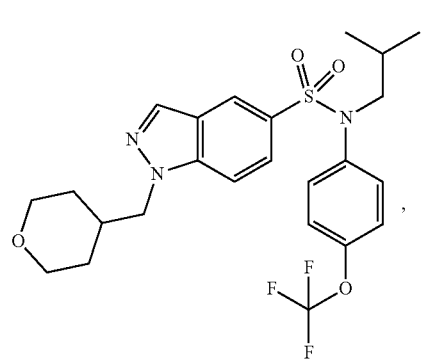

1-(tetrahydropyran-4-ylmethyl)-1H-
indazole-5-sulfonic acid
(4-trifluoromethoxyphenyl)isobutylamide Compound 50

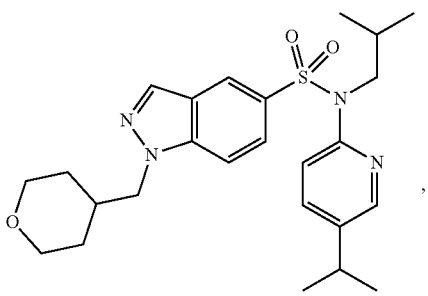

1-(tetrahydropyran-4-ylmethyl)-1H-indazole-5-
sulfonic acid isobutyl(5-isopropylpyridin-2-yl)amide Compound 51

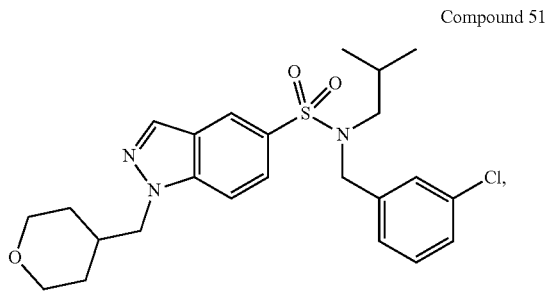

1-(tetrahydropyran-4-ylmethyl)-1H-indazole-5-
sulfonic acid (3-chloro-benzyl)isobutylamide Compound 52

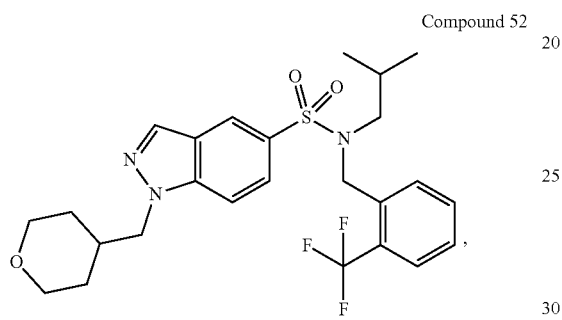

1-(tetrahydropyran-4-ylmethyl)-1H-indazole-5-
sulfonic acid isobutyl(2-trifluoromethylbenzyl)amide Compound 53

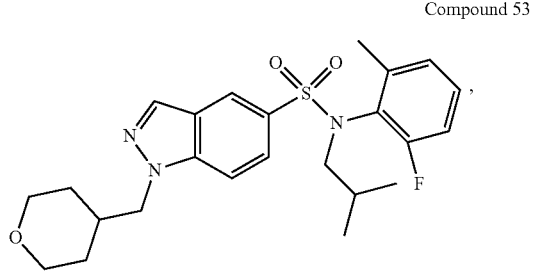

1-(tetrahydropyran-4-ylmethyl)-1H-indazole-5-sulfonic
acid (2-fluoro-6-methylphenyl)isobutylamide Compound 54

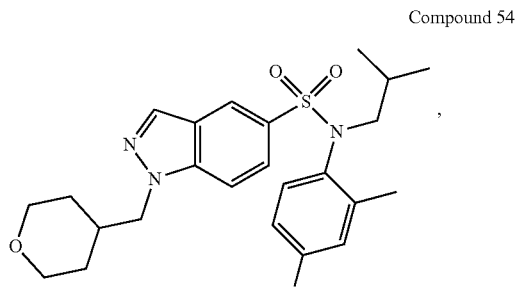

1-(tetrahydropyran-4-ylmethyl)-1H-indazole-5-sulfonic
acid (4-fluoro-2-methylphenyl)isobutylamide Compound 55

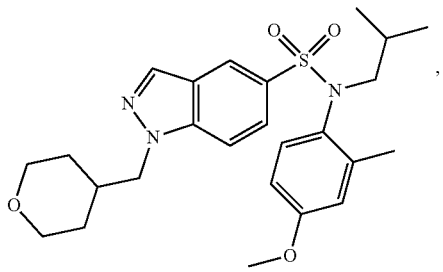

1-(tetrahydropyran-4-ylmethyl)-1H-indazole-5-sulfonic
acid isobutyl(4-methoxy-2-methylphenyl)amide Compound 56

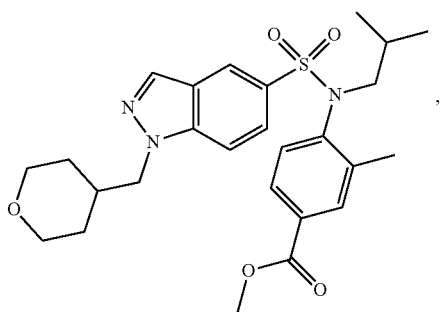

methyl 4-{isobutyl[1-(tetrahydropyran-4-ylmethyl)-1H-
indazole-5-sulfonyl]amino}-3-methylbenzoate Compound 57

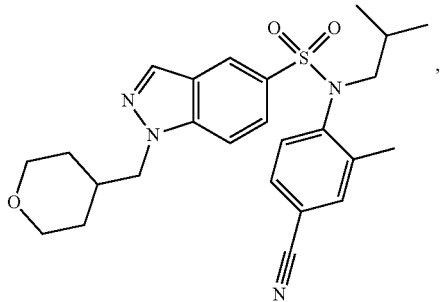

1-(tetrahydropyran-4-ylmethyl)-1H-indazole-5-sulfonic
acid (4-cyano-2-methylphenyl)isobutylamide Compound 58

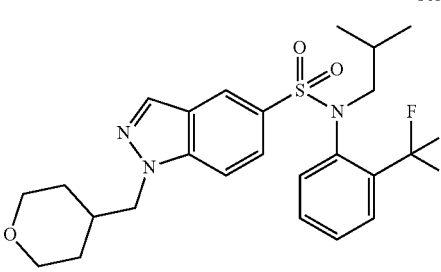

1-(tetrahydropyran-4-ylmethyl)-1H-indazole-5-sulfonic
acid isobutyl(2-trifluoromethylphenyl)amide Compound 59

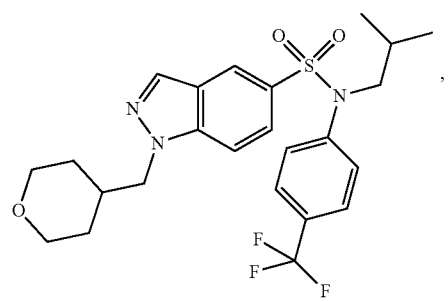

1-(tetrahydropyran-4-ylmethyl)-1H-indazole-5-sulfonic
acid isobutyl(4-trifluoromethylphenyl)amide Compound 60

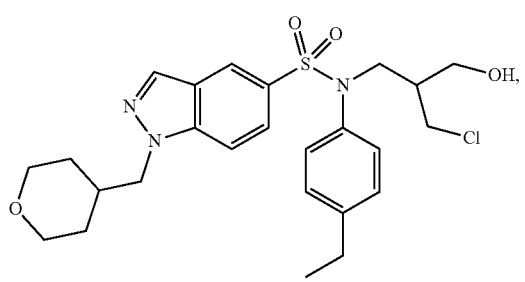

1-(tetrahydropyran-4-ylmethyl)-1H-indazole-5-sulfonic
acid (3-chloro-2-hydroxymethylpropyl)(4-ethylphenyl)amide Compound 61

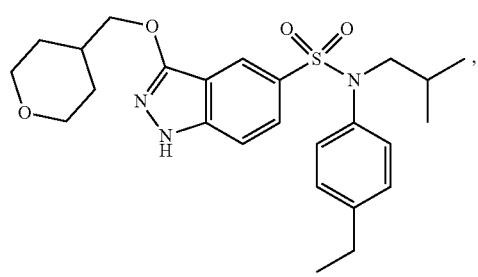

3-(tetrahydropyran-4-ylmethoxy)-1H-indazole-5-sulfonic
acid (4-ethylphenyl)isobutylamide Compound 62

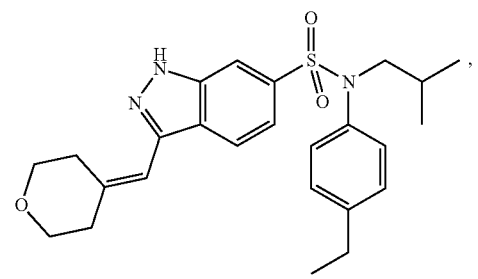

3-(tetrahydropyran-4-ylidenemethyl)-1H-indazole-
6-sulfonic acid (4-ethylphenyl)isobutylamide Compound 63

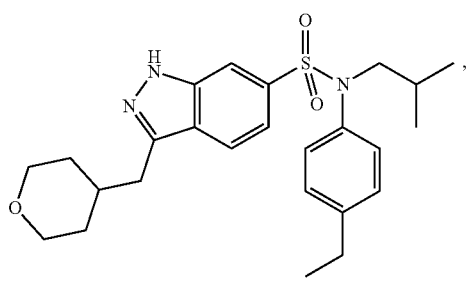

3-(tetrahydropyran-4-ylmethyl)-1H-indazole-6-sulfonic
acid (4-ethylphenyl)isobutylamide Compound 64

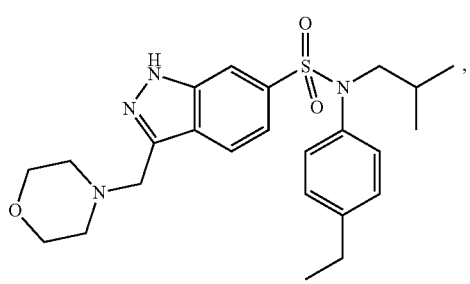

3-morpholin-4-ylmethyl-1H-indazole-6-sulfonic
acid (4-ethylphenyl)isobutylamide

Compound 65

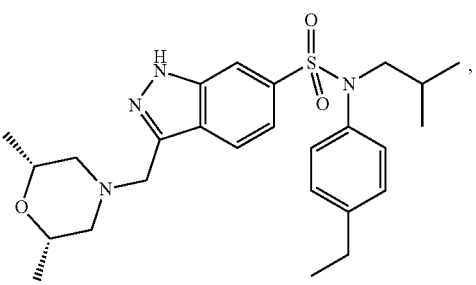

3-((cis)-2,6-dimethylmorpholin-4-ylmethyl)-1H-indazole-
6-sulfonic acid (4-ethylphenyl)isobutylamide Compound 66

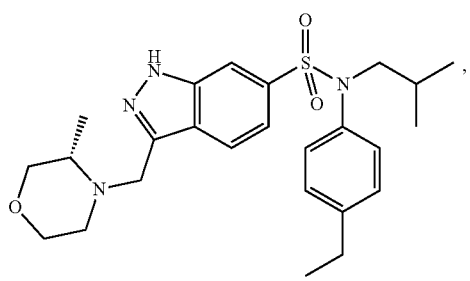

3-((S)-3-methylmorpholin-4-ylmethyl)-1H-indazole-
6-sulfonic acid (4-ethylphenyl)isobutylamide -continued Compound 69

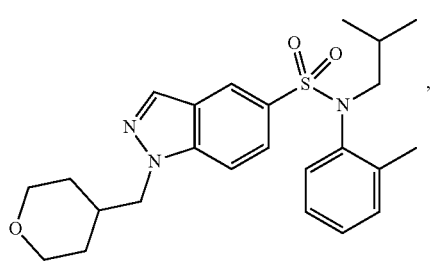

1-(tetrahydropyran-4-ylmethyl)-1H-indazole-
5-sulfonic acid isobutyl-o-tolylamide Compound 70

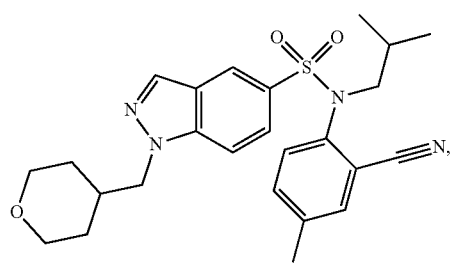

1-(tetrahydropyran-4-ylmethyl)-1H-indazole-5-sulfonic
acid (2-cyano-4-methylphenyl)isobutylamide Compound 71

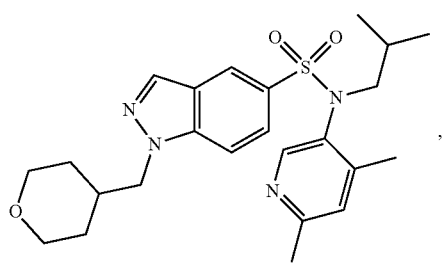

1-(tetrahydropyran-4-ylmethyl)-1H-indazole-5-
sulfonic acid (4,6-dimethylpyridin-3-yl)
isobutylamide -continued Compound 73

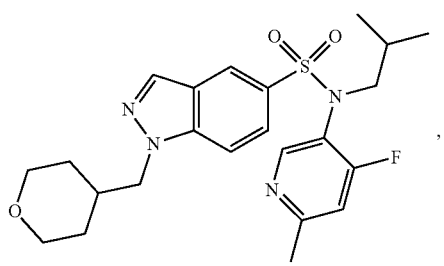

1-(tetrahydropyran-4-ylmethyl)-1H-indazole-5-
sulfonic acid (2-fluoro-4-methylphenyl)
isobutylamide Compound 75

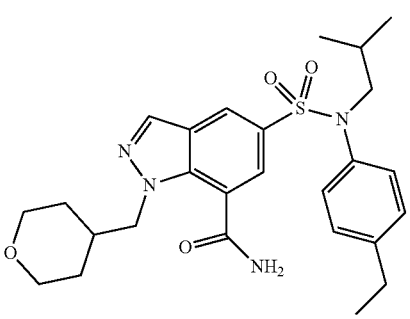

5-[(4-ethylphenyl)isobutylsulfamoyl]-1-
(tetrahydropyran-4-ylmethyl)-1H-indazole-7-
carboxylic acid amide, and.

\* \* \* \* \*